(12) United States Patent
Chu et al.

(10) Patent No.: US 6,620,828 B2
(45) Date of Patent: Sep. 16, 2003

(54) THIAZOLE COMPOUNDS AND PHARMACEUTICAL COMPOSITIONS FOR INHIBITING PROTEIN KINASES AND METHODS FOR THEIR USE

(75) Inventors: Shao Song Chu, Encinitas, CA (US); Larry Andrew Alegria, San Diego, CA (US); Steven Lee Bender, Oceanside, CA (US); Suzanne Pritchett Benedict, San Diego, CA (US); Allen J. Borchardt, San Diego, CA (US); Robert Steve Kania, San Diego, CA (US); Mitchell David Nambu, San Diego, CA (US); Anna Maria Tempczyk-Russell, San Diego, CA (US); Sepehr Sarshar, Cardiff by the Sea, CA (US); Dilip Bhumralkar, San Diego, CA (US); Zhengwei Peng, San Diego, CA (US); Michelle Yang, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 137 days.

(21) Appl. No.: 09/783,584

(22) Filed: Feb. 15, 2001

(65) Prior Publication Data

US 2002/0025976 A1 Feb. 28, 2002

Related U.S. Application Data

(63) Continuation of application No. 09/587,530, filed on Jun. 2, 2000, now abandoned.
(60) Provisional application No. 60/137,810, filed on Jun. 4, 1999.

(51) Int. Cl.[7] ..................... C07D 417/04; A01K 31/427
(52) U.S. Cl. .................. 514/364; 546/280; 514/370; 548/131; 548/181; 548/191; 548/912
(58) Field of Search ............................. 548/181, 191, 548/131, 142; 514/364, 370

(56) References Cited

U.S. PATENT DOCUMENTS

| | | | |
|---|---|---|---|
| 5,621,082 A | 4/1997 | Xiong et al. | |
| 5,705,499 A | 1/1998 | Cywin et al. | |
| 5,760,028 A | 6/1998 | Jadhav et al. | |
| 5,886,195 A | 3/1999 | Tang et al. | |

FOREIGN PATENT DOCUMENTS

| | | |
|---|---|---|
| DE | 273 062 | 11/1989 |
| EP | 0 066 270 | 8/1982 |
| EP | 0 816 357 | 1/1998 |
| WO | WO 86/05779 | 10/1986 |
| WO | WO 92/20642 | 11/1992 |
| WO | WO 93/19052 | 9/1993 |
| WO | WO 96/14843 | 5/1996 |
| WO | WO 96/23783 | 8/1996 |
| WO | WO 97/03967 | 2/1997 |
| WO | WO 97/16447 | 5/1997 |
| WO | WO 97/34876 | 9/1997 |
| WO | WO 98/09961 | 3/1998 |
| WO | WO 98/14451 | 4/1998 |
| WO | WO 99/21845 | 5/1999 |
| WO | WO 99/23076 | 5/1999 |
| WO | WO 99/23077 | 5/1999 |
| WO | WO 99/24416 | 5/1999 |
| WO | WO 99/65884 | 12/1999 |
| WO | WO 00/18761 | 4/2000 |

OTHER PUBLICATIONS

Al–Khodairy et al., *Molec. Biol. Cell*, 5, 147–160 (1994).
Alon, et. al, *Nat. Med.*, 1, 1024 (1995).
Bolen, *Oncogene*, 8, 2025–2031 (1993).
Hartwell et al., *Science*, 266, 1821–1828 (1994).
Hartwell et al., *Science*, 246, 629–634 (1989).
Jeffrey et al., *Nature*, 376, 313–320 (Jul. 27, 1995).
Kamb, *Trends in Genetics*, 11, 136–140 (1995).
Kamb et al., *Science*, 264, 436–440 (1994).
Lee et al., *Biochem*, 23, 4255 (1984).
Lutty and McLeod, *Arch. Ophthalmol.*, 110, 267 (1992.
Matsuoka, *Science*, 282, 1893–1897 (1998).
Merenmines et al., *Cell Growth & Differentiation*, 8, 3–10 (1997).
Mohammadi et al., *Mol. Cell. Biol.*, 16, 977–989 (1996).
Mylari et al., *J. Med. Chem.*, 35, 457–465 (1992).
Nurse, *Cell*, 91, 865–867 (1997).
O'Connor, *Cancer Surveys*, 29, 151–182 (1997).
Parast C. et al., *BioChemsitry*, 37, 16788–16801 (1998).
Peng et al., *Science*, 277, 1501–1505 (1997).
Penn et. al., *Invest. Ophthalmol. Vis. Sci.*, 36, 2063, (1995).
Rosenblatt et al., *J. Mol. Biol.*, 230, 1317–1319 (1993).
Sanchez et al., *Science*, 277, 1497–1501 (1997).
Still et al., *J. Org. Chem.*, 43, 2923 (1978).
J. Stone, et al, *J. Neurosci.*, 15, 4738 (1995).
Thompson, *Oncogene*, 15, 3025–3035 (1997).
Walworth et al., *Nature*, 363, 368–371 (1993).
Weinert, *Science*, 277, 1450–1451 (1997).

(List continued on next page.)

*Primary Examiner*—Robert Gerstl
(74) *Attorney, Agent, or Firm*—Bryan C. Zielinski; Joseph F. Reidy; Wendy Lei Hsu

(57) ABSTRACT

Diaminothiazole compounds that modulate and/or inhibit the activity of certain protein kinases are described. These compounds and pharmaceutical compositions containing them are capable of mediating tyrosine kinase signal transduction in order to modulate and/or inhibit unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, neovascular glaucoma, rheumatoid arthritis, and psoriasis, by administering effective amounts of such compounds.

13 Claims, No Drawings

OTHER PUBLICATIONS

Whitney, G.S. et al., DNA Cell Biol 9, 823–830, 1993.
Winters et al., *Oncogene,* 17, 673–684 (1998).
Zeng et al., *Nature,* 395, 507–510 (1998).
Bunz et al., *Science,* 282, 1497–1501 (1998).
Castro et al., *J. Med Chem,* 39:842–849
Cohen, *Curr. Op. Chem. Biol.,* 3, 459–65 (1999).
Folkman, *Nature Med.,* 1, 27–31 (1995).
Holash et al., *Oncogene,* 18, 5356–62 (1999).
Katsura et al., *Chem Pharm Biol,* 40(8), 2062–2072–140 (1992).
Klohs et al., *Curr. Op. Chem. Biol.,* 10, 544–49 (1999).
Klunder et al., *J. Med Chem,* 41, 2960–2971 (1998).
Lin et al., *J Med Chem.,* 15(6), 615 (1972).
Maisonpierre et al., *Science,* 277, 55–60 (1997).
McMahon et al., *Current Opinion in Drug Discovery & Development,* 1, 131–146 (1998).
McMahon et al, *Oncologist,* 5, 3–10 (2000).
Millauer et al., *Cancer Research,* 56, 1615–1620 (1996).
Mohammadi et al., *EMBO Journal,* 17, 5896–5904 (1998.
Sarodnick et al, *J. Prakt. Chem.* 339, 714–720 (1997).
Strawn et al., *Exp. Opin. Invest. Drugs,* 7, 553–573 (1998).
Thomas et al., *J. Biol. Chem.,* 274, 36684–92 (1999).
Rosowsky et al, *J. Med. Chem.,* 31, 763–768 (1988).
Yoshiji et al., *Cancer Research,* 57, 3924–3928 (1997).
Strawn et al., *Cancer Research,* 56, 3540–3545 (1996).

THIAZOLE COMPOUNDS AND PHARMACEUTICAL COMPOSITIONS FOR INHIBITING PROTEIN KINASES AND METHODS FOR THEIR USE

CROSS-REFERENCE TO RELATED APPLICATION

This application is a continuation of application Ser. No. 09/587,530; filed Jun. 2, 2000, now abandoned, which claims the benefit of U.S. Provisional Patent Application No. 60/137,810, filed Jun. 4, 1999.

FIELD OF THE INVENTION

This invention is directed to diaminothiazole compounds that modulate and/or inhibit the activity of certain protein kinases, and to pharmaceutical compositions containing such compounds. The invention is also directed to the therapeutic or prophylactic use of such compounds and compositions, and to methods of treating cancer as well as other disease states associated with unwanted angiogenesis and/or cellular proliferation, by administering effective amounts of such compounds.

BACKGROUND OF THE INVENTION

Protein kinases are a family of enzymes that catalyze phosphorylation of the hydroxy group of specific tyrosine, serine, or threonine residues in proteins. Typically, such phosphorylation dramatically perturbs the function of the protein, and thus protein kinases are pivotal in the regulation of a wide variety of cellular processes, including metabolisim, cell proliferation, cell differentiation, and cell survival. Of the many different cellular functions in which the activity of protein kinases is known to be required, some processes represent attractive targets for therapeutic intervention for certain disease states. Two examples are angiogenesis and cell-cycle control, in which protein kinases play a pivotal role; these processes are essential for the growth of solid tumors as well as for other diseases.

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., *Cell Growth & Differentiation*, 8, 3–10 (1997). On the other hand, unwanted angiogenesis is a hallmark of several diseases, such as retinopathies, psoriasis, rheumatoid arthritis, age-related macular degeneration (AMD), and cancer (solid tumors). Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540–3545 (1996)), as has been shown with mutants of VEGF-R2 which fail to mediate signal transduction. Millauer et al., *Cancer Research*, 56, 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924–3928 (1997). Unlike VEGF-R2, however, FGF-R is expressed in a number of different cell types throughout the body and may or may not play important roles in other normal physiological processes in the adult. Nonetheless, systemic administration of a small-molecule inhibitor of the kinase activity of FGF-R has been reported to block bFGF-induced angiogenesis in mice without apparent toxicity. Mohammadi et al., *EMBO Journal*, 17, 5896–5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277, 55–60 (1997).

As a result of the above-described developments, it has been proposed to treat angiogenesis by the use of compounds inhibiting the kinase activity of VEGF-R2, FGF-R, and/or TEK For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation and ocular diseases with retinal vessel proliferation.

In addition to its role in angiogenesis, protein kinases also play a crucial role in cell-cycle control. Uncontrolled cell proliferation is the insignia of cancer. Cell proliferation in response to various stimuli is manifested by a de-regulation of the cell division cycle, the process by which cells multiply and divide. Tumor cells typically have damage to the genes that directly or indirectly regulate progression through the cell division cycle.

Cyclin-dependent kinases (CDKs) are serine-threonine protein kinases that play critical roles in regulating the transitions between different phases of the cell cycle. See, e.g., the articles compiled in *Science*, 274, 1643–1677 (1996). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell cycle.

It is CDK4 complexed to the D cyclins that plays a critical part in initiating the cell-division cycle from a resting or quiescent stage to one in which cells become committed to cell division. This progression is subject to a variety of growth regulatory mechanisms, both negative and positive. Aberrations in this control system, particularly those that affect the function of CDK4, have been implicated in the advancement of cells to the highly proliferative state characteristic of malignancies, particularly familial melanomas, esophageal carcinomas, and pancreatic cancers. See, e.g., Kamb, *Trends in Genetics,* 11, 136–140 (1995); Kamb et al., *Science,* 264, 436–440 (1994).

The use of compounds as anti-proliferative therapeutic agents that inhibit CDKs is the subject of several patent publications. For example, U.S. Pat. No. 5,621,082 to Xiong et al. discloses nucleic acid encoding an inhibitor of CDK6, and European Patent Publication No. 0 666 270 A2 describes peptides and peptide mimetics that act as inhibitors of CDK1 and CDK2. WIPO International Publication No. WO 97/16447 discloses certain analogs of chromones that are inhibitors of cyclin-dependent kinases, in particular of CDK/cyclin complexes such as CDK4/cyclin D1, which may be used for inhibiting excessive or abnormal cell proliferation, and therefore for treating cancer. WIPO International Publication No. WO 99/21845 describes 4-aminothiazole derivatives that are useful as CDK inhibitors.

There is still a need, however, for small-molecule compounds that may be readily synthesized and are effective in inhibiting one or more CDKs or CDK/cyclin complexes. Because CDK4 may serve as a general activator of cell division in most cells, and complexes of CDK4 and D-type cyclins govern the early $G_1$ phase of the cell cycle, there is a need for effective inhibitors of CDK4, and D-type cyclin complexes thereof, for treating one or more types of tumors. Also, the pivotal roles of cyclin E/CDK2 and cyclin B/CDK1 kinases in the $G_1/S$ phase and $G_2/M$ transitions, respectively, offer additional targets for therapeutic intervention in suppressing deregulated cell-cycle progression in cancer.

Another protein kinase, CHK1, plays an important role as a checkpoint in cell-cycle progression. Checkpoints are control systems that coordinate cell-cycle progression by influencing the formation, activation and subsequent inactivation of the cyclin-dependent kinases. Checkpoints prevent cell-cycle progression at inappropriate times, maintain the metabolic balance of cells while the cell is arrested, and in some instances can induce apoptosis (programmed cell death) when the requirements of the checkpoint have not been met. See, e.g., O'Connor, *Cancer Surveys,* 29, 151–182 (1997); Nurse, *Cell,* 91, 865–867 (1997); Hartwell et al., *Science,* 266, 1821–1828 (1994); Hartwell et al., *Science,* 246, 629–634 (1989).

One series of checkpoints monitors the integrity of the genome and, upon sensing DNA damage, these "DNA damage checkpoints" block cell-cycle progression in $G_1$ and $G_2$ phases, and slow progression through S phase. O'Connor, *Cancer Surveys,* 29, 151–182 (1997); Hartwell et al., *Science,* 266, 1821–1828 (1994). This action enables DNA repair processes to complete their tasks before replication of the genome and subsequent separation of this genetic material into new daughter cells takes place. Importantly, the most commonly mutated gene in human cancer, the p53 tumor-suppressor gene, produces a DNA damage checkpoint protein that blocks cell-cycle progression in $G_1$ phase and/or induces apoptosis (programmed cell death) following DNA damage. Hartwell et al., *Science,* 266, 1821–1828 (1994). The p53 tumor suppressor has also been shown to strengthen the action of a DNA damage checkpoint in $G_2$ phase of the cell cycle. See, e.g., Bunz et al., *Science,* 282, 1497–1501 (1998); Winters et al., *Oncogene,* 17, 673–684 (1998); Thompson, *Oncogene,* 15, 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer-killing effects of DNA-damaging agents: the $G_2$ checkpoint. The $G_2$ checkpoint is regulated by a control system that has been conserved from yeast to humans. Important in this conserved system is a kinase, CHK1, which transduces signals from the DNA-damage sensory complex to inhibit activation of the cyclin B/Cdc2 kinase, which promotes mitotic entry. See, e.g., Peng et al., *Science,* 277, 1501–1505 (1997); Sanchez et al., *Science,* 277, 1497–1501 (1997). Inactivation of CHK1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell,* 91, 865–867 (1997); Weinert, *Science,* 277, 1450–1451 (1997); Walworth et al., *Nature,* 363, 368–371 (1993); and Al-Khodairy et al., *Molec. Biol. Cell,* 5, 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as Cds1/CHK2, a kinase recently discovered to cooperate with CHK1 in regulating S phase progression (see Zeng et al., *Nature,* 395, 507–510 (1998); Matsuoka, *Science,* 282, 1893–1897 (1998)), could provide valuable new therapeutic entities for the treatment of cancer.

Integrin receptor binding to ECM initiates intracellular signals mediated by FAK (Focal Adhesion Kinase) that are involved in cell motility, cellular proliferation, and survival. In human cancers, FAK overexpression is implicated in tumorigenesis and metastatic potential through its role in integrin mediated signaling pathways.

Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene,* 8, 2025–2031 (1993), which is incorporated herein by reference In addition to the protein kinases identified above, many other protein kinases have been considered to be therapeutic targets, and numerous publications disclose inhibitors of kinase activity, as reviewed in the following: McMahon et al, *Oncologist,* 5, 3–10 (2000); Holash et al., *Oncogene,* 18, 5356–62 (1999); Thomas et al., *J. Biol. Chem.,* 274, 36684–92 (1999); Cohen, *Curr. Op. Chem. Biol.,* 3, 459–65 (1999); Klohs et al., *Curr. Op. Chem. Biol.,* 10, 544–49 (1999); McMahon et al., *Current Opinion in Drug Discovery & Development,* 1, 131–146 (1998); Strawn et al., *Exp. Opin. Invest. Drugs,* 7, 553–573 (1998). WIPO International Publication WO 00/18761 discloses certain substituted 3-cyanoquinolines as protein kinase inhibitors. As is understood by those skilled in the art, it is desirable for kinase inhibitors to possess both high affinity for the target kinase as well as high selectivity versus other protein kinases.

SUMMARY OF THE INVENTION

The present invention relates to compounds falling within formula I below which modulate and/or inhibit the activity of protein kinases, as well as to pharmaceutically acceptable prodrugs, pharmaceutically active metabolites, and pharmaceutically acceptable salts thereof (such compounds, prodrugs, metabolites and salts are collectively referred to as "agents"). The invention is also directed to pharmaceutical compositions containing such agents and their therapeutic use in treating diseases mediated by kinase activity, such as cancer, as well as other disease states associated with unwanted angiogenesis and/or cellular proliferation, such as diabetic retinopathy, neovascular glaucoma, rheumatoid arthritis and psoriasis. Further, the invention is related to methods of modulating and/or inhibiting the kinase activity associated with VEGF-R, FGF-R, CDK complexes, TEK, CHK1, LCK, and FAK.

In one general aspect, the invention relates to protein kinase inhibitors of the Formula I:

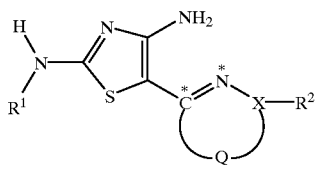

wherein:
  $R^1$ is hydrogen, a substituted or unsubstituted alkyl, cycloalkyl, heterocycloalkyl, aryl, or heteroaryl, or a group of the formula $R^6$—CO or $R^6$—CS where $R^6$ is substituted or unsubstituted alkyl, cycloalkyl, heterocycloalkyl, alkenyl, aryl, heteroaryl, alkoxy, or N—$R^7R^8$ where $R^7R^8$ are each independently hydrogen or substituted or unsubstituted alkyl, aryl, or heteroaryl;
  $R^2$ is hydroxy, halo, cyano, or nitro, or substituted or unsubstituted alkyl, alkenyl, cycloalkyl, heterocycloalkyl, aryl, or heteroaryl, or
a group of the formula (A)

where $R_a$ is hydrogen, alkyl, cycloalkyl, heterocycloalkyl, aryl, or heteroaryl, or
a group of the formula (B)

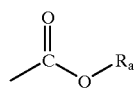

where $R_a$ is hydrogen, alkyl, cycloalkyl, heterocycloalkyl, aryl, or heteroaryl, or a group of the formula (C)

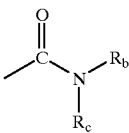

where $R_b$ and $R_c$ are independently hydrogen, alkyl, cycloalkyl, heterocycloalkyl, aryl, or heteroaryl, or
a group of the formula (D)

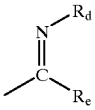

where $R_d$ is hydrogen, alkyl, cycloalkyl, heterocycloalkyl, aryl, heteroaryl, hydroxy, alkoxy, amino, alkylamino, dialkylamino, or acylamino, and $R_e$ is hydrogen, alkyl, cycloalkyl heterocycloalkyl, aryl, heteroaryl, amino, alkylamino, or dialkylamino, or
a group of the formula (E)

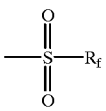

where $R_f$ is alkyl, cycloalkyl, heterocycloalkyl, aryl, or heteroaryl, or
a group of the formula (F)

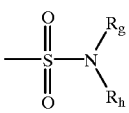

where $R_g$ and $R_h$ are each independently hydrogen, alkyl, cycloalkyl, heterocycloalkyl, aryl, or heteroaryl, or
a group of the formula (G)

where $R_i$ is alkyl, cycloalkyl, heterocycloalkyl, aryl, heteroaryl, or a group of formula (A), formula (B), formula (C), formula (H), or formula (I) as defined herein, or a group of the formula (H)

(H)

where $R_j$ is hydrogen, alkyl, cycloalkyl, heterocycloalkyl, aryl, heteroaryl, hydroxy, alkoxy, amino, or a group of formula (A), formula (B), formula (C) or formula (D) as defined herein, and $R_k$ is hydrogen, alkyl, cycloalkyl, heterocycloalkyl, aryl, heteroaryl, or a group of formula (A), formula (B), formula (C), formula (D), formula (E), or formula (F) as defined herein, or a group of the formula (I)

(I)

where $R_1$ is hydrogen, alkyl, cycloalkyl, heterocycloalkyl, aryl, heteroaryl, or a group of formula (C) as defined herein, or $R^2$ is a substituted or unsubstituted cycloalkyl, heterocycloalkyl, or aryl that is fused to Q;

X is C or N; and

Q is a divalent radical having 2 or 3 ring atoms (in the ring formed by Q together with X, C* and N* in Formula I) each independently selected from C, N, O, S, C—$R^5$ and N—$R^5$, where $R^5$ is alkyl, aryl, heteroaryl, alkoxy, hydroxy, halo, cyano, or amino, which together with C* and N* (in Formula I) form a five- or six-membered aromatic or nonaromatic ring.

The invention is also directed to pharmaceutically acceptable prodrugs, pharmaceutically active metabolites, and pharmaceutically acceptable salts of the compounds of Formula I.

In a preferred general embodiment, the invention relates to compounds having the Formula II:

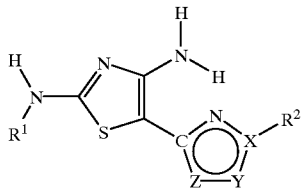

II wherein:

$R^1$ is substituted or unsubstituted aryl or heteroaryl, or a group of the formula $R^6$—CO or $R^6$—CS where $R^6$ is substituted or unsubstituted alkyl, cycloalkyl, heterocycloalkyl alkenyl, aryl, heteroaryl, alkoxy, or N—$R^7R^8$ where $R^7R^8$ are each independently hydrogen or a substituted or unsubstituted alkyl, aryl, or heteroaryl;

$R^2$ is as defined above;

X is C or N; and

Y and Z are each independently C, N, S, O, C—$R^5$ or N—$R^5$ where $R^5$ is as defined above;

and pharmaceutically acceptable prodrugs, pharmaceutically active metabolites, and pharmaceutically acceptable salts thereof. Advantageous methods of making the compounds of the Formula II are also described.

More preferably, the invention is directed to compounds of Formula II wherein: $R^1$ is substituted or unsubstituted aryl or heteroaryl, or $R^6$—CO or $R^6$—CS where $R^6$ is substituted or unsubstituted alkyl, cycloalkyl, heterocycloalkyl, alkenyl, aryl, heteroaryl, alkoxy, or N—$R^7R^8$ where $R^7R^8$ are each independently hydrogen or substituted or unsubstituted alkyl, aryl, or heteroaryl; $R^2$ is substituted or unsubstituted aryl or heteroaryl; X and Y are each independently C or N; and Z is S or O. In another preferred embodiment of compounds of the Formula II, $R^1$ and $R^2$ are each independently substituted aryl, X is C, Y is C or N, and Z is S or O. More preferably, $R^1$ is a substituted or unsubstituted alkyl, $R^2$ is a substituted aryl, X is C, Y is C or N, and Z is S or O.

In another preferred general embodiment, the invention relates to compounds of Formula III:

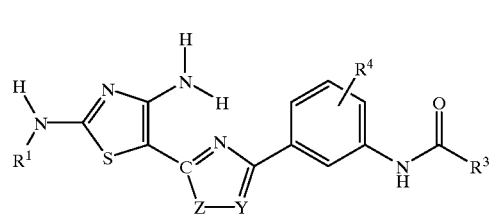

III wherein:

$R^1$ is substituted or unsubstituted aryl or heteroaryl, or $R^6$—CO or $R^6$—CS where $R^6$ is a substituted or unsubstituted alkyl, alkenyl, aryl, heteroaryl, alkoxy, or N—$R^7R^8$ where $R^7R^8$ are each independently hydrogen, alkyl, aryl, or heteroaryl;

$R^3$ is substituted or unsubstituted alkyl, cycloalkyl, heterocycloalkyl, aryl, heteroaryl, alkoxy, aryloxy, or N—$R^7R^8$ where $R^7R^8$ are each independently hydrogen, alkyl, aryl, or heteroaryl;

$R^4$ is hydrogen, hydroxy, lower alkyl, halo, lower alkoxy, amino, nitro, or trifluoromethyl; and Y and Z are each independently C, N, S, O, C—$R^5$ or N—$R^5$ where $R^5$ is unsubstituted or substituted alkyl or aryl;

as well as pharmaceutically acceptable prodrugs, pharmaceutically acceptable metabolites, and pharmaceutically acceptable salts thereof.

Especially preferred are compounds of Formula IV:

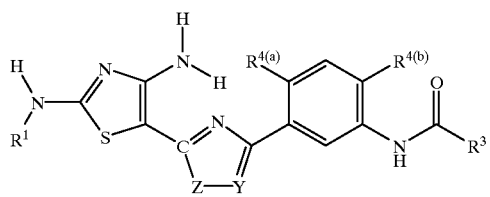

IV wherein:

$R^1$ is substituted or unsubstituted aryl or heteroaryl, or $R^6$—CO where $R^6$ is a substituted or unsubstituted alkyl, alkenyl, aryl, heteroaryl, alkoxy, cycloalkyl, heterocycloalkyl, or N—$R^7R^8$ where $R^7R^8$ are each independently hydrogen, alkyl, aryl, or heteroaryl;

$R^3$ is substituted or unsubstituted alkyl, cycloalkyl, heterocycloalkyl, aryl, heteroaryl, alkoxy, aryloxy, or N—$R^7R^8$ where $R^7R^8$ are each independently hydrogen, alkyl, aryl, or heteroaryl;

$R^4$ is independently selected from hydrogen, hydroxy, lower alkyl, halo, lower alkoxy, amino, nitro, and trifluoromethyl;

Y is C or N; and

Z is S or O;

as well as pharmaceutically acceptable prodrugs, pharmaceutically acceptable metabolites, and pharmaceutically acceptable salts thereof.

More preferably, the invention is directed to compounds of Formula IV, wherein:

$R^1$ is substituted or unsubstituted aryl or heteroaryl, or $R^6$—CO where $R^6$ is N—$R^7R^8$ where $R^7R^8$ are each independently hydrogen, alkyl, aryl, or heteroaryl; $R^3$ is substituted or unsubstituted alkyl, aryl, heteroaryl, or alkoxy; $R^{4(a)}$ and $R^{4(b)}$ are independently hydrogen, lower alkyl, or halo; Y is C or N; and Z is S or O. Even more preferred are compounds of Formula IV, wherein: $R^1$ is substituted or unsubstituted aryl or heteroaryl, or $R^6$—CO where $R^6$ is N—$R^7R^8$ where $R^7R^8$ are each independently hydrogen, alkyl, aryl, or heteroaryl; $R^3$ is substituted or unsubstituted aryl, heteroaryl, or alkoxy; $R^{4(a)}$ is chloro, fluoro, or methyl; $R^{4(b)}$ is fluoro; Y is N; and Z is O.

The invention also relates to a method of modulating and/or inhibiting the kinase activity of VEGF-R, FGF-R, TEK, a CDK complex, CHK1, TEK, LCK, and/or FAK by administering a compound of the formula I or a pharmaceutically acceptable prodrug, pharmaceutically active metabolites, or pharmaceutically acceptable salt thereof. There is also provided compounds of the present invention that have selective kinase activity—i.e., they possess significant activity against one specific kinase while possessing less or minimal activity against a different kinase. In one preferred embodiment of the invention, compounds of the present invention are those of Formula I possessing substantially higher potency against VEGF receptor tyrosine kinase than against FGF-R1 receptor tyrosine kinase. The invention is also directed to methods of modulating VEGF receptor tyrosine kinase activity without significantly modulating FGF receptor tyrosine kinase activity.

The invention also relates to pharmaceutical compositions each comprising: an effective amount of an agent selected from compounds of Formula I and pharmaceutically acceptable salts, pharmaceutically active metabolites, and pharmaceutically acceptable prodrugs thereof; and a pharmaceutically acceptable carrier or vehicle for such agent. The invention further provides methods of treating cancer as well as other disease states associated with unwanted angiogenesis and/or cellular proliferation, comprising administering effective amounts of such agents to a patient in need of such treatment.

DETAILED DESCRIPTION OF THE INVENTION AND PREFERRED EMBODIMENTS

The inventive compounds of the Formula I, II, III, and IV are useful for mediating the activity of protein kinases. More particularly, the compounds are useful as anti-angiogenesis agents and as agents for modulating and/or inhibiting the activity of protein kinases, thus providing treatments for cancer or other diseases associated with cellular proliferation mediated by protein kinases.

The term "alkyl" as used herein refers to straight- and branched-chain alkyl groups having one to twelve carbon atoms. Exemplary alkyl groups include methyl (Me), ethyl, n-propyl, isopropyl, butyl, isobutyl, sec-butyl, tert-butyl (t-Bu), pentyl, isopentyl, tert-pentyl, hexyl, isohexyl, and the like. The term "lower alkyl" designates an alkyl having from 1 to 8 carbon atoms (a $C_{1-8}$-alkyl). Suitable substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "cycloalkyl" refers to partially saturated or unsaturated carbocycles having from three to twelve carbon atoms, including bicyclic and tricyclic cycloalkyl structures. Suitable cycloalkyls include cyclopropyl, cyclobutyl, cyclopentyl, cyclohexyl, cycloheptyl, and the like.

A "heterocycloalkyl" is intended to mean a partially saturated or unsaturated monocyclic radical containing carbon atoms, preferably 4 or 5 ring carbon atoms, and at least one heteroatom selected from nitrogen, oxygen and sulfur.

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by one or more suitable substituents, for example, a substituent selected from a halogen (F, Cl, Br or I); lower alkyl; OH; $NO_2$; CN; $CO_2H$; O-lower alkyl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

The term "alkoxy" is intended to mean the radical —O-alkyl. Illustrative examples include methoxy, ethoxy, propoxy, and the like. The term "lower alkoxy" designates an alkoxy having from 1 to 8 carbon atoms The term "aryloxy" represents —O-aryl, where aryl is defined above.

The term "halogen" represents chlorine, fluorine, bromine or iodine. The term "halo" represents chloro, fluoro, bromo or iodo.

In general, the various moieties or functional groups for variables in the formulae may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

The terms "comprising" and "including" are used in an open, non-limiting sense.

Compounds of the invention are encompassed by Formula I. Although Formula I depicts a double bond between C* and N*, the artisan will understand that when Q together with C* and N* form a five- or six-membered aromatic ring, the presence of the double bond is not necessarily between C* and N*, as other canonical forms of the aromatic ring exist. It is therefore understood that all possible canonical forms of the aromatic ring formed by Q together with C* and N* are also intended to be covered by Formula I. The compounds of the invention are preferably those of the Formula II, more preferably those of the Formula III, and even more preferably those of the Formula IV.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of the Formula I, II, III, and IV, the invention includes pharmaceutically acceptable prodrugs, pharmaceutically active metabolites, and pharmaceutically acceptable salts of such compounds.

A "pharmaceutically acceptable prodrug" is a compound that may be converted under physiological conditions or by solvolysis to the specified compound or to a pharmaceutically acceptable salt of such compound.

A "pharmaceutically active metabolite" is intended to mean a pharmacologically active product produced through metabolism in the body of a specified compound or salt thereof. Metabolites of compound may be identified using routine techniques known in the art and their activities determined using tests such as those described herein.

A "pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tryosine kinases. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated. The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described below, employing the techniques available in the art using starting materials that are readily available.

In one general synthetic process, compounds of Formula I are prepared according to the following reaction scheme:

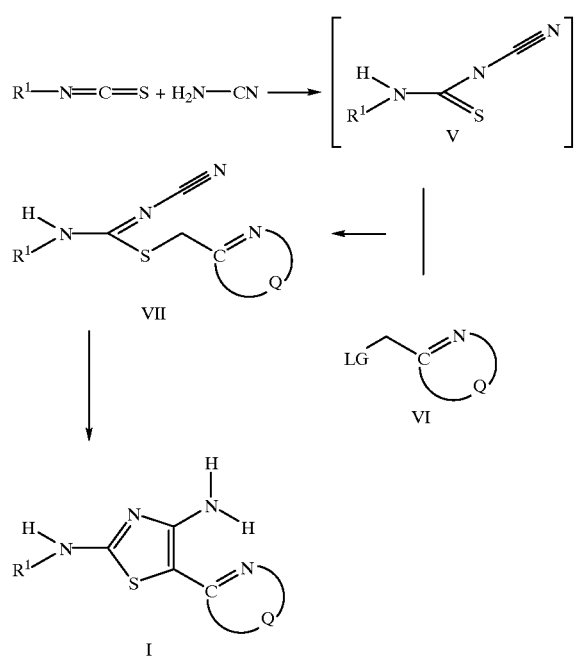

A solution of an isothiocyanate, e.g., $R^1$—N=C=S and cyanamide is reacted with 1.1 to 1.5 molar equivalents of 1,8-diazabicylclo[5.4.0]undec-7-ene ("DBU") in a suitable solvent, such as acetonitrile, at an appropriate temperature (preferably room temperature) for approximately 40–80 minutes, generating intermediate V. Without isolation, intermediate V is further allowed to react with a compound of Formula VI, where LG is a suitable leaving group such as chloro, bromo, or mesyloxy, under the same conditions for an additional 0.5 to 24 hours (h) to yield a compound of Formula VII.

In some instances, the compound of Formula VII is not isolated, but is directly converted to the compound of Formula I by continued reaction at a temperature between room temperature and 80° C., preferably 50° C., for 1 to 24 h. Conventional work-up and purification yields final compound I. Alternatively, a compound of Formula VII is isolated and purified, and then is converted to a compound of Formula I by treatment with a suitable base, such as potassium t-butoxide, lithium hexamethyldisilazide, or lithium diisopropylamide, in an appropriate solvent, such as THF, for 0.5 to 24 h at a temperature between −78° C. and room temperature. Various compounds of Formula VI are commercially available or known, for example, 2-(chloromethyl)benzimidazole, 2-(chloromethyl)quinoline, 2-picolyl chloride, 2-acetamido-4-(chloromethyl)thiazole, 6-(chloromethyl)-2-isopropylpyrimidin-4-ol, 4-chloromethyl-2-(4-chlorophenyl)thiazole, 3-(chloromethyl)-1,2,4-oxadiazole, 3-(chloromethyl)-5-(3,5-dimethylisoxazol-4-yl)-1,2,4-oxadiazole, 3-bromomethyl-6,7-dimethoxy-1-methyl-2(1h)-quinoxalinone, 2-chloromethyl-5-methoxybenzimidazole, 5-(tert-butyl)-3-(chloromethyl)-1,2,4-oxadiazole, 5-chloro-3-(chloromethyl)-1,2,4-thiadiazole, 3-(chloromethyl)-5-(3-thienyl)-1,2,4-oxadiazole, 5-[4-(chloromethyl)-1,3-thiazol-2-yl]isoxazole, 5-(chloromethyl)-3-[3,5-di(trifluoromethyl) styryl]-1,2,4-oxadiazole, 5-chloro-4-(chloromethyl)-1,2,3-thiadiazole, 5-(chloromethyl)-3-(4-chlorophenyl)-1,2,4-oxadiazole, 3-chloro-2-(chloromethyl)-5-(trifluoromethyl) pyridine, 5-(chloromethyl)-3-[(2-pyridylsulfonyl)methyl]-1,2,4-oxadiazole, 3-(chloromethyl)-5-methylisoxazole, 2-chloromethyl-4,6-dimethoxypyrimidine, 3-(chloromethyl)-5-(4-chlorophenyl)-4H-1,2,4-triazole, 2-(chloromethyl)-5-(4-chlorophenyl)-1,3,4-oxadiazole, 4-chloromethyl-5-methyl-2-phenyl-oxazole, 3-(chloromethyl)-1-(3,5-dichlorophenyl)-5-methyl-1h-pyrazole, and 3-(chloromethyl)-5-(1,2,3-thiadiazol-4-yl)-1, 2,4-oxadiazole. Compounds of Formula VI may also be prepared by methods known to those skilled in the art. See, e.g., Mylari et al., *J. Med. Chem.*, 35, 457–465 (1992); Baiocchi et al., *Heterocyclic Chem.*, 16, 1469–1474 (1979), which are incorporated by reference herein.

A compound of Formula VIII may be prepared by conventional acylation of 3-aminobenzonitrile, followed by heating at 60–100° C. with hydroxylamine in a suitable solvent, such as ethanol or isopropanol, for 1 to 24 hours. A compound of Formula VI(a) may be prepared by treatment of a compound of Formula VIII with chloroacetyl chloride and a suitable base, such as diispropylethylamine ("DIEA"), in an appropriate solvent, such as dichloromethane. Conventional aqueous work-up provides a crude intermediate, which is further heated at 100° C. in a suitable solvent, such as dioxane, for 0.5 to 4 hours, to yield, after conventional isolation and purification, a compound of Formula VI(a).

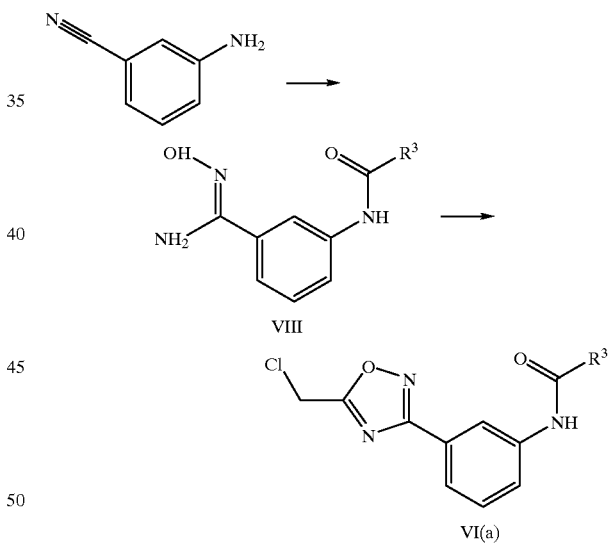

Compounds of Formula II, where X is C and Y and Z are independently C, N, or O, may also be prepared by the above described general procedure. To an $R^1$-isothiocyanate solution in acetonitrile is added cyanamide, followed by the addition of DBU, while maintaining the internal temperature of the reaction at approximately 15–30° C. After stirring 1–2 hours, a suitable reactant that allows for the cyclization and formation as described above of a compound of Formula II is added in the presence of a catalytic amount of tetrabutylammonium iodide. For example, the reaction of 3-chloromethyl-5-$R^2$-[1,2,4]oxadiazole (VI(a)) with compound VII for about two hours at approximately 50° C. provides after purification the cyclized compound II(a).

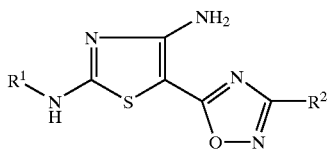

II(a)

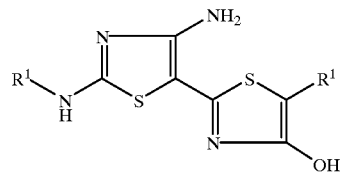

II(c)

Inventive compounds of Formulas II, III, and IV may also be prepared by other processes, including the general procedure shown in the following reaction scheme.

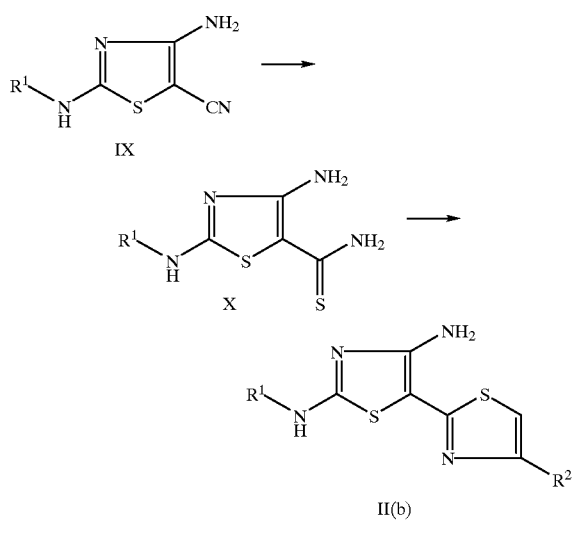

II(b)

A compound of Formula II, where X and Y are C and Z is S, may be prepared by adding DBU to a solution of $R^1$-isothiocyanato and cyanamide in a suitable solvent at an appropriate temperature, preferably acetonitrile at room temperature for approximately 40–80 minutes. To this reaction mixture is added bromo-acetonitrile and additional DBU, to yield, after conventional work-up and purification, an intermediate 2-$R^1$-amino-4-amino-thiazole-5-carbonitrile intermediate IX. The reaction of intermediate IX with dihydrogen sulfide in triethylamine/pyridine at about 0° C. provides intermediate X. Intermediate X is converted to a compound II(b) by stirring a solution of compound X and 2-bromo-1-$R^2$-ethanone in methanol overnight at room temperature. After removal of the methanol, the crude compound II(b) is worked up using conventional isolation techniques and purified using silica column chromatography.

Compounds of Formula II(c) may also be prepared directly from compound X by reacting it with a α-bromoacetic acid ester or a α-bromolactone under the same conditions as described in the preparation of compounds II(b).

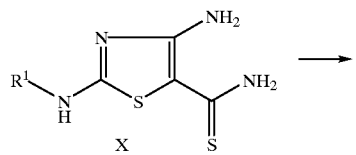

By treating compound IX with a suitable 2-amino-alcohol and a catalytic amount of $ZnCl_2$, a compound of Formula II(d) is produced after standard acid work-up and purification by silica chromatography. Compounds of Formula II(e) may also be prepared from compounds IX by refluxing in a suitable aprotic solvent, such as toluene, a solution of IX, $TMSN_3$, and a catalytic amount of $Bu_2SnO$. After refluxing, the solvent is removed and the residue is redissolved in ethyl acetate, washed with a appropriate aqueous acid solution, and dried over a suitable drying agent. After the removal of the solvent, the residue is triturated in ethyl ether and compound II(e) is collected by filtration.

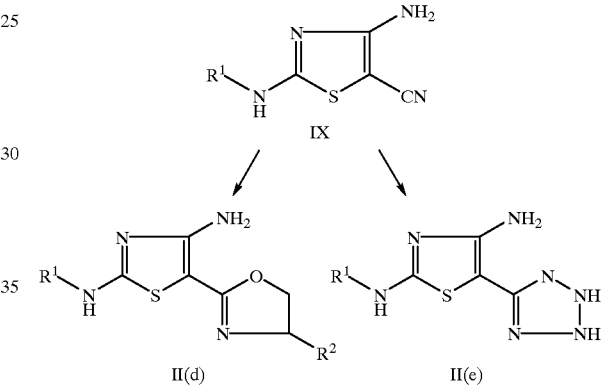

Compounds of Formula III may also be prepared directly from compound II(b) where $R^2$ is 3-nitrophenyl by reducing the nitro group with a suitable reducing agent to form the amino substituted phenyl (II(f)). Preferably, a solution of compound II(b) where $R^2$ is 3-nitrophenyl and stannous chloride is dissolved in dimethylformamide ("DMF") under inert atmosphere conditions and stirred at between 40–60° C. until II(f) is formed.

The intermediate II(f) may be reacted with a suitable acylating agent under standard acylating conditions to form a compound of the Formula III(a). A preferable acylating procedure involves dissolving compound II(f) in DMF and tetrahydrofuran ("THF") and adding pyridine and a suitable acid chloride or acyl chloroformate at −30 to 0° C. The reaction is quenched with a proton source (e.g., methanol) and purified by preparative C-18 reverse phase HPLC to provide compound III(a).

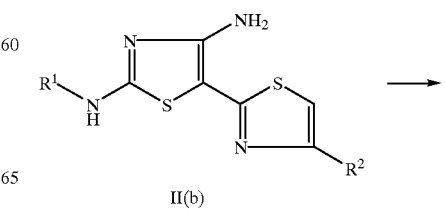

II(b)

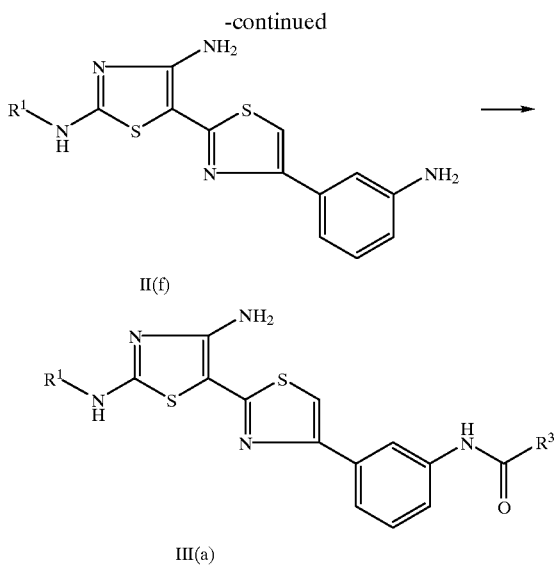

Other compounds of Formula I may be prepared in manners analogous to the general procedures described above or the detailed procedures described in the examples herein. The affinity of the compounds of the invention for a receptor may be enhanced by providing multiple copies of the ligand in close proximity, preferably using a scaffolding provided by a carrier moiety. It has been shown that provision of such multiple valence compounds with optimal spacing between the moieties dramatically improves binding to a receptor. See for example, Lee et al., *Biochem*, 23, 4255 (1984). The multivalency and spacing can be controlled by selection of a suitable carrier moiety or linker units. Such moieties include molecular supports which contain a multiplicity of functional groups that can be reacted with functional groups associated with the compounds of the invention. Of course, a variety of carriers can be used, including proteins such as BSA or HAS, a multiplicity of peptides including, for example, pentapeptides, decapeptides, pentadecapeptides, and the like. The peptides or proteins can contain the desired number of amino acid residues having free amino groups in their side chains; however, other functional groups, such as sulfhydryl groups or hydroxyl groups, can also be used to obtain stable linkages.

Compounds that potently regulate, modulate, or inhibit the protein kinase activity associated with receptors, FGF, CDK complexes, TEK, CHK1, LCK, and FAK, among others, and which inhibit angiogenesis and/or cellular profileration is desirable and is one preferred embodiment of the present invention. The present invention is further directed to methods of modulating or inhibiting protein kinase activity, for example in mammalian tissue, by administering an inventive agent. The activity of the inventive compounds as modulators of protein kinase activity, such as the activity of kinases, may be measured by any of the methods available to those skilled in the art, including in vivo and/or in vitro assays. Examples of suitable assays for activity measurements include those described in Parast C. et al., *BioChemistry*, 37, 16788–16801 (1998); Jeffrey et al., *Nature*, 376, 313–320 (Jul. 27, 1995); WIPO International Publication No. WO 97/34876; and WIPO International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I, II, III or IV and an inert, pharmaceutically acceptable carrier or diluent. In one embodiment of the pharmaceutical compositions, efficacious levels of the inventive agents are provided so as to provide therapeutic benefits involving modulation of protein kinases. By "efficacious levels" is meant levels in which the effects of protein kinases are, at a minimum, regulated. These compositions are prepared in unit-dosage form appropriate for the mode of administration, e.g., parenteral or oral administration.

An inventive agent is administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals. Administration of prodrugs are typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the Formula I, II, III, or IV is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously, intramuscularly, or intraocularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) cotains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylforamide (DMF) were purchased from Aldrich in Sure seal bottles and used as received. All solvents were purified using standard methods readily known to those skilled in the art, unless otherwise indicated.

The reactions set forth below were done generally under a positive pressure of nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the tip plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel: crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers (cm$^{-1}$). The mass spectra were obtained using LSIMS or electrospray. All melting points (mp) are uncorrected.

EXAMPLE A(1)

4-(4'-Amino-4-phenyl-[2,5']bithiazolyl-2'-ylamino)-benzenesulfonamide

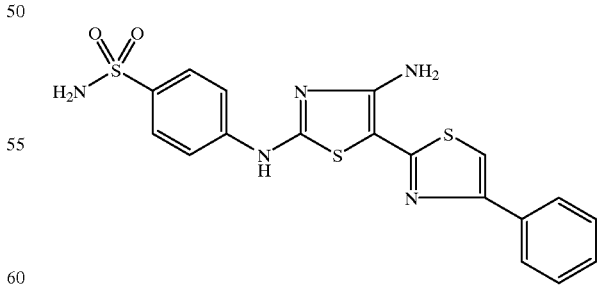

The starting material was prepared using Steps (i) and (ii) described below.

Step (i): To a solution of 4-(aminosulfonyl) phenylisothiocyanate (1.12 g, 5.0 mmol) and cyanamide (0.23 g, 5.5 mmol) in acetonitrile (50 ml) was added DBU (0.83 g, 5.5 mmol), and the resulting mixture was stirred at room temperature for 60 minutes. To the reaction mixture was added bromo-acetonitrile (0.66 g, 5.5 mmol) followed by DBU (0.83 g, 5.5 mmol) 30 minutes afterward. The reaction mixture was stirred overnight at room temperature, the solvent was removed at the reduced pressure, and the residue was dissolved in EtOAc (200 ml). The EtOAc solution was washed with 0.1 N HCl (150 ml×3) and brine and dried with MgSO$_4$ and concentrated. The residue was purified by silica gel chromatography (EtOAc) to provide 0.73 g (48%) of 2-(4-aminosulfonylphenyl)amino-4-amino-thiazole-5-carbonitrile.

Step (ii): To a solution of 2-(4-aminosulfonylphenyl) amino-4-amino-thiazole-5-carbonitrile (0.59 g, 2 mmol) in 20% triethylamine/pyridine (50 ml) was bubbled H$_2$S gas at ice-water temperature for 30 minutes. Then the reaction solution was sealed and stirred at room temperature overnight. Argon gas was bubbled through the reaction solution for 60 minutes to replace the H$_2$S, and then the solvents were removed at reduced pressure. The residue was dissolved in EtOAc, and the EtOAc solution was then washed with 5% citric acid (50 ml×3) followed by brine. The solvent was removed in vacuo and the residue was triturated in Et$_2$O. The product 2-(4-aminosulfonylphenyl)amino-4-amino-thiazole-5-carbothioamide was collected by filtration (0.56 g, 95%). To prepare the title compound, a solution of 2-(4-aminosulfonylphenyl)amino-4-amino-thiazole-5-carbothioamide (164 mg, 0.5 mmol) and α-bromoacetophenone (110 mg, 0.55 mmol) in MeOH (20 ml) was stirred at room temperature overnight. The solvent was removed in vacuo and the residue was dissolved in EtOAc (50 ml). The EtOAc solution was washed with saturated NaHCO$_3$ (10 ml), followed by brine. Purification of the residue by silica gel chromatography provided 4-(4'-amino-4-phenyl-[2,5']bithiazolyl-2'-ylamino)-benzenesulfonamide. Mp 233–235° C. (decomp.). $^1$H NMR (CD$_3$OD): δ7.96 (s, 1H), 7.82 (s, 4H), 7.44–7.25 (m, 4H). ESIMS (MH$^+$): 430; (M–H$^-$): 428.

Anal. Calcd for C$_{18}$H$_{15}$N$_5$O$_2$S$_3$: C, 50.33; H, 3.52; N, 16.30; S, 22.39. Found: C, 50.62; H, 3.54; N, 16.03; S, 22.12. In a manner similar to that used to prepare Example A(1), the following Examples A(2) through A(71) were prepared.

EXAMPLE A(2)

4-[4'-Amino-4-(4-methoxy-phenyl)-[2,5']bithiazolyl-2'-ylamino]-benzenesulfonamide

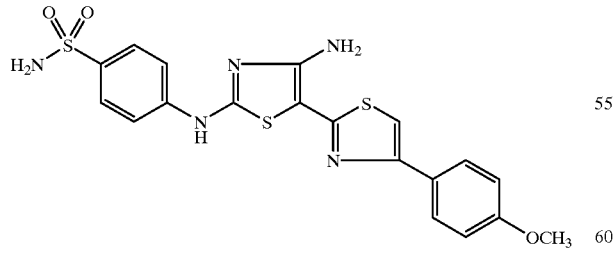

mp 195–198° C. $^1$H NMR (CD$_3$OD): δ 7.78 (d, J=8.80 Hz, 2H), 7.75 (s, 4H), 7.13 (s, 1H), 6.88 (d, J=8.86 Hz, 2H), 3.75 (s, 3H). FABMS (MH$^+$): 460. Anal. Calcd for C$_{18}$H$_{15}$N$_5$O$_2$S$_3$: C, 50.33; H, 3.52; N, 16.30; S, 22.39. Found: C, 50.62; H, 3.54; N, 16.03; S, 22.12.

EXAMPLE A(3)

4-[4'-Amino-4-(2-methoxy-phenyl)-[2,5']bithiazolyl-2'-ylamino]-benzenesulfonamide

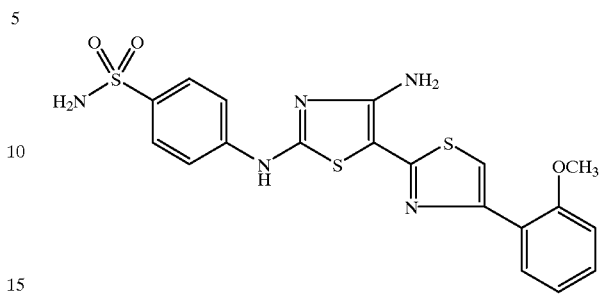

mp 231–235° C. (decomp). R$_f$ (75% EtOAc/Hex)=0.56. $^1$H NMR (CD$_3$OD): δ 8.10 (dd, J=7.79, 1.73 Hz, 1H), 7.79–7.70 (m, 4H), 7.57 (s, 1H), 7.25–7.19 (m, 1H), 7.03–6.93 (m, 2H), 3.84 (s, 3). FABMS (MH$^-$): 460.

EXAMPLE A(4)

4-[4'-Amino-4-(2,4-difluoro-phenyl)-[2,5']bithiazolyl-2'-ylamino]-benzenesulfonamide

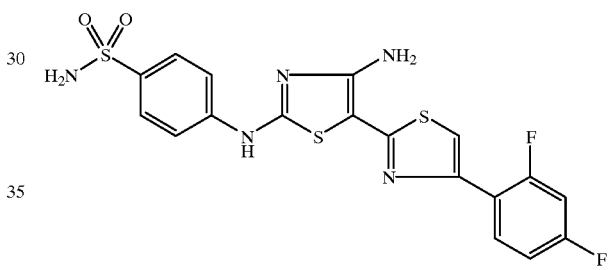

mp 233–238° C. $^1$H NMR (CD$_3$OD): δ 8.26–8.21 (m, 1H), 7.88 (s, 4H), 7.47 (s, 1H), 7.14–7.07 (m, 2). ESIMS (MH$^+$): 466; [M–H$^-$]: 464. Anal. Calcd for C$_{18}$H$_{13}$F$_2$N$_5$O$_2$S$_3$·0.4 H$_2$O: C, 45.73; H, 2.94; N, 14.82; S, 20.35. Found: C, 45.82; H, 2.78; N, 14.77; S, 20.38.

EXAMPLE A(5)

4-[4'-Amino-4-(4-fluoro-phenyl)-[2,5']bithiazolyl-2'-ylamino]-benzenesulfonamide

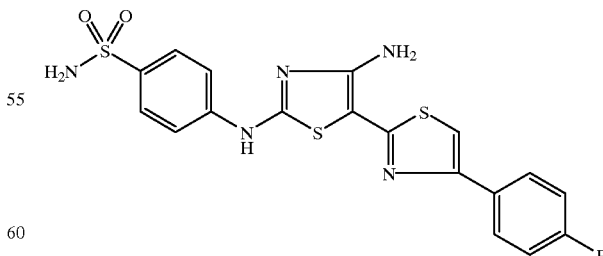

mp 254–257° C. $^1$H NMR (CD$_3$OD): δ 8.01–7.91 (m, 2H), 7.88–7.76 (m, 4H), 7.35 (s, 1H), 7.20–7.09 (m, 2H). Anal. Calcd for C$_{18}$H$_{14}$FN$_5$O$_2$S$_3$: C, 48.31; H, 3.15; N, 15.65; S, 21.49. Found: C, 48.40; H, 3.26; N, 15.44; S, 21.68.

EXAMPLE A(6)
4-[4'-Amino-4-(2,4-dichloro-phenyl)-[2,5']bithiazolyl-2'-ylamino]-benzenesulfonamide

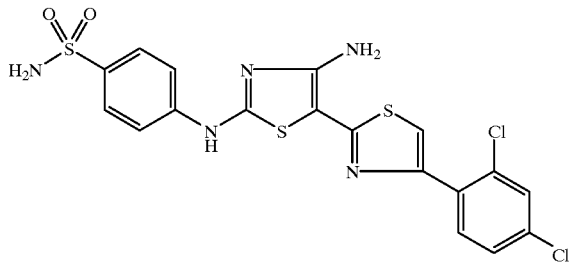

mp 173–175° C. (decomp). $^1$H NMR (CD$_3$OD): δ 7.97–7.93 (m, 1H), 7.87–7.81 (m, 4H), 7.67–7.59 (m, 1H), 7.57 (s, 1H), 7.45–7.39 (m, 1H). FABMS (MH$^+$): 498. Anal. Calcd for C$_{18}$H$_{13}$Cl$_2$N$_5$O$_2$S$_3$: C, 43.38; H, 2.63; N, 14.05; S, 19.30. Found: C, 43.32; H, 2.78; N, 13.84; S, 19.06%.

EXAMPLE A(7)
4-[4'-Amino-4-(3-chloro-5-fluoro-4-methyl-phenyl)-[2,5']bithiazolyl-2'-ylamino]-benzenesulfonamide

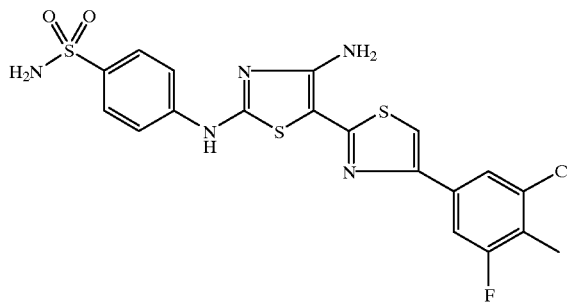

mp 208–212° C. $^1$H NMR (DMSO-d$_6$): δ 10.63 (s, NH), 7.95 (t, J=8.42 Hz, 1H), 7.73 (q, J=9.00 Hz, 4H), 7.55 (d, J=2.32 Hz, 1H), 7.35 (d, J=8.55 Hz, 1H, 7.17 (s, NH$_2$), 6.96 (s, NH$_2$), 2.28 (s, 3H). ESIMS (MH$^-$): 496. Anal. Calcd for C$_{19}$H$_{15}$ClFN$_5$O$_2$S$_3$: C, 46.01; H, 3.05; N, 14.12; S, 19.12. Found: C, 45.93; H, 3.23; N, 13.86; S, 19.47.

EXAMPLE A(8)
4-[4'-Amino-4-(4-hydroxy-phenyl)-[2,5']bithiazolyl-2'-ylamino]-benzenesulfonamide

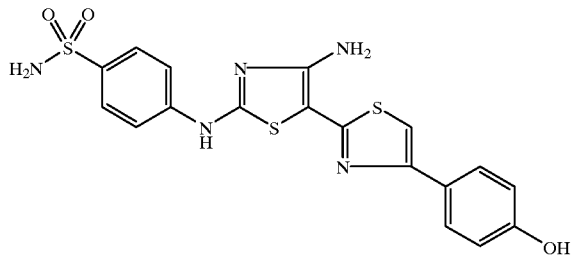

mp 168–170° C. (decomp). $^1$H NMR (CD$_3$OD): δ 7.83 (s, 4H), 7.79–7.76 (d, J=8.59 Hz, 2H), 7.16 (s, 1H), 6.85–6.82 (d, J=8.46 Hz, 2H). FABMS (MH$^+$): 446. Anal. Calcd for C$_{18}$H$_{15}$N$_5$O$_3$S$_3$.0.5 H$_2$O: C, 47.56; H, 3.55; N, 15.41; S, 21.16. Found: C, 47.87; H, 3.59; N, 15.09; S, 21.11.

EXAMPLE A(9)
4-(2,4-Difluoro-phenyl)-N$^{2'}$-(3,4,5-trimethoxy-phenyl)-[2,5']bithiazolyl-2',4'-diamine

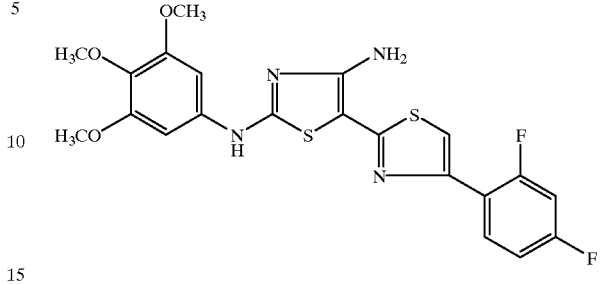

mp 180–183° C. (decomp). $^1$H NMR (CD$_3$OD): δ 8.26–8.23 (m, 1H), 7.41 (d, J=2.2 Hz, 1H), 7.13–7.05 (m, 2H), 7.02 (s, 2H), 3.90 (s, 6H), 3.78 (s, 3H). FABMS (MH$^+$): 476. Anal. Calcd for C$_{21}$H$_{18}$F$_2$N$_4$O$_3$S$_2$: C, 52.93; H, 3.81; N, 11.76; S, 13.46. Found: C, 52.81; H, 3.72; N, 11.58; S, 13.45.

EXAMPLE A(10)
4-[4'-Amino-2'-(3,4,5-trimethoxy-phenylamino)-[2,5']bithiazolyl-4-yl]-phenol

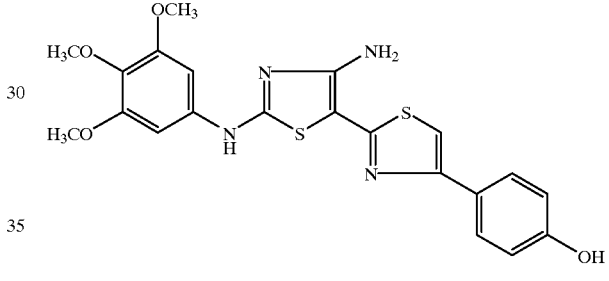

mp 129–133° C. (decomp). $^1$H NMR (CD$_3$OD): δ 7.80 (d, J=8.09 Hz, 2H), 7.16 (s, 1H), 7.02 (s, 2H), 6.86 (d, J=8.09 Hz, 2H), 3.90 (s, 6H), 3.78 (s, 3H). ESIMS (MH+): 457; (M–H)$^-$: 455. Anal. Calcd for C$_{21}$H$_{20}$N$_4$O$_4$S$_2$.1.0 Et$_2$O: C, 56.58; H, 5.70; N, 10.56; S, 12.08. Found: C, 56.27; H, 5.48; N, 10.69; S, 12.00.

EXAMPLE A(11)
4-[4'-Amino-2'-(3,4,5-trimethoxy-phenylamino)-[2,5']bithiazolyl-4-yl]-benzoic acid ethyl ester

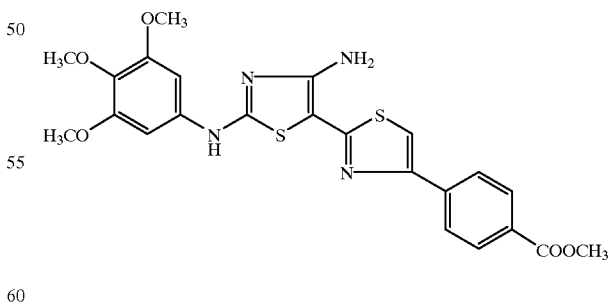

mp 240–245° C. (decomp). $^1$H NMR (CD$_3$OD): δ 8.18–8.16 (d, J=8.46 Hz, 2H), 8.09–8.06 (d, J=8.09 Hz, 2H), 7.06 (s, 1H), 4.38 (q, J=7.35 Hz, 2H), 3.85 (s, 6H), 3.68 (s, 3H), 1.41–1.37 (t, J=6.99 Hz, 3H). FABMS (MH$^+$): 513. Anal. Calcd for C$_{22}$H$_{20}$N$_4$O$_5$S$_2$.0.3 Et$_2$O: C, 56.59; H, 5.09; N, 10.48; S, 11.99. Found: C, 56.24; H, 4.83; N, 10.26; S, 11.86.

EXAMPLE A(12)

4-[4'-Amino-2'-(3,4,5-trimethoxy-phenylamino)-[2,5']bithiazolyl-4-yl]-benzene-1,2-diol

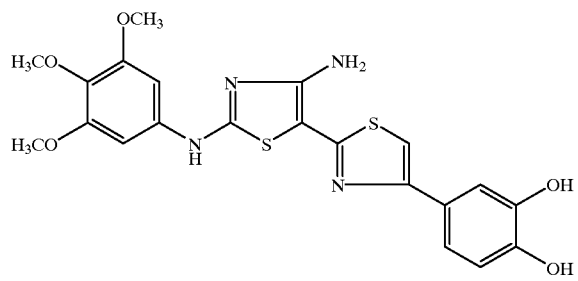

mp 132–137° C. (decomp). $^1$H NMR (CD$_3$OD): δ 7.42–7.41 (d, J=2.20 Hz, 1H), 7.32–7.28 (dd, J=7.65, 1.84 Hz, 1H), 7.11 (s, 1H), 7.07 (s, 2H), 6.85–6.82 (d, J=8.45 Hz, 1H), 3.90 (s, 6H), 3.78 (s, 3H). FABMS (MH$^+$): 473.

EXAMPLE A(13)

4-[4'-Amino-2'-(3,4,5-trimethoxy-phenylamino)-[2,5']bithiazolyl-4-yl]-2-methoxyphenol

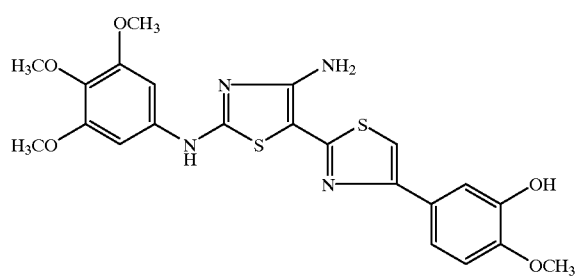

mp 202–203° C. $^1$H NMR (CD$_3$OD): δ 7.42 (s, 1H), 7.39 (d, J=2.11 Hz, 1H), 7.15 (s, 1H), 6.99 (s, 2H), 6.97 (d, J=2.10 Hz, 1H), 3.91 (s, 3H), 3.88 (s, 6H), 3.76 (s, 3H). FABMS (MH$^+$): 487. Anal. Calcd for C$_{22}$H$_{22}$N$_4$O$_5$S$_2$: C, 54.31; H, 4.56; N, 11.51; S, 13.18. Found: C, 54.52; H, 4.70; N, 11.26; S, 13.32.

EXAMPLE A(14)

4-[4'-Amino-4-(4-fluoro-phenyl)-5-methyl-[2,5']bithiazolyl-2'-ylamino]-benzenesulfonamide

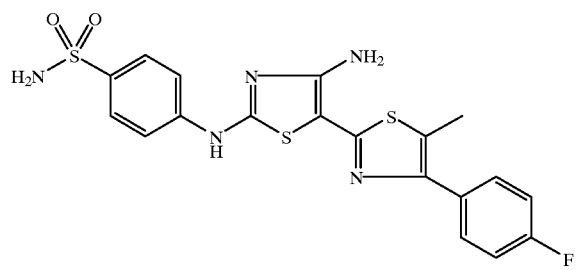

mp 145–148° C. (decomp). $^1$H NMR (CD$_3$OD): δ 7.90–7.82 (m, 4H), 7.76–7.70 (m, 2H), 7.22–7.17 (m, 2H), 2.56 (s, 3H). HRFABMS: Calcd. for C$_{19}$H$_{16}$FN$_5$O$_2$S$_3$(MH$^+$): 461.0450. Found: 461.0466.

EXAMPLE A(15)

4-[4'-Amino-5-(4-fluoro-benzyl)-4-methyl-[2,5']bithiazolyl-2'-ylamino]-benzenesulfonamide

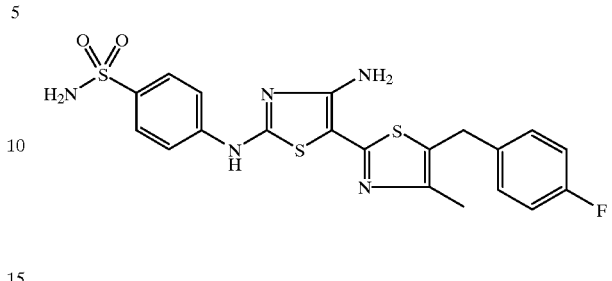

mp 130–135° C. (decomp). $^1$H NMR (CD$_3$OD): δ 7.76–7.68 (m, 4H), 7.17–7.12 (m, 2H), 6.97–6.90 (m, 2H), 3.97 (s, 2H), 2.23 (s, 3H). Anal. Calcd for C$_{20}$H$_{18}$FN$_5$O$_2$S$_3$: C, 50.51; H, 3.81; N, 14.73; S, 20.23. Found: C, 50.40; H, 3.73; N, 14.64; S, 20.37.

EXAMPLE A(16)

4-[4'-Amino-4-(3-hydroxy-phenyl)-[2,5']bithiazolyl-2'-ylamino]-benzenesulfonamide

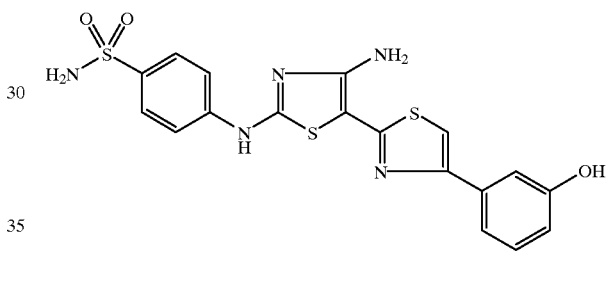

mp 205–209° C. (decomp). $^1$H NMR (CD$_3$OD): δ 7.94–7.81 (m, 4H), 7.43–7.39 (m, 2H), 7.33 (s, 1H), 7.24 (t, J=8.17 Hz, 1H), 6.80–6.75 (m, 1H). FABMS (MH$^+$): 445. Anal. Calcd for C$_{18}$H$_{15}$N$_5$O$_3$S$_3$: C, 48.53; H, 3.39; N, 15.72; S, 21.59. Found: C, 48.74; H, 3.47; N, 15.44; S, 21.31.

EXAMPLE A(17)

3-[4'-Amino-2'-(3,4,5-trimethoxy-phenylamino)-[2,5']bithiazolyl-4-yl]-phenol

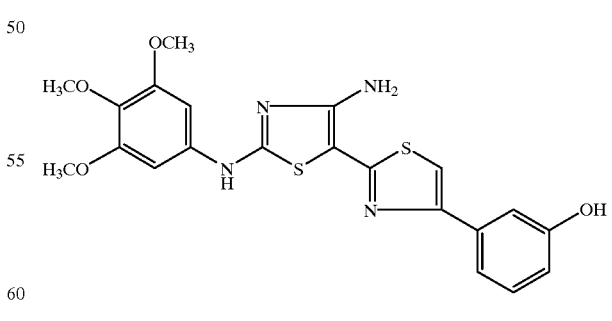

mp 226–230° C. $^1$H NMR (CD$_3$OD): δ 7.43–7.41 (m, 2H), 7.31 (s, 1H), 7.28–7.23 (m, 1H), 7.02 (s, 2H), 6.80–6.77 (m, 1H), 3.90 (s, 6H), 3.78 (s, 3H). FABMS (MH$^+$): 456. Anal. Calcd for C$_{21}$H$_{20}$N$_4$O$_4$S$_2$: C, 55.25; H, 4.42; N, 12.27; S, 14.05. Found: C, 55.39; H, 4.56; N, 12.07; S, 14.05.

EXAMPLE A(18)
5-[4'-Amino-2'-(3,4,5-trimethoxy-phenylamino)-[2,5']bithiazolyl-4-yl]-benzene-1,3-diol

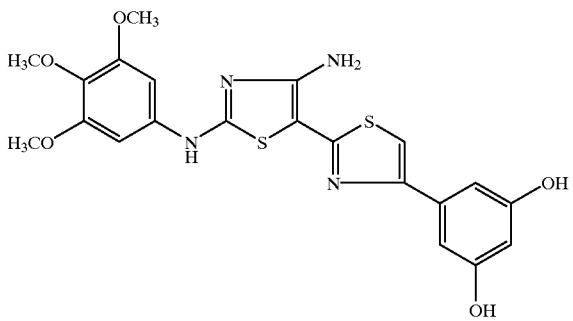

mp 198–202° C. $^1$H NMR (CD$_3$OD): δ 7.21 (s, 1H), 6.99 (s, 2H), 6.91 (d, J=2.06 Hz, 2H), 6.27 (t, J=2.03 Hz, 1H), 3.88 (s, 6H), 3.77 (s, 3H). FABMS (MH$^+$): 473. Anal. Calcd for C$_{21}$H$_{20}$N$_4$O$_5$S$_2$.0.5 H$_2$O: C, 52.38; H, 4.40; N, 11.63; S, 13.32. Found: C, 52.53; H, 4.44; N, 11.83; S, 13.47.

EXAMPLE A(19)
3-[4'-Amino-2'-(3,4,5-trimethoxy-phenylamino)-[2,5']bithiazolyl-4-yl]-5-methoxyphenol

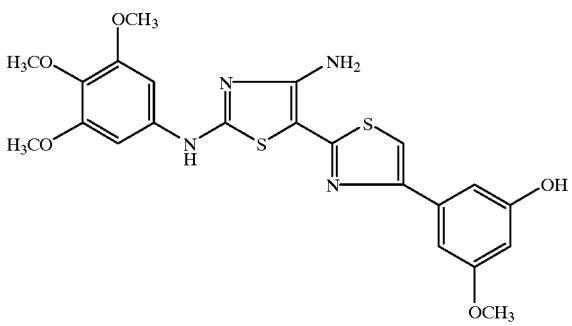

mp 208–210° C. $^1$H NMR (CD$_3$OD): δ 7.14 (s, 1H), 6.89–6.86 (m, 2H), 6.85 (s, 2H), 6.23 (t, J=2.06 Hz, 1H), 3.75 (s, 6H), 3.69 (s, 3H), 3.63 (s, 3H). FABMS (MH$^+$): 486. Anal. Calcd for C$_{22}$H$_{22}$N$_4$O$_5$S$_2$.0.5 H$_2$O: C, 54.20; H, 4.57; N, 11.49; S, 13.16. Found: C, 54.02; H, 4.71; N, 11.09; S, 13.56.

EXAMPLE A(20)
4-[4'-Amino-4-(4-hydroxy-phenyl)-[2,5']bithiazolyl-2'-ylamino]-benzenesulfonamide

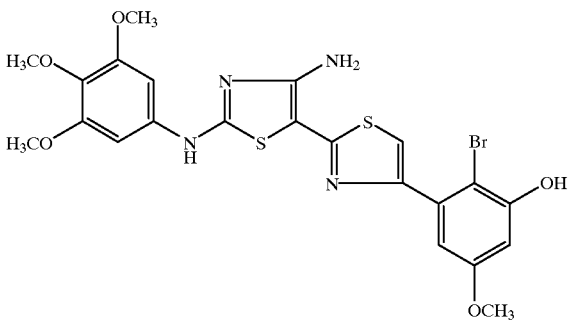

mp 200–203° C. (decomp). $^1$H NMR (CD$_3$OD): δ 7.30 (s, 1H), 6.98 (s, 2H), 6.83 (d, J=2.93 Hz, 1H), 6.56 (d, J=2.93 Hz, 1H), 3.88 (s, 6H), 3.81 (s, 3H), 3.76 (s, 3H); FABMS (MH$^+$): 565/567. Anal. Calcd for C$_{22}$H$_{21}$BrN$_4$O$_5$S$_2$.0.5 H$_2$O: C, 46.00; H, 3.86; N, 9.75; S, 11.16. Found: C, 46.26; H, 3.69; N, 9.55; S, 11.09.

EXAMPLE A(21)
3-[4'-Amino-2'-(4-sulfamoyl-phenylamino)-[2,5']bithiazolyl-4-yl]-benzoic acid

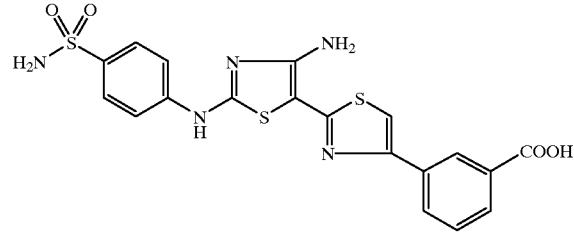

$^1$H NMR (DMSO-d$_6$): δ 10.94 (s, OH), 8.46 (s, 1H), 8.18 (d, J=7.80 Hz, 1H), 7.92 (d, J=7.80 Hz, 1H, 7.78 (m, 4H), 7.56 (t, J=7.80 Hz, 1H), 7.22 (brd, NH$_2$), 7.04 (brd, NH$_2$). Anal. Calcd for C$_{19}$H$_{15}$N$_5$O$_4$S$_3$.0.3 EtOAc: C, 48.52; H, 3.51; N, 14.01; S, 19.24. Found: C, 48.37; H, 3.67; N, 13.97; S, 19.24.

EXAMPLE A(22)
5-[4'-Amino-2'-(3,4,5-trimethoxy-phenylamino)-[2,5']bithiazolyl-4-yl]-2-chloro-phenol

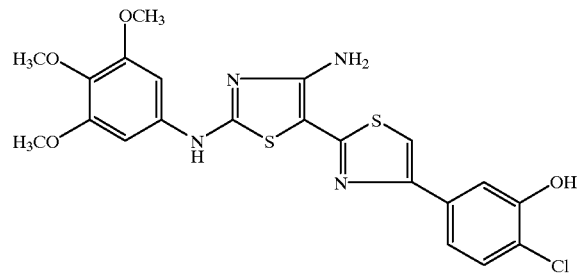

mp 235–238° C. $^1$H NMR (CD$_3$OD): δ 7.61 (d, J=1.92 Hz, 1H), 7.47–7.39 (m, 2H), 7.37 (s, 1H), 7.05 (s, 2H), 3.94 (s, 6H), 3.82 (s, 3H). FABMS (MH$^+$): 490. Anal. Calcd for C$_{21}$H$_{19}$ClN$_4$O$_4$S$_2$: C, 51.37; H, 3.90; N, 11.41; S, 13.06. Found: C, 51.38; H, 3.95; N, 11.32; S, 12.72.

EXAMPLE A(23)
2-[4'-Amino-2'-(3,4,5-trimethoxy-phenylamino)-[2,5']bithiazolyl-4-yl]-phenol

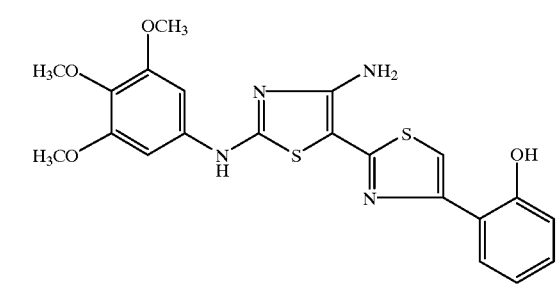

mp 186–190° C. (decomp). $^1$H NMR (CD$_3$OD): δ 7.88 (dd, J=7.99, 1.61 Hz, 1H,), 7.62 (s, 1H), 7.27–7.20 (m, 1H), 7.04 (s, 2H), 6.98–6.91 (m, 2H), 3.92 (s, 6H), 3.80 (s, 3H).

FABMS (MH⁺): 457. Anal. Calcd for $C_{21}H_{20}N_4O_4S_2$: C, 55.25; H, 4.42; N, 12.27; S, 14.05. Found: C, 55.28; H, 4.62; N, 11.96; S, 13.72.

EXAMPLE A(24)

4-(4'-Amino-4-p-tolyl-[2,5']bithiazolyl-2'-ylamino)-benzenesulfonamide

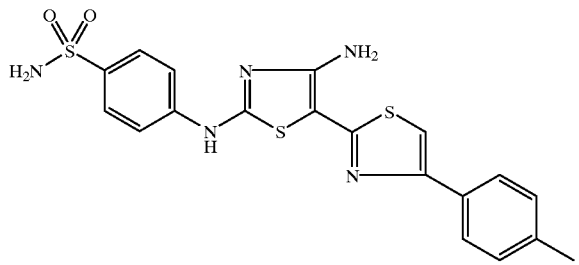

¹H NMR (DMSO): δ 7.92–7.84 (m, 4H), 7.32 (m, 3H), 7.11 (s, 2H), 2.39 (s, 3H). FABMS (M⁺): 443; (MNa⁺): 466.

EXAMPLE A(25)

2-(4'-Amino-2'-(3,4,5-trimethoxy-phenylamino)-[2,5'] bithiazolyl-4-yl]-benzene-1,4-diol

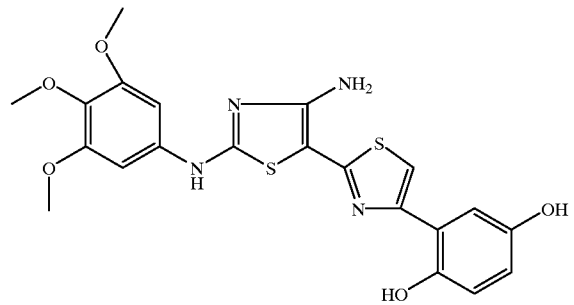

mp 208–212° C. (decomp).; ¹H NMR (CD₃OD): δ 7.56 (s, 1H), 7.31 (d, J=2.80 Hz, 1H), 7.00 (s, 2H), 6.77 (d, J=8.69 Hz, 1H), 6.68 (dd, J=8.72, 2.87 Hz, 1H), 3.89 (s, 6H, 3.77 (s, 3H). ESIMS (MH⁺): 473. Anal. Calcd for $C_{21}H_{20}N_4O_5S_2 \cdot 0.4\ H_2O$: C, 52.47; H, 4.38; N, 11.66; S, 13.34. Found: C, 52.77; H, 4.48; N, 11.23; S, 12.98.

EXAMPLE A(26)

3-[4'-Amino-2'-(3,4,5-trimethoxy-phenylamino)-[2,5'] bithiazolyl-4-yl]-4-bromophenol

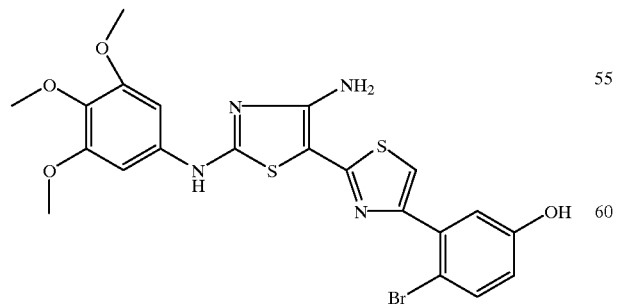

mp 214–216° C. ¹H NMR (CD₃OD): δ 7.47 (d, J=8.67 Hz, 1H), 7.38 (s, 1H), 7.26 (d, J=3.02 Hz, 1H), 7.07 (s, 2H), 6.72 (dd, J=8.69, 3.07 Hz, 1H), 3.89 (s, 6H), 3.76 (s, 3H). FABMS (MH⁺): 535/537. Anal. Calcd for $C_{21}H_{19}BrN_4O_4S_2$: C, 47.11; H, 3.58; N, 10.46; S, 11.85. Found: C, 47.31; H, 3.65; N, 10.26; S, 11.85.

EXAMPLE A(27)

2-(4'-Amino-4-benzo[b]thiophen-3-yl-[2,5']bithiazolyl-2'-ylamino)-benzenesulfonamide

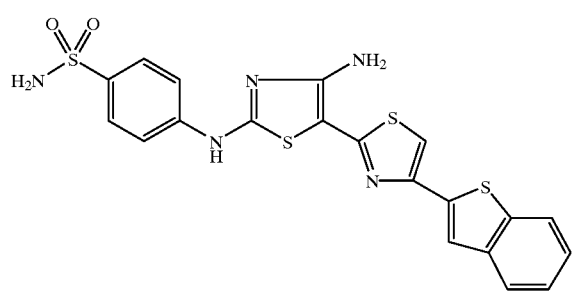

mp 155–160° C. (decomp). ¹H NMR (CD₃OD): δ 8.39 (d, J=7.94 Hz, 1H), 8.01 (s, 1H), 7.96 (d, J=7.72 Hz, 1H), 7.86 (s, 4H), 7.50–7.39 (m, 3H). FABMS (MH⁺): 485.

EXAMPLE A(28)

4-{4'-Amino-4-[4-(2,4-dichloro-phenyl)-furan-2-yl]-[2,5'] bithiazolyl-2'-ylamino}-benzenesulfonamide

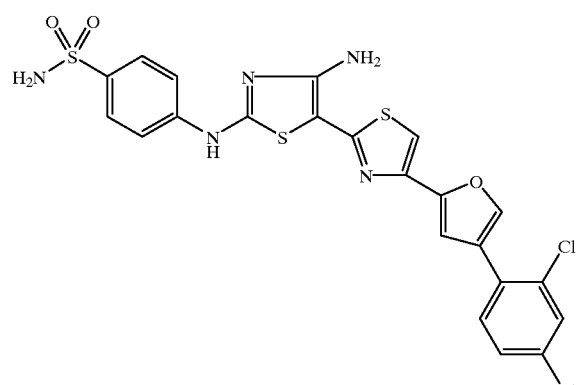

mp 225–230° C. (decomp). ¹H NMR (CD₃OD): δ 8.00 (d, J=8.62, 1H), 7.86 (s, 4H), 7.58 (d, J=2.10, 1H), 7.45 (dd, J=8.60, 2.12 Hz, 1H), 7.40 (s, 1H), 7.29 (d, J=3.61 Hz, 1H), 6.97 (d, J=3.59 Hz, 1H). FABMS (MH⁺): 564/566.

EXAMPLE A(29)
3-(4'-Amino-2'-propylamino-[2,5']bithiazolyl-4-yl)-phenol

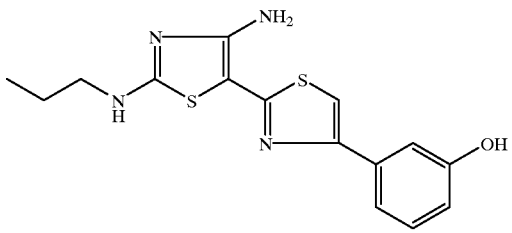

$^1$H NMR (CD$_3$COCD$_3$): δ 8.43 (s, 1H), 7.50 (d, 1H), 7.43 (d, 1H), 7.30–7.20 (m, 3H), 6.55 (s, 2H), 3.40 (t, 2H), 1.69 (sextet, 2H), 0.97 (t, 3H). ESIMS (MH$^+$): 333; (MNa$^+$): 355; (MH$^-$): 331.

EXAMPLE A(30)
3-(4'-Amino-2'-methylamino-[2,5']bithiazolyl-4-yl)-phenol

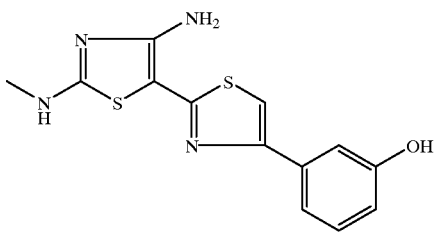

$^1$H NMR (CD$_3$COCD$_3$): δ 8.40 (s, 1H), 7.50 (d, 1H), 7.43 (d, 1H), 7.31–7.15 (m, 3H), 6.63 (s, 2H), 3.00 (d, 3H). ESIMS (MH$^+$): 305; (M–H$^-$): 303.

EXAMPLE A(31)
3-[4'-Amino-2'-(3,4,5-trimethoxy-phenylamino)-[2,5']bithiazolyl-4-yl]-N-phenethyl-benzamide

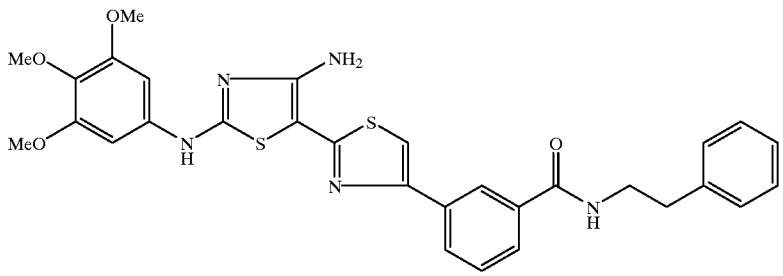

ESMS (MH$^+$): 588. Anal. Calcd for C$_{30}$H$_{29}$N$_5$O$_4$S$_2$: C, 61.31; H, 4.97; N, 11.92; S, 10.91. Found: C, 61.02; H, 4.86; N, 11.72; S, 10.83.

EXAMPLE A(32)
3-[4'-Amino-2'-(3,4,5-trimethoxy-phenylamino)-[2,5']bithiazolyl-4-yl]-N-benzyl-benzamide

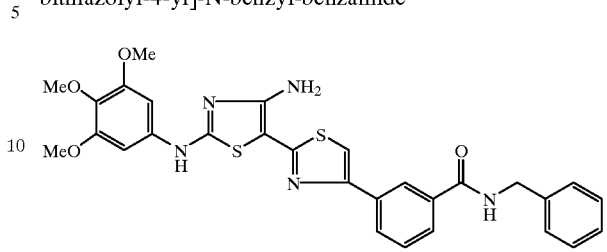

ESMS (MH$^+$): 574.

EXAMPLE A(33)
3-[4'-Amino-2'-(3,4,5-trimethoxy-phenylamino)-[2,5']bithiazolyl-4-yl]-N-phenyl-benzamide

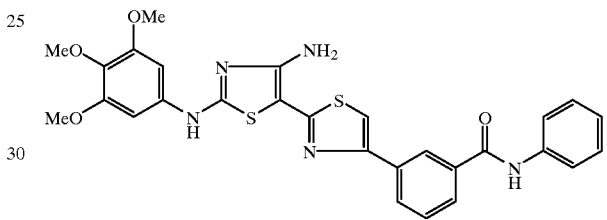

ESMS (MH$^+$): 560. Anal. Calcd for C$_{28}$H$_{25}$N$_5$O$_4$S$_2$.0.8 H$_2$O: C, 58.58; H, 4.67; N, 12.20; S, 11.17. Found: C, 58.68; H, 4.49; N, 12.23; S, 11.33.

EXAMPLE A(34)
3-[4'-Amino-2'-(3,4,5-trimethoxy-phenylamino)-[2,5']bithiazolyl-4-yl]-N-(4-isopropyl-3-methyl-phenyl)-benzamide

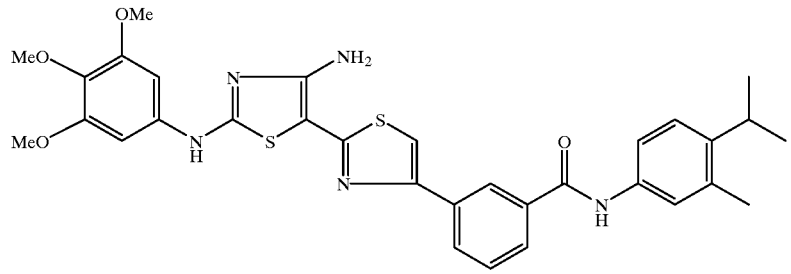

ESMS (MH+): 616. Anal. Calcd for C32H33N5O4S2.0.4 H2O: C, 61.69; H, 5.47; N, 11.24; S, 10.29. Found: C, 61.76; H, 5.26; N, 11.08; S, 10.18.

EXAMPLE A(35)

3-[4'-Amino-2'-(3,4,5-trimethoxy-phenylamino)-[2,5'] bithiazolyl-4-yl]-N-(2-methyl-quinolin-6-yl)-benzamide

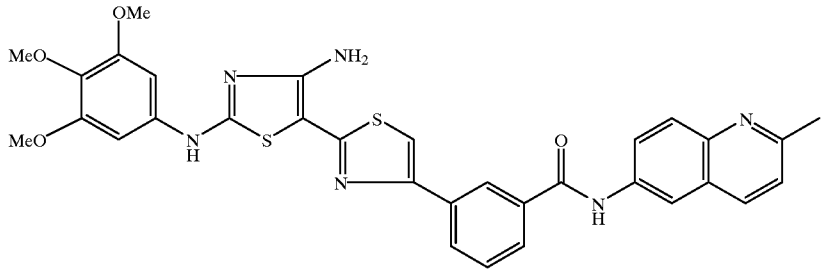

ESMS (MH+): 625. Anal. Calcd for C32H28N6O4S2.0.2 H2O: C, 58.41; H, 4.36; N, 12.65; S, 9.66. Found: C, 58.40; H, 4.31; N, 12.28; S, 9.54.

EXAMPLE A(36)

[3-(4'-Amino-2'-p-tolylamino-[2,5']bithiazolyl-4-yl)-phenyl]-carbamic acid benzyl ester

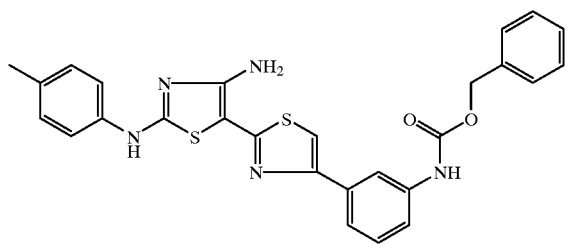

1H NMR (CD3COCD3): δ 8.85 (s, 1H), 8.21 (s, 1H), 7.70–7.25 (m, 14H), 6.52 (s, 2H), 5.30 (s, 2H), 2.41 (s, 3H). ESIMS (MH+): 514; (MH−): 512.

EXAMPLE A(37)

N-{3-[4'-Amino-2'-(3-diethylamino-propylamino)-[2,5'] bithiazolyl-4-yl]-phenyl}-benzamide

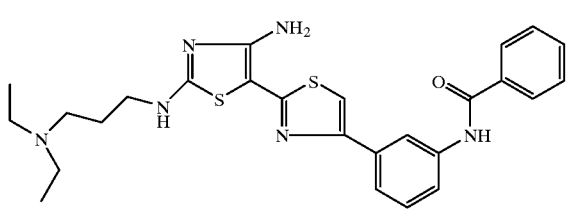

1H NMR (DMSO-D6): δ 10.39 (s, 1H), 9.12 (s, 1H, 8.35 (s, 2H), 7.96 (m, 3H), 7.79 (m, 1H), 7.69–7.39 (m, 6H), 3.36 (m, 2H), 3.12 (m, 6H), 2.93 (m, 2H), 1.20 (m, 6H). ESIMS (MH+): 507.

EXAMPLE A(38)

N-[3-(4'-Amino-2'-phenethylamino-[2,5']bithiazolyl-4-yl)-phenyl]-benzamide

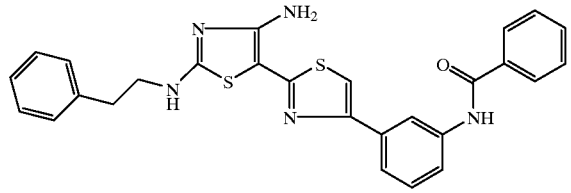

1H NMR (DMSO-D6): δ 10.39 (s, 1H), 8.42–7.15 (m, 16H), 6.85 (s, 1H), 5.20 (broad s, 2H), 2.90 (m, 2H), 3.50 (m, 2H). ESIMS (MH+): 498.

EXAMPLE A(39)

3-[4'-Amino-4-(3-benzoylaminophenyl)-[2,5']bithiazolyl-2'-ylamino]-benzoic acid methyl ester

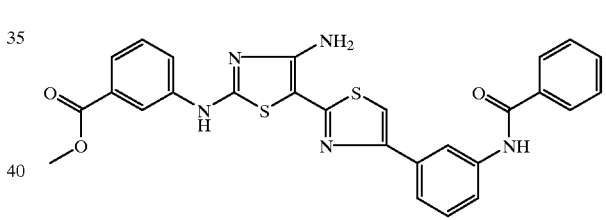

1H NMR (DMSO-D6): δ 10.39 (s, 1H), 10.38 (s, 1H), 8.37 (s, 1H), 8.16 (s, 1H), 8.18 (d, 1H), 7.98 (d, 2H), 7.84 (d, 1H), 7.70 (d, 1H), 7.65–7.39 (m, 8H), 7.10 (broad s, 2H), 3.89 (s, 3H). ESIMS (MH+): 528; (MNa+): 550; (MH−): 526.

EXAMPLE A(40)

3-[4'-Amino-4-(3-benzoylaminophenyl)-[2,5']bithiazolyl-2'-ylamino]-benzoic acid ethyl ester

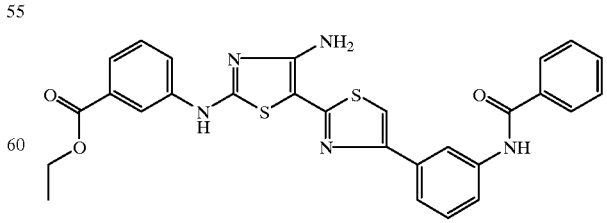

1H NMR (DMSO-D6): δ 10.80 (s, 1H), 10.38 (s, 1H), 8.37 (s, 1H), 8.16 (s, 1H), 8.15 (d, 2H), 8.00 (d, 2H), 7.88 (d, 1H), 7.75–7.40 (m, 8H), 7.10 (broad s, 1H), 4.38 (quartet, 2H), 1.39 (t, 3H). ESIMS (MH$^+$): 542; (MNa$^+$): 564.

EXAMPLE A(41)

N-{3-[4'-Amino-2'-(benzo[1,3]dioxol-5-ylamino)-[2,5']bithiazolyl-4-yl]-phenyl}-benzamide

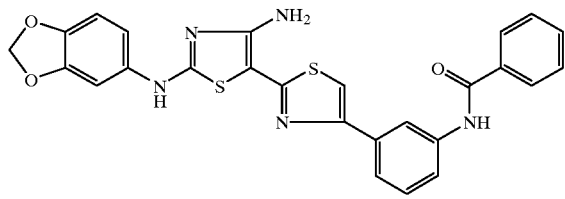

$^1$H NMR (DMSO-D$_6$): δ 10.41 (m, 2H), 8.35 (s, 1H), 8.00–6.88 (m, 14H), 6.10 (s, 2H). ESIMS (MH$^+$): 514; (MH$^-$): 512.

EXAMPLE A(42)

N-{3-[4'-Amino-2'-(3,5-dimethylphenylamino)-[2,5']bithiazolyl-4-yl]-phenyl}-benzamide

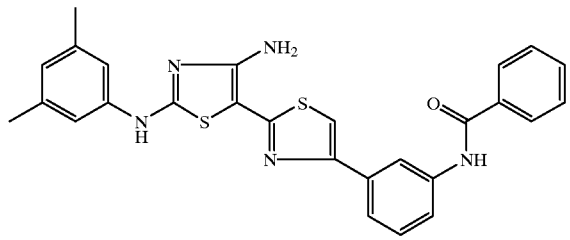

$^1$H NMR (CD$_3$OD): δ 8.36–6.79 (m, 16H), 6.68 (s, 1H) 2.28 (s, 6H). ESIMS (MW$^+$)*: 993; (MNa$^+$)*: 1015.

EXAMPLE A(43)

N-{3-[4'-Amino-2'-(indan-5-ylamino)-[2,5']bithiazolyl-2'-ylamino]-phenyl}-benzamide

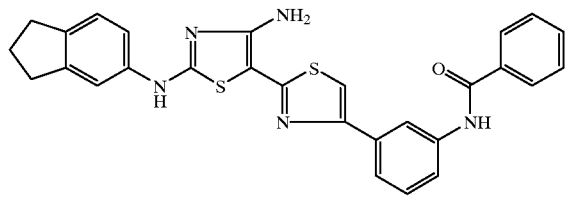

$^1$H NMR (CD$_3$OD): δ 8.50–7.15 (m, 17H), 2.95 (m, 4H), 2.15 (m, 2H). ESIMS (MH$^+$): 510; (MNa$^+$): 532; (MH$^-$): 508.

EXAMPLE A(44)

[3-(4'-Amino-2'-m-tolylamino-[2,5']bithiazolyl-4-yl)-phenyl]-benzamide

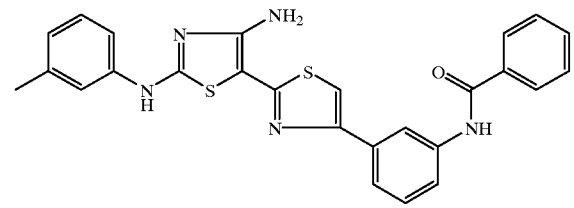

$^1$H NMR (CD$_3$OD): δ 8.25–6.81 (m, 18H), 2.29 (s, 3H). ESIMS (MH$^+$): 484; (MNa$^+$): 506.

EXAMPLE A(45)

N-{3-[4'-Amino-2'-(2,3-dihydro-benzo[1,4]dioxin-6-ylamino)-[2,5']bithiazolyl-4-yl]-phenyl}-benzamide

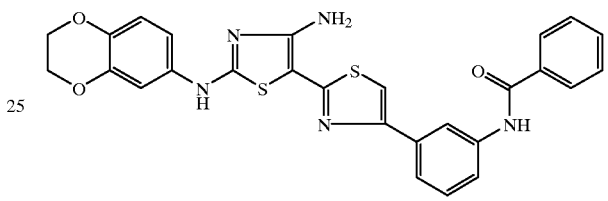

$^1$H NMR (CD$_3$OD): δ 8.42–6.83 (m, 17H), 4.29 (m, 4H). ESIMS (MH$^+$): 528; (MNa$^+$): 550.

EXAMPLE A(46)

N-{3-[4'-Amino-2'-(3-methylsulfanyl-phenylamino)-[2,5']bithiazolyl-4-yl]-phenyl}-benzamide

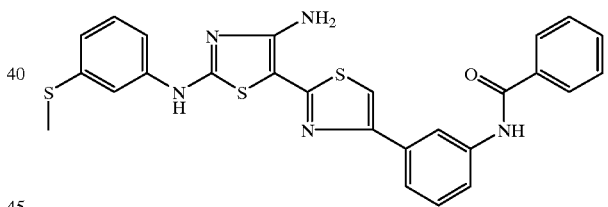

$^1$H NMR (DMSO-D$_6$): δ 10.39 (s, 1H), 8.89 (d, 2H), 8.51–6.91 (m, 18H). ESIMS (MH$^+$)*: 1029.

EXAMPLE A(47)

N-{3-[4'-Amino-2'-(3,4-dimethoxy-phenylamino)-[2,5']bithiazolyl-4-yl]-phenyl}-benzamide

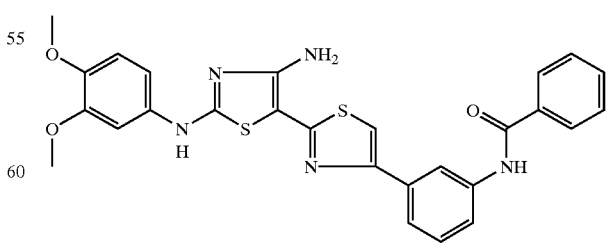

$^1$H NMR (CD$_3$OD): δ 8.32 (s, 1H), 7.98 (d, 2H), 7.78–6.91 (m, 14H), 3.88 (s, 3H), 3.81 (s, 3H). ESIMS (MH$^+$): 530; (MNa+): 552.

EXAMPLE A(48)
N-{3-[2'-(3-Acetylamino-4-methyl-phenylamino)-4'-amino-[2,5']bithiazolyl-4-yl]-phenyl}-benzamide

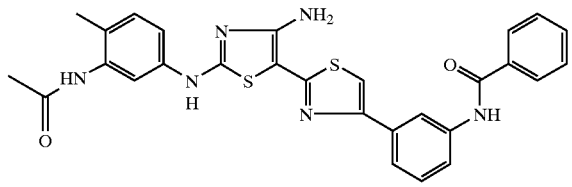

$^1$H NMR (CD$_3$OD): δ 8.32 (s, 1H), 7.98 (d, 2H), 7.72–7.15 (m, 15H), 2.22 (s, 3H), 1.98 (s, 3H). ESIMS (MH$^+$): 541; (MNa$^+$): 563; (MK$^+$): 579; (MH$^-$): 539.

EXAMPLE A(49)
N-{3-[4'-Amino-2'-(1,4-dioxo-1,2,3,4-tetrahydro-phthalazin-6-ylamino)-[2,5']bithiazolyl-4-yl]-phenyl}-benzamide

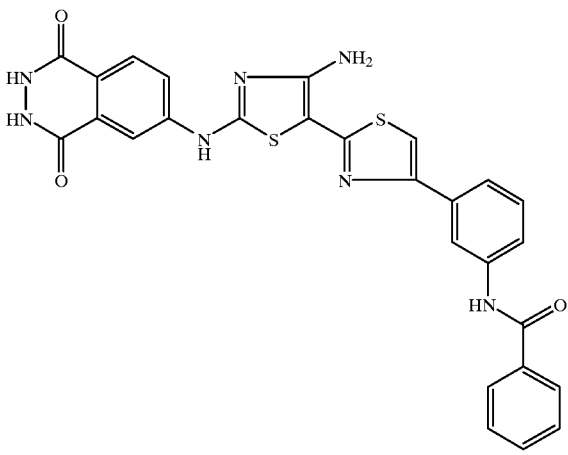

$^1$H NMR (DMSO-D$_6$): δ 11.11 (s, 1H), 10.39 (s, 1H), 8.35–7.10 (m, 17H). ESIMS (MNa$^+$): 576; (MH$^-$): 552.

EXAMPLE A(50)
3-[4'-Amino-4-(3-benzoylamino-phenyl)-[2,5']bithiazolyl-2'-ylamino]-benzoic acid

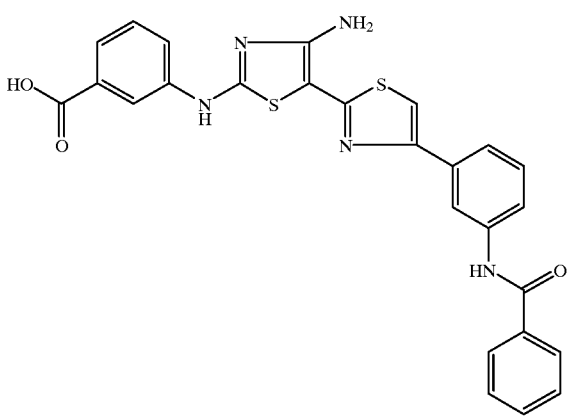

$^1$H NMR (DMSO-D$_6$): δ 10.79 (s, 1H), 10.39 (s, 1H), 8.35 (s, 1H), 8.18–7.34 (m, 16H). ESIMS (MH$^+$): 514; (MNa$^+$): 536; (MH$^-$): 512.

EXAMPLE A(51)
4-(4'-Amino-4-(3-benzamidophenyl)-[2,5']bithiazolyl-2'-ylamino)-ethylbenzoate

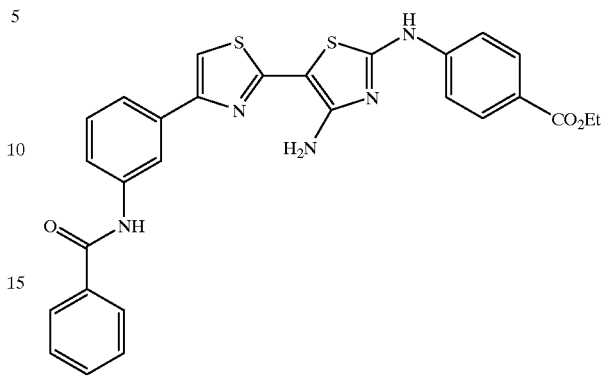

$^1$H NMR (d$_6$-DMSO): δ 1.2 (t, 3H), 4.3 (q, 2H), 7.4 (t, 1H), 7.5–8.0 (m, 14H), 8.35 (s br, 1H), 10.4 (s, 1H), 10.95 (s, 1H). ESIMS (MH$^+$): 542; (M–H$^-$): 540.

EXAMPLE A(52)
4-(4'-Amino-4-(3-benzamidophenyl)-[2,5']bithiazolyl-2'-ylamino)-methoxyphenyl

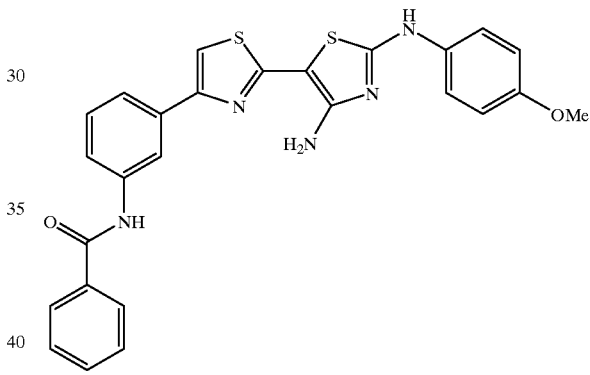

$^1$H NMR (CD$_3$OD): δ 2.6 (s, 3H), 7.2–7.8 (m, 11H), 8.35 (s br, 1H), 7.9 (d, 2H), 8.2 (s br, 1H). ESIMS (MH$^+$): 500; (M+Na+): 522; (M+K+): 538.

EXAMPLE A(53)
3-(4'-Amino-4-(3-benzamidophenyl)-[2,5']bithiazolyl-2'-ylamino)-pyridine

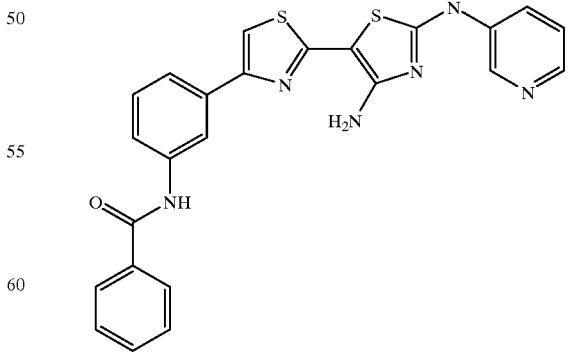

$^1$H NMR (d$_6$-DMSO): δ 7.1 (s br, 1H), 7.4 (t, 1H), 7.5–7.7 (m, 7H), 7.85 (m, 1H), 8.0 (m, 2H), 8.25–8.4 (m, 3H), 9.0 (d, 1H), 10.4 (s, 1H), 10.95 (s, 1H). ESIMS (M+Na$^+$): 493; (M-H): 469.

EXAMPLE A(54)
2-(4'-Amino-4-(3-benzamidophenyl)-[2,5']bithiazolyl-2'-ylamino)-thiophene carboxylic acid methyl ester

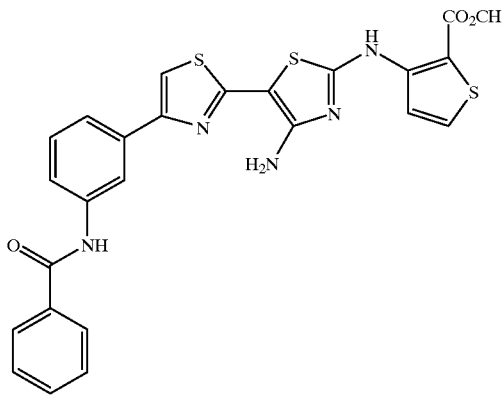

¹H NMR (d₆-DMSO): δ 3.8 (s, 3H), 7.0 (s br, 2H), 7.4 (t, 1H), 7.5–7.7 (m, 6H), 7.85 (m, 1H), 8.0 (m, 3H), 8.15 (d, 1H), 8.35 (m, 1H), 10.4 (m, 1H). ESIMS (MH⁺): 534; (M+Na⁺): 556; (M−H⁻): 532.

EXAMPLE A(55)
4-(4'-Amino-4-(3-benzamidophenyl)-[2,5']bithiazolyl-2'-ylamino)-phenylsulfonylpiperidine

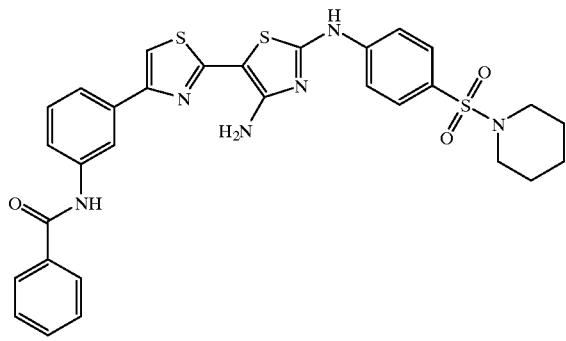

¹H NMR (d₆-DMSO): δ 1.2–1.6 (m, 6H), 3.1 (m, 4H), 7.3–8.5 (m, 14H), 8.9 (d, 1H), 10.4 (s, 1H), 10.5 (s, 1H), 11.2 (s, 1H). ESIMS (MH⁺): 617; (M−H): 615.

EXAMPLE A(56)
4-(4'-Amino-4-(3-benzamidophenyl)-[2,5']bithiazolyl-2'-ylamino)-nitrophenyl

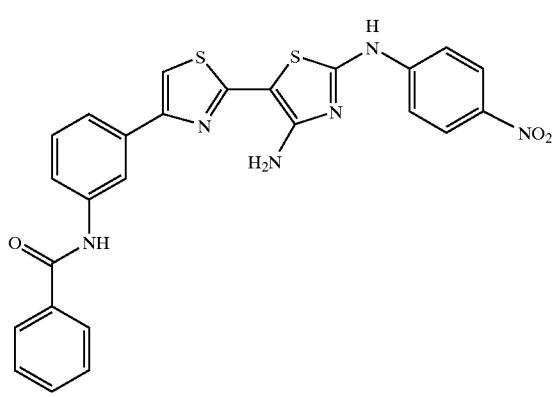

¹H NMR (d₆-DMSO): δ 7.2–7.9 (m, 13H), 8.2 (d, 2H), 8.3 (s, 1H), 10.3 (s, 1H), 11.2 (s, 1H). ESIMS (MH⁺): 515; (M−H)⁻: 513.

EXAMPLE A(57)
4-(4'-Amino-4-(3-benzamidophenyl)-[2,5']bithiazolyl-2'-ylamino)-trans-benzoyl-DL-homoserine lactone

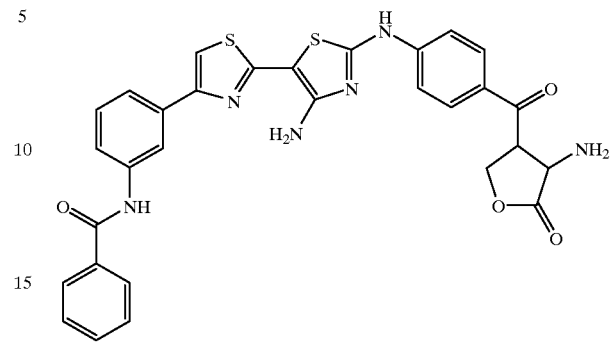

¹H NMR (d₆-DMSO): δ 2.5 (m, 1H, 2.7 (m, 1H), 4.35 (m, 1H), 4.5 (m, 1H), 4.8 (m, 1H), 7.2 (m, 1H), 7.45 (m, 3H), 7.55 (m, 4H), 7.75 (m, 5H), 7.85 (m, 3H), 8.0 (m, 3H), 8.35 (m, 1H). ESIMS (MH⁺): 597; (M+Na⁺): 619.

EXAMPLE A(58)
4-(4'-Amino-4-(3-benzamidophenyl)-[2,5']bithiazolyl-2'-ylamino)-acetophenone

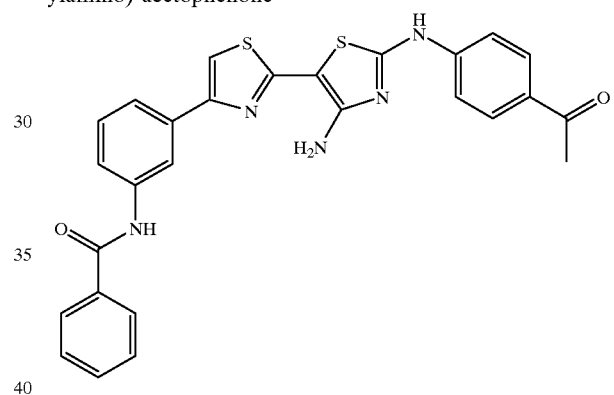

¹H NMR (d₆-DMSO): δ 2.5 (s, 3H), 7.1 (s br, 1H), 7.42 (t, 1H), 7.5–7.7 (m, 6H), 7.8 (m, 4H), 8.0 (m, 5H), 8.35 (t br, 1H). ESIMS (MH⁻): 512; (M+Na⁻): 534; (M−H)⁻: 510.

EXAMPLE A(59)
(4'-Amino-4-(3-benzamidophenyl)-[2,5']bithiazolyl-2'-ylamino)-cyclohexane

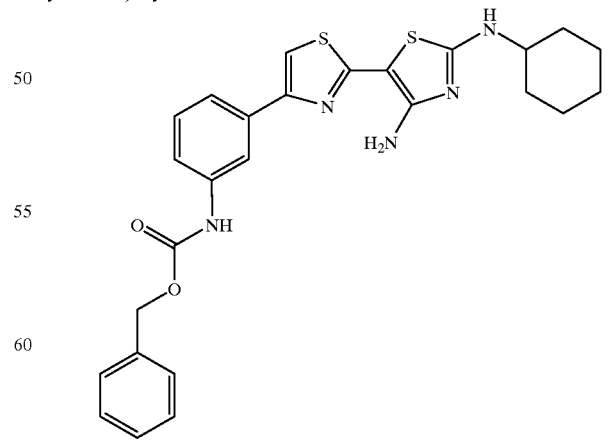

¹H NMR (CDCl₃): δ 1.0–2.0 (m, 10H), 3.2 (m br, 1H), 5.2 (s, 2H), 7.0 (d, 1H), 7.4–8.0 (m, 11H). ESIMS (MH⁺): 506; (M−H)⁻: 504.

EXAMPLE A(60)

3-(4'-Amino-4-(3-benzamidophenyl)-[2,5']bithiazolyl-2'-ylamino)-methoxypropane

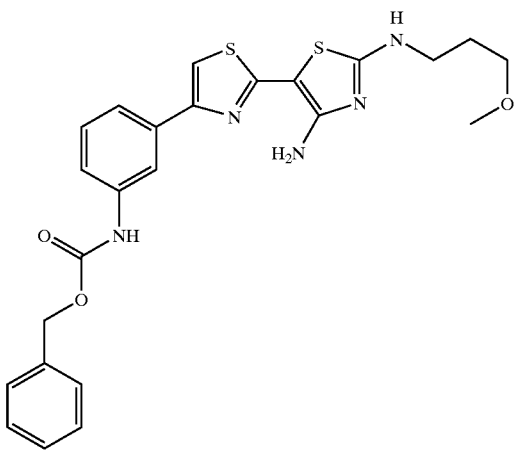

$^1$H NMR (CDCl$_3$): δ 1.5 (m, 1H), 1.8 (m, 1H), 2.0 (m, 2H), 3.1 (s, 3H), 3.3 (m, 2H), 5.0 (s, 2H), 7.2–7.4 (m, 12H). ESIMS (MH$^+$): 496; (M–H)$^-$: 494.

EXAMPLE A(61)

4-[4'-Amino-4-(3-benzyloxy-5-hydroxy-phenyl)-[2,5]bithiazolyl-2'-ylamino]-benzenesulfonamide

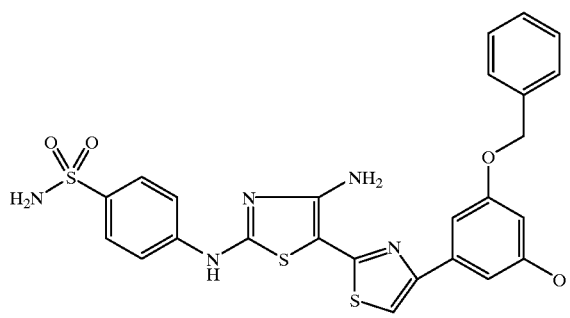

mp 185–187° C. (decomp). $^1$H NMR (CD$_3$OD): δ 7.88 (s, 4H), 7.56–7.32 (m, 6H), 7.10–7.03 (m, 2H), 6.45 (t, J=2.23 Hz, 1H), 5.13 (s, 2H). ESIMS (MH$^+$): 552; (M–H)$^-$:; 550. Anal. Calcd for C$_{25}$H$_{21}$N$_5$O$_4$S$_3$.0.3 EtOAc: C, 54.43; H, 4.08; N, 12.12; S, 16.64. Found: C, 54.54; H, 4.00; N, 12.06; S, 16.59.

EXAMPLE A(62)

4-[4-(3-Allyloxy-5-hydroxyphenyl)-4'-amino-[2,5']bithiazolyl-2'-ylamino]-benzenesulfonamide

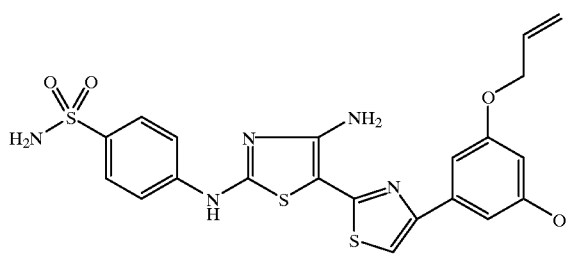

mp 200–202° C. $^1$H NMR (CD$_3$OD): δ 11.12 (s, NH), 9.81 (s, NH$_2$), 8.07–8.00 (m, 4H), 7.86 (s, NH$_2$), 7.48 (s, 1H), 7.30–7.23 (m, 2H), 6.57 (s, 1H), 6.34–6.23 (m, 1H), 5.68–5.52 (m, 2H), 5.32–5.28 (m, 2H). ESIMS (MH+): 502; (M–H–): 501. Anal. Calcd for C$_{21}$H$_{19}$N$_5$O$_4$S$_3$: C, 50.29; H, 3.82; N, 13.96; S, 19.18. Found: C, 50.31; H, 3.93; N, 13.74; S, 19.05.

EXAMPLE A(63)

4-(4'-Amino-4-styryl-[2,5']bithiazolyl-2'-ylamino)-benzenesulfonamide

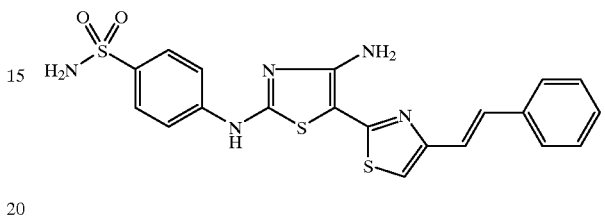

mp 140–143° C. (decomp). $^1$H NMR (CD$_3$OD): δ 7.80–7.72 (m, 4H), 7.50–7.46 (m, 1H), 7.38–7.06 (m, 6H), 6.95 (s, 1H). FABMS Calcd for C$_{20}$H$_{17}$N$_5$O$_2$S$_3$: 455.0544. Found 455.0529.

EXAMPLE A(64)

4-{4'-Amino-4-[2-(4-hydroxy-phenyl)-vinyl]-[2,5']bithiazolyl-2'-ylamino}-benzenesulfonamide

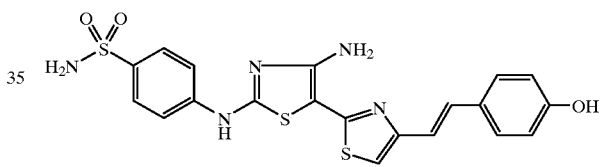

mp 138–140° C. (decomp). $^1$H NMR (CD$_3$OD): δ 10.90 (s, NH), 7.73 (q, J=15.32 Hz, 4H), 7.36 (d, J=8.75 Hz, 2H), 7.22 (d, J=15.80 Hz, 1H), 7.18 (s, NH$_2$), 7.06 (s, 1H), 6.90 (d, J=16.1 Hz, 1H), 6.84 (s, NH$_2$), 6.70 (d, J=8.62, 2H). FABMS Calcd for C$_{20}$H$_{17}$N$_5$O$_3$S$_3$: 471.0494. Found: 471.0502.

EXAMPLE A(65)

4-{4'-Amino-4-[2-(3-hydroxy-4-methoxy-phenyl)-ethenyl]-[2,5']bithiazolyl-2'-ylamino}-benzenesulfonamide

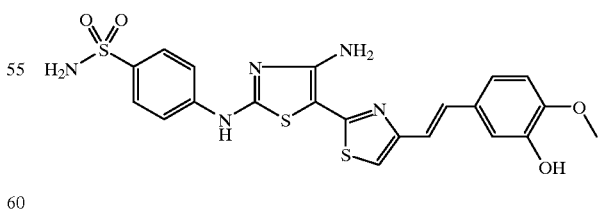

mp 190–193° C. (decomp). $^1$H NMR (CD$_3$OD): δ 10.71 (s, NH$_2$), 9.83 (s, NH2), 7.63 (q, J=15.40, 4H), 7.10–7.03 (m, 2H), 6.98 (s, 1H), 6.86 (s, NH$_2$), 6.83–6.72 (m, 3H, NH$_2$), 3.60 (s, 3H). ESIMS (MNa+): 524. Anal. Calcd for C$_{21}$H$_{19}$N$_5$O$_4$S$_3$.0.4 EtOAc: C, 50.56; H, 4.17; N, 13.05; S, 17.92. Found: C, 50.50; H, 4.35; N, 12.75; S, 17.88.

EXAMPLE A(66)
4-[4'-Amino-4-(4-phenyl-buta-1,3-dienyl)-[2,5']bithiazolyl-2'-ylamino]-benzenesulfonamide

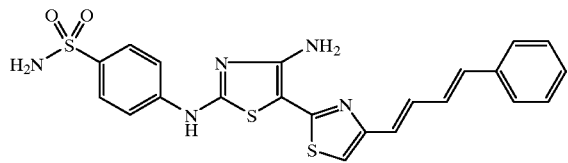

mp 193–195° C. (decomp). $^1$H NMR (CD$_3$OD): δ 10.92 (s, NH), 7.82 (q, J=15.92, 4H), 7.53 (d, J=7.42, 2H), 7.36 (t, J=7.41 Hz, 2H), 7.28–7.06 (m, 2H, 2NH$_2$), 6.77 (m, 2H). ESIMS (MH+): 482.

EXAMPLE A(67)
4-(4'-Amino-4-benzoyl-[2,5']bithiazolyl-2'-ylamino)-benzenesulfonamide

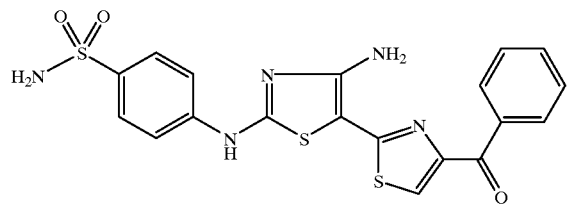

mp 255–260 0C (decomp). $^1$H NMR (CD$_3$OD): δ 10.99 (s, 1H), 8.12 (s, 1H), 8.04–8.02 (m, 2H), 7.78 (q, J=12.1 Hz, 4H), 7.72–7.66 (m, 1H), 7.60–7.55 (m, 2H), 7.26 (s, NH$_2$), 7.05 (br, NH$_2$). ESIMS (MNa+): 480; (M–H–): 456.

EXAMPLE A(68)
Ethyl 4'-amino-2'-(4-sulfamoyl-phenylamino)-[2,5'] bithiazolyl-4-carboxylate

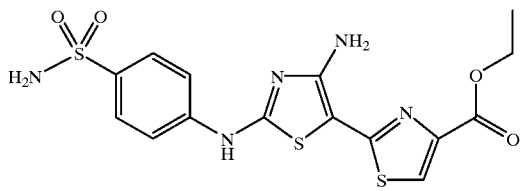

$^1$H NMR (DMSO-D$_6$): δ 11.0 (s, NH, 8.12 (s, H), 7.80 (m, 4H), 7.32 (s, NH$_2$), 7.08 (br, NH$_2$), 4.35 (q, J=8.7 Hz, 2H), 1.30 (t, J=8.7 Hz, 3H). FABMS Calcd for C$_{15}$H$_6$N$_5$O$_4$S$_3$ (MH+): 426.0364. Found: 426.0356.

EXAMPLE A(69)
4-[4'-Amino-4-(4-chloro-3-hydroxy-phenyl)-[2,5'] bithiazolyl-2'-ylamino]-benzenesulfonamide

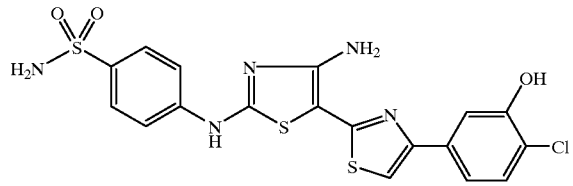

$^1$H NMR (CD$_3$OD): δ 7.97 (s, 4H), 7.63 (s, 1H), 7.58–7.46 (m, 3H). FABMS (MH+): 480.

EXAMPLE A(70)
4-(4'-Amino-4-biphenyl-4-yl-[2,5']bithiazolyl-2'-ylamino)-benzenesulfonamide

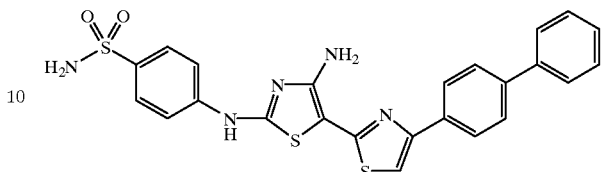

$^1$H NMR (CD$_3$OD): δ 8.09–8.00 (m, 1H), 7.88 (s, 4H), 7.72–7.63 (m, 3H), 7.51–7.40 (m, 3H), 7.38–7.29 (m, 1H). EIMS (M–H$^-$): 504. Anal. Calcd for C$_{24}$H$_{19}$N$_5$O$_2$S$_3$: C, 57.01; H, 3.79; N, 13.85; S, 19.02. Found: C, 56.87; H, 3.81; N, 13.57; S, 19.16.

EXAMPLE A(71)
4-(4'-Amino-4-benzoyl-[2,5']bithiazolyl-2'-ylamino)-N-(2-dimethylamino-ethyl)-benzenesulfonamide

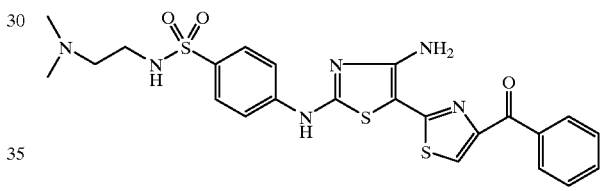

$^1$H NMR (CD$_3$OD): δ 7.88 (s, 1H), 7.84–7.78 (m, 2H), 7.69–7.47 (m, 5H), 7.40–7.34 (m, 2), 2.63 (t, J=6.70 Hz, 2H), 2.06 (t, J=6.60 Hz, 2H), 1.84 (s, 6H). FABMS Calcd for C$_{23}$H$_{24}$N$_6$O$_3$S$_3$: 529.1150. Found: 529.1158.

EXAMPLE A(72)
4-[4-Amino-4-(3-amino-benzoyl)-[2,5']bithiazoyl-2'-ylamino]-benzenesulfonamide

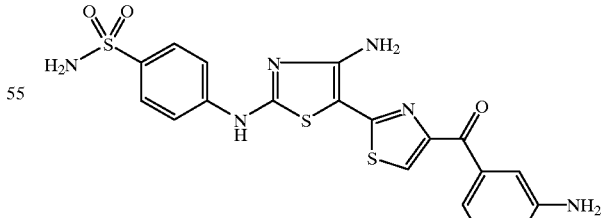

$^1$H NMR (DMSO): δ 10.91 (s, 1H), 7.99 (s, 1H), 7.86–7.84 (m, 4H), 7.27 (s, 2H), 7.23–7.06 (m, 5H), 6.81–6.90 (m, 1H), 5.38 (s, 2H). HRFABMS (M+Na$^+$): Calcd.: 495.0344. Found: 495.0330.

EXAMPLE A(73)
4'-Amino-5-benzyl-2'-(4-sulfamoyl-phenylamino)-[2,5']bithiazolyl-4-carboxylic acid ethyl ester

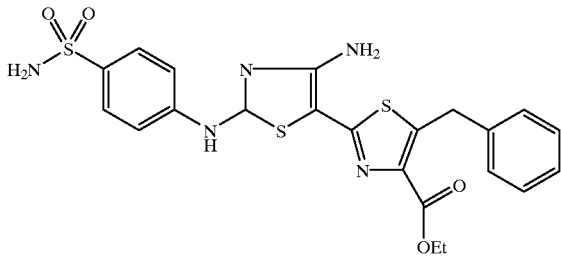

$^1$H NMR (CD3OD): δ 7.76 (s, 4H), 7.18 (m, 5H), 4.40 (s, 2H), 4.30 (q, J=7.8 Hz, 2H), 1.26 (t, J=7.8 Hz, 3H).

EXAMPLE B(1)
(3-{5-[4-Amino-2-(trityl-amino)-thiazol-5-yl]-[1,2,4]oxadiazol-3-yl}-phenyl)-carbamic acid tert-butyl ester

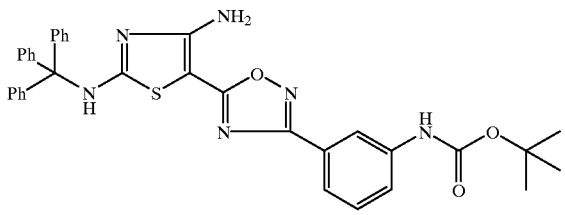

The starting material for use in preparing the title compound was prepared according to the following Steps (i) and (ii).

Step (i): To a solution of 3.15 g (26.7 mmol, 1.0 eq.) of 3-aminobenzonitrile in 10 mL of CH$_2$Cl$_2$ was added a solution of 6.4 g (29.4 mmol, 1.1 eq.) of di-tertbutyl dicarbonate in 10 mL of CH$_2$Cl$_2$, followed by 320 mg (2.7 mmol, 0.1 eq.) of DMAP and 8 mL (80.1 mmol, 3.0 eq.) of pyridine. CO$_2$ evolved and the reaction was followed by TLC until completion. The solvent was pumped off, the residue was taken up in EtOAc, and washed with 1N HCl and brine. The organic layer was dried over Na$_2$SO$_4$ and the solvent was removed. The crude product was purified on SiO$_2$ (2% Et$_2$O—CH$_2$Cl$_2$ eluant) to yield 5.4 g of 3-(t-butoxycarbamoyl)benzonitrile (yield 93%). Rf=0.9 (10% Et$_2$O—CH$_2$Cl$_2$). $^1$H NMR (CDCl$_3$): δ 1.5 (s, 9H), 6.6 (s br, 1H), 7.35 (m, 2H), 7.55 (m, 1H), 7.82 (m, 1H).

Step (ii): To a solution of 2 g (9.17 mmol, 1.0 eq.) of 3-(t-butoxycarbamoyl)benzonitrile in 25 mL of EtOH was added 0.84 mL (13.76 mmol, 1.5 eq.) of 50% aqueous solution of NH$_2$OH. The reaction was placed in an oil bath at 80° C. and heated to 85° C. for 4 h. The solvent was removed in vacuo, and residual water was removed by azeotroping the residue with THF-toluene. Without purification, the crude hydroxyamidine (R$_f$=0.1 in 10% Et$_2$O—CH$_2$Cl$_2$) was dissolved in 45 mL of DMF and 2.1 mL (12 mmol, 1.3 eq.) of diisopropylethyl amine and 110 mg (0.92 mmol, 0.1 eq.) of DMAP were added. The mixture was cooled to −50° C., and a solution of 0.88 mL (11 mmol, 1.2 eq.) of chloroacetyl chloride in 15 mL of CH$_2$Cl$_2$ (or DMF) was added dropwise, under argon. The reaction was stirred at −50° C. for 1 h, and then poured into EtOAc and washed with 1N HCl and brine. The organic layer was dried over Na$_2$SO$_4$ and the solvent was removed. The residue was taken up in 50 mL of dioxane and placed in an oil bath at 110° C. for about 1 h. The solvent was removed and the residue was purified on SiO$_2$ (Et$_2$O-hexane eluant) to yield 2 g of 5-chloromethyl-3-(3-(t-butoxy-carbamoyl)phenyl)-[1,2,4]-oxadiazole as a white solid (70% overall yield for three steps). R$_f$=0.9 (10% Et$_2$O—CH$_2$Cl$_2$). $^1$H NMR (CDCl$_3$): δ 1.5 (s, 9H), 4.75 (s, 2H), 6.62 (s br, 1H), 7.45 (dd, 1H), 7.62 (d br, 1H), 7.75 (m, 1H), 8.05 (m, 1H).

The title compound was prepared as follows. To a solution of tritylisothiocyanate (5.0 mmol) and cyanamide (5.5 mmol) dissolved in anhydrous THF (10 mL) was added 1,8-diazabicyclo [5.4.0]undec-7-ene (5.5 mmol). After stirring for 2 hours, the reaction was diluted with acetonitrile (15 mL) and then treated with 5-chloromethyl-3-(3-(t-butoxy-carbamoyl)phenyl)-[1,2,4]-oxadiazole (2.5 mmol) and 1,8-diazabicyclo [5.4.0]undec-7-ene (2.75 mmol). The product was isolated after 1 hour by concentrating the crude reaction in vacuo, and chromatographing the resulting oil (gradient elution, 20% EtOAc/hexane to 40% EtOAc/hexane), giving 1.30 g of product (84% yield). $^1$H NMR (CDCl$_3$): δ 7.79 (1H, s), 7.60 (2H, m), 7.24 (16H, m), 6.91 (1H, s), 6.48 (1H, s), 5.77 (2H, s), 1.52 (3H, s), 1.46 (6H, s). ESIMS (MH$^+$): 617.

The following Examples B(2) through B(36) were prepared in a similar fashion to Example B(1).

EXAMPLE B(2)
3-(3-tert-Butyloxycarboxy-aminophenyl)-5-[2-[(3,4,5-trimethoxyphenyl)amino]-4-amino-5-thiazolyl]-1,2,4-oxadiazole

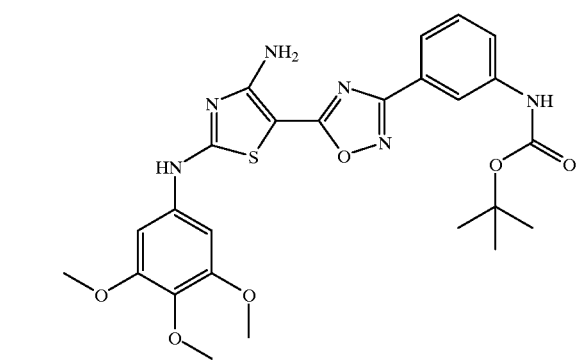

$^1$H NMR (d$_6$-acetone): δ 1.5 (s, 9H), 3.7 (s, 3H), 3.85 (s, 6H), 7.0 (s br, 2H), 7.05 (s, 2H), 7.4 (t, 1H), 7.75 (d, 2H), 8.35 (s, 1H), 8.6 (s br, 1H), 9.7 (s br, 1H). ESIMS (MH$^+$): 541; (M–H$^-$): 539. Anal. Calcd for C$_{25}$H$_{28}$N$_6$O$_6$S: C, 55.54; H, 5.22; N, 15.55; S, 5.93. Found: C, 56.45; H, 5.67; N, 14.88; S, 5.58.

EXAMPLE B(3)
5-[3-(4-tert-Butyl-phenyl)-[1,2,4]oxadiazol-5-yl]-N$^2$-(3,4,5-trimethoxy-phenyl)-thiazole-2,4-diamine

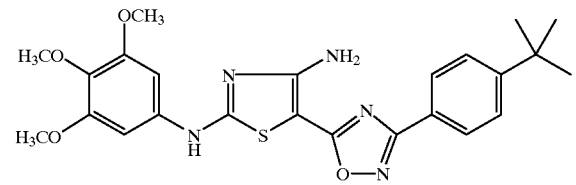

MS (FAB) [m+]/z Calc'd: 481. Found 481. Anal. Calc'd: C, 59.86; H, 5.65; N, 14.54; S, 6.66. Found: C, 58.36; H, 5.53; N, 13.95; S, 6.36.

EXAMPLE B(4)

5-[3-(3-Methoxymethoxy-phenyl)-[1,2,4]oxadiazol-5-yl]-$N^2$-(3,4,5-trimethoxy-phenyl)-thiazole-2,4-diamine

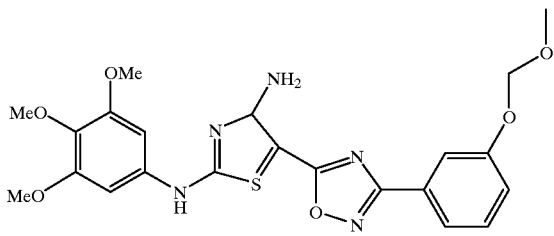

$^1$H NMR (300 MHz, DMSO-$d_6$): δ 3.41 (s, 3H), 3.64 (s, 3H), 3.81 (s, 6H), 5.29 (s, 2H), 7.01 (s, 2H), 7.22 (m, 1H), 7.34 (br s, 2H), 7.47 (m, 1H), 7.70 (m, 2H), 10.76 (s, 1H). Anal. Calcd for $C_{22}H_{23}N_5O_6S·H_2O$: C, 52.48; H, 5.00; N, 13.91. Found: C, 52.47; H, 4.98; N, 13.75.

EXAMPLE B(5)

3-(3-(tert-butyloxycarboxyamino)-6-fluoro-phenyl)-5-[2-[(3,4,5-trimethoxyphenyl)amino]-4-amino-5-thiazolyl]-1,2,4-oxadiazole

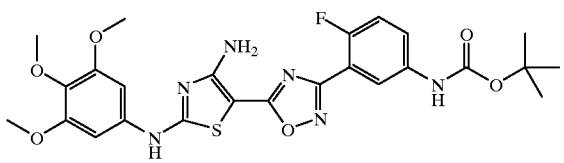

$^1$H NMR (CDCl$_3$): δ 1.5 (s, 9H), 3.7 (s, 3H), 3.85 (s, 6H), 6.6 (s br, 2H), 6.7 (s br, 1H), 7.05 (t, 1H), 7.55 (m br, 1H), 7.85 (m, 1H). ESIMS [MH]$^+$: 559.

EXAMPLE B(6)

3-(2-methyl-5-(tert-butyloxycarboxyamino)-phenyl)-5-[2-[(3,4,5 trimethoxyphenyl)-amino]-4-amino-5-thiazolyl]-1,2,4-oxadiazole

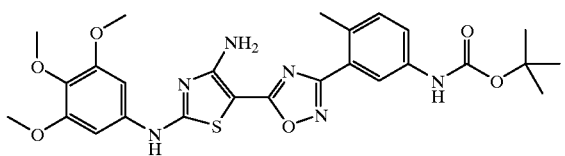

$^1$H NMR (CDCl$_3$): δ 1.5 (s, 9H), 2.55 (s, 3H), 3.85 (s, 3H), 3.87 (s, 6H), 6.65 (s br, 2H), 7.22 (d br, 1H), 7.28 (s, 1H), 7.55 (d br, 1H), 7.85 (m br, 1H). ESIMS [MH]$^-$: 555.

EXAMPLE B(7)

3-[3-[(3-methoxybenzoyl)amino]-6-methyl-phenyl]-5-[2-[4-(N,N-dimethylaminophenyl)amino]-4-amino-5-thiazolyl]-1,2,4-oxadiazole

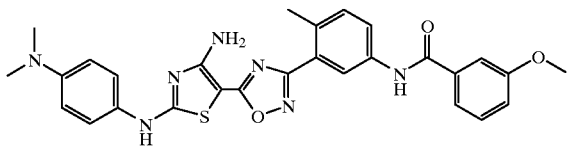

$^1$H NMR (d$_6$-DMSO): δ 2.55 (s, 3H), 2.9 (s, 6H), 3.85 (s, 3H), 6.75 (m, 2H), 7.18 (m, 3H), 7.35–7.6 (m, 6H), 7.95 (dd, 1H), 8.35 (d, 1H), 10.3 (s br, 1H), 10.4 (s br, 1H). ESIMS [MH]$^+$: 542, [M+Na]$^+$: 564. Anal. Calcd. for C28 H27 N7 O3 S: C, 58.22; H, 5.41, N, 16.97; S, 5.55. Found: C, 58.01; H, 5.54, N, 16.13; S, 5.22.

EXAMPLE B(8)

3-[3-[(1-ethyl-3-methyl-1H-Pyrazole-5-carboxy)-amino]-6-methylphenyl]-5-[2-(3-hydroxymethylphenyl)amino]-4-amino-5-thiazolyl]-1,2,4-oxadiazole

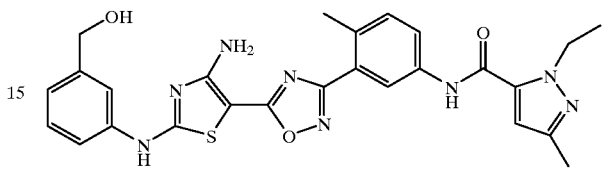

$^1$H NMR (MeOD): δ 1.4 (t, 3H), 2.3 (s, 3H), 2.6 (s, 3H), 4.5 (q, 2H), 4.65 (s, 2H), 6.75 (s, 1H), 7.1 (d br, 1H), 7.35 (m, 2H), 7.55 (m, 1H), 7.65 (m br, 1H), 7.8 (dd, 1H), 8.25 (d, 1H). ESIMS [MH]$^+$: 531.

EXAMPLE B(9)

3-[3-[(1-ethyl-3-methyl-1H-Pyrazole-5-carboxy)-amino]-6-methylphenyl]-5-[2-(3-methylpyrrolidinephenyl)amino]-4-amino-5-thiazolyl]-1,2,4-oxadiazole

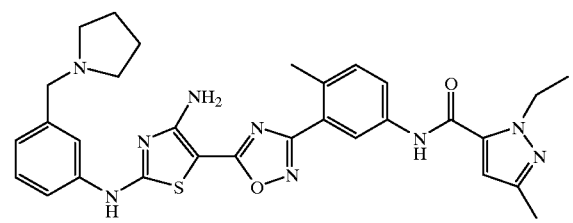

$^1$H NMR (MeOD): δ 1.4 (t, 3H), 1.8 (m br, 4H), 2.3 (s, 3H), 2.6 (s br, 7H), 3.7 (s, 2H), 4.5 (q, 2H), 6.75 (s, 1H), 7.18 (m, 3H), 7.35 (m, 2H), 7.55 (m br, 1H), 7.65 (s br, 1H), 7.8 (dd, 1H), 8.28 (d, 1H). ESIMS [MH]$^+$: 584.

EXAMPLE B(10)

3-[3-[(1-ethyl-3-methyl-1H-Pyrazole-5-carboxy)-amino]-6-methylphenyl]-5-[2-(4-methylpyrrolidinephenyl)amino]-4-amino-5-thiazolyl]-1,2,4-oxadiazole

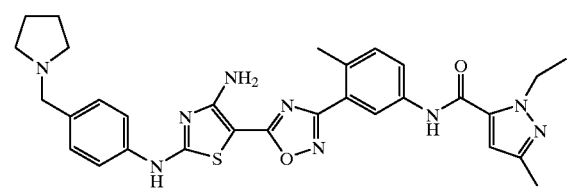

$^1$H NMR (d$_6$-DMSO): δ 1.32 (t, 3H), 1.7 (m br, 4H), 2.2 (s, 3H), 2.6 (s, 3H), 3.3 (m, 4H), 3.6 (s, 2H), 4.45 (q, 2H), 6.85 (s, 1H), 7.3 (m, 5H), 7.6 (d, 2H), 7.92 (dd, 1H), 8.28 (d, 1H), 10.25 (s, 1H), 10.8 (s br, 1H). ESIMS [MH]$^+$: 584. Anal. Calcd. for C30 H33 N9 O2 S: C, 61.73; H, 5.70, N, 21.60; S, 5.49. Found: C, 61.52; H, 5.61, N, 21.52; S, 5.46.

EXAMPLE B(11)

(R,S)-3-[3-(2-hydroxy-4-methyl pentanoyl)amino]-6-methylphenyl]-5-[2-(3-methylpyrrolidinephenyl)amino]-4-amino-5-thiazolyl]-1,2,4 oxadiazole

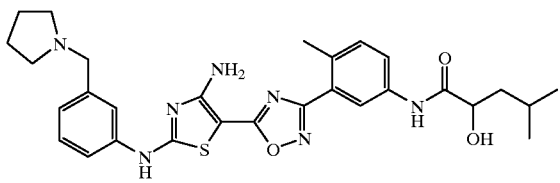

$^1$H NMR (MeOD): δ 1.0 (dd, 6H), 1.65 (m, 3H), 1.9 (m, 4H), 2.6 (s, 3H), 2.8 (m br, 4H), 3.85 (s, 2H), 4.2 (dd, 1H), 7.13 (d br, 1H), 7.35 (m, 3H), 7.56 (m br, 1H), 7.72 (m br, 2H), 8.28 (d, 1H).

EXAMPLE B(12)N (3-{5-[4-Amino-2-(3,4,5-trimethoxy-phenylamino)-thiazol-5-yl]-[1,2,4]oxadiazoyl}-4-chloro-phenyl)-carbamic acid tert-butyl ester

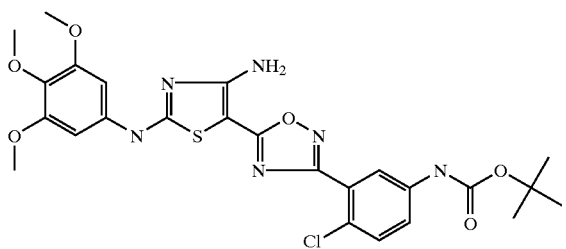

$^1$H-NMR (d$_6$-acetone): δ 9.71 (s, 1H), 8.71 (s, 1H), 8.20 (m, 1H), 7.78 (m, 1H), 7.52 (m, 1H), 7.06 (s, 2H), 6.95 (s, 2H), 3.85 (s, 6H), 3.72 (s, 3H), 1.50 (s, 9H). ESIMS: (MH)$^+$: 575(100%), 577(30%).

EXAMPLE B(13)

(5-{5-[4-Amino-2-(3,4,5-trimethoxy-phenylamino)-thiazol-5-yl]-[1,2,4]oxadiazol-3-yl}-2,4-difluoro-phenyl)-carbamic acid tert-butyl ester

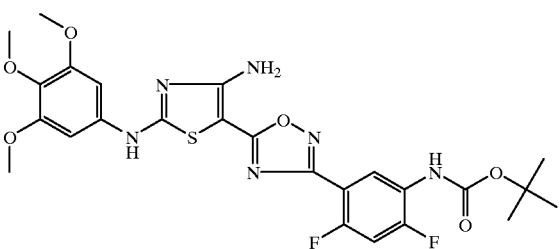

$^1$H-NMR (d$_6$-acetone) δ 9.71 (s, 1H), 8.68 (m, 1H), 8.24 (m, 1H), 7.28 (m, 1H), 7.04 (s, 2H), 6.99 (s, 2H), 3.85 (s, 6H), 3.72 (s, 3H), 1.51 (s, 9H). ESIMS (MH)$^+$: 577.

EXAMPLE B(14)

(5-{5-[4-Amino-2-(3,4,5-trimethoxy-phenylamino)-thiazol-5-yl]-[1,2,4]oxadiazol-3-yl}-4-chloro-2-fluoro-phenyl)-carbamic acid tert-butyl ester

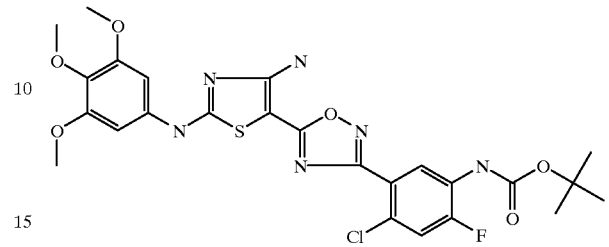

$^1$H-NMR (d$_6$-acetone): δ 9.72 (s, 1H), 8.68 (m, 1H), 7.49 (m, 1H), 7.07 (s, 2H), 6.97 (s, 2H), 3.85 (s, 6H), 3.72 (s, 3H), 1.51 (s, 9H). ESIMS(MH)$^+$: 593(100%), 595(30%).

EXAMPLE B(15)

(5-{5-[4-Amino-2-(3,4,5-trimethoxy-phenylamino)-thiazol-5-yl]-[1,2,4]oxadiazol-3-yl}-2,4-dichloro-phenyl)-carbamic acid tert-butyl ester

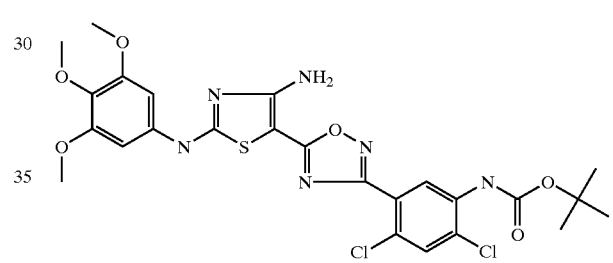

$^1$H-NMR (d$_6$-acetone): δ 9.73 (s, 1H), 8.71 (s, 1H), 7.96 (s, 1H), 7.72 (s, 1H), 7.07 (s, 2H), 6.98 (s, 2H), 3.85 (s, 6H), 3.72 (s, 3H), 1.52 (s, 9H). ESIMS(MH)$^+$: 609(100%), 611 (60%).

EXAMPLE B(16)

N-(3-{5-[4-Amino-2-(3,4,5-methylamino)-thiazol-5-yl]-[1,2,4]oxadiazol-3-yl]-4-methyl-phenyl}-carbamic acid tert-butyl

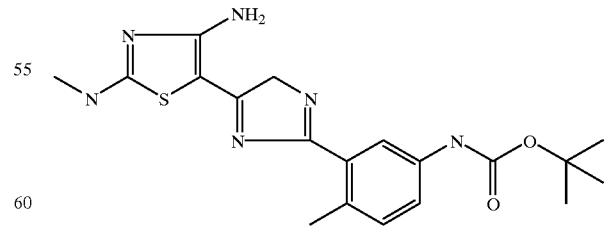

$^1$H-NMR (d$_6$-acetone): δ 8.48 (s, 1H), 8.20 (m, 1H), 7.69 (m, 1H), 7.55 (m, 1H), 7.28 (m, 1H), 6.77 (s, 2H), 3.02 (d, 3H), 2.55 (s, 3H), 1.55 (s, 9H). ESIMS: (MH)$^+$: 403, (MNa)$^+$: 425.

EXAMPLE B(17)
N-(3-{5-[4-Amino-2-(3,4,5-methylamino)-thiazol-5-yl]-[1,2,4]oxadiazol-3-yl]-4-methyl-phenyl}-3-methoxy-benzamide

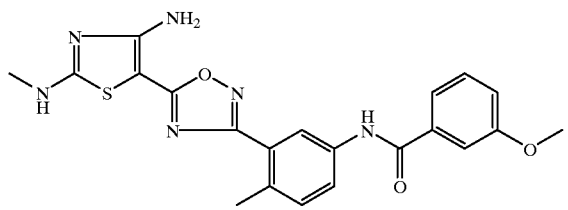

¹H-NMR (d₆-dmso): δ 10.33 (s, 1H), 8.59 (m, 1H), 8.35 (m, 1H), 7.95 (m, 1H), 7.55 (m, 2H), 7.45 (m, 2H), 7.36 (m, 1H), 7.19 (m, 2H), 3.88 (s, 3H), 2.91 (m, 3H), 2.50 (s, 3H). ESIMS: (MH)⁺:437, (MNa)⁺: 459.

EXAMPLE B(18)
N-(5-{5-[4-Amino-2-(6-morpholin-4-yl-pyridin-3-ylamino)-thiazol-5-yl]-[1,2,4]oxadiazol-3-yl}-2,4-difluoro-phenyl)-3-methoxy-benzamide

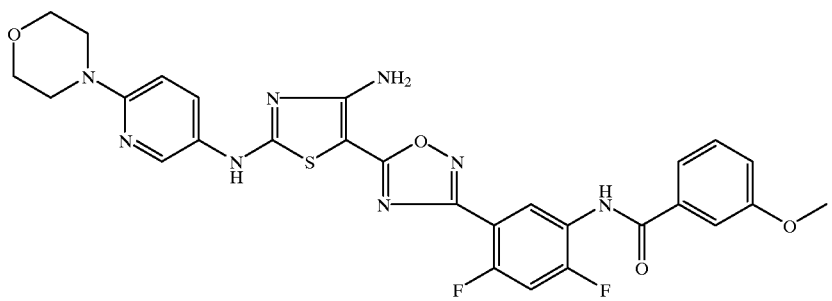

¹H-NMR (d₆-dmso): δ 10.62 (s, 1H), 10.27 (s, 1H), 8.39 (m, 1H), 8.33 (m, 1H), 7.85 (m, 1H), 7.63 (m, 3H), 7.48 (m, 1H), 7.30 (s, 2H), 7.20 (m, 1H), 6.88 (m, 1H), 3.85 (s, 3H), 3.70 (m, 4H), 3.42 (m, 4H). ESIMS: (MH)⁺: 607.

EXAMPLE B(19)
N-{5-[5-(4-Amino-2-isopropylamino-thiazol-5-yl)-[1,2,4]oxadiazol-3-yl]-2,4-difluoro-phenyl}-3-methoxy-benzamide

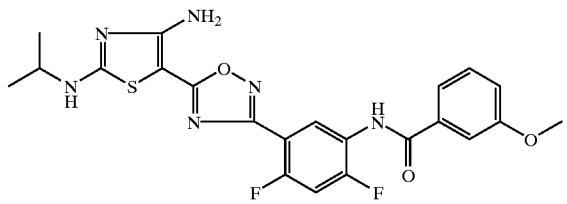

¹H-NMR (d₆-acetone): δ 9.37 (s, 1H), 8.70 (m, 1H), 7.65–7.60 (m, 3H), 7.45 (m, 1H), 7.34 (m, 1H), 7.18 (m, 1H), 6.78 (s, 2H), 3.96 (m, 1H), 3.90 (s, 3H), 1.30 (d, 6H). ESIMS: (MH)⁺: 487.

EXAMPLE B(20)
N-(5-{5-[4-Amino-2-(pyridin-3-ylamino)-thiazol-5-yl]-[1,2,4]oxadiazol-3-yl}-2,4-difluoro-phenyl)-3-methoxy-benzamide-TFA salt

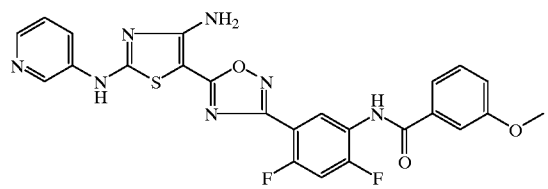

¹H-NMR (d₆-acetone and d₆-dmso): δ 11.07 (s, 1H), 9.94 (s, 1H), 8.98 (m, 1H), 8.54 (m, 1H), 8.30 (m, 2H), 7.64 (m, 3H), 7.48–7.36 (m, 4H), 7.18 (m, 2H), 3.89 (s, 3H). ESIMS: (MH)⁺: 522.

EXAMPLE B(21)
{5-[5-(4-Amino-2-isopropylamino-thiazol-5-yl)-[1,2,4]oxadiazol-3-yl]-2,4-difluoro-phenyl}-carbamic acid tert-butyl ester

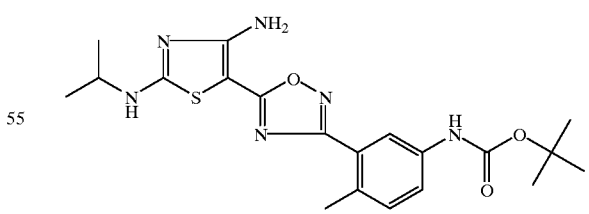

¹H-NMR (d₆-acetone): δ 8.42 (s, 1H, 8.18 (m, 1H), 7.70 (m, 1H), 7.67 (m, 1H), 7.26 (m, 1H), 6.73 (s, 2H), 3.97 (m, 1H), 2.54 (s, 3H), 1.50 (s, 9H), 1.29 (d, 6H). ESIMS: (MH)⁺: 431.

EXAMPLE B(22)

N-{3-[5-(4-Amino-2-isopropylamino-thiazol-5-yl)-[1,2,4]oxadiazol-3-yl]-4-methyl-phenyl}-3-methoxy-benzamide

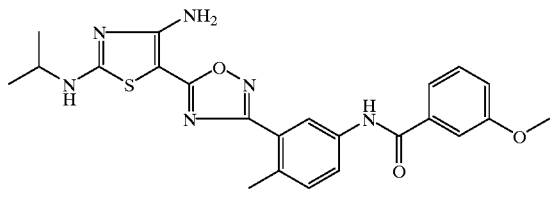

¹H-NMR (d₆-acetone): δ 9.59 (s, 1H), 8.42 (m, 1H), 8.03 (m, 1H), 7.57 (m, 2H), 7.43–7.7.37 (m, 3H), 7.14 (m, 1H), 6.73 (s, 2H), 3.97 (m, 1H), 3.88 (s, 3H), 2.60 (s, 3H), 1.29 (d, 6H). ESIMS: (MH)⁺: 465.

EXAMPLE B(23)

{3-[5-(4-Amino-2-phenyl-thiazol-5-yl)-[1,2,4]oxadiazol-3-yl]-4-methyl-phenyl}-carbamic acid tert-butyl ester

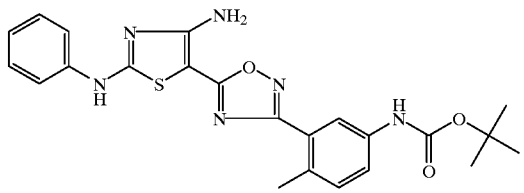

¹H-NMR (d₆-acetone): δ 9.78 (s, 1H), 8.44 (s, 1H), 7.72 (m, 3H), 7.42 (m, 2H), 7.39 (m, 1H), 7.11 (m, 1H), 6.91 (s, 2H), 2.57 (s, 3H), 1.51 (s, 9H). ESIMS: (MH)⁺: 465.

EXAMPLE B(24)

(3-{5-[4-Amino-2-(1H-benzoimidazol-5-yl)-thiazol-5-yl]-[1,2,4]oxadiazol-3-yl}-4-methyl-phenyl)-carbamic acid tert-butyl ester

EXAMPLE B(25)

(3-{5-[4-Amino-2-(3,4,5-trimethoxy-phenyl)-thiazol-5-yl]-[1,2,4]oxadiazol-3-yl}-4-methyl-phenyl)-carbamic acid tert-butyl ester

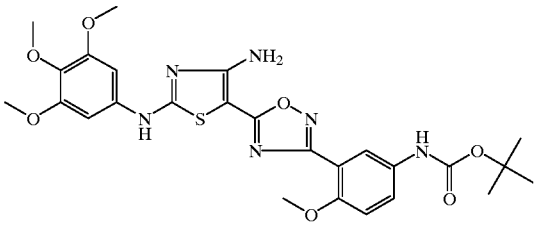

¹H-NMR (d₆-acetone): δ 9.62 (s, 1H), 8.23 (m, 1H), 8.09 (m, 1H), 7.15–7.05 (m, 2H), 7.39 (m, 3H), 6.82 (s, 2H), 6.91 (s, 2H), 4.07–3.85 (s, 9H), 3.76 (s, 3H), 1.49 (s, 9H). ESIMS: (MH)⁺: 571.

EXAMPLE B(26)

2-Ethyl-5-methyl-2H-pyrazole-3-carboxylic acid {3-[5-(4-amino-2-phenyl-thiazol-5-yl)-[1,2,4]oxadiazol-3-yl]-4-methyl-phenyl}-amide

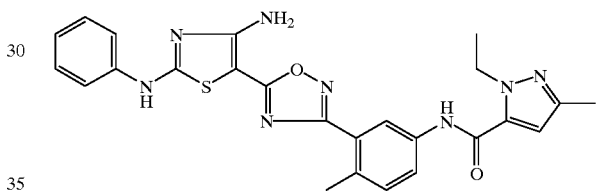

¹H-NMR (d₆-acetone): δ 10.75 (s, 1H), 9.42 (m, 1H), 8.38 (m, 1H), 7.99 (m, 1H), 7.20 (m, 2H), 7.45–7.35 (m, 3H), 7.12 (m, 1H), 6.90 (s, 2H), 6.74 (s, 1H), 4.55 (quartet, 2H), 2.62 (s, 3H), 2.21 (s, 3H), 1.39 (t, 3H). ESIMS: (MH)⁺: 500, (MNa)⁻: 523.

EXAMPLE B(27)

2-Ethyl-5-methyl-2H-pyrazole-3-carboxylic acid [3-(5-{4-amino-2-[6-(4-methyl-piperazin-1-yl)-pyridin-3-yl]-thiazol-5-yl}-[1,2,4]oxadiazol-3-yl)-4-methyl-phenyl]-amide

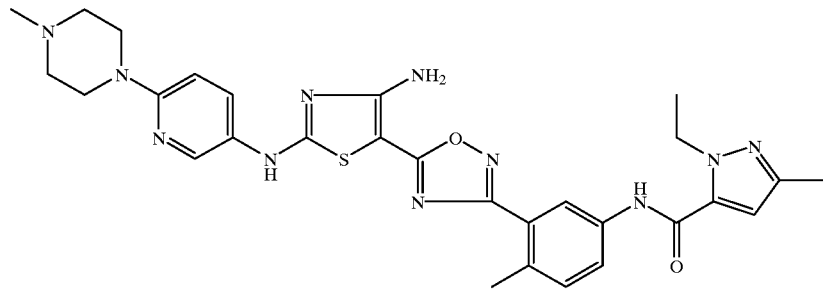

¹H-NMR (CD₃OD): δ 8.37 (m, 1H), 8.25 (m, 1H), 7.89 (m, 1H), 7.77 (m, 1H), 7.34 (m, 1H), 6.87 (m, 1H), 6.73 (m, 1H), 4.51 (quartet, 2H), 3.58 (m, 4H), 2.72 (m, 4H), 2.58 (s, 3H), 2.46 (s, 3H), 2.28 (s, 3H), 1.42 (t, 3H). ESIMS: (MH)⁺: 600.

EXAMPLE B(28)
N-[5-(5-{4-Amino-2-[6-(4-methyl-piperazin-1-yl)-pyridin-3-yl]-thiazol-5-yl}-[1,2,4]oxadiazol-3-yl)-2-chloro-4-methyl-phenyl]-3-methoxy-benzamide

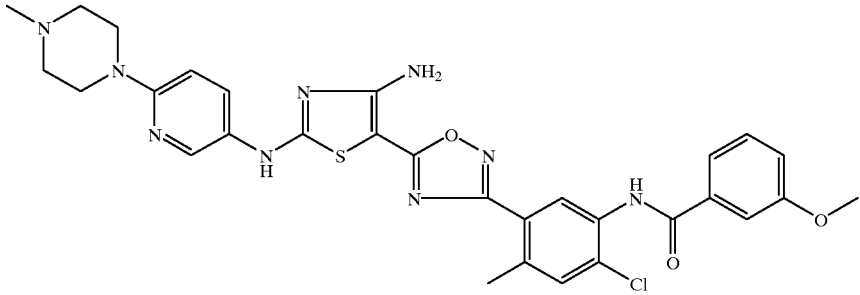

$^1$H-NMR (d$_6$-acetone and d$_6$-dmso): δ 10.51 (s, 1H) 9.89 (s, 1H), 8.47 (m, 2H), 7.91 (m, 1H), 7.70–7.51 (m, 3H), 7.45 (m, 1H), 7.20–7.14 (m, 3H), 6.89 (m, 1H), 3.91 (s, 3H), 3.58 (m, 4H), 2.67 (s, 3H), 2.58 (m, 4H), 2.36 (s, 3H). ESIMS: (MH)$^+$: 632.

EXAMPLE B(29)
2-Hydroxy-4-methyl-pentanoic acid [3-(5-{4-amino-2-[6-(4-methyl-piperazin-1-yl)-pyridin-3-yl]-thiazol-5-yl}-[1,2,4]oxadiazol-3-yl)-4-methyl-phenyl]-amide

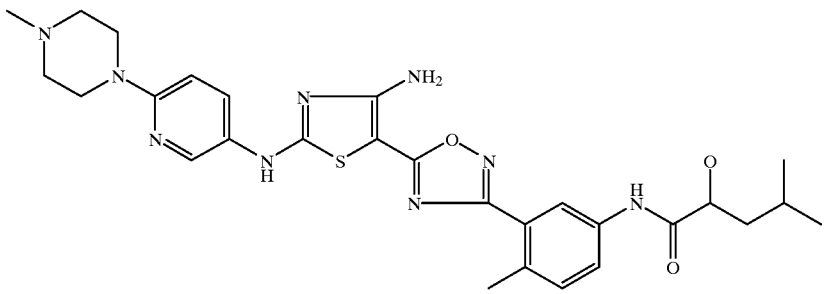

$^1$H-NMR (CD$_3$OD): δ 8.47 (m, 1H), 8.28 (m, 1H), 8.01 (m, 1H), 7.68 (m, 1H), 7.32 (m, 1H), 7.00 (m, 1H), 4.20 (m, 1H), 3.41–3.31 (m, 7h), 2.99 (m, 4H), 2.59 (s, 3H), 1.93 (m, 1H), 1.65 (m, 2H), 1.10 (d, 6H). ESIMS: (MH)$^+$: 578.

EXAMPLE B(30)
2-Ethyl-5-methyl-2H-pyrazole-3-carboxylic acid (3-{5-[4-amino-2-(4-hydroxy-phenyl)-thiazol-5-yl]-[1,2,4]oxadiazol-3-yl}-4-methyl-phenyl)-amide

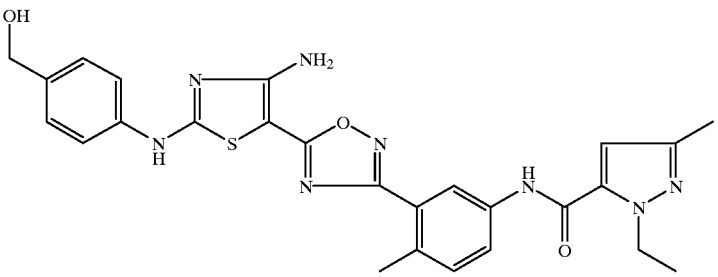

$^1$H-NMR (d$_6$-acetone): δ 9.77 (s, 1H), 9.43 (s, 1H), 8.36 (m, 1H), 7.98 (m, 1H), 7.66 (m, 2H), 7.41–7.36 (m, 3H), 6.90 (s, 2H), 6.75 (s, 1H), 4.64 (m, 2H), 4.54 (quartet, 2H), 4.14 (m, 1H), 2.61 (s, 3H), 2.20 (s, 3H), 1.39 (t, 3H). ESIMS: (MH)$^-$: 531.

EXAMPLE B(31)

(Z)-2-Methyl-but-2-enoic acid [3-(5-{4-amino-2-[4-(4-methyl-piperazin-1-yl)-phenyl]-thiazol-5-yl}-[1,2,4]oxadiazol-3-yl)-4-methyl-phenyl]-amide

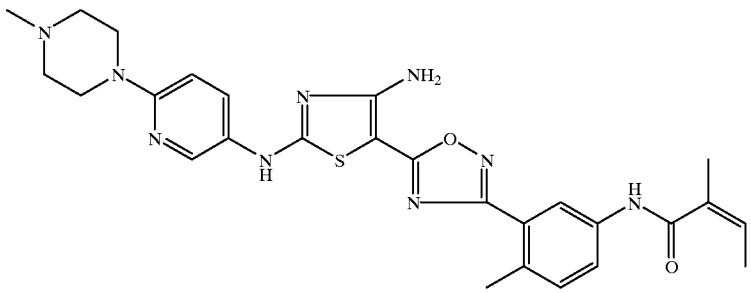

¹H-NMR (d₆-acetone): δ 10.55 (s, 1H), 9.92 (s, 1H), 8.60 (m, 1H), 8.24 (m, 1H), 7.81 (m, 2H), 7.31 (m, 1H), 7.22 (s, 2H), 6.87 (m, 1H), 5.61 (m, 1H), 3.45 (m, 4H), 2.50 (s, 3H), 2.40 (m, 4H), 2.22 (s, 3H), 1.92 (s, 3H), 1.72 (d, 3H). ESIMS: (MH)⁺: 546.

EXAMPLE B(32)

(Z)-2-Methyl-but-2-enoic acid (3-{5-[4-amino-2-(3-pyrrolidin-1-ylmethyl-phenyl)-thiazol-5-yl]-[1,2,4]oxadiazol-3-yl}-4-methyl-phenyl)-amide

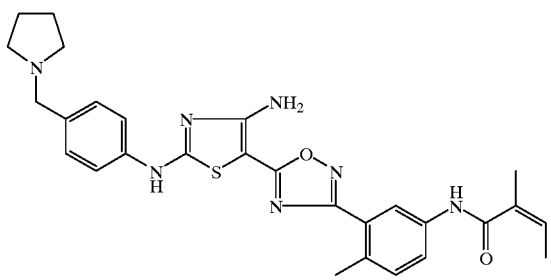

¹H-NMR (CD₃OD): δ 8.31 (m, 1H), 7.80 (m, 2H), 7.68 (m, 1H), 7.50 (m, 2H), 7.32 (m, 1H), 5.70 (m, 1H), 4.33 (s, 2H), 2.59 (s, 3H), 2.16 (s, 3H), 2.10 (m, 4H), 1.99 (m, 4H), 1.80 (m, 3H). ESIMS: (MH)⁺: 530.

EXAMPLE B(33)

(3-{5-[4-Amino-2-(3-pyrrolidin-1-ylmethyl-phenyl)-thiazol-5-yl]-[1,2,4]oxadiazol-3-yl}-4-methyl-phenyl)-carbamic acid tert-butyl ester

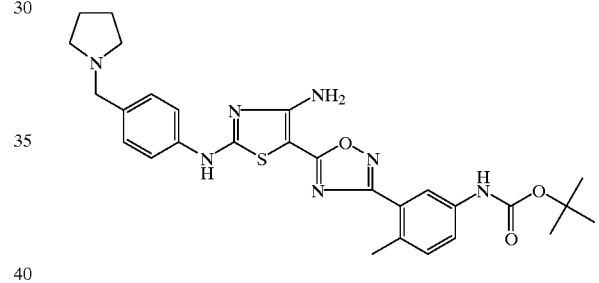

¹H-NMR (d₆-acetone): δ 10.48 (s, 1H), 8.61 (m, 1H), 8.47 (m, 1H), 8.23 (m, 1H), 7.74 (m, 1H), 7.63 (m, 1H), 7.38–7.28 (m, 5H), 4.33 (s, 2H), 3.47 (m, 4H), 2.80 (m, 4H), 2.58 (s, 3H), 1.51 (s, 9H), ESIMS: (MH)⁺: 548.

EXAMPLE B(34)

(3-{5-[4-Amino-2-(3-pyrrolidin-1-ylmethyl-phenyl)-thiazol-5-yl]-[1,2,4]oxadiazol-3-yl}4-methyl-phenyl)-carbamic acid isobutyl ester

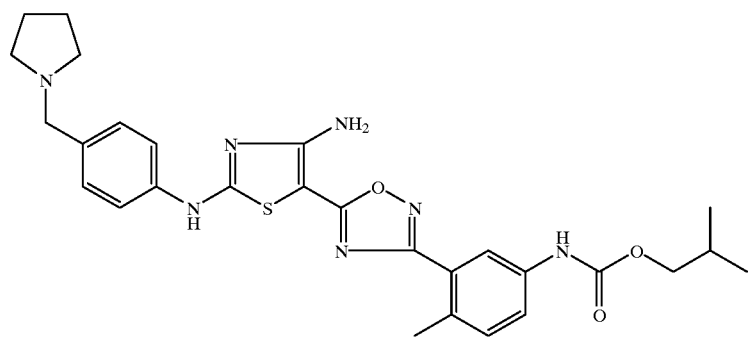

$^1$H-NMR (d$_6$-acetone): δ 10.46 (s, 1H), 8.75 (m, 1H), 8.52 (m, 1H), 8.26 (m, 1H), 7.74 (m, 1H), 7.63 (m, 1H), 7.36–7.27 (m, 3H), 7.22 (s, 2H), 4.29 (s, 2H), 3.92 (d, 2H), 3.22 (m, 4H), 3.09 (m, 4H), 2.57 (s, 3H), 1.98 (m, 1H), 0.97 (d, 6H), ESIMS: (MH)$^+$:548.

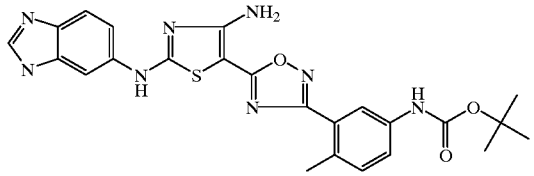

$^1$H-NMR (d$_6$-acetone): δ 9.79 (s, 1H), 8.45 (s, 1H), 8.11–8.15 (m, 2H), 7.71 (m, 1H), 7.64 (m, 1H) 7.39 (m, 1H), 7.29 (m, 1H), 6.79 (s, 2H), 2.57 (s, 3H), 1.51 (s, 9H). ESIMS: (MH)$^+$: 505.

EXAMPLE B(35)
3-[3-[(3-methoxybenzoyl)amino]-6-methyl-phenyl]-5-(2-phenylamino)-4-amino-5-thiazolyl]-1,2,4-oxadiazole

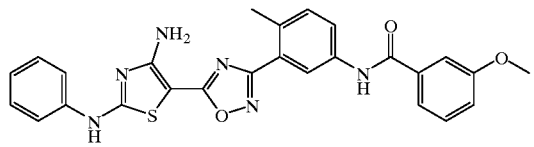

$^1$H NMR (d$_6$-DMSO): δ 2.55 (s, 3H), 3.85 (s, 3H), 7.1 (m, 1H), 7.18 (m, 1H), 7.2 (s br, 2H), 7.4 (m, 2H), 7.45 (m, 2H), 7.55 (m, 2H), 7.7 (dd, 2H), 7.95 (dd, 1H), 8.35 (d, 1H), 10.35 (s br, 1H), 10.85 (s br, 1H). ESIMS [MH]$^+$: 499. Anal. Calcd. for C26 H22 N6 O3 S: C, 62.64; H, 4.45, N, 16.86; S, 6.43. Found: C, 62.41; H, 4.54, N, 16.72; S, 6.30.

EXAMPLE B(36)
3-[3-[(3-methoxybenzoyl)amino]-6-methyl-phenyl]-5-[2-[3-amino-6-(4-morpholinyl)-pyridinyl]-4-amino-5-thiazolyl]-1,2,4-oxadiazole

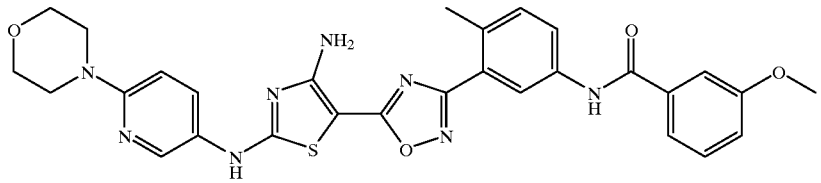

$^1$H NMR (d$_6$-DMSO): δ 2.55 (s, 3H), 3.4 (m, 4H), 3.7 (m, 4H), 3.85 (s, 3H), 6.9 (d, 1H), 7.15 (m, 1H), 7.22 (s br, 1H), 7.35 (d, 1H), 7.45 (m, 1H), 7.55 (m, 2H), 7.85 (dd, 1H), 7.95 (dd, 1H), 8.4 (dd, 2H), 9.75 (s br, 1H), 10.35 (s br, 1H), 10.7 (s br, 1H). ESIMS [MH]$^+$: 585.

EXAMPLE B(37)
5-{3-[3-(5-Methyl-2H-[1,2,4]triazol-3-yl)-phenyl]-[1,2,4]-oxadiazol-5-yl}-N2-(3,4,5-trimethoxy-phenyl)-thiazole-2,4-diamine

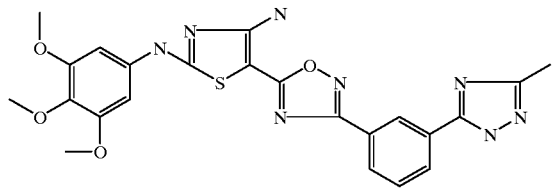

(A) To 1 (6.0 g, 37.5 mmol) in 120 mL EtOH was added hydrazine (6.24 mL, 200 mmol, 5.3 eq.) dropwise. The resulting solution was placed in a 90° C. oil bath. The reaction was allowed to stir until 1 disappeared by TLC (~2 h). The reaction was allowed to cool, the solvent was reduced to ~50 mL by rotary evaporation, and 2 precipitated as a white solid. The solid was collected by filtration. The volume of the filtrate was further reduced to ~20 mL and diluted with ether (10 mL) allowing a second crop of 2 to be collected. The two crops were combined after $^1$H NMR showed them to be equally pure (yield: 5.07 g, 83%). Rf 1=0.8 (25%CH$_2$Cl$_2$-EtOAc), Rf 2=0.2 (25%CH$_2$Cl$_2$-EtOAc). 2: $^1$H-NMR (d$_6$-dmso): δ 9.98 (s, 1H), 8.21 (m, 1H), 8.14 (m, 1H), 8.00 (m, 1H), 7.71 (m, 1H), 4.60 (s, 2H).

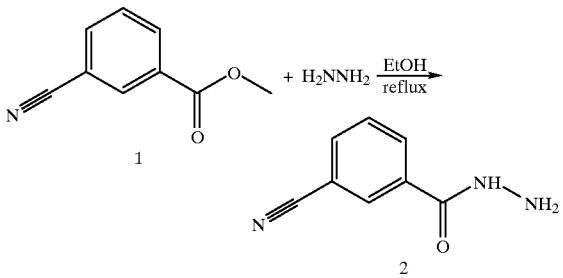

(B) To a solution of acetamidine HCl (2.3 g, 24.6 mmol, 1 eq) in 20 mL anhydrous ethanol was added NaOEt (24.6 mL, 1 M in EtOH, 1 eq) under argon. After 30 min. the cloudy solution was filtered through a fritted funnel packed with celite. To the resulting clear solution was added 2. Upon addition of 2 the reaction turns yellow and cloudy. The solution clears after ~5 min. of stirring and then a heavy precipitate forms. The reaction is allowed to stir until 2 disappears by TLC (3 h). Rf 2=0.75 (30%EtOH: 30%CHCl3: 40%EtOAc), Rf of uncyclized intermediate= 0.2 (30%EtOH: 30%CHCl3: 40%EtOAc). The reaction was stirred on ice for 30 min. and then filtered to yield a white solid (2.125 g, 85%). 2.07 g of this intermediate was dissolved in 10 mL xylenes and 0.52 mL 1-octanol and placed in a 150° C. oil bath. After ~15 h full conversion to 3 was observed by TLC and white crystals had precipitated. The reaction was placed in an ice-MeOH bath for 15 min. and then filtered. The crystals were washed with cold xylenes and then dried to yield 1.636 g 3 (83%). Rf 3=0.6 (30%EtOH: 30%CHCl3: 40%EtOAc). 3: $^1$H-NMR (d$_6$-dmso): δ 13.89 (s, 1H), 8.27 (m, 2H), 7.86 (m, 1H), 7.67 (m, 1H), 2.43 (s, 3H).

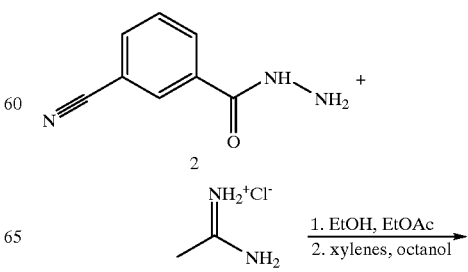

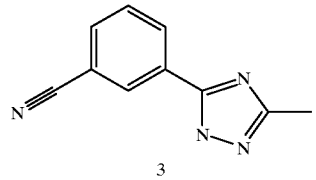

Compound 3 was further reacted in a similar manner according to the procedure of B(1) to form Example B(37). $^1$H-NMR (d$_6$ acetone): δ 8.85 (m, 1H), 8.26 (m, 1H), 8.15 (m, 1H), 7.63 (m, 1H), 7.09 (s, 2H), 7.01 (s, 2H), 3.86 (s, 6H), 3.72 (s, 3H), 2.49 (s, 3H). ESIMS: (MH)$^+$: 507.

Examples B(38) and B(39) are formed in a similar manner to the procedure described in B(37).

EXAMPLE B(38)
5-{3-[3-(5-isopropyl-2H-[1,2,4]triazol-3-yl)-phenyl]-[1,2,4]oxadiazol-5-yl}-N2-(3,4,5-trimethoxy-phenyl)-thiazole-2,4-diamine

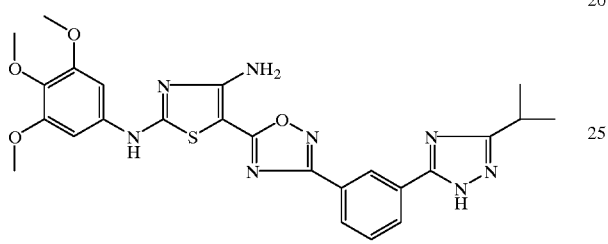

$^1$H-NMR (d$_6$-acetone): δ 13.79 (s, 1H), 10.78 (s, 1H), 8.63 (m, 1H), 8.15 (m, 2H), 7.63 (m, 1H), 7.36 (s, 2H), 7.02 (s, 2H), 3.81 (s, 6H), 3.72 (s, 3H), 3.13 (septet, 1H), 1.33 (d, 6H). ESIMS: (MH)$^+$: 535.

EXAMPLE B(39)
5-(3-{5-[5-Isobutyl-2H-[1,2,4]triazol-3-yl)-phenyl-[1,2,4]oxadiazol-5-yl)-N2-(3,4,5-trimethoxy-phenyl)-thiazole-2,4-diamine

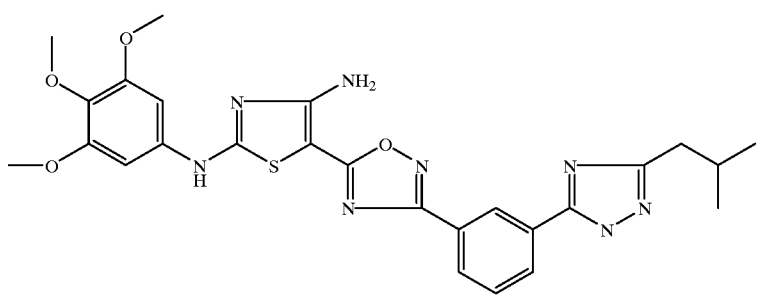

$^1$H-NMR (d$_6$-acetone): δ 12.75 (s, 1H), 9.68 (s, 1H), 8.81 (m, 1H), 8.23 (m, 1H), 8.11 (m, 1H), 7.58 (m, 1H), 7.02 (s, 2H), 6.93 (s, 2H), 3.77 (s, 6H), 3.67 (s, 3H), 2.51 (d, 2H), 2.01 (m, 1H), 0.98 (d, 6H). ESIMS: (MH)$^+$: 549.

EXAMPLE B(40)

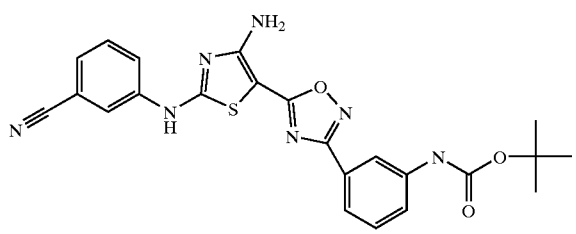

EXAMPLE B(41)

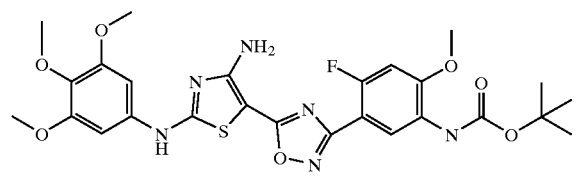

EXAMPLE B(42)

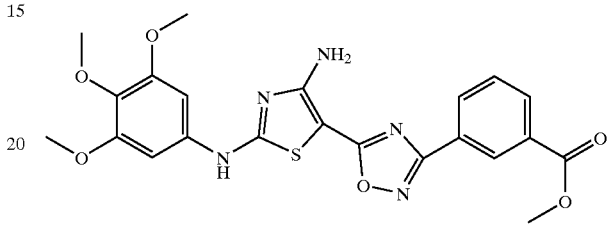

EXAMPLE B(43)

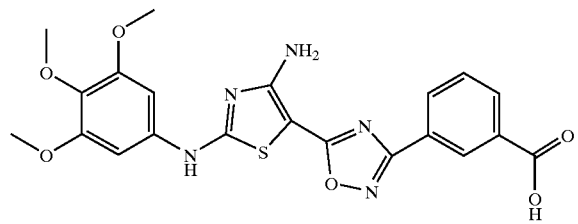

EXAMPLE C(1)
4-(3-Aminophenyl)-N$^{2'}$-[(3,4,5-trimethoxyphenyl)-[2,5']bithiazolyl-2',4'-diamine

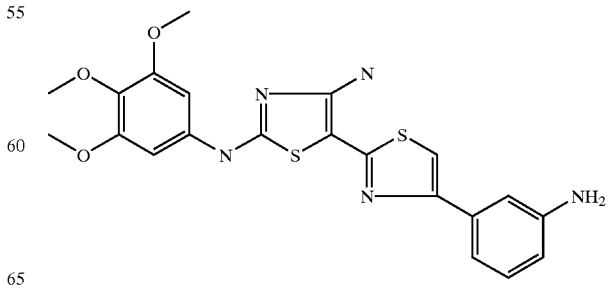

A solution of (3-nitrophenyl)-N$^{2'}$-trimethoxyphenyl-[2,5']bithiazolyl-2',4'-diamine (1 mmol), prepared as in Example A(1), and stannous chloride (3 mmol) in DMF (3 mL), under an argon atmosphere, was stirred at 50° C. (internal temperature) for 2.5 h. The resulting dark-brown solution was diluted with ethyl acetate (10 mL) and NaHCO₃ (10 mL), causing formation of a precipitate, which was removed by filtration and rinsed with 50% DMF/ethyl acetate (20 mL) until the filtrate was nearly colorless. The filtrate was then washed with NaHCO₃ (30 mL), brine (30 mL), dried over MgSO₄, filtered, stripped of solvent, and purified by flash chromatography (gradient elution, 10% acetone/CH₂Cl₂ to 40% acetone/CH₂Cl₂) to give 4-(3-aminophenyl)-N²'-(3,4,5-trimethoxyphenyl)-[2,5']bithiazolyl-2',4'-diamine. Mp 205–210° C. (decomp.) ¹H NMR (DMSO-d₆): δ 10.35 (br d, NH₂), 7.41 (s, 1H), 7.18 (s, 1H), 7.07 (d, 1H, J=4.82 Hz, 1H), 7.00 (s, 2H), 6.95 (s, 1H), 6.57–6.52 (m, 1H), 5.13 (br d, NH₂), 3.80 (s, 6H), 3.65 (s, 3H). FABMS (MH⁺): 456. Anal. Calcd for C₂₁H₂₁N₅O₃S₂: C, 55.37; H, 4.65; N, 15.37; S, 14.08. Found: C, 55.59; H, 4.72; N, 15.11; S, 13.92.

EXAMPLE C(2)

3-[3-Aminophenyl]-5-[2-[(3,4,5-trimethoxyphenyl)amino]-4-amino-5-thiazolyl]-1,2,4-oxadiazole

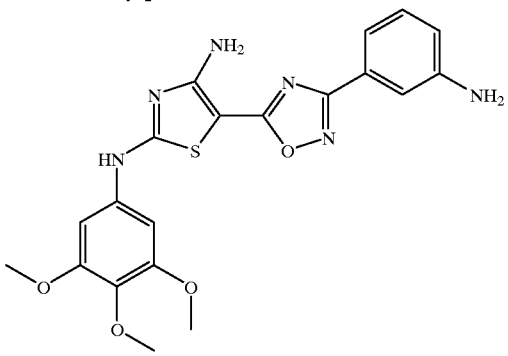

A solution of 267 mg (0.49 mmol) of 3-(3-t-butyloxycarboxy-aminophenyl)-5-[2-[(3,4,5-trimethoxyphenyl)amino]-4-amino-5-thiazolyl]-1,2,4-oxadiazole (prepared according to Example B(2)) in 3 mL of 50% trifluoroacetic acid in dichloromethane was stirred for 60 minutes at ambient temperature and then poured onto ice. 3N NaOH was added dropwise until the solution was basic, and the mixture was extracted with EtOAc. The organic layer was washed with NaHCO₃ and brine, and dried over Na₂SO₄. The solvent was removed to yield 204 mg (95% yield) of the title compound as a light yellow solid.
¹H NMR (d₆-acetone): δ 3.6 (s, 3H), 3.75 (s, 6H), 4.8 (s br, 2H), 6.75 (m, 1H), 6.85 (s br, 2H), 6.95 (s, 2H), 7.1 (t, 1H), 7.25 (m, 1H), 7.35 (m, 1H), 9.6 (s br, 1H). ESIMS (MH⁺): 441; (M–H⁻): 439. Anal. Calcd for C₂₀H₂₀N₆O₄S: C, 54.53; H, 4.58; N, 19.08; S, 7.28. Found: C, 54.79; H, 4.59; N, 18.81; S, 7.09.

EXAMPLE C(3)

4-[4'-Amino-4-(3-amino-phenyl)-[bithiazolyl-2'-ylamino]-benzenesulfonamide

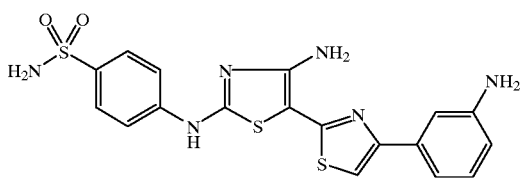

In a similar manner to that described above for Examples C(1) and C(2), the title compound was prepared.

¹H NMR (CD₃OD): δ 7.88 (s, 4H), 7.42 (s, 1H), 7.40–7.29 (m, 2H), 7.25–7.18 (m, 1H), 6.80–6.72 (m, 1H). FABMS (MH⁺): 445.

EXAMPLE C(4)

3-[3-amino-6-fluorophenyl]-5-[2-[(3,4,5-trimethoxyphenyl)amino]-4-amino-5-thiazolyl]-1,2,4-oxadiazole

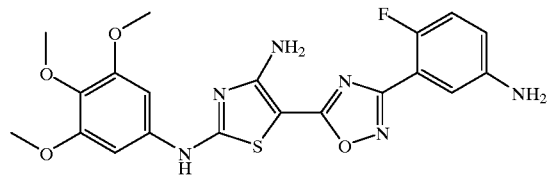

¹H NMR (CDCl₃—MeOD 10:1): δ 3.85 (s, 3H), 3.95 (s, 6H), 6.75 (m, 2H), 7.1 (m, 2H), 7.7 (s br, 1H). ESIMS [MH]⁺: 459.

EXAMPLE C(5)

3-[2-fluoro-4-methoxy-5-aminophenyl]-5-[2-[(3,4,5-trimethoxyphenyl)amino]-4-amino-5-thiazolyl]-1,2,4-oxadiazole

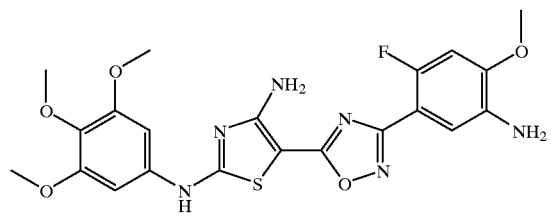

¹H NMR (d₆-DMSO): δ 3.6 (s, 3H), 3.8 (s, 6H), 4.0 (s, 3H), 6.95 (s br, 2H), 7.2 (m, 3H), 8.65 (d, 1H), 9.05 (s br, 1H). ESIMS [MH]⁺: 489.

EXAMPLE C(6)

3-(3-amino-6-methyl-phenyl)-5-[2-[(3,4,5 trimethoxyphenyl)-amino]-4-amino-5-thiazolyl]-1,2,4-oxadiazole

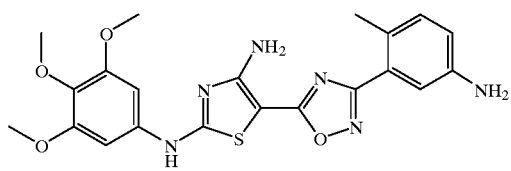

¹H NMR (CDCl₃): δ 2.05 (s, 3H), 3.8 (s, 9H), 6.2 (s br, 2H), 6.6 (s br, 2H), 6.8 (m br, 1H), 7.05 (m br, 1H), 7.45 (s br, 1H). ESIMS [MH]⁺: 455.

EXAMPLE C(7)

5-[3-(5-Amino-2-chloro-phenyl)-[1,2,4]oxadiazol-5-yl]-N2-(3,4,5-trimethoxy-phenyl)-thiazole-2,4-diamine

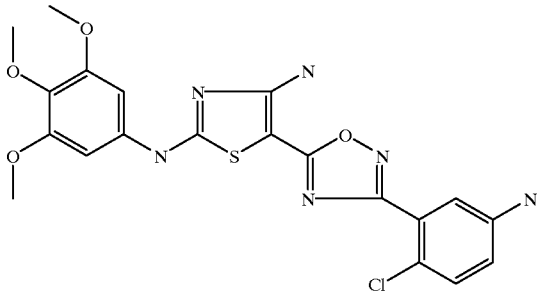

$^1$H-NMR (d$_6$-acetone): δ 9.58 (s, 1H), 7.13 (m, 2H), 6.92 (s, 2H), 6.78 (s, 2H), 6.70 (m, 1H), 4.91 (s, 2H), 3.78 (s, 6H), 3.58 (s, 3H). ESIMS:(MH)$^+$: 475 (100%), 477 (30%.)

EXAMPLE C(8)

5-[3-(5-Amino-2,4,-difluoro-phenyl)-[1,2,4]oxadiazol-5-yl]-N2-(3,4,5-trimethoxy-phenyl)-thiazole-2,4-diamine

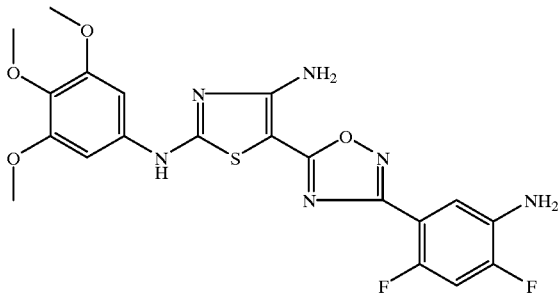

$^1$H-NMR (d$_6$-acetone): δ 9.72 (s, 1H), 7.63 (m, 1H), 7.09 (m, 1H), 7.05 (s, 2H), 6.94 (s, 2H), 4.83 (s, 2H), 3.85 (s, 6H), 3.72 (s, 3H). ESIMS (MH)$^+$: 477.

EXAMPLE C(9)

5-[3-(5-Amino-2-chloro-4-fluoro-phenyl)-[1,2,4]oxadiazol-5-yl]-N-(3,4,5-trimethoxy-phenyl)-thiazole-2,4-diamine

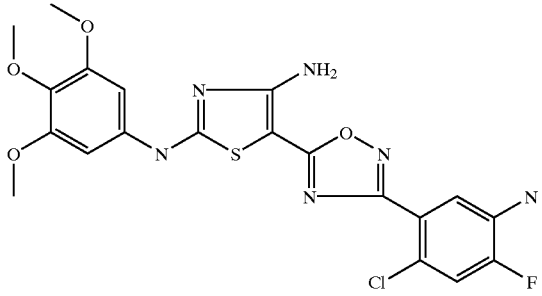

$^1$H-NMR (d$_6$-dmso) δ 10.76 (s, 1H), 7.36 (m, 2H), 7.18 (s, 2H), 6.93 (s, 2H), 5.60 (s, 2H), 3.86 (s, 6H), 3.73 (s, 3H). ESIMS (MH)$^+$ 493(100%), 495(30%).

EXAMPLE D(1)

N-{3-[4'-Amino-2'-(3,4,5-trimethoxy-phenylamino)-[2,5']bithiazolyl-4-yl]-phenyl}acetamide

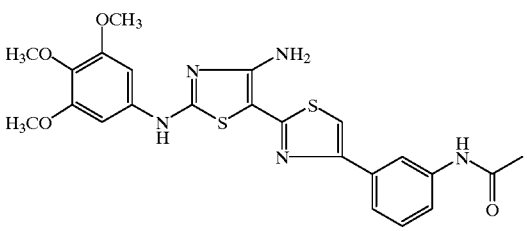

Acetic anhydride (21.3 μL, 0.2250 mmol) was added to a solution of 4-(3-aminophenyl)-N$^2$'-(3,4,5-trimethoxyphenyl)-[2,5']bithiazolyl-2',4'-diamine (50.0 mg, 0.1125 mmol), prepared as described in Example C(1), dissolved in pyridine (28.5 μL, 0.352 mmol), DMF (70 μL), and THF (700 μL) at −15° C. (bath temperature). After 30 minutes, the reaction was quenched with MeOH (0.5 mL), concentrated, and purified by preparative C-18 reverse-phase HPLC (gradient elution, 95% H$_2$O/0.1% TFA/CH$_3$CN to 5% H$_2$O/0.1% TFA/CH$_3$CN), giving 46 mg (82% yield) of N-{3-[4'-amino-2'-(3,4,5-trimethoxy-phenylamino)-[2,5']bithiazolyl-4-yl]-phenyl}acetamide.

$^1$H NMR (CDCl$_3$): δ 7.97 (s, 1H), 7.56 (d, J=7.7 Hz, 1H), 7.44 (d, J=7.8 Hz, 1H), 7.30 (t, J=7.6 Hz, 1H), 7.27 (s, 1H), 7.19 (s, 1H), 6.55 (s, 2H), 5.90–6.10 (bs, 1H), 3.82 (s, 6H), 3.78 (s, 3H), 2.14 (s, 3H). ESIMS (MH$^+$): 498. Anal. Calcd. for C$_{23}$H$_{23}$N$_5$O$_4$S$_2$.(0.5 H$_2$O, 0.5 acetone): C, 54.93; H, 5.08; N, 13.08; S, 11.97. Found: C, 54.73; H, 4.80; N, 13.21; S, 11.98.

In a manner analogous to that described for Example D(1), the following Examples D(2) through D(57) were prepared.

EXAMPLE D(2)

N-{3-[4'-Amino-2'-(3,4,5-trimethoxy-phenylamino)-[2,5']bithiazolyl-4-yl]-phenyl}-C-phenyl-methanesul-fonamide

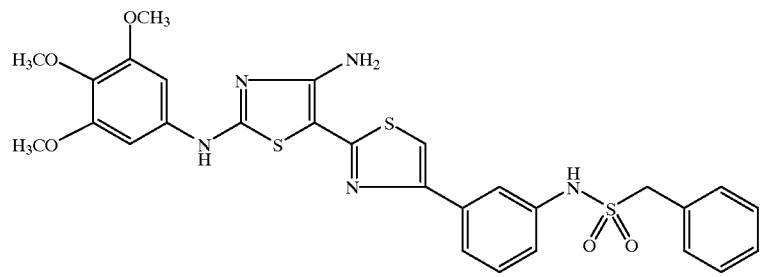

¹H NMR (CDCl₃): δ 7.61 (s, 1H), 7.55 (d, J=7.9 Hz, 1H), 7.32 (d, J=7.9 Hz, 1H), 7.26–7.16 (m, 5H), 7.03 (s, 1H), 7.00 (s, 2H), 6.51 (s, 2H), 6.42 (s, 1H), 5.90–6.00 (bs, 2H), 4.26 (s, 2H), 3.78 (s, 6H), 3.74 (s, 3H). ESIMS (MH⁺): 610. Anal. Calcd. for $C_{28}H_{27}N_5O_5S_3 \cdot 0.3 H_2O$: C, 54.67; H, 4.52; N, 11.39. Found: C, 54.70; H, 4.52; N, 11.04.

EXAMPLE D(3)

N-{3-[4'-Amino-2'-(3,4,5-trimethoxy-phenylamino)-[2,5']bithiazolyl-4-yl]-phenyl}-methanesulfonamide

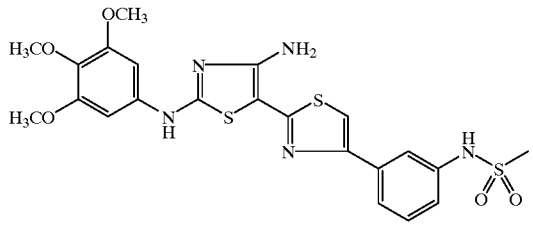

¹H NMR (CDCl₃): δ 7.81 (s, 1H), 7.69 (d, J=7.8 Hz, 1H), 7.45 (t, J=7.9 Hz, 1H), 7.26 (s, 1H), 7.24 (s, 1H), 6.73 (bs, 1H), 6.70 (s, 2H), 3.92 (s, 6H), 3.89 (s, 3H), 3.12 (s, 3H). ESIMS (MH⁺): 534. Anal. Calcd. for $C_{22}H_{23}N_5O_5S_3 \cdot 0.9$ TFA: C, 44.92; H, 3.79; N, 11.01; S, 15.12. Found: C, 44.94; H, 3.87; N, 11.12.

EXAMPLE D(4)

{3-[4'-Amino-2'-(3,4,5-trimethoxy-phenylamino)-[2,5']bithiazolyl-4-yl]-phenyl}-carbamic acid phenyl ester

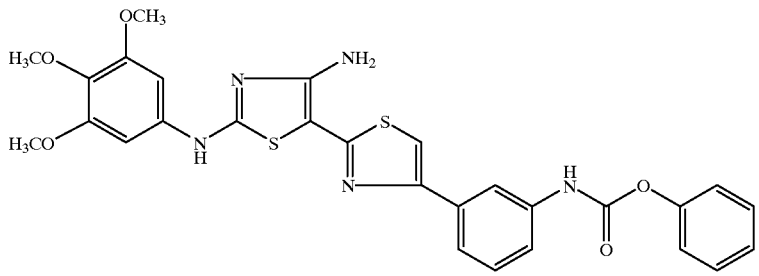

¹H NMR (CDCl₃): δ 8.04 (s, 1H), 7.64 (t, J=7.2 Hz, 1H), 7.46–7.38 (m, 5H), 7.28–7.18 (m, 4H), 7.14 (s, 1H), 7.05 (s, 1H), 6.64 (s, 2H), 6.09 (bs, 1H), 3.91 (s, 6H), 3.87 (s, 3H). ESIMS (MH⁺): 576. Anal. Calcd. for $C_{28}H_{25}N_5O_5S_2 \cdot 0.3$ DMF: C, 58.08; H, 4.57; N, 12.42; S, 10.73. Found: C, 58.33; H, 4.39; N, 11.53; S, 10.68.

EXAMPLE D(5)

N-{3-[4'-Amino-2'-(3,4,5-trimethoxy-phenylamino)-[2,5']bithiazolyl-4-yl]-phenyl}-2-phenyl-acetamide

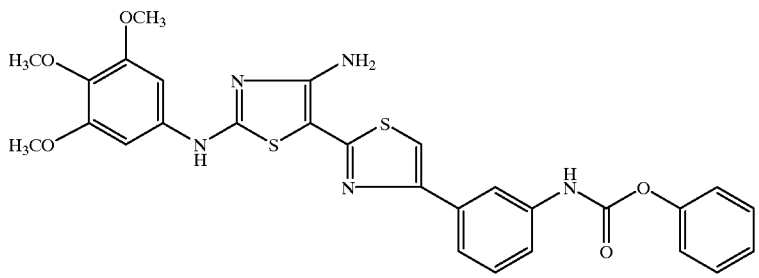

¹H NMR (CDCl₃): δ 7.89 (s, 1H), 7.64 (d, J=7.4 Hz, 1H), 7.47–7.32 (m, 7H), 7.14 (s, 1H), 7.10 (s, 1H), 6.64 (s, 2H), 6.06 (bs, 2H), 3.91 (s, 6H), 3.87 (s, 3H), 3.79 (s, 2H). ESIMS (MH⁺): 574. Anal. Calcd. for $C_{29}H_{27}N_5O_4S_2$: C, 60.71; H, 4.74; N, 12.21; S, 11.18. Found: C, 60.88; H, 4.78; N, 12.00; S, 11.14.

EXAMPLE D(6)

{3-[4'-Amino-2'-(3,4,5-trimethoxy-phenylamino)-[2,5']bithiazolyl-4-yl]-phenyl}-carbamic acid methyl ester

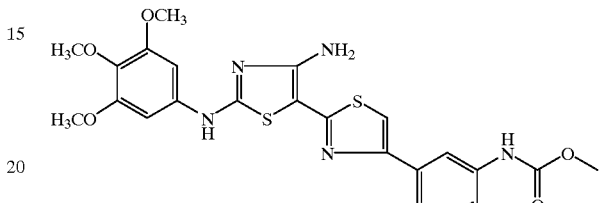

¹H NMR (CDCl₃): δ 8.14 (s, 1H), 7.82 (d, J=6.9 Hz, 1H), 7.59 (m, 3H), 7.34 (s, 1H), 6.90 (s, 1H), 6.85 (s, 2H), 6.40–6.20 (bs, 1H), 4.12 (s, 6H), 3.78 (s, 3H), 2.14 (s, 3H). ESIMS (MH): 514. Anal. Calcd. for $C_{23}H_{23}N_5O_5S_2 \cdot 0.305 H_2O$: C, 53.13; H, 4.60; N, 13.47; S, 12.34. Found: C, 53.10; H, 4.58; N, 13.34; S, 12.11.

EXAMPLE D(7)

1-{3-[4'-Amino-2'-(3,4,5-trimethoxy-phenylamino)-[2,5']bithiazolyl-4-yl]-phenyl}-3-methyl-urea

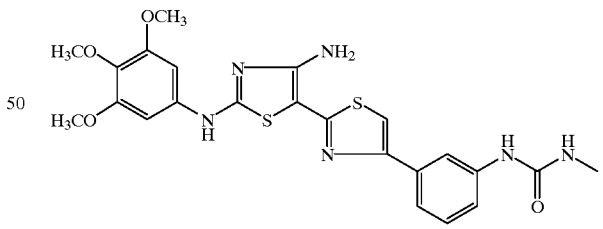

¹H NMR (CDCl₃): δ 8.63 (bs, 1H), 7.90 (s, 1H), 7.61 (s, 1H), 7.49 (d, J=8.0 Hz, 1H), 7.39 (d, J=8.2 Hz, 1H), 7.31 (s, 1H), 7.07 (s, 1H), 6.75 (s, 2H), 6.00–6.10 (bs, 1H), 5.35 (bs, 1H), 3.87 (s, 6H), 3.81 (s, 3H), 2.80 (d, J=4.3 Hz, 3H). ESIMS (MH⁺): 513. Anal. Calcd. for $C_{23}H_{24}N_6O_4S_2 \cdot 0.4$ H₂O: C, 53.14; H, 4.81; N, 16.17; S, 12.34. Found: C, 53.15; H, 4.75; N, 16.12; S, 12.46.

EXAMPLE D(8)

N-{3-[4'-Amino-2'-(3,4,5-trimethoxy-phenylamino)-[2,5'] bithiazolyl-4-yl]-phenyl}-propionamide

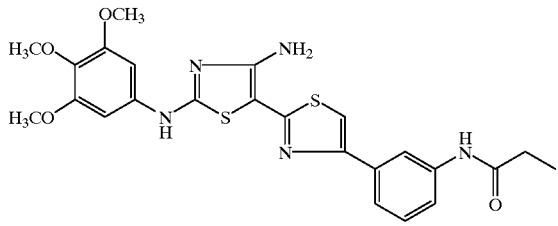

¹H NMR (CDCl₃): δ 8.27 (s, 1H), 7.85 (d, J=7.5 Hz, 1H), 7.74 (d, J=8.0 Hz, 1H), 7.59 (t, J=7.9 Hz, 1H), 7.41 (s, 1H), 7.33 (s, 1H), 6.84 (s, 2H), 6.20–6.35 (bs, 1H), 4.11 (s, 6H), 4.07 (s, 3H), 2.64 (q, J=7.6 Hz, 2H), 1.50 (t, J=7.5 Hz, 3H). ESIMS (MH): 512. Anal. Calcd. for $C_{24}H_{25}N_5O_4S_2$: C, 56.34; H, 4.93; N, 13.69; S, 12.54. Found: C, 56.22; H, 5.01; N, 13.48; S, 12.73.

EXAMPLE D(9)

N-{3-[4'-Amino-2'-(3,4,5-trimethoxy-phenylamino)-[2,5'] bithiazolyl-4-yl]-phenyl}-isobutyramide

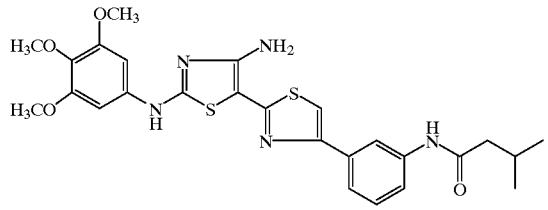

¹H NMR (CDCl₃): δ 9.16 (s, 1H), 8.54 (s, 1H), 8.06 (s, 1H), 7.57 (d, J=8.1 Hz, 1H), 7.53 (d, J=7.8 Hz, 1H), 7.27 (t, J=8.0 Hz, 1H), 7.03 (s, 1H), 6.77 (s, 2H), 6.00–6.20 (bs, 1H), 3.81 (s, 6H), 3.75 (s, 3H), 2.18 (m, 3H), 0.95 (d, J=6.3 Hz, 6H).

ESIMS (MH⁺): 540. Anal. Calcd. for $C_{26}H_{29}N_5O_4S_2 \cdot 0.5$ H₂O: C, 56.91; H, 5.51; N, 12.76; S, 11.69. Found: C, 57.33; H, 5.57; N, 12.28; S, 11.64.

EXAMPLE D(10)

{3-[4'-Amino-2'-(3,4,5-trimethoxy-phenylamino)-[2,5'] bithiazolyl-4-yl]-phenyl}-carbamic acid isopropyl ester

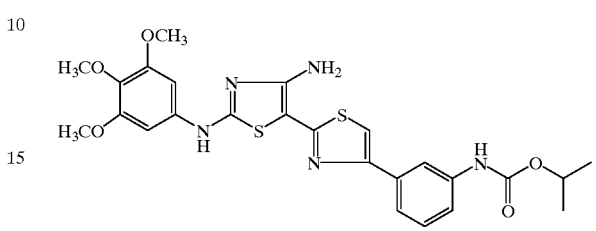

¹H NMR (CDCl₃): δ 7.93 (s, 1H), 7.60 (d, J=6.9 Hz, 1H), 7.40 (m, 3H), 7.13 (s, 1H), 6.65 (s, 2H), 6.62 (s, 1H), 6.08 (bs, 2H), 5.06 (m, J=6.4 Hz, 1H), 3.92 (s, 6H), 3.87 (s, 3H), 1.33 (d, J=6.4 Hz, 6H). ESIMS (MH⁺): 542. Anal. Calcd. for $C_{25}H_{27}N_5O_5S_2$: C, 55.44; H, 5.02; N, 12.93; S, 11.84. Found: C, 55.15; H, 5.14; N, 12.46; S, 11.75.

EXAMPLE D(11)

4-Chloro-pyridine-2-carboxylic acid {3-[4'-amino-2'-(3,4,5-trimethoxy-phenylamino)-[2,5']bithiazolyl-4-yl]-phenyl}-amide

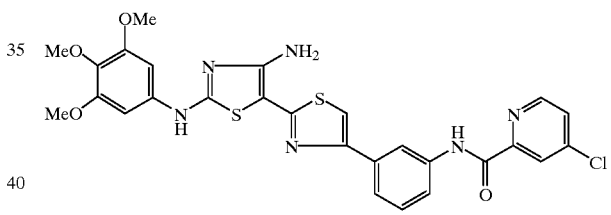

HRFABMS: Calcd. for $C_{27}H_{23}ClN_6O_4S_2$ (MH⁺): 594.0911. Found: 594.0927. Anal. Calcd for $C_{27}H_{23}ClN_6O_4S_2$: C, 54.94; H, 3.90; N, 14.12; S, 10.78. Found: C, 54.43; H, 3.87; N, 14.01; S, 10.92.

EXAMPLE D(12)

{3-[4'-Amino-2'-(3,4,5-trimethoxy-phenylamino)-[2,5'] bithiazolyl-4-yl]-phenyl}-carbamic acid benzyl ester

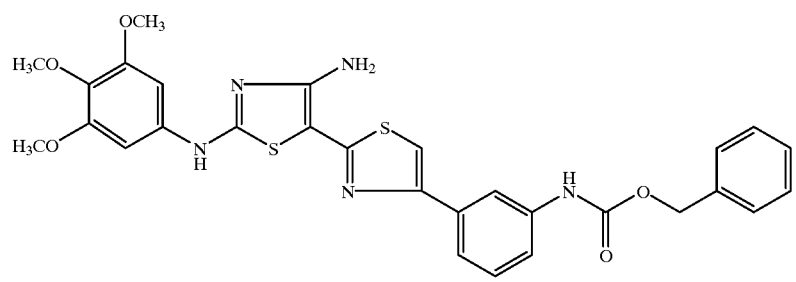

¹H NMR (CDCl₃): δ 7.93 (s, 1H), 7.61 (d, J=7.0 Hz, 1H), 7.40 (m, 7H), 7.12 (s, 1H), 6.76 (s 1H), 6.64 (s, 2H), 6.07 (bs, 2H), 5.25 (s, 2H), 3.91 (s, 6H), 3.87 (s, 3H). ESIMS (MH⁺): 590. Anal. Calcd. for $C_{29}H_{27}N_5O_5S_2$: C, 59.07; H, 4.62; N, 11.88; S, 10.88. Found: C, 58.84; H, 4.64; N, 11.71; S, 11.07.

3.89 (s, 3H), 3.52 (s, 1H). ESIMS (MH⁺): 534. HRMS (FAB), m/z Calcd. for $C_{23}H_{21}F_2N_5O_4S_2$ (M+Cs⁺): 666.0057. Found: 666.0032.

EXAMPLE D(15)

N-{3-[4'-Amino-2'-(3,4,5-trimethoxy-phenylamino)-[2,5'] bithiazolyl-4-yl]-phenyl}-2-phenoxy-acetamide

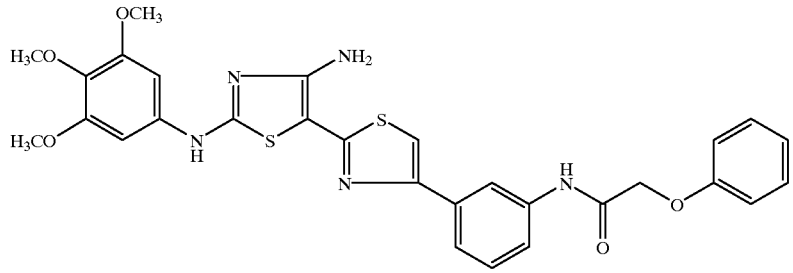

¹H NMR (CDCl₃): δ 8.27 (s, 1H), 8.06 (s, 1H), 7.63 (d, J=7.8 Hz, 1H), 7.51 (d, J=8.0 Hz, 1), 7.32 (m, 4H), 7.07 (s, 1H), 6.56 (s, 2H), 6.01 (bs, 2H), 4.58 (s, 2), 3.82 (s, 6H), 3.78 (s, 3H). ESIMS (MH⁺): 590. Anal. Calcd. for $C_{29}H_{27}N_5O_5S_2$.(0.7 H₂O, 0.2 EtOAc): C, 57.73; H, 4.88; N, 11.30; S, 15.74. Found: C, 57.97; H, 4.59; N, 11.08; S, 10.33.

EXAMPLE D(13)

N-{³-[4'-Amino-2'-(3,4,5-trimethoxy-phenylamino)-[2,5'] bithiazolyl-4-yl]-phenyl}-2,2,2-trifluoro-acetamide

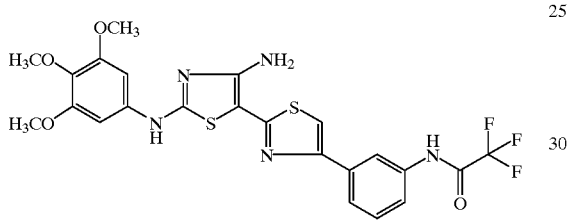

¹H NMR (CDCl₃): δ 8.14 (s, 1H), 7.96 (bs, 1H), 7.79 (d, J=6.4 Hz, 1H), 7.48 (d, J=8.0 Hz, 1H), 7.17 (s, 1H), 6.65 (s, 2H), 6.05 (bs, 2H), 3.92 (s, 6H), 3.87 (s, 3H). ESIMS (MH⁺): 552. HRMS (FAB), m/z Calcd. for $C_{23}H_{20}F_3N_5O_4S_2$ (MH⁺): 552.0987. Found: 552.0981.

EXAMPLE D(16)

N-{3-[4'-Amino-2'-(3,4,5-trimethoxy-phenylamino)-[2,5'] bithiazolyl-4-yl]-phenyl}-3-phenyl-propionamide

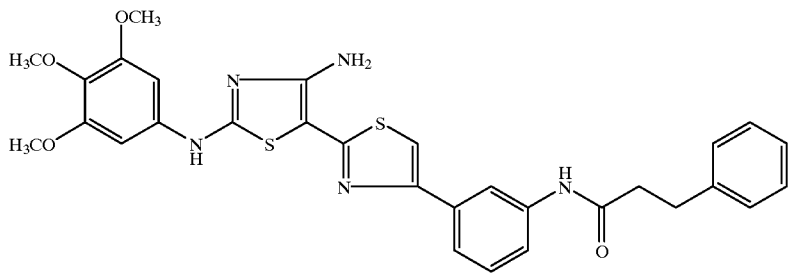

EXAMPLE D(14)

N-{3-[4'-Amino-2'-(3,4,5-trimethoxy-phenylamino)-[2,5'] bithiazolyl-4-yl]-phenyl}-2,2-difluoro-acetamide

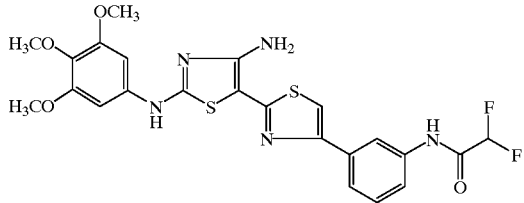

¹H NMR (CDCl₃): δ 8.15 (s, 1H), 7.98 (bs, 1H), 7.75 (d, J=7.5 Hz, 1H), 7.61 (d, J=8.1 Hz, 1H), 7.46 (t, J=8.0 Hz, 1H), 7.17 (s, 1H), 6.66 (s, 2H), 6.08 (bs, 2H), 3.93 (s, 6H),

¹H NMR (CDCl₃): δ 7.97 (s, 1H), 7.63 (d, J=8.0 Hz, 1H), 7.46 (d, J=7.9 Hz, 1H), 7.40 (m, 3H), 7.12 (s, 1H), 7.06 (s, 1H), 6.64 (s, 2H), 6.07 (bs, 1H), 3.91 (s, 6H), 3.87 (s, 3H), 3.11 (t, J=7.5 Hz, 2H), 2.72 (t, J=7.5 Hz, 2H). ESIMS (MH⁺): 588. Anal. Calcd. for $C_{30}H_{29}N_5O_5S_2$: C, 61.31; H, 4.97; N, 11.92; S, 10.91. Found: C, 60.67; H, 5.09; N, 11.77; S, 10.69.

EXAMPLE D(17)
{3-[4'-Amino-2'-(2,4-dimethoxy-phenylamino)-[2,5']bithiazolyl-4-yl]-phenyl}-carbamic acid benzyl ester $^1$H NMR (CDCl$_3$): δ 7.65 (s, 1H), 7.48 (d, J=9.4 Hz, 1H), 7.37 (d, J=7.3 Hz, 1H), 7.16 (m, 7H), 6.85 (s, 1H), 6.54 (s, 1H), 6.31 (m, 3H), 6.00–5.70 (bs, 2H), 5.00 (s, 2H), 3.65 (s, 3H), 3.60 (s, 3H). ESIMS (MH$^+$): 560. Anal. Calcd. for C$_{28}$H$_{25}$N$_5$O$_4$S$_2$.0.7 H$_2$O: C, 59.14; H, 4.61; N, 12.32; S, 11.28. Found: C, 59.51; H, 4.41; N, 11.82; S, 10.90.

EXAMPLE D(18)
{3-[4'-Amino-2'-(2,5-dimethoxy-phenylamino)-[2,5']bithiazolyl-4-yl]-phenyl}-carbamic acid benzyl ester $^1$H NMR (CDCl$_3$): δ 7.91 (s, 1H), 7.65 (d, J=9.4 Hz, 1H), 7.37 (d, J=7.3 Hz, 1H), 7.16 (m, 7H), 6.85 (s, 1H), 6.54 (s, 1H), 6.31 (m, 3H), 6.00–5.70 (bs, 2H), 5.00 (s, 2H), 3.65 (s, 6H), 3.60 (s, 3H). ESIMS (MH$^+$): 560. Anal. Calcd. for C$_{28}$H$_{25}$N$_5$O$_4$S$_2$: C, 60.09; H, 4.50; N, 12.51; S, 11.46. Found: C, 60.52; H, 4.64; N, 12.00; S, 10.96.

EXAMPLE D(19)
{3-[4'-Amino-2'-(4-phenoxy-phenylamino)-[2,5']bithiazolyl-4-yl]-phenyl}-carbamic acid benzyl ester $^1$H NMR (CDCl$_3$): δ 7.90 (s, 1H), 7.61 (d, J=7.4 Hz, 1W, 7.46 (m, 10H), 7.11 (m, 8H), 6.81 (s, 1H), 6.08 (bs, 2H), 5.25 (s, 2H). ESIMS (MH$^+$): 592. Anal. Calcd. for C$_{32}$H$_{25}$N$_5$O$_3$S$_2$: C, 64.96; H, 4.26; N, 11.84; S, 10.84. Found: C, 64.68; H, 4.36; N, 11.58; S, 10.65.

EXAMPLE D(20)
[3-(4'-Amino-2'-phenylamino-[2,5']bithiazolyl-4-yl)-phenyl]-carbamic acid benzyl ester $^1$H NMR (CDCl$_3$): δ 7.81 (s, 1H), 7.55 (d, J=7.3 Hz, 1H), 7.30 (m, 12H), 7.10 (m, 1H), 7.02 (s, 1H), 6.68 (s, 1H), 6.10–5.90 (bs, 2H), 5.15 (s, 2H). ESIMS (MH$^+$): 500. HRMS (FAB), m/z Calcd. for C$_{26}$H$_{21}$N$_5$O$_2$S$_2$ (MH$^+$): 500.1215. Found: 500.1232.

EXAMPLE D(21)
Benzofuran-2-carboxylic acid {3-[4'-amino-2'-(3,4,5-trimethoxy-phenylamino)-[2,5']bithiazolyl-4-yl]-phenyl}-amide ESMS (MH$^+$): 600. Anal. Calcd for C$_{30}$H$_{25}$N$_5$O$_5$S$_2$.0.75 H$_2$O: C, 58.76; H, 4.36; N, 11.42; S, 10.46. Found: C, 58.74; H, 4.08; N, 11.46; S, 10.41.

EXAMPLE D(22)

{3-[4'-Amino-2'-(3,4,5-trimethoxy-phenylamino)-[2,5']bi-thiazolyl-4-yl]-phenyl}-carbamic acid naphthalen-1-yl ester

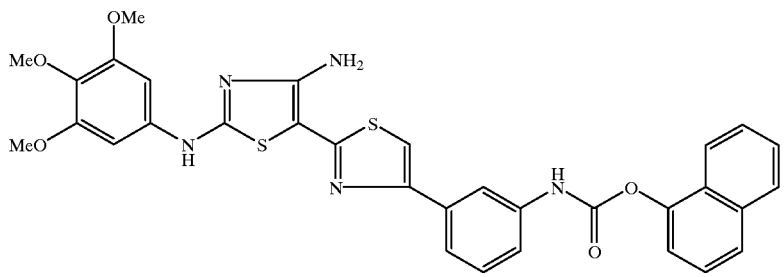

ESMS (MH$^+$): 626. Anal. Calcd for $C_{32}H_{27}N_5O_5S_2 \cdot 0.7$ H$_2$O: C, 60.21; H, 4.48; N, 10.97; S, 10.05. Found: C, 60.24; H, 4.31; N, 10.72; S, 10.03.

EXAMPLE D(23)

{3-[4'-Amino-2'-(3,4,5-trimethoxy-phenylamino)-[2,5'] bithiazolyl-4-yl]-phenyl}-carbamic acid 1-R-phenyl-ethyl ester

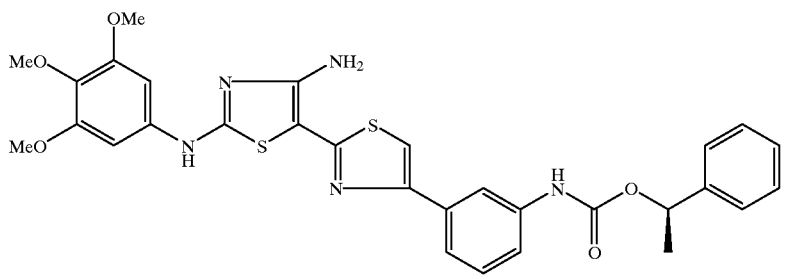

ESMS (MH$^+$): 604. Anal. Calcd for $C_{30}H_{29}N_5O_5S_2 \cdot 0.4$ H$_2$O: C, 58.98; H, 4.92; N, 11.46; S, 10.50. Found: C, 58.93; H, 4.90; N, 11.41; S, 10.27.

EXAMPLE D(24)

N-{3-[4'-Amino-2'-(3,4,5-trimethoxy-phenylamino)-[2,5'] bithiazolyl-4-yl]-phenyl}-benzamide

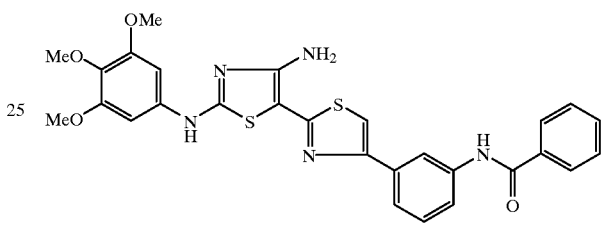

ESMS (MH$^+$): 560. Anal. Calcd for $C_{28}H_{25}N_5O_4S_2$: C, 60.09; H, 4.50; N, 12.51; S, 11.46. Found: C, 60.07; H, 4.54; N, 12.45; S, 11.42.

EXAMPLE D(25)

{3-[4'-Amino-2'-(4-sulfamoyl-phenylamino)-[2,5'] bithiazolyl-4-yl]-phenyl}-carbamic acid benzyl ester

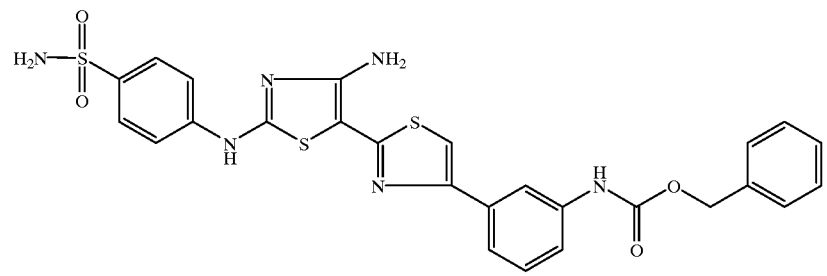

ESMS (MH$^+$): 579.

EXAMPLE D(26)

4-{3-4'-Amino-2'-(3,4,5-trimethoxy-phenylamino)-[2,5']bithiazolyl-4-yl]-phenylcarbamoyloxymethyl}-benzoic acid methyl ester

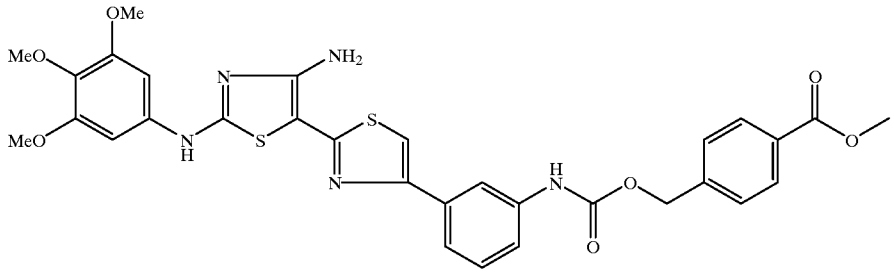

ESMS (MH+): 648. Anal. Calcd for $C_{31}H_{29}N_5O_7S_2$: C, 57.48; H, 4.51; N, 10.81; S, 9.90. Found: C, 57.66; H, 4.52; N, 10.64; S, 10.08.

EXAMPLE D(27)

N-{3-[4'-Amino-2'-(3,4,5-trimethoxy-phenylamino)-[2,5']bithiazolyl-4-yl]-phenyl}-3-isopropyl-benzamide

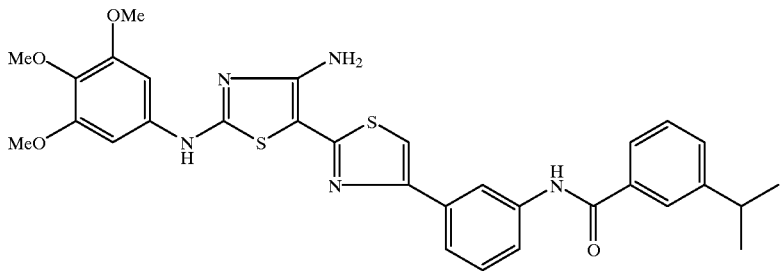

ESMS (MH+): 602. Anal. Calcd for $C_{31}H_{31}N_5O_4S_2$: C, 61.88; H, 5.19; N, 11.64; S, 10.66. Found: C, 61.45; H, 5.38; N, 11.30; S, 10.38.

EXAMPLE D(28)

N-{3-[4'-Amino-2'-(3,4,5-trimethoxy-phenylamino)-[2,5']bithiazolyl-4-yl]-phenyl}-4-fluoro-benzamide

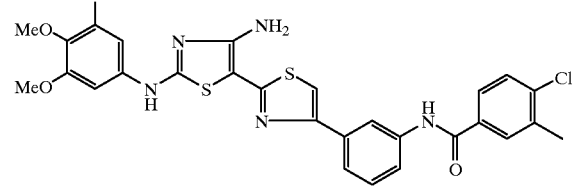

ESMS (MH+): 578. Anal. Calcd for $C_{28}H_{24}N_5O_4S_2$·0.3 $H_2O$: C, 57.68; H, 4.25; N, 12.01; S, 11.00. Found: C, 57.64; H, 4.32; N, 11.79; S, 10.97.

EXAMPLE D(29)

N-{3-[4'-Amino-2'-(3,4,5-trimethoxy-phenylamino)-[2,5']bithiazolyl-4-yl]-phenyl}-3-bromo-benzamide

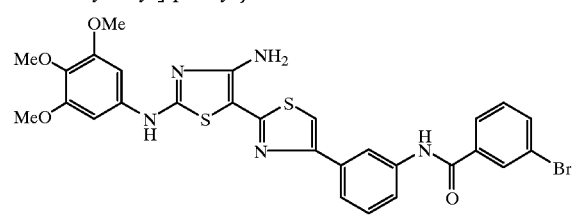

ESMS (MH+): 638/640. Anal. Calcd for $C_{28}H_{24}BrN_5O_4S_2$: C, 52.67; H, 3.79; N, 10.97; S, 10.04. Found: C, 52.49; H, 3.99; N, 10.36; S, 9.71.

EXAMPLE D(30)

N-{3-[4'-Amino-2'-(3,4,5-trimethoxy-phenylamino)-[2,5']bithiazolyl-4-yl]-phenyl}-4-chloro-3-methyl-benzamide

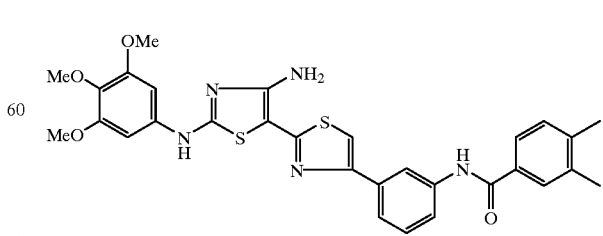

ESMS (MH+): 608/610. Anal. Calcd for $C_{29}H_{26}ClN_5O_4S_2$·0.6 $H_2O$: C, 56.27; H, 4.43; N, 11.32; S, 10.36. Found: C, 56.36; H, 4.38; N, 11.14; S, 10.14.

EXAMPLE D(31)

N-{3-[4'-Amino-2'-(3,4,5-trimethoxy-phenylamino)-[2,5']bithiazolyl-4-yl]-phenyl}-3,4-dimethyl-benzamide

ESMS (MH+): 588.

EXAMPLE D(32)
N-{3-[4'-Amino-2'-(3,4,5-trimethoxy-phenylamino)-[2,5']bithiazolyl-4-yl]-phenyl}-3-methoxy-4-methyl-benzamide

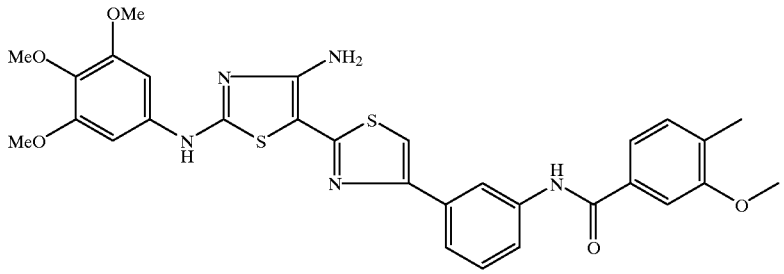

ESMS (MH+): 604. Anal. Calcd for $C_{30}H_{29}N_5O_5S_2.0.6$ $H_2O$: C, 58.52; H, 5.07; N, 11.08; S, 10.14. Found: C, 58.48; H, 5.03; N, 10.75; S, 9.95.

EXAMPLE D(33)
2,4-Dimethyl-thiazole-5-carboxylic acid {3-[4'-amino-2'-(3,4,5-trimethoxy-phenylamino)-[2,5']bithiazolyl-4-yl]-phenyl}-amide

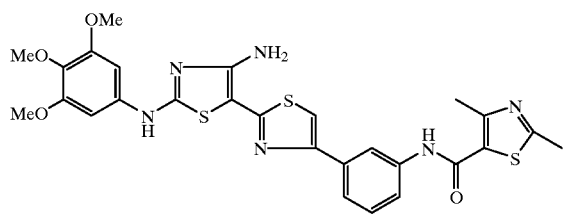

ESMS (MH): 595. Anal. Calcd for $C_{27}H_{26}N_6O_4S_3.0.2$ $H_2O$: C, 54.22; H, 4.77; N, 13.08; S, 14.97. Found: C, 54.59; H, 4.89; N, 12.61; S, 14.73.

EXAMPLE D(34)
5-Methyl-thiophene-2-carboxylic acid {3-[4'-amino-2'-(3,4,5-trimethoxy-phenylamino)-[2,5']bithiazolyl-4-yl]-phenyl}-amide ESMS (MH+): 580. Anal. Calcd for $C_{27}H_{25}N_5O_4S_3$: C, 55.94; H, 4.35; N, 12.08; S, 16.59. Found: C, 55.78; H, 4.26; N, 11.80; S, 16.58.

EXAMPLE D(35)
5-Chloro-thiophene-2-carboxylic acid {3-[4'-amino-2'-(3,4,5-trimethoxy-phenylamino)-[2,5']bithiazolyl-4-yl]-phenyl}-amide

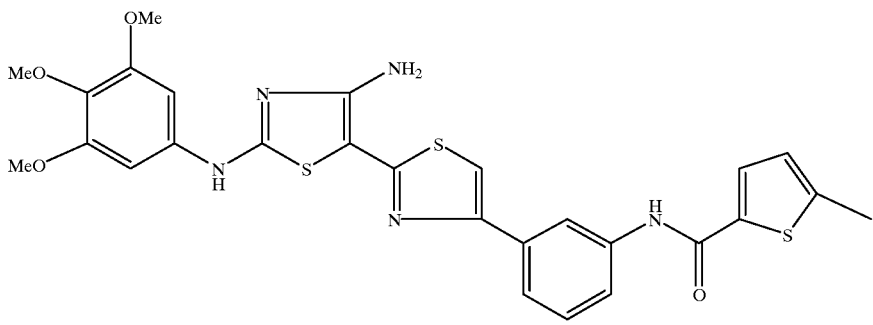

ESMS (MH+): 600/602. Anal. Calcd for $C_{26}H_{22}ClN_5O_4S_3$: C, 52.03; H, 3.69; N, 11.67; S, 16.03. Found: C, 51.61; H, 3.82; N, 11.46; S, 16.01.

EXAMPLE D(36)

5-Bromo-thiophene-2-carboxylic acid {3-[4'-amino-2'-(3,4,5-trimethoxy-phenylamino)-[2,5']bithiazolyl-4-yl]-phenyl}-amide

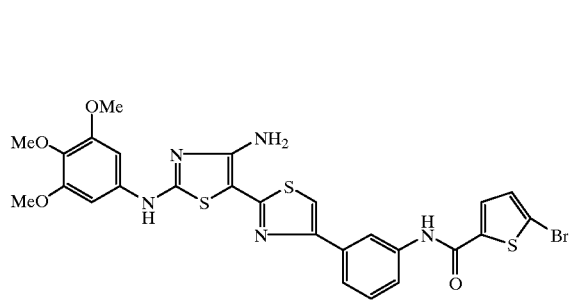

ESMS (MH$^+$): 644/646. Anal. Calcd for $C_{26}H_{22}BrN_5O_4S_3$.0.8 H$_2$O: C, 47.39; H, 3.61; N, 10.63; S, 14.60. Found: C, 47:31; H, 3.51; N, 10.57; S, 14.70.

EXAMPLE D(37)

5-Bromo-furan-2-carboxylic acid {3-[4'-amino-2'-(3,4,5-trimethoxy-phenylamino)-[2,5']bithiazolyl-4-yl]-phenyl}-amide

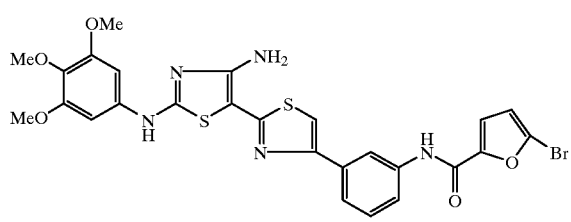

ESMS (MH$^+$): 628/630. Anal. Calcd for $C_{26}H_{22}BrN_5O_5S_2$.0.5 H$_2$O: C, 48.98; H, 3.64; N, 10.99; S, 10.06. Found: C, 48.98; H, 3.43; N, 10.79; S, 9.80.

EXAMPLE D(38)

N-{3-[4'-Amino-2'-(3,4,5-trimethoxy-phenylamino)-[2,5']bithiazolyl-4-yl]-phenyl}-3-methyl-benzamide

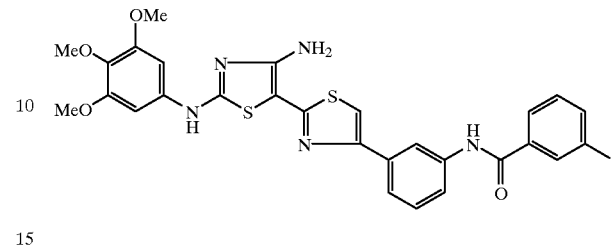

ESMS (MH$^+$): 574. Anal. Calcd for $C_{29}H_{27}N_5O_4S_2$.0.5 H$_2$O.0.5 CH$_2$Cl$_2$: C, 56.67; H, 4.68; N, 11.20; S, 10.26. Found: C, 56.76; H, 4.39; N, 11.04; S, 10.12.

EXAMPLE D(39)

N-{3-[4'-Amino-2'-(3,4,5-trimethoxy-phenylamino)-[2,5']bithiazolyl-4-yl]-phenyl}-3-ethyl-benzamide

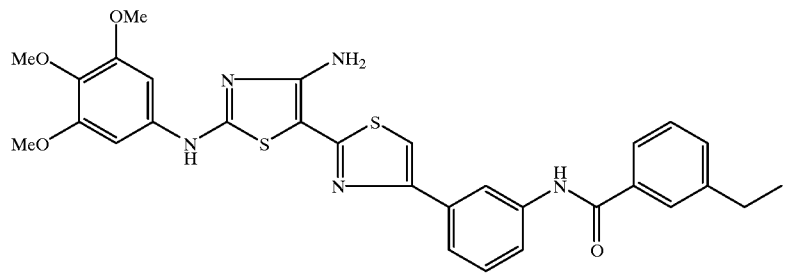

ESMS (MH$^+$): 588. Anal. Calcd for $C_{30}H_{29}N_5O_4S_2$.0.4 H$_2$O: C, 60.56; H, 5.05; N, 11.77; S, 10.78. Found: C, 6063; H, 4.87; N, 11.57; S, 10.65.

EXAMPLE D(40)

N-{3-[4'-Amino-2'-(3,4,5-trimethoxy-phenylamino)-[2,5']bithiazolyl-4-yl]-phenyl}-3-chloro-benzamide

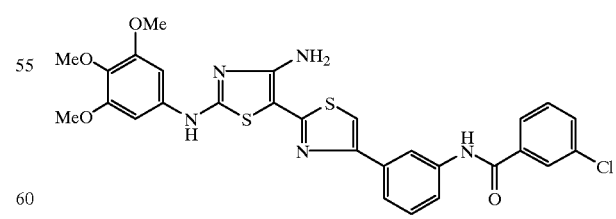

ESMS (MH$^+$): 594/596. Anal. Calcd for $C_{28}H_{24}ClN_5O_4S_2$.0.5 H$_2$O.0.3 CH$_2$Cl$_2$: C, 54.07; H, 4.11; N, 11.14; S, 10.20. Found: C, 54.16; H, 3.88; N, 10.95; S, 10.10.

EXAMPLE D(41)

N-{3-[4'-Amino-2'-(3,4,5-trimethoxy-phenylamino)-[2,5']bithiazolyl-4-yl]-phenyl}-3-methoxy-benzamide

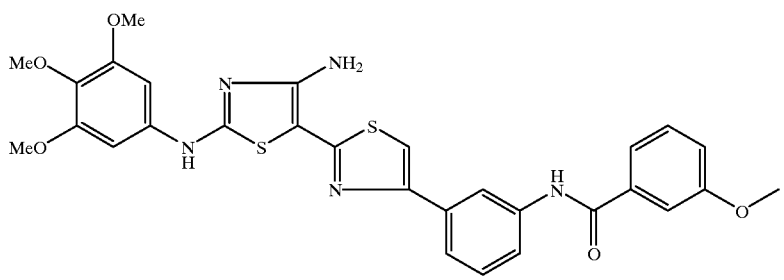

ESMS (MH⁺): 590. Anal. Calcd for $C_{29}H_{27}N_5O_5S_2.0.85$ $H_2O$: C, 57.57; H, 4.78; N, 11.58; S, 10.60. Found: C, 57.62; H, 4.58; N, 11.40; S, 10.53.

EXAMPLE D(42)

5-Methyl-thiazole-2-carboxylic acid {3-[4'-amino-2'-(3,4,5-trimethoxy-phenylamino)-[2,5']bithiazolyl-4-yl]-phenyl}-amide

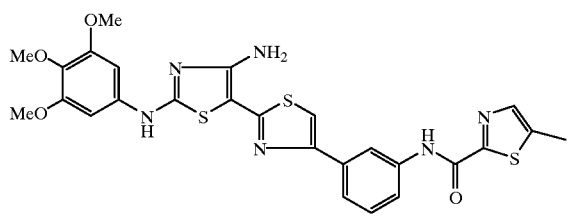

ESMS (MH⁺): 581. Anal. Calcd for $C_{26}H_{24}N_6O_4S_3$: C, 53.78; H, 4.17; N, 14.47; S, 16.57. Found: C, 53.57; H, 4.24; N, 14.23; S, 16.47.

EXAMPLE D(43)

{3-[4'-Amino-2'-(3,4,5-trimethoxy-phenylamino)-[2,5']bithiazolyl-4-yl]-phenyl}-carbamic acid tert-butyl ester

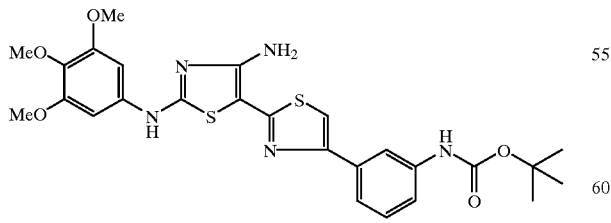

ESMS (MH⁺): 556. Anal. Calcd for $C_{26}H_{29}N_5O_5S_2.0.4$ $H_2O$: C, 55.48; H, 35.34; N, 12.44; S, 11.39. Found: C, 55.33; H, 5.28; N, 12.55; S, 11.12.

EXAMPLE D(44)

3-[3-Benzyloxycarboxy-aminophenyl]-5-[2-[(3,4,5-trimethoxyphenyl)amino]-4-amino-5-thiazolyl]-1,2,4-oxadiazole

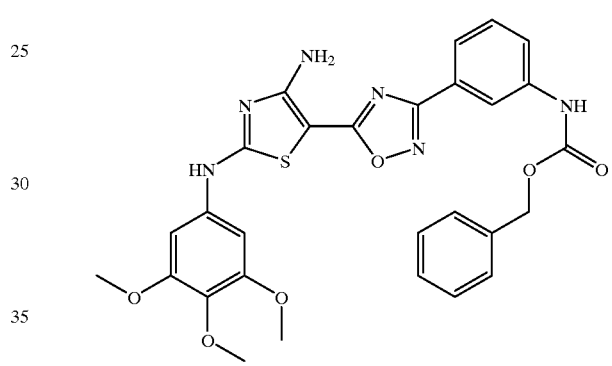

¹H NMR ($d_6$-acetone): δ 3.7 (s, 3H), 3.85 (s, 6H), 5.2 (s, 2H), 6.95 (s br, 2H), 7.05 (s, 2H), 7.4 (m, 6H), 7.8 (d, 2H), 8.35 (s, 1H), 8.95 (s br, 1H), 9.7 (s br, 1H). ESIMS (MH⁺): 575; (M-H⁻): 573.

EXAMPLE D(45)

3-[3-Acetamidophenyl]-5-[2-[(3,4,5-trimethoxyphenyl)amino]-4-amino-5-thiazolyl]-1,2,4-oxadiazole

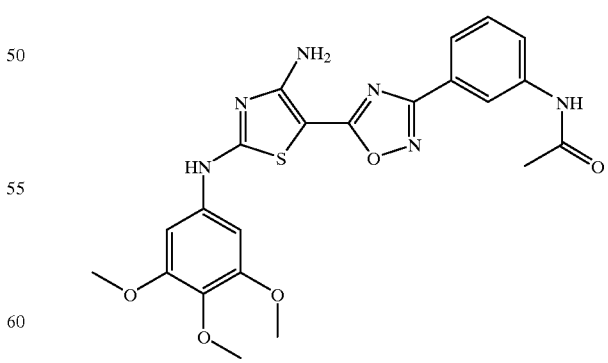

¹H NMR ($d_6$-DMSO): δ 2.0 (s, 3H), 3.6 (s, 3H), 3.75 (s, 6H), 6.95 (s, 2H), 7.25 (s br, 2H), 7.4 (t, 1H), 7.75 (m, 2H), 8.2 (s, 1H), 10.1 (s br, 1H), 10.7 (s br, 1 H). ESIMS (M+Na⁺): 505; (M-H⁻): 481.

EXAMPLE D(46)

3-[3-Benzamidophenyl]-5-[2-[(3,4,5-trimethoxyphenyl)amino]-4-amino-5-thiazolyl]-1,2,4-oxadiazole

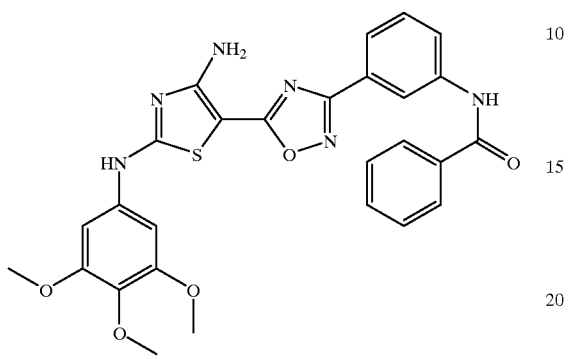

$^1$H NMR (d$_6$-acetone): δ 3.7 (s, 3H), 3.85 (s, 6H), 7.0 (s br, 2H), 7.05 (s, 2H), 7.6 (m, 4H), 7.9 (m, 1H), 8.05 (m, 2H), 8.1 (m, 1H), 8.6 (m br, 1H), 9.75 (s br, 1H). ESIMS (MH$^-$): 545; (M+Na$^+$): 567; (M–H$^-$): 543.

EXAMPLE D(47)

3-[3-(3-Methylbenzamido)phenyl]-5-[2-[(3,4,5-trimethoxyphenyl)amino]-4-amino-5-thiazolyl]-1,2,4-oxadiazole

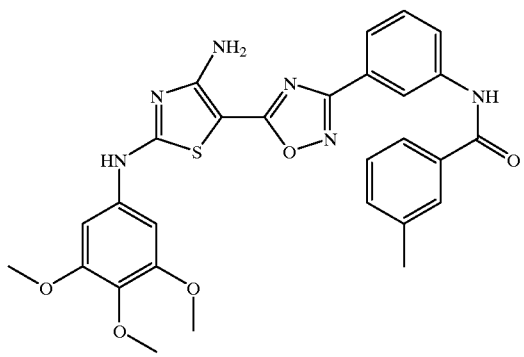

$^1$H NMR (d$_6$-acetone): δ 2.2 (s, 3H), 3.5 (s, 3H), 3.65 (s, 6H), 6.75 (s br, 2H), 6.85 (s, 2H), 7.2 (d, 2H), 7.3 (t, 1H), 7.65 (m, 3H), 7.95 (d, 1H), 8.35 (s br, 1H), 9.5 (s br, 2H). ESIMS (MH$^+$): 559; (M+Na$^-$): 581; (M–H$^-$): 557. Anal. Calcd for C$_{28}$H$_{26}$N$_6$O$_5$S: C, 60.20; H, 4.69; N, 15.04; S, 5.74. Found: C, 60.34; H, 4.82; N, 14.39; S, 5.50.

EXAMPLE D(48)

3-[3-(3-Methoxybenzamido)phenyl]-5-[2-[(3,4,5-trimethoxyphenyl)amino]-4-amino-5-thiazolyl]-1,2,4-oxadiazole

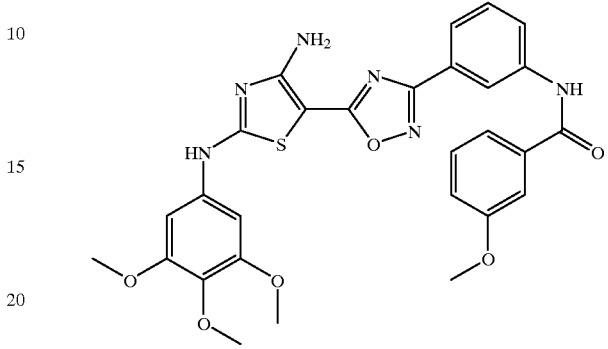

$^1$H NMR (d$_6$-acetone): δ 3.7 (s, 3H), 3.85 (s, 6H), 3.9 (s, 3H), 7.0 (s br, 2H), 7.1 (s, 2H, 7.15 (m, 1H), 7.45 (t, 1H), 7.55 (t, 1H), 7.65 (m, 2H), 7.9 (m, 1H), 8.15 (m, 1H), 8.6 (m, 1H), 9.7 (d br, 2H). ESIMS (MH$^+$): 575; (M+Na$^+$): 597; (M–H$^-$): 573. Anal. Calcd for C$_{28}$H$_{26}$N$_6$O$_6$S: C, 58.53; H, 4.56; N, 14.63; S, 5.58. Found: C, 58.89; H, 4.78; N, 13.88; S, 5.35.

EXAMPLE D(49)

3-[3-(3-Trifluoromethylbenzamido)phenyl]-5-[2-[(3,4,5-trimethoxyphenyl)amino]-4-amino-5-thiazolyl]-1,2,4-oxadiazole

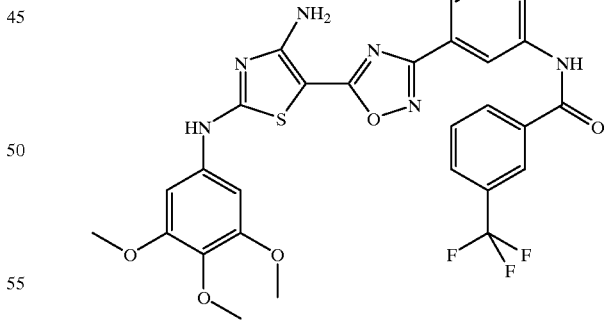

$^1$H NMR (d$_6$-DMSO): δ 3.65 (s, 3H), 3.85 (s, 6H), 7.0 (s, 2H), 7.25 (s br, 2H), 7.55 (t, 1H), 7.8 (m, 2H), 8.0 (d, 1H), 8.1 (d, 1H), 8.32 (d, 1H), 8.35 (d, 1H), 8.45 (s br, 1H), 10.7 (s, 1H), 10.8 (s, 1H). ESIMS (MH$^+$): 613; (M+Na$^+$):; 635; (M–H$^-$): 611. Anal. Calcd for C$_{28}$H$_{23}$F$_3$N$_6$O$_5$S: C, 54.90; H, 3.78; F, 9.30; N, 13.72; S, 5.23. Found: C, 53.55; H, 3.95; N, 12.24; S, 4.67.

EXAMPLE D(50)

3-[3-(3-Chlorobenzamido)phenyl]-5-[2-[(3,4,5-trimethoxyphenyl)amino]-4-amino-5-thiazolyl]-1,2,4-oxadiazole

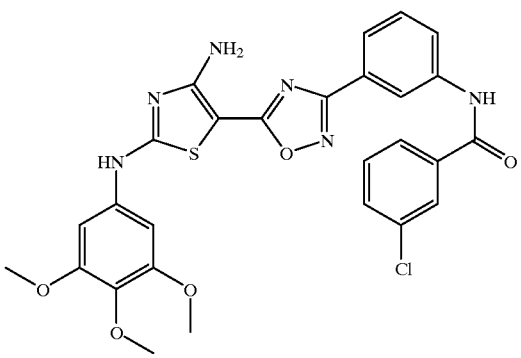

¹H NMR (d₆-acetone): δ 3.6 (s, 3H), 3.75 (s, 6H), 6.85 (s br, 2H), 6.95 (s, 2H), 7.45 (m, 3H), 7.75 (d, 1H), 7.9 (d, 1H), 8.0 (m, 2H), 8.45 (s, 1H), 9.6 (s br, 1H), 9.7 (s br, 1H). ESIMS (MH⁺): 579/581; (M–H⁻): 577/579. Anal. Calcd for C$_{27}$H$_{23}$ClN$_6$O$_5$S: C, 56.01; H, 4.00; Cl, 6.12; N, 14.51; S, 5.54. Found: C, 55.53; H, 4.23; Cl, 6.31; N, 14.00; S, 5.33.

EXAMPLE D(51)

3-[3-(2-Carboxy-5-methylthiazolyl)-aminophenyl]-5-[2-[(3,4,5-trimethoxyphenyl)amino]-4-amino-5-thiazolyl]-1,2,4-oxadiazole

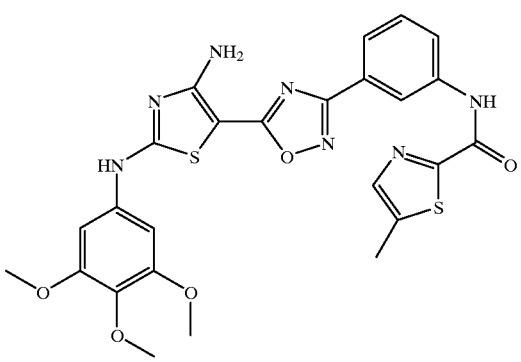

¹H NMR (d₆-DMSO): δ 2.6 (s, 3H), 3.65 (s, 3H), 3.85 (s, 6H), 7.0 (s, 2H), 7.38 (s br, 2H), 7.55 (t, 1H), 7.85 (m, 2H), 8.05 (m, 1H), 8.65 (m, 1H), 10.75 (s, 1H), 10.95 (s, 1H). ESIMS (M+Na⁺): 588; (M–H⁻): 564. Anal. Calcd for C$_{25}$H$_{23}$N$_7$O$_5$S$_2$: C, 53.09; H, 4.10; N, 17.33; S, 11.34. Found: C, 50.46; H, 4.39; N, 16.10; S, 10.47.

EXAMPLE D(52)

3-[3-(3-Chlorobenzamido)phenyl]-5-[2-(3-aminopyridyl)-4-amino-5-thiazolyl]-1,2,4-oxadiazole

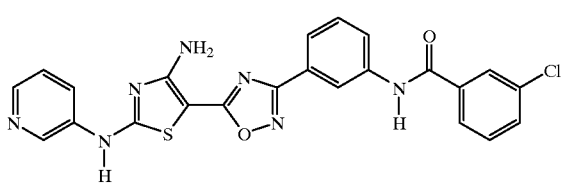

¹H NMR (d₆-DMSO): δ 7.42 (m, 3H), 7.57 (m, 2H), 7.7 (m, 1H), 7.85 (m, 1H), 7.98 (m, 1H), 8.07 (m, 2H), 8.2 (m, 1H), 8.3 (m, 1H), 8.48 (m, 1H), 8.88 (d br, 1H), 10.6 (s br, 1H), 11.1 (s br, 1H). ESIMS (MH⁺): 490/492; (M–H⁻): 577/579. Anal. Calcd for C$_{23}$H$_{16}$ClN$_7$O$_2$S: C, 56.38; H, 3.29; N, 20.01; S, 6.54. Found: C, 53.07; H, 3.41; N, 18.01; S, 5.90.

EXAMPLE D(53)

2-Methyl-thiazole-5-carboxylic acid {3-[4'-amino-2'-(3,4,5-trimethoxy-phenylamino)-[2,5']bithiazolyl-4-yl]-phenyl}-amide

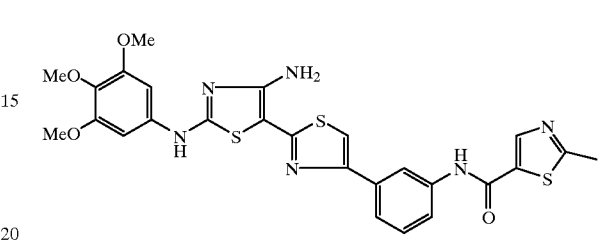

ESMS (MH⁺): 581. Anal. Calcd for C$_{26}$H$_{24}$N$_6$O$_4$S$_3$.0.5 H$_2$O: C, 52.95; H, 4.27; N, 14.25; S, 16.31. Found: C, 52.99; H, 4.27; N, 14.21; S, 16.39.

EXAMPLE D(54)

6-Chloro-pyridine-2-carboxylic acid {3-[4'-amino-2'-(3,4,5-trimethoxy-phenylamino)-[2,5']bithiazolyl-4-yl]-phenyl}-amide

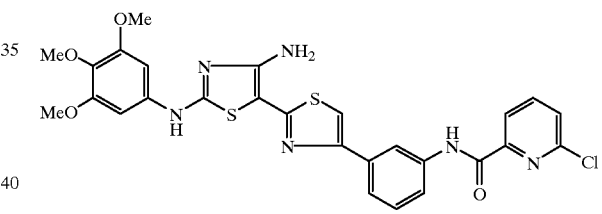

ESMS (MH⁺): 595/597. Anal. Calcd for C$_{27}$H$_{23}$ClN$_6$O$_4$S$_2$.(0.5 H$_2$O, 0.5 CH$_2$Cl$_2$): C, 51.08; H, 3.90; N, 13.00; S, 9.92. Found: C, 51.04; H, 3.65; N, 12.54; S, 9.63.

EXAMPLE D(55)

N-{3-[4'-Amino-2'-(3,4,5-trimethoxy-phenylamino)-[2,5']bithiazolyl-4 yl]-phenyl}-2-chloro-isonicotinamide

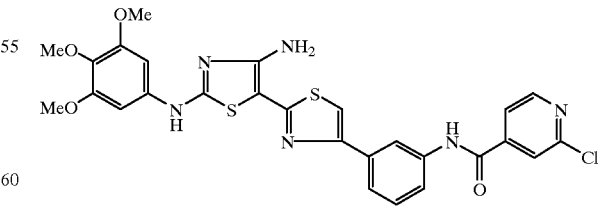

HRFABMS: Calcd. for C$_{27}$H$_{23}$ClN$_6$O$_4$S$_2$ (MNa⁺): 617.0808. Found: 617.0832. Anal. Calcd for C$_{27}$H$_{23}$ClN$_6$O$_4$S$_2$.0.6 H$_2$O: C, 53.52; H, 4.03; N, 13.87; S, 10.58. Found: C, 53.53; H, 3.85; N, 13.39; S, 10.42.

EXAMPLE D(56)

N-(3-{5-[4-Amino-2-(3,4,5-trimethoxy-phenylamino)-thiazol-5-yl]-[1,2,4]oxadiazol-3-yl}-phenyl)-3,5-dimethyl-benzamide trifluoroacetate salt

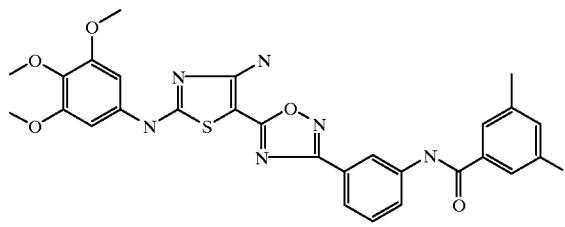

$^1$H NMR (CD$_3$COCD$_3$): δ 9.65 (s, 1H), 8.56 (s, 1H), 8.13 (d, 1H), 7.88 (d, 1H), 7.67 (s, 2H), 7.53 (m, 1H), 7.24 (s, 1H), 7.07 (s, 3H), 3.86 (s, 6H), 3.75 (s, 3H), 2.39 (s, 6H). ESIMS: (MH$^+$): 573; (MNa$^+$): 595; (MH$^-$): 571.

EXAMPLE D(57)

N-(3-{5-[4-Amino-2-(3,4,5-trimethoxy-phenylamino)-thiazol-5-yl]-[1,2,4]oxadiazol-3-yl}-phenyl)-2-methyl-benzamide trifluoroacetate salt

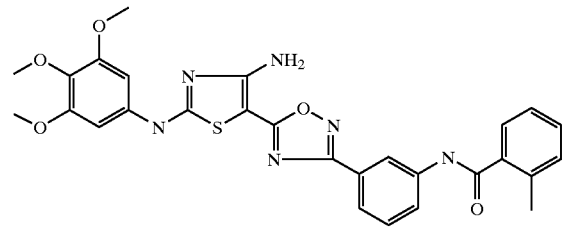

$^1$H NMR (CD$_3$COCD$_3$): δ 9.58 (s, 1H), 8.60 (s, 1H), 8.08 (d, 1H), 7.89 (d, 1H), 7.67 (s, 2H), 7.56 (m, 2H), 7.36 (m, 3H), 7.07 (s, 3H), 3.86 (s, 6H), 3.73 (s, 3H), 2.49 (s, 3H). ESIMS: (MH$^+$): 559; (MNa$^+$): 581; (MH$^-$): 557.

EXAMPLE D(58)

N-{3-[4'-Amino-2'-(3,4,5-trimethoxy-phenylamino)-[2,5']bithiazolyl-4-yl]-phenyl}-4-hydroxy-3,5-dimethyl-benzamide

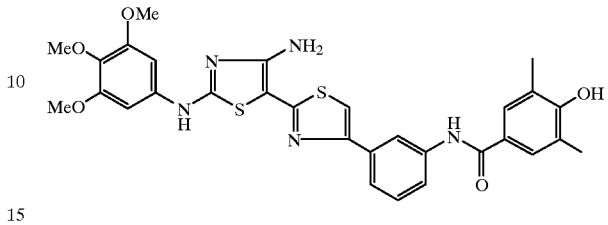

A solution of 4-(3-aminophenyl)-N$^{2'}$-(3,4,5-trimethoxyphenyl)-[2,5']bithiazolyl-2',4'-diamine (100 mg, 0.2195 mmol) from example C(1), 4-hydroxy-3,5-dimethylbenzoic acid (38.3 mg, 0.2305 mmol), triethylamine (64 μL, 0.4609 mmol), and DMF (1.0 mL) were treated with HATU (O-(7-azabenzotriazol-1-yl)-N,N,N',N'-tetramethyluronium hexafluorophosphate) (87.6 mg, 0.2305 mmol), and stirred for 30 minutes at room temperature. The crude product was purified by preparative C-18 reverse phase HPLC (gradient elution, 95% H$_2$O/0.1% TFA/CH$_3$CN to 5% H$_2$O/0.1% TFA/CH$_3$CN), giving 33 mg (25% yield) of title compound as a yellow powder.

Anal. Calcd. for C$_{30}$H$_{29}$N$_5$O$_5$S$_2$.0.5 H$_2$O: C, 58.81; H, 4.94; N, 11.43; S, 14.36. Found: C, 58.81; H, 4.87; N, 11.50; S, 10.50. ESIMS (MNa$^+$): 626.

The following examples D(59) through D(61) were prepared in manner analogous to D(58).

EXAMPLE D(59)

N-{3-[4'-Amino-2'-(3,4,5-trimethoxy-phenylamino)-[2,5']bithiazolyl-4-yl]-phenyl}-2-bicyclo[2.2.1]hept-2-yl-acetamide

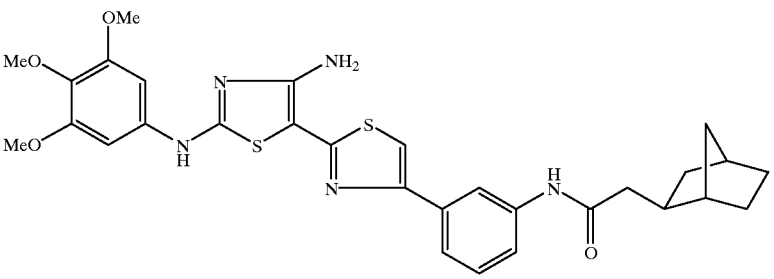

Anal. Calcd. for C$_{30}$H$_{33}$N$_5$O$_4$S$_2$.0.8 H$_2$O: C, 59.44; H, 5.75; N, 11.55; S, 10.58. Found: C, 59.43; H, 5.55; N, 11.40; S, 10.54. ESIMS (MH$^+$): 592.

EXAMPLE D(60)

Quinoline-3-carboxylic acid {3-[4'-amino-2'-(3,4,5-trimethoxy-phenylamino)-[2,5']bithiazolyl-4-yl]-phenyl}-amide

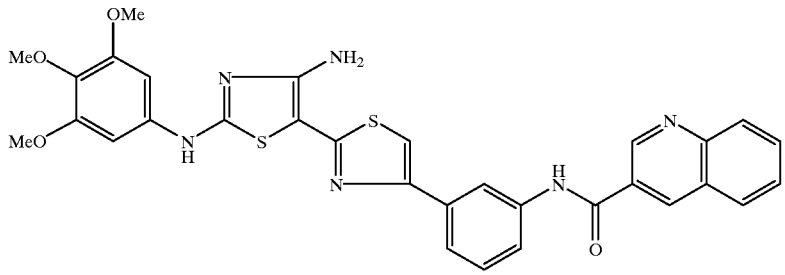

Anal. Calcd. for $C_{31}H_{26}N_6O_4S_2 \cdot 0.3\ H_2O$: C, 60.43; H, 4.35; N, 13.64; S, 10.41. Found: C, 60.49; H, 4.36; N, 13.77; S, 10.40. ESIMS $(MH^+)$: 611.

EXAMPLE D(61)

5-Phenyl-oxazole-4-carboxylic acid {3-[4'-amino-2'-(3,4,5-trimethoxy-phenylamino)-[2,5']bithiazolyl-4-yl]-phenyl}-amide

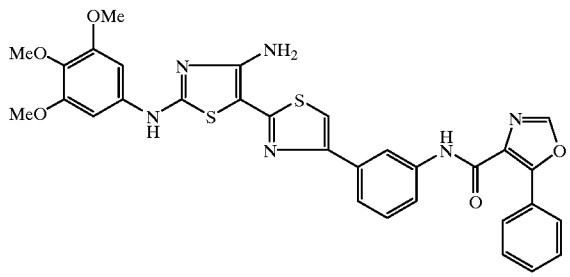

ESIMS $(MH^+)$: 627. In a manner analogous to that described for Example D(1), the following Examples D(62) through D(77) were prepared.

EXAMPLE D(62)

Hex-5-ynoic acid (3-{5-[4-amino-2-(3,4,5-trimethoxy-phenylamino)-thiazol-5-yl]-[1,2,4]oxadiazol-3-yl}-phenyl)-amide

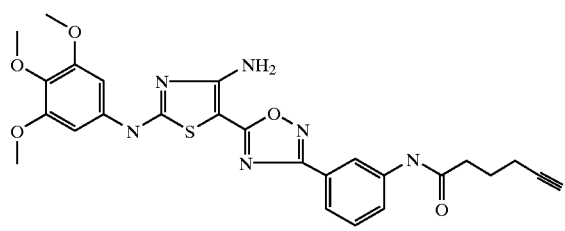

$^1$H-NMR ($d_6$-acetone): δ 9.72 (s, 1H), 9.35 (s, 1H), 8.39 (m, 1H), 7.92 (m, 1H), 7.82 (m, 1H), 7.46 (m, 1H), 7.06 (s, 2H), 6.98 (s, 2H), 3.85 (s, 6H), 3.72 (s, 3H), 2.57 (s, 2H), 2.33 (t, 2H), 1.93 (m, 3H). ESIMS: $(MH)^-$: 535, $(MH)^-$: 533.

EXAMPLE D(63)

N-[3(5-{4-Amino-2-[3-(2H-tetrazol-5-yl)-phenylamino]-thiazol-5-yl]-[1,2,4]oxadiazol-3-yl)-phenyl]-3-chloro-benzamide

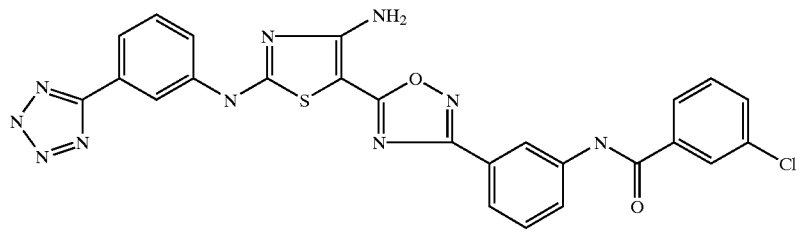

$^1$H-NMR ($d_6$-dmso): δ 11.04 (s, 1H), 10.59 (s, 1H), 8.46 (s, 1H), 8.17 (m, 1H), 8.11 (m, 2H), 7.98 (m, 1H), 7.83 (m, 2H), 7.69 (m, 2H), 7.56 (m, 3H), 7.42 (m, 3H). ESIMS: $(MH)^+$: 557(100%), 559(30%).

EXAMPLE D(64)

N-(3-{5-[4-Amino-2-(3,4,5-trimethoxy-phenylamino)-thiazol-5-yl]-,2,4]oxadiazol-3-yl}-4-chloro-phenyl)-3-chloro-benzamide

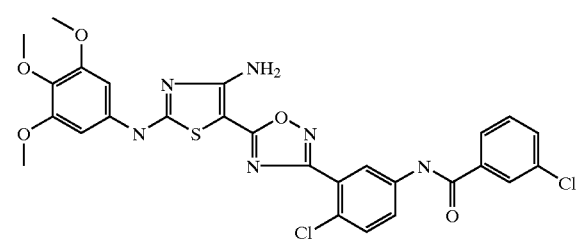

$^1$H-NMR ($d_6$-DMSO): δ 10.79 (s, 1H), 10.66 (s, 1H), 8.39 (m, 1H), 8.06 (m, 3H), 7.68 (m, 1H), 7.65 (m, 2H), 7.33 (s, 2H), 7.02 (s, 2H), 3.81 (s, 6H), 3.65 (s, 3H). ESIMS: $(MH)^+$: 613 (100%), 615 (60%).

EXAMPLE D(65)

N-(3-{5-[4-Amino-2-(3,4,5-trimethoxy-phenylamino)-thiazol-5-yl]-[1,2,4]oxadiazyl}-4-chloro-phenyl)-3-methoxy-benzamide

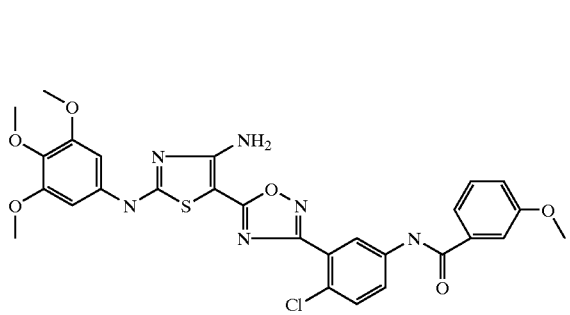

¹H-NMR (d₆-DMSO): δ 10.79 (s, 1H), 10.53 (s, 1H), 8.40 (m, 1H), 8.07 (m, 1H), 7.66 (m, 1H), 7.55 (m, 3H), 7.33 (s, 2H), 7.19 (m, 1H), 6.96 (s, 2H), 3.85 (s, 3H), 3.81 (s, 6H), 3.65 (s, 3H). ESIMS: (MH)⁺: 609 (100%), 611 (30%).

EXAMPLE D(66)

N-(5-{5-[4-Amino-2-(3,4,5-trimethoxy-phenylamino)-thiazol-5-yl]-[1,2,4]oxadiazol-3-yl}-2,4-difluoro-phenyl)-3-chloro-benzamide

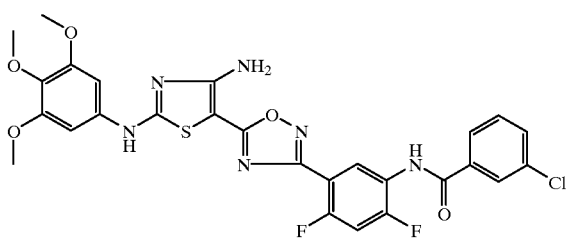

¹H-NMR (d₆ acetone) δ 9.73 (s, 1H), 9.58 (s, 1H), 8.73 (m, 1H), 8.07 (m, 1H), 8.02 (m, 1H), 7.65 (m, 2H), 7.42 (m, 1H), 7.06 (s, 2H), 6.98 (s, 2H), 3.85 (s, 6H), 3.72 (s, 3H). ESIMS: (MH)⁺: 615(100%), 617(30%).

EXAMPLE D(67)

N-(5-{5-[4-Amino-2-(3,4,5-trimethoxy-pheny-1-amino)-thiazol-5-yl]-[1,2,4]oxadiazol-3-yl}-2,4-difluoro-phenyl)-3-methoxy-benzamide

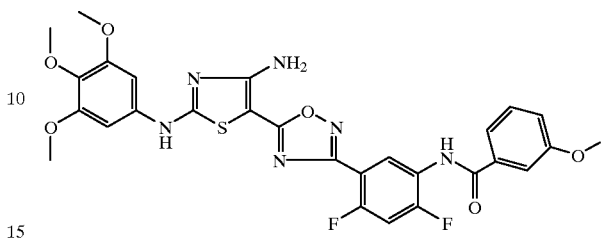

¹H-NMR (d₆ acetone): δ 9.71 (s, 1H), 9.41 (s, 1H), 8.73 (m, 1H), 7.61 (m, 2H), 7.47 (m, 1H), 7.37 (m, 1H), 7.21 (m, 1H), 7.06 (s, 2H), 6.98 {s, 2H), 3.90 (s, 3H), 3.85 (s, 6H), 3.72 (s, 3H). ESIMS: (MH)⁺: 611.

EXAMPLE D(68)

N-(3-{5-[4-Amino-2-(3,4,5-trimethoxy-phenylamino)-thiazol-5-yl]-[1,2,4]oxadiazol-3-yl}-phenyl)-yl}-phenyl)-3-cyano-benzamide

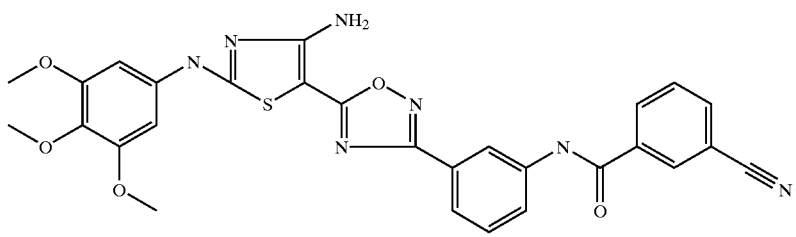

¹H-NMR (d₆-acetone): δ 9.91 (s, 1H), 9.73 (s, 1H), 8.55 (m, 1H), 8.45 (m, 1H), 8.38 (m, 1H), 8.13 (m, 1H), 8.03 (m, 1H), 7.92 (m, 1H), 7.80 (m, 1H), 7.56 (m, 1H), 7.07 (s, 2H), 7.00 (s, 2H), 3.86 (s, 6H), 3.73 (s, 3H). ESIMS: (MH)⁺: 570.

EXAMPLE D(69)

N-(5-{5-[4-Amino-2-(3,4,5-trimethoxy-phenylamino)-thiazol-5-yl]-[1,2,4]oxadiazol-3-yl}-4-chloro-2-fluoro-phenyl)-3-chloro-benzamide

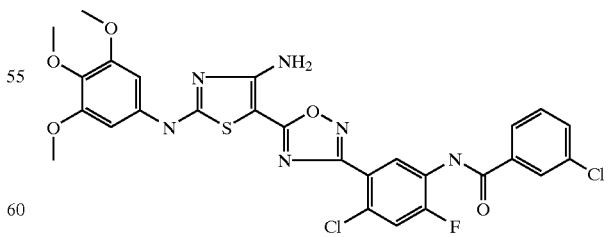

¹H-NMR (d₆-acetone}: δ 9.73 (s, 1H), 9.63 (s, 1H), 8.74 (m, 1H), 8.07 (m, 1H), 8.03 (m, 1H), 7.68 (m, 2H), 7.63 (m, 1H), 7.07 (s, 2H), 6.98 (s, 2H), 3.86 (s, 6H), 3.73 (s, 3H). ESIMS: (MH)⁺: 631(100%), 633(60%), 635(10%).

EXAMPLE D(70)

N-(5-{5-[4-Amino-2-(3,4,5-trimethoxy-phenylamino)-thiazol-5-yl]-[1,2,4]oxadiazol-3-yl}-4-chloro-2-fluoro-phenyl)-3-methoxy-benzamide TFA salt

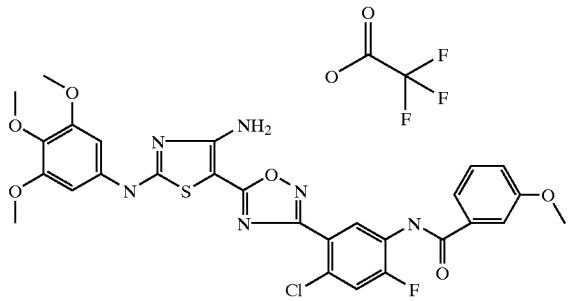

$^1$H-NMR (d$_6$-acetone): δ 9.74 (s, 1H), 9.45 (s, 1H), 8.74 (m, 1H), 7.61 (m, 2H), 1.46 (m, 1H), 7.19 (m, 1H), 7.06 (s, 3H), 6.97 (s, 2H), 3.89 (s, 3H), 3.85 (s, 6H), 3.72 (s, 3H). ESIMS: (MH)$^+$: 627(100%), 629(30%).

EXAMPLE D(71)

N-(3-{5-[4-Amino-2-(3,4,5-trimethoxy-phenylamino)-thiazol-5-yl]-[1,2,4]oxadiazol-3-yl-phenyl)-3-carboxyimido-benzamide

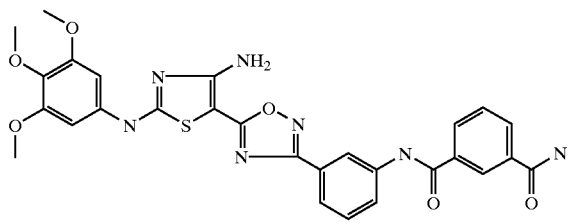

$^1$H-NMR (d$_6$-acetone): δ 9.91 (s, 1H), 9.73 (s, 1H), 8.58 (m, 2H), 8.21 (m, 1H), 8.15 (m, 2H), 7.85 (m, 1H), 7.66 (m, 2H), 7.57 (m, 1H), 7.06 (s, 2H), 7.00 (s, 2H), 3.85 (s, 6H), 3.72 (s, 3H). ESIMS: (MH)$^+$: 588.

EXAMPLE D(72)

Example: 3-[2-fluoro-5-[(3-methoxybenzoyl)amino]-phenyl]-5-[2-[(3,4,5-trimethoxyphenyl)amino]-4-amino-5-thiazolyl]-1,2,4-oxadiazole

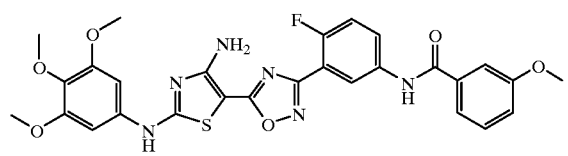

$^1$H NMR (d$_6$-DMSO): δ 3.7 (s, 3H), 3.85 (s, 6H), 3.9 (s, 3H), 7.05 (s, 2H), 7.25 (m, 1H), 7.6 (m, 6H), 8.15 (m, 1H), 8.55 (m, 1H), 10.5 (s, 1H), 10.85 (s, 1H). ESIMS [MH]$^+$: 593. Anal. Calcd: C, 56.75; H, 4.25; F, 3.21, N, 14.18; S, 5.41. Found: C, 56.55; H, 4.48, N, 13.20; S, 5.39.

EXAMPLE D(73)

3-[3-(3-chlorobenzoyl)amino)-6-fluoro-phenyl]-5-[2-[(3,4,5-trimethoxyphenyl)amino]-4-amino-5-thiazolyl]-1,2,4-oxadiazole

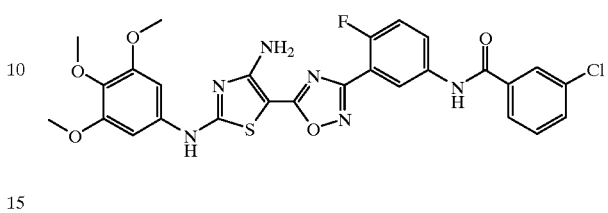

$^1$H NMR (d$_6$-DMSO): δ 3.7 (s, 3H), 3.85 (s, 6H), 6.95 (s, 2H), 7.05 (s, 2H), 7.35 (t, 1H), 7.6 (m, 2H), 8.0 (m, 2H), 8.15 (m, 1H), 8.55 (m, 1H), 9.7 (s br, 1H), 9.85 (s br, 1H). ESIMS [MH]$^-$: 597, 599.

EXAMPLE D(74)

3-[3-[(3-methoxybenzoyl)amino]-6-methyl-phenyl]-5-[2-[(3,4,5-trimethoxyphenyl)amino]-4-amino-5-thiazolyl]-1,2,4-oxadiazole

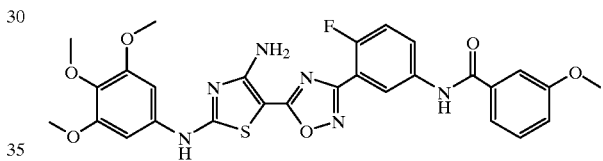

$^1$H NMR (MeOD): δ 2.6 (s, 3H), 3.75 (s, 3H), 3.85 (s, 6H), 3.9 (s, 3H), 7.0 (s, 2H), 7.15 (m, 1H), 7.35 (d, 1H), 7.45 (t, 1H), 7.55 (m, 2H), 7.8 (m, 1H), 8.35 (d, 1H). ESIMS [MH]$^+$: 589. Anal. Calcd. for C29 H28 N6 O6 S: C, 59.17; H, 4.79, N, 14.28; S, 5.45. Found: C, 60.07; H, 5.30, N, 13.69; S, 5.07.

EXAMPLE D(75)

3-[3-[(3-chlorobenzoyl)amino]-6-methyl-phenyl]-5-[2-[(3,4,5-trimethoxyphenyl)amino]-4-amino-5-thiazolyl]-1,2,4-oxadiazole

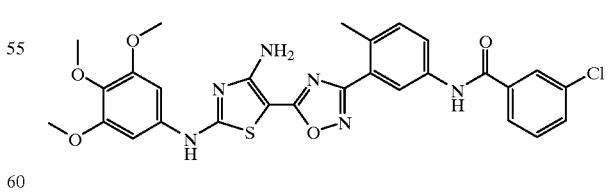

$^1$H NMR (MeOD): δ 2.6 (s, 3H), 3.75 (s, 3H), 3.85 (s, 6H), 7.0 (s, 2H), 7.35 (m, 1H), 7.57 (m, 2H), 7.8 (m, 1H), 7.9 (m, 1H), 8.0 (m, 1H), 8.35 (d, 1H). ESIMS [MH]$^+$: 593, 595. Anal. Calcd. for C28 H25 Cl N6 O5 S: C, 56.71; H, 4.25, N, 14.17; S, 5.41. Found: C, 56.66; H, 4.38, N, 13.54; S, 4.89.

EXAMPLE D(76)

3-[3-[(4-morpholinylmethyl)benzoyl]amino]phenyl]-5-[2-[(3,4,5-trimethoxyphenyl)amino]-4-amino-5-thiazolyl]-1,2,4-oxadiazole

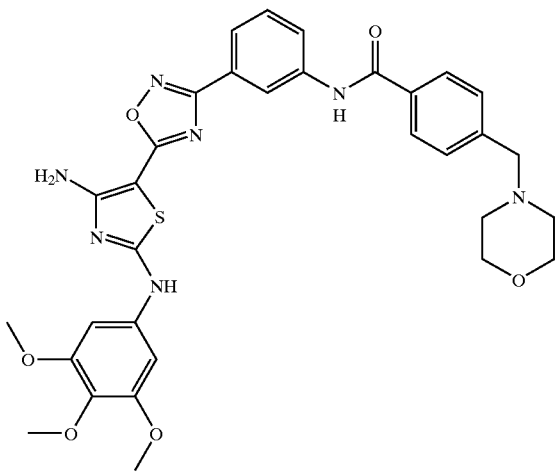

$^1$H NMR (d$_6$-acetone): δ 2.6 (m, 4H), 3.7 (s, 2H), 3.8 (m, 4H), 3.9 (s, 3H), 4.0 (s, 6H), 7.1 (s, 2H), 7.2 (s, 2H), 7.65 (m, 3H), 8.0 (d br, 1H), 8.15 (d, 2H), 8.3 (d br, 1H), 9.8 (s br, 1H), 10.05 (s br, 1H). ESIMS [MH]$^-$: 644.

EXAMPLE D(77)

3-[3-[4-[(4-methyl-1-piperazinyl)methyl]-benzoyl]amino]phenyl]-5-[2-[(3,4,5-trimethoxyphenyl)amino]-4-amino-5-thiazolyl]-1,2,4-oxadiazole

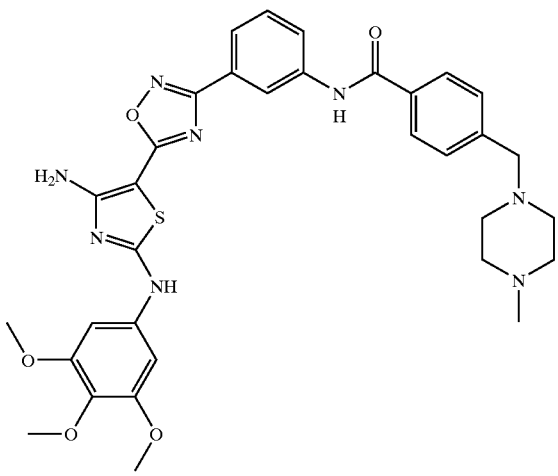

$^1$H NMR (d$_6$-acetone): δ 2.6 (m br, 8H), 3.5 (s br, 2H), 3.6 (s, 3H), 3.7 (s, 6H), 6.8 (s, 2H), 6.9 (s, 2H), 7.4 (m, 3H), 7.75 (m, 1H), 7.9 (d, 2H), 8.0 (m, 1H), 8.4 (m, 1H), 9.55 (s br, 1H), 9.65 (s br, 1H). ESIMS [MH]$^+$: 657.

EXAMPLE D(78)

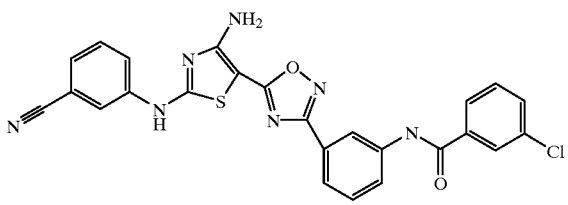

EXAMPLE E(1)
{3-[5-(2,4-Diaminothiazol-5-yl)-[1,2,4]oxadiazol-3-yl]-phenyl}-carbamic acid tert-butyl ester

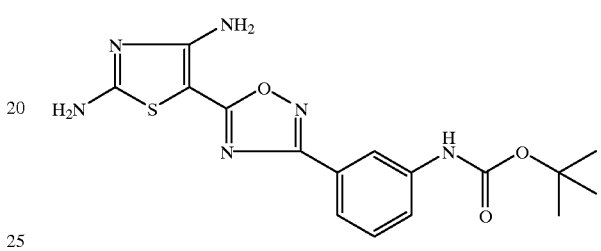

A solution of 1.3 mmol of (3-{5-[4-amino-2-(tritylamino)-thiazol-5-yl]-[1,2,4]oxadiazol-3-yl}-phenyl)-carbamic acid tert-butyl ester, prepared as described in Example B(1), dissolved in 8 ml of 1:1 formic acid/diethyl ether was stirred at room temperature until the starting material had been consumed by TLC (typically 5 h). The resulting light yellow solution was stripped of all solvent in vacuo, heated gently under high vacuum to remove residual formic acid, and then recrystallized from methylene chloride, giving 255 mg of the title compound (53% yield) as a light-yellow powder.
$^1$H NMR (DMSO-d$_6$): δ 9.54 (s, 1H), 8.177 (s, 1H), 8.07 (s, 2H), 7.65–7.59 (m, 3H), 7.39 (t, 1H), 7.12 (bs, 2H), 1.49 (s, 9H). ESMS (MH$^+$): 375. Anal. Calcd for C$_{19}$H$_{15}$ClN$_6$O$_2$S$_3$: C, 46.48; H, 3.08; N, 17.12; S, 19.59. Found: C, 46.47; H, 3.21; N, 17.10; S, 19.43.

EXAMPLE E(2)
N-[3-(2',4'-Diamino-[2,5']bithiazolyl-4-yl)-phenyl]benzamide

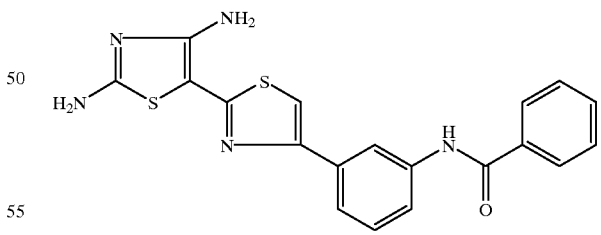

A solution of 4-amino-2-(trityl-amino)-thiazole-5-carbothioic acid amide (304 mg, 0.73 mmol) and N-(3-Bromoacetyl-phenyl)-benzamide (300 mg, 0.94 mmol) in MeOH (30 ml) was stirred at room temperature overnight. The solvent was removed in vacuo and the residue was dissolved in EtOAc (100 ml). The EtOAc solution was washed with a saturated aqueous solution of NaHCO3 (3×25 ml). The organic layer was separated, dried over MgSO4, and concentrated. Purification of the residue was achieved by silica gel chromatography (75% EtOAc/DCM) providing N-[3-(2',4'-diamino-[2,5']bithiazolyl-4-yl)-phenyl]-benzamide (110 mg, 39% yield). mp 159–163° C. (decomp). $^1$H NMR (CD$_3$OD): δ 8.33 (s, 1H), 8.00–7.97 (m, 2H), 7.75–7.71 (m, 2H), 7.64–7.52 (m, 3H), 7.43 (t, J=7.74 Hz, 1H), 7.33 (s, 1H). FABMS Calcd for C$_{19}$H$_{15}$N$_5$OS$_2$: 394.0796. Found: 394.0802.

EXAMPLE E(3)

N-[3-(2',4'-Diamino-[2,5']bithiazolyl-4-yl)phenyl]-5-chloro-thiophene-2-carboxamide

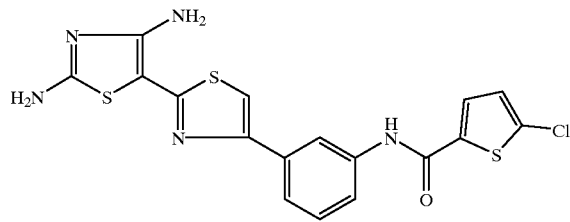

Starting material was prepared following Steps (i) and (ii) described below.

Step (i): Oxalyl chloride (4.9 mL, 56.00 mmol) was added to solution of 5-chloro-thiophene-2-carboxylic acid (4.78 g, 29.40 mmol), DMF (0.25 mL), and CH$_2$Cl$_2$ (50 ml) at room temperature. After stirring overnight, the reaction was stripped of solvent and unreacted oxalyl choride in vacuo, giving a colorless oil. The oil was dissolved in CH$_2$Cl$_2$ (50 mL), and treated with 3-aminoacetophenone (3.78 g, 28.00 mmol) and triethylamine (4.68 mL, 33.60 mmol). After stirring for 1 h, the mixture was diluted with 800 mL of ethyl acetate, extracted with 1N HCl, 1N NaHCO$_3$, brine, and dried over MgSO$_4$. The resulting solution was concentrated in vacuo to a volume of 100 mL, giving 5-chloro-thiophene-2-carboxylic acid (3-acetyl-phenyl)-amide as a white powder, which was collected by filtration and dried under high vacuum (8.12 g, 81% yield).

Step (ii): A solution of 5-chloro-thiophene-2-carboxylic acid (3-acetyl-phenyl)-amide (2.0 g, 7.17 mmol) and CuBr$_2$ (3.19 g, 14.34 mmol) in EtOAc (100 ml) was heated to reflux. Progress of the reaction was monitored every 30 minutes by TLC. After 2.5 h, starting material was still present, so additional CuBr$_2$ (0.75 g) was added. After an additional 1.5 h, TLC indicated that all starting material had been consumed. The reaction was reduced in volume by 50% in vacuo, diluted with CH$_2$Cl$_2$ (50 mL), filtered through a plug of silica, which was eluted with 40% ethyl acetate/CH$_2$Cl$_2$ (300 mL). The resulting solution was concentrated in vacuo, giving a colorless oil, which was taken up in CH$_2$Cl$_2$ (2 mL) and precipitated with diethyl ether (10 mL), giving 5-chloro-thiophene-2-carboxylic acid (3-bromoacetyl-phenyl)-amide (2.06 g, 80% yield) as white powder.

The title compound was prepared as follows. To a solution of 1.07 g (3.0 mmol) of 4-amino-2-(trityl-amino)-thiazole-5-carbothioic acid amide (prepared analogously to the starting material described in step (ii) of Example A(1)) dissolved in DMF (12 mL), was added 5-chloro-thiophene-2-carboxylic acid (3-bromoacetyl-phenyl)-amide. After 15 minutes, the reaction was diluted with MeOH (12 mL), treated with TFA (4 mL), and stirred overnight. The resulting solution was concentrated in vacuo, diluted with ethyl acetate, extracted with 1M NaHCO$_3$, extracted with brine, dried over MgSO$_4$, concentrated, and purified by flash chromatography (gradient elution: 5% CH$_3$CN/CH$_2$Cl$_2$ to 30% CH$_3$CN/CH$_2$Cl$_2$), giving 0.47 g (36% yield) of N-[3-(2',4'-diamino-[2,5']bithiazolyl-4-yl)phenyl]-5-chloro-thiophene-2-carboxamide.

$^1$H NMR (DMSO-d$_6$): δ 10.41 (s, 1H), 8.23 (s, 1H), 7.95 (d, J=4.1 Hz, 2H), 7.73–7.65 (m, 4H), 7.48 (s, 1H), 7.41 (t, J=8.1 Hz, 1H), 7.29 (d, J=4.1 Hz, 1H), 6.90 (s, 2H).

EXAMPLE E(4)

(2',4'-Diamino-[2,5']bithiazolyl-4-yl)-phenyl-methanone

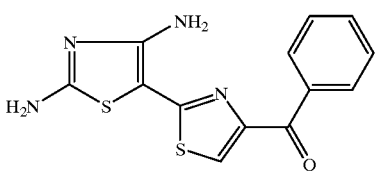

The title compound was prepared in a manner similar to Example E(3). $^1$H NMR (CD$_3$OD): δ 8.02–7.99 (m, 2H), 7.94 (s, 1H), 7.76 (s, NH$_2$), 7.70–7.64 (m, 1H), 7.57–7.52 (m, 2H), 6.85 (bs, NH$_2$). FABMS (MH$^+$): 303. FABMS Calcd for C$_{13}$H$_{10}$N$_4$OS$_2$ (MNa+): 325.0194. Found: 325.0182.

EXAMPLE F(1)

5-Chloro-thiophene-2-carboxylic acid {3-[4'-amino-2'-(3-methyl-ureido)-[2,5']bithiazolyl-4-yl]-phenyl}-amide

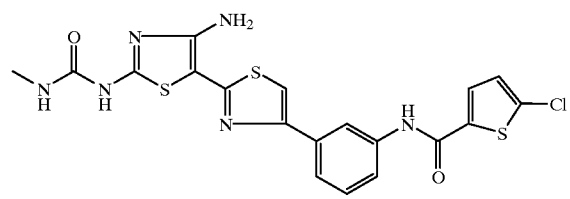

A solution of N-[3-(2',4'-diamino-[2,5']bithiazolyl-4-yl)phenyl]-5-chloro-thiophene-2-carboxamide (0.2307 mmol) (prepared as in Example E(3)), dissolved in anhydrous THF (5.0 mL) and anhydrous N-methylpyrolidinone (1.0 mL) at −78° C., was treated phenyllithium (0.2307 mmol), followed by methylisocyanate (0.3461 mmol). After 5 minutes a second portion of phenyllithium (0.2307 mmol) was added slowly. After stirring for an additional 15 minutes, the reaction was quenched with acetic acid (0.6921 mmol), and methanol (0.5 mL), concentrated, and purified by reverse phase HPLC. The major component was collected, dissolved in ethyl acetate, extracted with NaHCO$_3$, brine, dried over MgSO$_4$, concentrated until a precipitate formed, and filtered. Mass of the resulting light-yellow powder after drying under high vacuum was 46 mg (41% yield).

ESMS (MH$^+$): 491/493. Anal. Calcd for C$_{19}$H$_{15}$ClN$_6$O$_2$S$_3$: C, 46.48; H, 3.08; N, 17.12; S, 19.59. Found: C, 46.47; H, 3.21; N, 17.10; S, 19.43.

In an analogous manner to that described in Example F(1), the following Examples F(2) through F(15) were prepared.

EXAMPLE F(2)
N-[3-(2'-Acetylamino-4'-amino-[2,5']bithiazolyl-4-yl)-phenyl]-5-chloro-thiophene-2-carboxamide

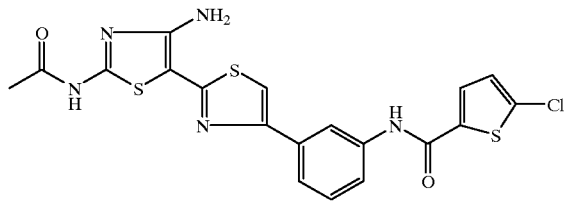

ESMS (MH$^+$): 476/478. Anal. Calcd for C$_{19}$H$_{14}$N$_5$O$_2$S$_3$: C, 47.94; H, 2.96; N, 14.17; S, 19.46. Found: C, 47.66; H, 3.39; N, 13.87; S, 19.21.

EXAMPLE F(3)
(4'-Amino-4-{3-[(5-chloro-thiophene-2-carbonyl)-amino]-phenyl}-[2,5']bithiazolyl-2'-yl)-carbamic acid methyl ester

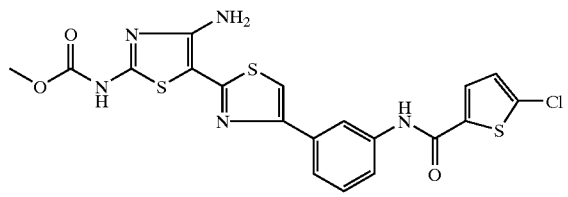

ESMS (MH$^-$): 492/494.

EXAMPLE F(4)
N-{3-[5-(2-Acetylamino-4-amino-thiazol-5-yl)-[1,2,4]oxadiazol-3-yl]-phenyl}-3-chloro-benzamide

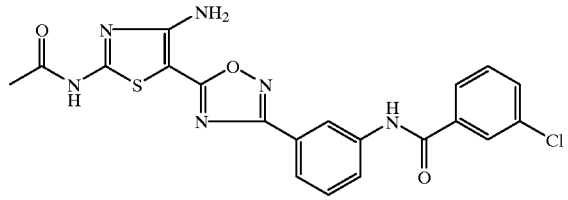

$^1$H NMR (CD$_3$COCD$_3$/DMSO-d$_6$): δ 10.55 (s, 1H), 8.60 (m, 1H), 8.20 (m, 2H), 8.15 (m, 1H), 8.19 (m, 1H), 7.66–7.50 (m, 4H), 7.12 (s, 2H), 2.22 (s, 3H). ESIMS: (MNa$^+$): 477; (MH$^-$): 453.

EXAMPLE F(5)
Thiophene-2-carboxylic acid (4-amino-5-{3-[3-(3-chloro-benzoylamino)-phenyl]-[1,2,4]oxadiazol-5-yl}-thiazol-2-yl)-amide

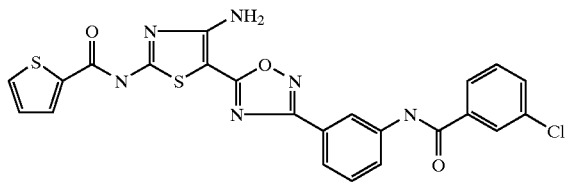

$^1$H NMR (DMSO-d$_6$): δ 13.19 (s, 1H), 10.60 (s, 1H), 8.52 (s, 1H), 8.32 (m, 1H), 8.09–7.88 (m, 5H), 7.72–7.56 (m, 3H), 7.29 (m, 1H), 7.22 (s, 2H). ESIMS: (MH$^+$): 523; (MNa$^+$): 545; (MH$^-$): 521.

EXAMPLE F(6)
N-{3-[5-(4-Amino-2-propionylamino-thiazol-5-yl)-[1,2,4]oxadiazol-3-yl]-phenyl}-3-chloro-benzamide

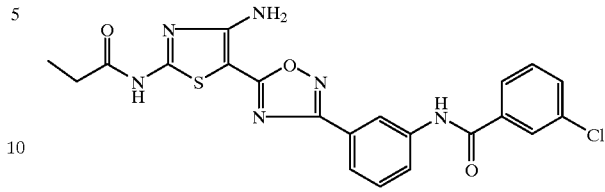

$^1$H NMR (DMSO-d$_6$): δ 12.41 (s, 1H), 10.57 (s, 1H), 8.48 (s, 1H), 8.06 (m, 2H), 7.96 (m, 1H), 7.85 (m, 1H), 7.70 (m, 1H), 7.67–7.55 (m, 2H), 7.15 (s, 2H), 2.46 (q, 2H), 1.09 (t, 3H). ESIMS: (MNa$^+$): 491; (MH$^-$): 467.

EXAMPLE F(7)
N-{3-[5-(4-amino-2-benzoylamino-thiazol-5-yl)-[1,2,4]oxadiazol-3-yl]-phenyl}-3-chloro-benzamide

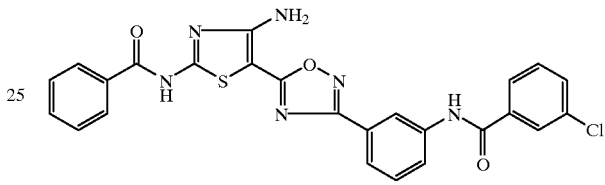

$^1$H NMR (DMSO-d$_6$): δ 13.08 (s, 1H), 10.57 (s, 1H), 8.50 (s, 1H), 8.43–8.10 (m, 4H), 8.07 (m, 1H), 7.97 (m, 1H), 7.86 (m, 1H), 7.71–7.52 (m, 6H), 7.14 (s, 2H). ESIMS: (MH$^+$): 517; (MNa$^+$): 539; (MH$^-$): 515.

EXAMPLE F(8)
N-(3-[5-[4-Amino-2-(3-methyl-ureido)-thiazol-5-yl]-[1,2,4]oxadiazol-3-yl]-phenyl)-3-methyl-benzamide

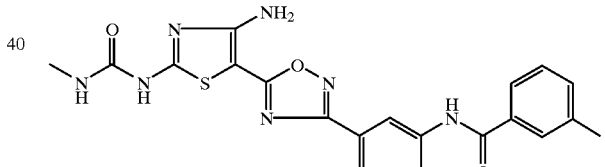

ESMS (MH$^-$): 450. Anal. Calcd for C$_{21}$H$_{19}$N$_7$O$_3$S: C, 56.11; H, 4.26; N, 21.81; S, 7.13. Found: C, 55.97; H, 4.39; N, 21.54; S, 6.89.

EXAMPLE F(9)
N-[3-(2'-Acetylamino-4'-amino-[2,5']bithiazolyl-4-yl)-phenyl]benzamide

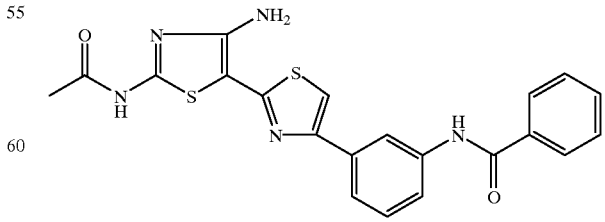

$^1$H NMR (CD$_3$OD): δ 8.27–8.24 (m, 1H), 7.89–7.85 (m, 2H), 7.67–7.61 (m, 2H), 7.51–7.31 (m, 5H), 2.14 (s, 3H). ESIMS (MH$^+$): 436; (M−H$^-$): 434.

EXAMPLE F(10)

N-{3-[4'-Amino-2'-(3-methyl-ureido)-[2,5']bithiazolyl-4-yl]-phenyl}-3-chloro-benzamide

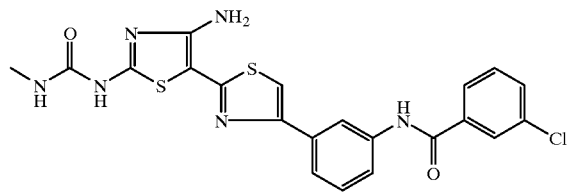

Anal. Calcd. for $C_{21}H_{17}ClN_6O_2S_2 \cdot 1.0$ $H_2O$: C, 50.14; H, 3.81; N, 16.71; S, 12.75. Found: C, 51.12; H, 3.64; N, 16.96; S, 12.87. ESIMS (MH$^+$): 485/487.

EXAMPLE F(11)

N-{3-[4'-Amino-2'-(3-methyl-ureido)-[2,5']bithiazolyl-4-yl]-phenyl}-3-methoxy-benzamide

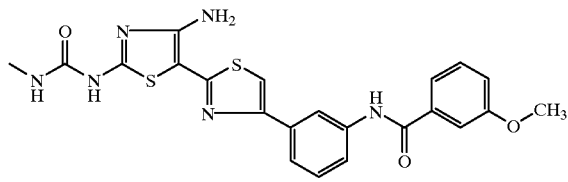

Anal. Calcd. for $C_{22}H_{20}N_6O_3S_2 \cdot 0.7$ $H_2O$: C, 53.58; H, 4.37; N, 17.04; S, 13.00. Found: C, 53.60; H, 4.34; N, 17.04; S, 12.93. ESIMS (M−H$^-$): 479.

EXAMPLE F(12)

N-(3-{5-[4-Amino-2-(3-phenyl-ureido)-thiazol-5-yl]-[1,2,4]oxadiazol-3-yl}-phenyl)-3-methyl-benzamide

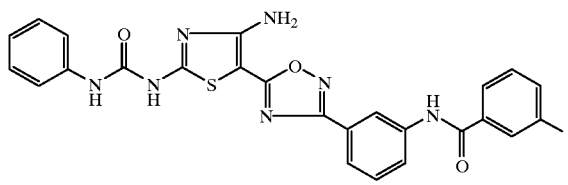

Anal. Calcd. for $C_{26}H_{21}N_7O_3S$: C, 61.04; H, 4.14; N, 19.17; S, 6.27. Found: C, 60.78; H, 4.18; N, 19.05; S, 6.08. ESIMS (MH$^+$): 512.

EXAMPLE F(13)

N-(3-{5-[4-Amino-2-(3-isopropyl-ureido)-thiazol-5-yl]-[1,2,4]oxadiazol-3-yl}-phenyl)-3-methyl-benzamide

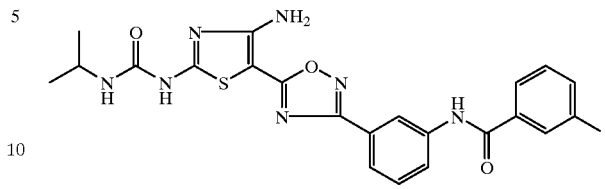

Anal. Calcd. for $C_{23}H_{23}N_7O_3S$: C, 57.85; H, 4.85; N, 20.53; S, 6.71. Found: C, 57.65; H, 4.97; N, 20.47; S, 6.64. ESIMS (MH$^+$): 478.

EXAMPLE F(14)

N-(3-{5-[4-Amino-2-(3-benzyl-ureido)-thiazol-5-yl]-[1,2,4]oxadiazol-3-yl}-phenyl)-3-methyl-benzamide

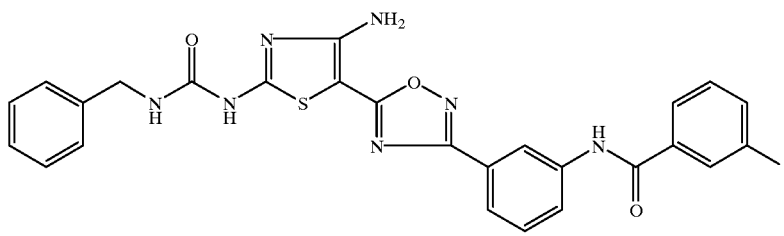

Anal. Calcd. for $C_{27}H_{23}N_7O_3S \cdot 0.9$ $H_2O$: C, 59.85; H, 4.61; N, 18.10; S, 5.92. Found: C, 59.86; H, 4.55; N, 17.86; S, 5.78. ESIMS (MH$^+$): 526.

EXAMPLE F(15)

N-{3-[5-(4-Amino-2-methanesulfonylamino-thiazol-5-yl)-[1,2,4]oxadiazol-3-yl]-phenyl}-3-methyl-benzamide

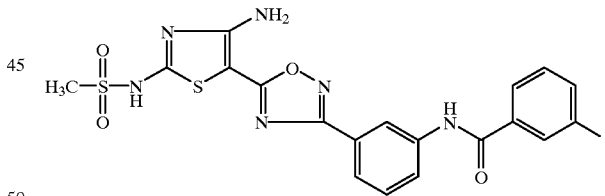

ESIMS (MNa$^+$): 493.

EXAMPLE F(16)

N-(4'-Amino-4-benzoyl-[2,5']bithiazolyl-2'-yl)-acetamide

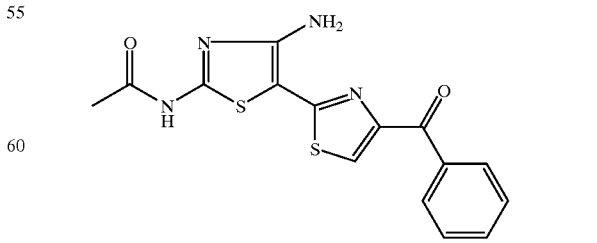

$^1$H NMR (CD$_3$OD): δ 6.81–6.69 (m, 2H), 6.41–6.18 (m, 3H), 6.07–5.91 (m, 1H), 0.93 (s, 3H). FABMS Calcd for $C_{15}H_{12}N_4O_2S_2Na$: 367.0299. Found: 367.0991.

EXAMPLE G(1)
5-Pyridin-2-yl-N²-(3,4,5-trimethoxy-phenyl)-thiazole-2,4-diamine

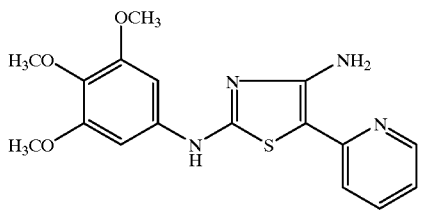

3,4,5-Trimethoxyphenyl isothiocynate (250 mg, 1.11 mmol, 1 equiv.) and cyanamide (56 mg, 1.33 mmol, 1.2 equiv.) were taken up in acetonitrile-tert-butanol (1:1, 10 mL) at 23° C. To this was added KO-t-Bu (286 mg, 2.55 mmol, 2.3 equiv.) and 2-chloromethylpyridine hydrochloride (182 mg, 1.11 mmol, 1.00 equiv.). The reaction mixture was allowed to stir for 1.5 h at 23° C. The mixture was diluted with water (20 mL) and the white solids were filtered, washed with ether and dried (257 mg). The dried residue (60 mg, 0.167 mmol, 1.00 equiv.) was dissolved in THF (3 mL), cooled to −78° C. and was treated with n-butyllithium (0.261 mL, 1.6 M, 2.5 equiv.). The mixture was allowed to warm to 23° C., was quenched with saturated sodium bicarbonate, and organics were extracted into ethyl acetate. The concentrated residue was purified by silica gel chromatography (ethyl acetate/hexane: 1:1, 48.3 mg, 80%). MS (FAB) [m+]/z Calcd: 359. Found: 359. MS (FAB) [m−]/z Calcd: 357. Found: 357. Anal. Calcd: C, 56.97; H, 5.06; N, 15.63; S, 8.95. Found: C, 56.18; H, 5.10; N, 15.31; S, 8.68.

The following Examples G(2) through G(9) were prepared in a similar manner to Example G(1).

EXAMPLE G(2)
N²-Phenyl-5-pyridin-2-yl-thiazole-2,4-diamine

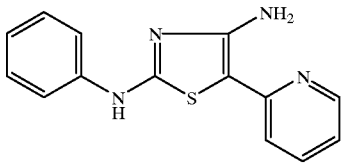

MS (FAB) [m+]/z Calcd: 269. Found: 269. Anal. Calcd: C, 62.66; H, 4.51; N, 20.88; S, 11.95. Found: C, 62.71; H, 4.46; N, 20.76; S, 11.91.

EXAMPLE G(3)
N²-(2,3-Dihydro-benzo[1,4]dioxin-6-yl)-5-pyridin-2-yl-thiazole-2,4-diamine

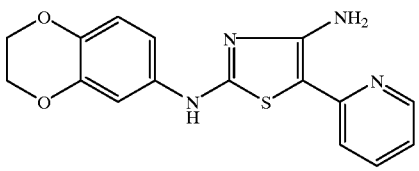

MS (FAB) [m+]/z Calcd: 327. Found: 327. Anal. Calc'd: C, 58.88; H, 4.32; N, 17.17; S, 9.82. Found: C, 59.00; H, 4.29; N, 16.92; S, 9.58.

EXAMPLE G(4)
N²-(3,4-Dimethoxy-phenyl)-5-pyridin-2-yl-thiazole-2,4-diamine

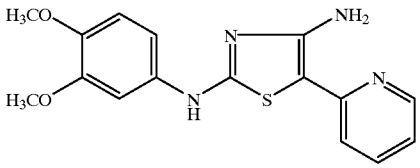

MS (FAB) [m+]/z Calcd: 329. Found: 329. Anal. Calcd: C, 58.52; H, 4.91; N, 17.06; S, 9.76. Found: C, 58.43; H, 4.89; N, 17.03; S, 9.67.

EXAMPLE G(5)
5-Quinolin-2-yl-N²-(3,4,5-trimethoxy-phenyl)-thiazole-2,4-diamine

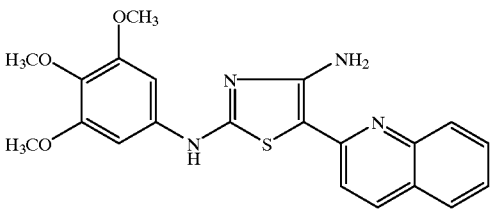

MS (FAB) [m+]/z Calcd: 408. Found: 408. Anal. Calcd: C, 61.75; H, 4.94; N, 13.72; S, 7.85. Found: C, 61.96; H, 4.80; N, 13.05; S, 7.54.

EXAMPLE G(6)
5-(6-Bromo-pyridin-2-yl)-2-N-(3,4,5-trimethoxy-phenyl)-thiazole-2,4-diamine

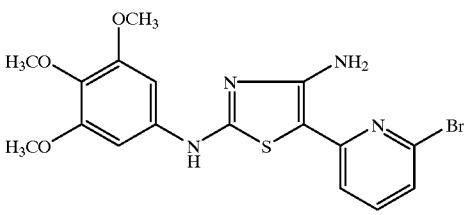

¹H NMR (300 MHz, CDCl₃): δ 7.35 (t, 1H), 6.98 (d, 1H), 6.76 (d, 1H), 6.62 (s, 2H), 3.85 (s, 6H), 3.82 (s, 3H). MS (FAB) [m+H]/z Calcd: 437. Found: 438. Anal. Calcd: C, 46.69; H, 3.92; N, 12.81; S, 7.33. Found: C, 46.66; H, 3.84; N, 12.68; S, 7.25.

EXAMPLE G(7)
5-(5-Thiophen-3-yl-[1,2,4]oxadiazol-3-yl)-N²-(3,4,5-trimethoxy-phenyl)-thiazole-2,4-diamine

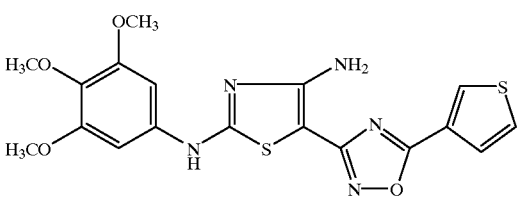

MS (FAB) [m+]/z Calcd: 431. Found: 431. Anal. Calcd: C, 50.10; H, 3.97; N, 16.23; S, 14.86. Found: C, 50.45; H, 3.96; N, 15.31; S, 14.46.

EXAMPLE G(8)
4-{4-Amino-5-[1-(4-chloro-benzyl)-1H-imidazol-2-yl]-thiazol-2-ylamino}-benzenesulfonamide

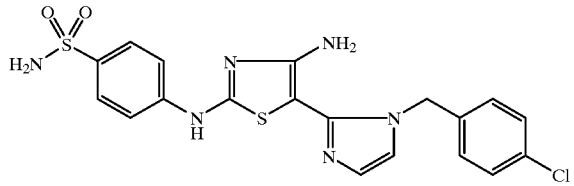

EXAMPLE G(9)
4-[4-Amino-5-(5-nitro-benzothiazol-2-yl)-thiazol-2-ylamino]-benzenesulfonamide

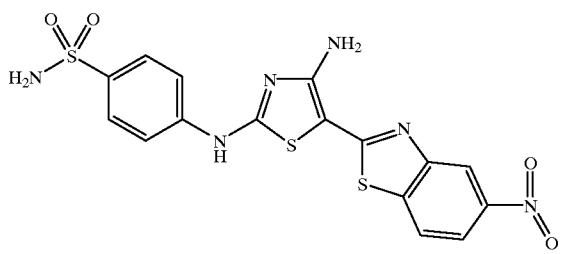

$^1$H NMR (DMSO-d$_6$): δ 8.35 (s, 1H), 8.02 (d, J=6.5 Hz, 1H), 7.90 (d, J=6.5 Hz, 1H), 7.72 (m, 4H), 7.64 (br, NH$_2$), 7.22 (br, NH$_2$).

EXAMPLE H(1)
4-(4'-Amino-4-hydroxy-[2,5']bithiazolyl-2'-ylamino)-benzenesulfonamide

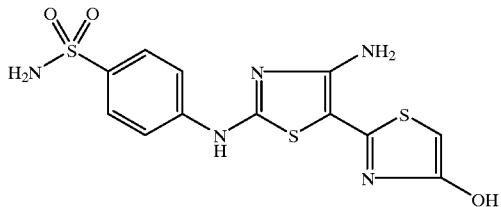

The title compound of this example and Examples H(2) through H(6) were prepared in a manner similar to that described in Example A(1) et seq. from 2-arylaminoamino-thiazole-5-carbothioamides and α-bromo esters, α-bromo-lactones, or α-bromo-nitriles, as appropriate.

$^1$H NMR (DMSO-d$_6$): δ 7.88 (s, 4H), 7.39 (s, 1H). ESIMS (MH$^+$): 370; (M–H)$^-$: 368.

EXAMPLE H(2)
4-[4'-Amino-4-hydroxy-5-(4-hydroxy-phenyl)-[2,5']bithiazolyl-2'-yl-amino]-benzenesulfonamide

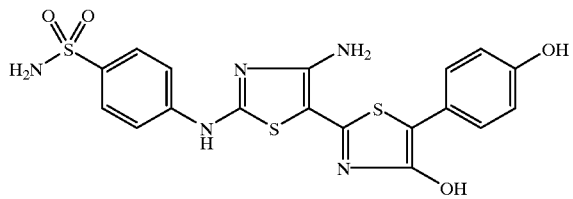

$^1$H NMR (DMSO-d$_6$): δ 9.52 (s, 1H), 7.83 (m, 4H), 7.32, (s, 2H), 7.06 (d, J=8.0 Hz, 2H), 7.42 (d, J=8.0 Hz, 2H), 5.38 (s, 1H). ESIMS (MH$^+$): 462. Anal. Calcd for C$_{18}$H$_{15}$N$_5$O$_4$S$_3$.0.2 H$_2$O.0.2 Et$_2$O: C, 47.04; H, 3.65; N, 14.59; S, 20.04. Found: C, 46.78; H, 3.59; N, 14.36; S, 20.73.

EXAMPLE H(3)
4'-Amino-2'-(4-dimethylamino-phenylamino)-5-(2-hydroxy-phenyl)-[2,5']bithiazoly-4-ol

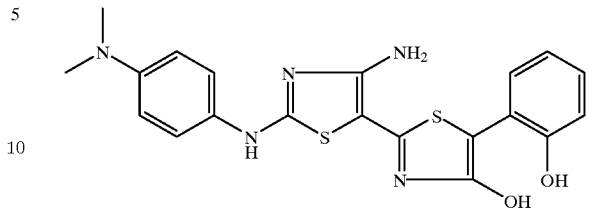

$^1$H NMR (DMSO-d$_6$): δ 7.30 (m, 2H), 7.04 (m, 2H), 6.68 (m, 4H), 2.88 (s, 6H). ESIMS (MH$^+$): 426; (M–H)$^-$: 424.

EXAMPLE H(4)
4-[4'-Amino-4-hydroxy-5-(2-hydroxy-phenyl)-[2,5']bithiazoly-2'-ylamino]-benzenesulfonamide

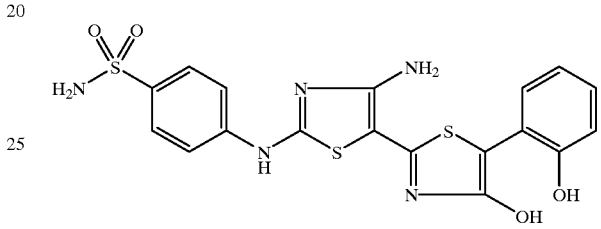

$^1$H NMR (CD$_3$OD): δ 7.82 (m, 4H), 7.02 (m, 2H), 6.62 (m, 2H). ESIMS (MH$^+$): 462; (M–H)$^-$: 460.

EXAMPLE H(5)
4-[4'-Amino-4-hydroxy-5-(2-hydroxy-ethyl)-3'H-1'-[2,5]bithiazolyl-2'-ylamino]-benzenesulfonamide

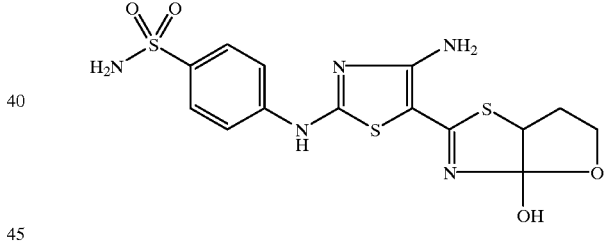

$^1$H NMR (DMSO-d$_6$): δ 7.83 (s, 4H), 4.72 (m, 1H), 4.26 (m, 1H), 3.52 (m, 2H), 2.30 (m, 1H), 1.78 (m, 1H). ESIMS (MH$^+$): 414; (M–H)$^-$: 412. Anal. Calcd for C$_{14}$H$_{15}$N$_5$O$_4$S$_3$: C, 40.67; H, 3.66; N, 16.94; S, 23.26. Found: C, 40.81; H, 3.76; N, 1676; S, 23.02.

EXAMPLE H(6)
4-(4,4'-Diamino-[2,5']bithiazolyl-2'-ylamino)-benzenesulfonamide

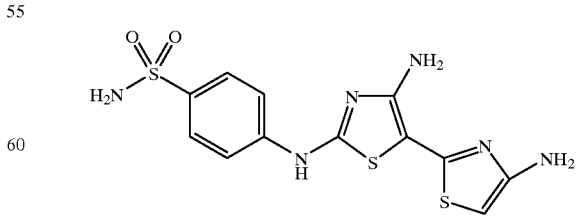

$^1$H NMR (DMSO-D$_6$): δ 11.0 (s, NH), 8.12 (s, H), 7.80 (m, 4H), 7.32 (s, NH$_2$), 7.08 (br s, NH$_2$), 7.02 (s, NH$_2$). ESIMS (MH+): 369; (M–H−): 367.

EXAMPLE I(1)

S-5-(4-Benzyl-4,5-dihydro-oxazol-2-yl)-$N^2$-(3,4,5-trimethoxyl-pheny)-thiazole-2,4-diamine

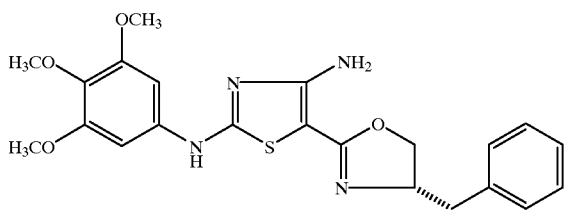

A mixture of 4-amino-2-(3,4,5-trimethoxy-phenylamino)-thiazole-5-carbonitrile (153 mg, 0.5 mmol), 2(S)-amino-3-phenyl-propan-1-ol (84 mg, 0.55 mmol), and a catalytic amount of dry $ZnCl_2$ in chlorobenzene (15 ml) was refluxed for four hours. The solvent was removed under reduced pressure. The residue was dissolved in ethyl acetate and washed with 0.1 N HCl, brine and dried with MgSO4. The product (53 mg) was obtained after silica chromatography purification (hexanes/ethyl acetate=1/1).

$^1$H NMR ($CDCl_3$): δ 7.33–7.22 (m, 5H), 6.58 (s, 2H), 4.50 (m, 1H), 4.24 (t, J=9.0 H, 1H), 4.01 (t, J=9.0 Hz, 1H), 3.86 (s, 6H), 3.82 (s, 3H), 3.11 (m, 1H), 2.70 (m, 1H). ESIMS ($MH^+$): 441; ($M-H^-$): 439.

The following Examples I(2) through I(19) were prepared in a similar manner:

EXAMPLE I(2)

R-5-(4-Benzyl-4,5-dihydro-oxazol-2-yl)-$N^2$-(3,4,5-trimethoxyl-phenyl)-thiazole-2,4-diamine

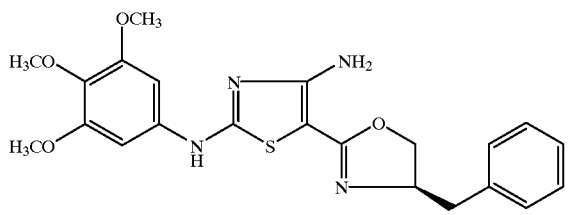

$^1$H NMR ($CDCl_3$): δ 7.33–7.22 (m, 5H), 6.58 (s, 2H), 4.50 (m, 1H), 4.24 (t, J=9.0 Hz, 1H), 4.01 (t, J=9.0 Hz, 1H), 3.86 (s, 6H), 3.82 (s, 3H), 3.11 (m, 1H), 2.70 (m, 1H). Anal. Calcd for $C_{22}H_{24}N_4O_4S$: C, 59.98; H, 5.49; N, 12.72; S, 7.28. Found: C, 59.88; H, 5.54; N, 12.67; S, 7.21.

EXAMPLE I(3)

S-5-(4-Isobutyl-4,5-dihydro-oxazol-2-yl)-$N^2$-(3,4,5-trimethoxyl-phenyl)-thiazole-2,4-diamine

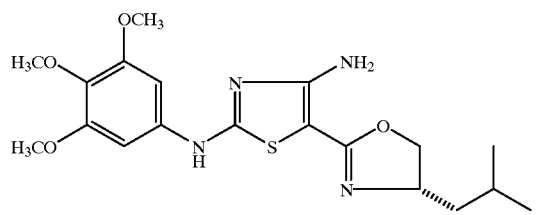

$^1$H NMR ($CDCl_3$): δ 6.57 (s, 2H), 5.71 (brd, $NH_2$), 4.36 (m, 1H), 4.26 (m, 1H), 3.85–3.80 (m, 10H), 1.80 (m, 1H), 1.62 (m, 1H), 1.35 (m, 1H), 0.95 (m, 6H). ESIMS ($MH^+$): 407.

EXAMPLE I(4)

5-{(4R)-[(1R)-Benzyloxy-ethyl]-4,5-dihydro-oxazol-2-yl}-$N^2$-(3,4,5-trimethoxyl-phenyl)-thiazole-2,4-diamine

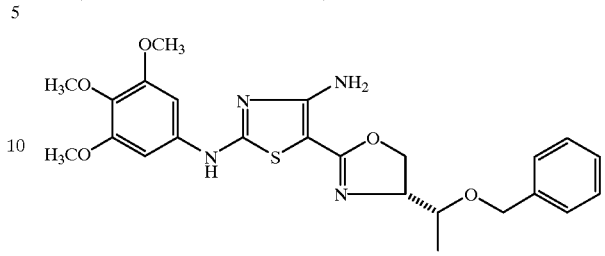

$^1$H NMR ($CDCl_3$): δ 7.35–7.25 (m, 5H), 6.58 (s, 2H), 5.70 (brd, $NH_2$), 4.70–4.59 (m, 2H), 4.48 (m, 1H), 4.25 (m, 2H), 3.86 (s, 6H), 3.83 (s, 3H), 3.77 (m, 1H), 1.14 (m, 3H). ESIMS ($MH^+$): 485.

EXAMPLE I(5)

S-4-[4-Amino-5-(4-phenyl-4,5-dihydro-oxazol-2-yl)-thiazol-2-ylamino]-benzenesulfonamide

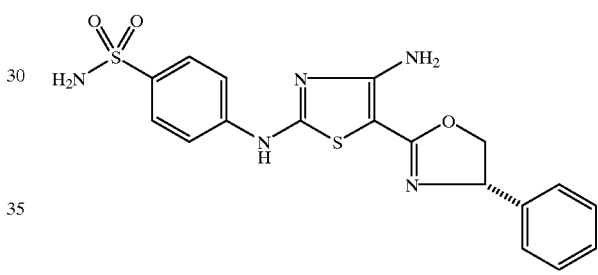

$^1$H NMR ($CD_3OD$): δ 7.82 (m, 4H), 7.34 (m, 5H), 5.26 (t, J=8 Hz, 1H), 4.72 (t, J=7.80 Hz, 1H), 4.16 (t, J=7.80 Hz, 1H). Anal. Calcd for $C_{18}H_{17}N_5O_3S_2 \cdot 0.5\ Et_2O$: C, 53.08; H, 4.90; N, 15.48; S, 14.17. Found: C, 53.36; H, 4.79; N, 15.66, S, 14.33.

EXAMPLE I(6)

S-5-(4-Phenyl-4,5-dihydro-oxazol-2-yl)-$N^2$-(3,4,5-trimethoxyl-phenyl)-thiazole-2,4-diamine

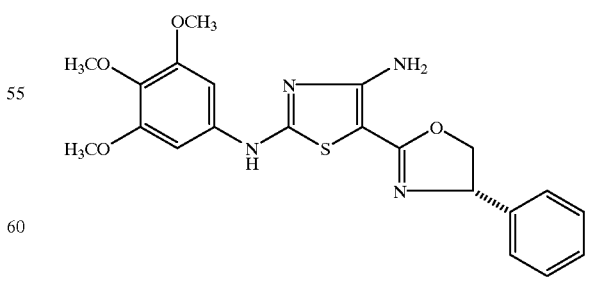

$^1$H NMR ($CDCl_3$): δ 7.37–7.26 (m, 5H), 6.59 (s, 2H), 5.80 (brd, $NH_2$), 5.32 (t, J=7.80 Hz, 1H), 4.65 (t, J=7.80 Hz, 1H), 4.09 (t, J=7.80 Hz, 1H). FABMS ($MH^+$): 427.

EXAMPLE I(7)

R-5-(4-Phenyl-4,5-dihydro-oxazol-2-yl)-N²-(3,4,5-trimethoxyl-phenyl)-thiazole-2,4-diamine

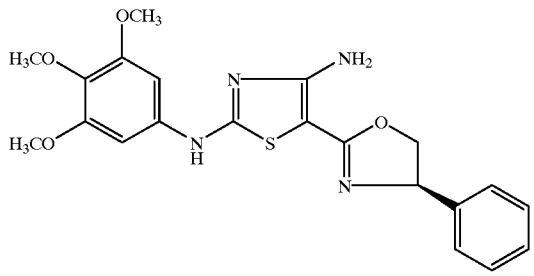

¹H NMR (CDCl₃): δ 7.37–7.26 (m, 5H), 6.59 (s, 2H), 5.80 (brd, NH₂), 5.32 (t, J=7.80 Hz, 1H), 4.65 (t, J=7.80 Hz, 1H), 4.09 (t, J=7.80 Hz, 1H). FABMS (MH⁺): 427.

EXAMPLE I(8)

S-5-[4-(3-Benzyloxy-phenyl)-4,5-dihydro-oxazol-2-yl]-N²-(3,4,5-trimethoxy-phenyl)-thiazole-2,4-diamine

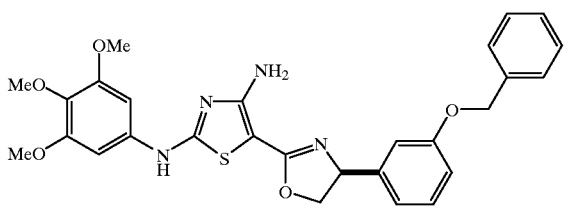

¹HNMR (300 MHz, CDCl₃): δ 3.83 (s, 3H), 3.87 (s, 6H), 4.08 (dd, J=8, 8 Hz, 1H), 4.62 (dd, J=8, 10 Hz, 1H), 5.05 (s, 2H), 5.30 (dd, J=8, 8 Hz, 1H), 5.80 (s, 2H), 6.59 (s, 2H), 6.90 (m, 3H), 7.33 (m, 6H). HRMS (FAB) (MH⁺⁾) Calcd: 533.1859. Found: 533.18477.

EXAMPLE I(9)

S-3-{2-[4-Amino-2-(3,4,5-trimethoxy-phenylamino)-thiazol-5-yl]-4,5-dihydro-oxazol-4-yl}-phenol

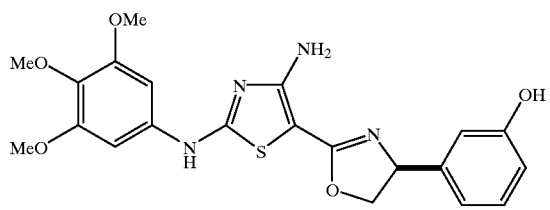

To a solution of S-5-[4-(3-benzyloxyphenyl)-4,5-dihydro-oxazo-2-yl]-N2-(3,4,5-trimethoxy-phenyl)-thiazole-2,4-diamine (prepared as described in Example I(8)) (20 mg, 0.038 mmol) in DMF (0.5 ml), Pd black (10 mg) and ammonium formate (10 mg, 0.14 mmol) were added. The reaction mixture was stirred at room temperature for 42 h. The reaction mixture was diluted with CH₂Cl₂ (5 ml) and filtered through Celite. The product (4 mg) was obtained after the removing of the solvent.

¹HNMR (300 MHz, CD₃OD): δ 3.74 (s, 3H), 3.85 (s, 6H), 4.28 (dd, J=8, 8 Hz, 1H), 4.84 (m, 1H), 5.20 (dd, J=8, 9 Hz, 1H), 6.74 (m, 3H), 6.93 (s, 2H), 7.18 (dd, J=8, 8 Hz, 1H). HRMS (FAB) (MH⁺) Calcd: 443.1389. Found: 443.1377.

EXAMPLE I(10)

S-5-[4-(4-Benzyloxy-phenyl)-4,5-dihydro-oxazol-2-yl]-N²-(3,4,5-trimethoxy-phenyl)-thiazole-2,4-diamine

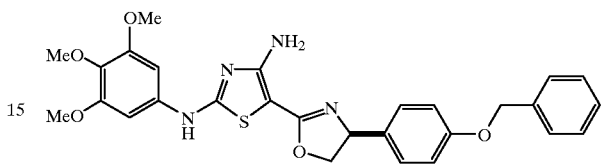

¹HNMR (300 MHz, CDCl₃): δ 3.82 (br s, 9H), 4.06 (dd, J=8, 8 Hz, 1H), 4.60 (dd, J=9, 9 Hz, 1H), 5.05 (s, 2H), 5.26 (dd, J=9, 9 Hz, 1H), 5.89 (br s, 2H), 6.58 (s, 2H), 6.94 (d, J=9 Hz, 2H), 7.20 (J=9 Hz, 2H), 7.39 (m, 5H). HRMS (FAB) (MH⁺) Calcd: 533.1859. Found: 533.1876.

EXAMPLE I(11)

S-4-{2-[4-Amino-2-(3,4,5-trimethoxy-phenylamino)-thiazol-5-yl]-4,5-dihydro-oxazol-4-yl}-phenol

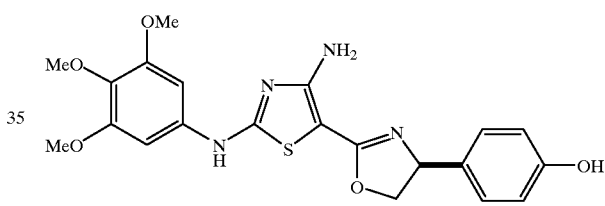

The title compound was prepared from the compound of Example I(10) in a manner similar to that described for Example 1(9).

¹HNMR (300 MHz, CD₃OD): δ 3.73 (s, 3H), 3.80 (s, 6H), 4.12 (dd, J=8, 8 Hz, 1H), 4.70 (dd, J=9, 9 Hz, 1H), 5.16 (dd, J=8, 8 Hz, 1H), 6.70 (d, J=8 Hz, 2H), 6.92 (s, 2H), 7.12 (d, J=8 Hz, 2H). HRMS (FAB) (MH⁺) Calcd: 443.1389. Found: 443.1377.

EXAMPLE I(12)

(R/S)-5-[4-(4-Bromo-phenyl)-4,5-dihydro-oxazol-2-yl]-N²-(3,4,5-trimethoxy-phenyl)-thiazole-2,4-diamine

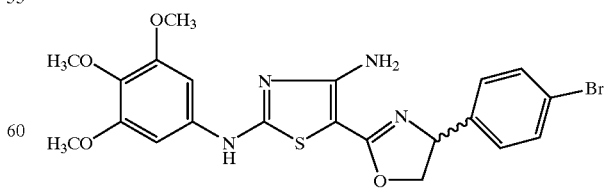

MS (FAB) [m+H]/z Calcd: 505. Found: 505. Anal. Calcd: C, 49.91; H, 4.19; N, 11.09; S, 6.34. Found: C, 49.32; H, 4.02; N, 10.59; S, 6.05.

EXAMPLE I(13)
(R/S)-5-[4-(2-Bromo-phenyl)-4,5-dihydro-oxazol-2-yl]-$N^2$-(3,4,5-trimethoxy-phenyl)-thiazole-2,4-diamine

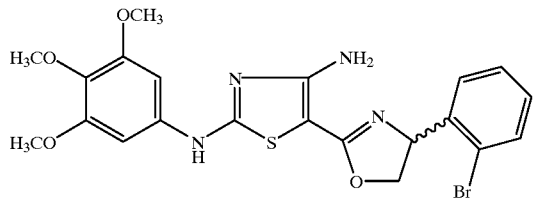

MS (FAB) [m+H]/z Calcd: 505. Found: 505. Anal. Calcd: C, 49.91; H, 4.19; N, 11.09; S, 6.34. Found: C, 49.32; H, 4.02; N, 10.59; S, 6.05.

EXAMPLE I(14)
(R/S)-5-[4-(3-Bromo-phenyl)-4,5-dihydro-oxazol-2-yl]-$N^2$-(3,4,5-trimethoxy-phenyl)-thiazole-2,4-diamine

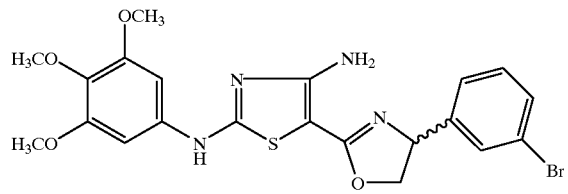

MS (FAB) [m+H]/z Calcd: 505. Found: 505. Anal. Calcd: C, 49.91; H, 4.19; N, 11.09; S, 6.34. Found: C, 50.16; H, 4.41; N, 9.64; S, 5.4.

EXAMPLE I(15)
(R/S)-5-(4-Methyl-4,5-dihydro-oxazol-2-yl)-$N^2$-(3,4,5-trimethoxy-phenyl)-thiazole-2,4-diamine

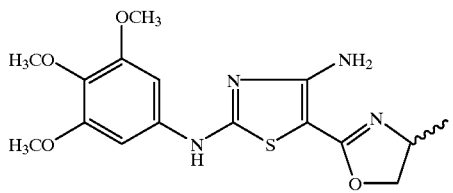

MS (FAB) [m+]/z Calcd: 364. Found: 364. Anal. Calcd: C, 52.73; H, 5.53; N, 15.37; S, 8.8. Found: C, 50.58; H, 5.36; N, 13.92; S, 7.84.

EXAMPLE I(16)
5-(4-Methyl-5-phenyl-4,5-dihydro-oxazol-2-yl)-$N^2$-(3,4,5-trimethoxy-phenyl)-thiazole-2,4-diamine

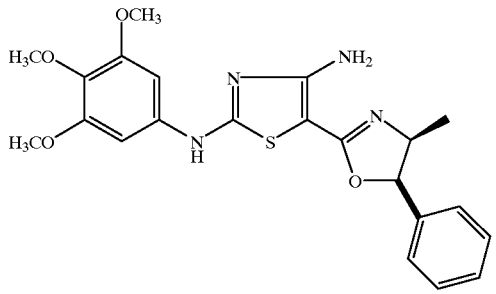

MS (FAB) [m+H]/z Calcd: 441. Found: 441. Anal. Calcd: C, 59.98; H, 5.49; N, 12.72; S, 7.28. Found: C, 59.38; H, 5.49; N, 12.50; S, 7.16.

EXAMPLE I(17)
(R/S)-5-(4-Isopropyl-4,5-dihydro-oxazol-2-yl)-$N^2$-(3,4,5-trimethoxy-phenyl)-thiazole-2,4-diamine

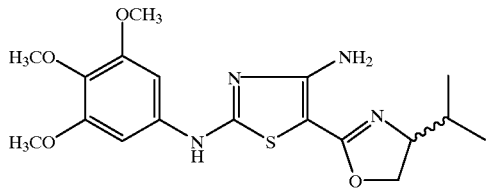

MS (FAB) [m+H]/z Calcd: 393. Found: 393. Anal. Calcd: C, 55.08; H, 6.16; N, 14.28; S, 8.17. Found: C, 55.62; H, 6.33; N, 13.07; S, 7.73.

EXAMPLE I(18)
5-(4(R)-Methyl-5(S)-phenyl-4,5-dihydro-oxazol-2-yl)-$N^2$-(3,4,5-trimethoxy-phenyl)-thiazole-2,4-diamine

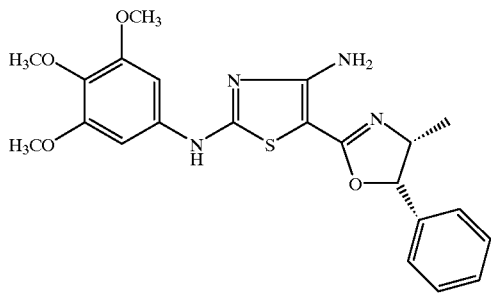

MS (FAB) [m+H]/z Calcd: 441. Found: 441. Anal. Calcd: C, 59.98; H, 5.49; N, 12.72; S, 7.28. Found: C, 59.38; H, 5.49; N, 12.50; S, 7.16.

EXAMPLE I(19)
(R/S)-5-(5-Methyl-4,5-dihydro-oxazol-2-yl)-$N^2$-(3,4,5-trimethoxy-phenyl)-thiazole-2,4-diamine

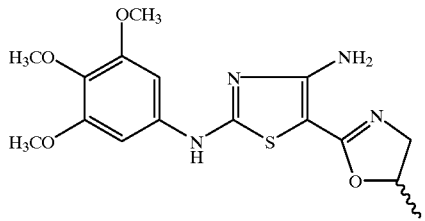

MS (FAB) [m+H]/z Calcd: 365. Found: 365. Anal. Calcd: C, 52.73; H, 5.53; N, 15.37; S, 8.8. Found: C, 50.91; H, 5.27; N, 14.03; S, 8.09.

EXAMPLE I(20)

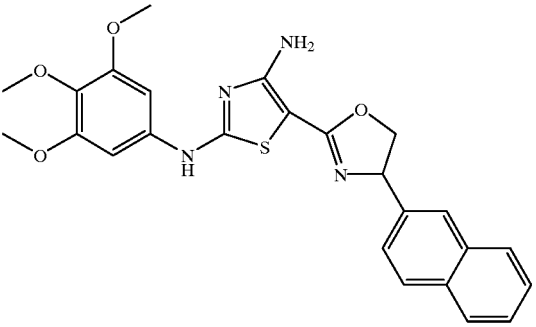

EXAMPLE J(1)
5-(2H-Tetrazol-5-yl-)-N-(3,4,5-trimethoxyl)-thiazole-2,4-diamine

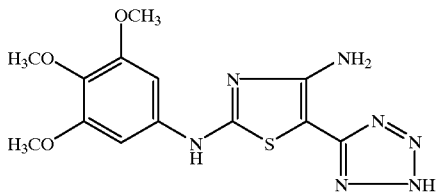

A solution of 4-amino-2-(3,4,5-trimethoxy-phenylamino)-thiazole-5-carbonitrile (110 mg, 0.35 mmol), TMSN$_3$ (115 mg, 1.0 mmol) and catalytic amount of Bu$_2$SnO in toluene was refluxed for four days (additional amounts of TMSN$_3$ and Bu$_2$SnO were added during the reaction). Solvent was removed under reduced pressure. The residue was dissolved in ethyl acetate and washed with 0.1 N HCl, brine and dried with MgSO$_4$. The solvent was removed and the residue was triturated in ethyl ether. The final product (30 mg) was collected by filtration:
$^1$H NMR (CD$_3$OD): δ 6.99 (s, 2H), 3.89 (s, 6H), 3.77 (s, 3H). ESIMS (MH$^+$): 350; (M–H)$^-$: 348.

The following example was prepared in a similar manner:

EXAMPLE J(2)
N-(4-Dimethylamino-phenyl)-5-(2H-tetrazol-5-yl)-thiazole-2,4-diamine

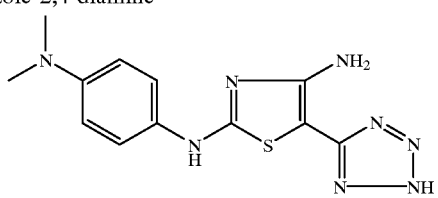

$^1$H NMR (CD$_3$OD): δ 7.38 (d, J=5.40 Hz, 2H), 6.85 (d, J=5.40 Hz, 2H), 2.95 (s, 6H). ESIMS (MH$^+$): 302; (M–H$^-$): 301.

EXAMPLE K(1)
3-{5-[4-Amino-2-(3,4,5-trimethoxy-phenylamino)-thiazol-5-yl]-[1,2,4]oxadiazol-3-yl}-phenol

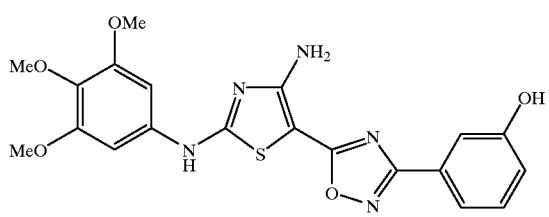

To a solution of 200 mg (0.412 mmol) of 5-[3-(3-methoxymethoxy-phenyl)-[1,2,4]oxadiazol-5-yl]-N$^2$-(3,4,5-trimethoxy-phenyl)-thiazole-2,4-diamine (prepared in Example B(4)) in 8 mL of 50% aqueous dioxane was added trifluoroacetic acid (8 mL) with water bath cooling at 15° C. After 2 hours at room temperature, toluene was added, and the solution was concentrated in vacuo with the water bath at 22° C. With five milliliters of solvent left, the solution was poured into cold aqueous sodium bicarbonate. This solution was extracted with two portions of dichloromethane, which was subsequently washed with brine and dried over sodium sulfate. Radial silica chromatography eluting with 5–10% methanol/dichloromethane gave 3-{5-[4-amino-2-(3,4,5-trimethoxy-phenylamino)-thiazol-5-yl]-[1,2,4]oxadiazol-3-yl}-phenol (60 mg) as a pale-yellow solid.

$^1$HNMR (300 MHz, DMSO-d$_6$): δ 3.64 (s, 3H), 3.81 (s, 6H), 6.95 (m, 3H), 7.34 (m, 2H), 7.49 (m, 2H), 9.76 (s, 1H), 10.76 (s, 1H). Anal. Calcd for C$_{20}$H$_{19}$N$_5$O$_5$S: C, 54.41; H, 4.34; N, 15.86. Found: C, 54.40; H, 4.40; N, 15.86.

EXAMPLE L(1)
5-{6-(Furan-2-yl)-pyridin-2-yl}-N$^2$-(3,4,5-trimethoxy-phenyl)-thiazole-2,4-diamine

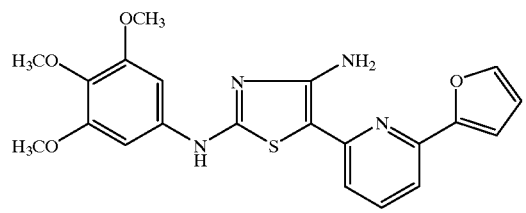

To a solution of 5-(6-Bromo-pyridin-2-yl-2-N-(3,4,5-trimethoxy-phenyl)-thiazole-2,4-diamine (prepared as in Example G(6)) (60 mg, 0.137 mmol, 1.0 equiv) in DMF (0.7 mL) was added 2-furantributyltin (130 μL, 0.411 mmol, 3.0 equiv), triethylamine (95 μL, 0.685 mmol, 5.0 equiv) and dichlorobis(triphenylphosphine)-palladium (19 mg, 0.027 mmol, 0.2 equiv.). The reaction mixture was heated to 85° C. for 18 h, cooled and partitioned between ethyl acetate and sodium bicarbonate. The organic layer was dried over sodium sulfate, decanted and concentrated. The material was purified by silica gel chromatography (1:1 ethyl acetate/hexane) to give 5-{6-(furan-2-yl)pyridin-2-yl}-N$^2$-(3,4,5-trimethoxy-phenyl)-thiazole-2,4-diamine (30.5 mg, 53% yield).
MS (FAB) [m+]/z Calcd: 424. Found: 424. Anal. Calcd: C, 59.42; H, 4.75; N, 13.20; S, 7.55. Found: C, 59.56; H, 4.71; N, 13.10; S, 7.44.

The following Examples L(2) and L(3) were prepared in a similar fashion as Example L(1).

EXAMPLE L(2)
5-(6-Thiophen-2-yl-pyridin-2-yl)-N$^2$-(3,4,5-trimethoxy-phenyl)-thiazole-2,4-diamine

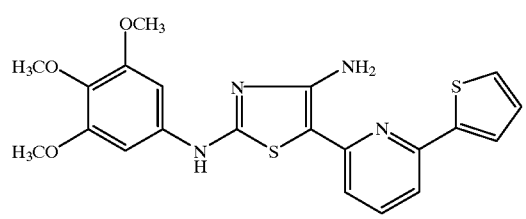

MS (FAB) [m+H]/z Calcd: 441. Found: 441. Anal. Calcd: C, 57.25; H, 4.58; N, 12.72; S, 14.56. Found: C, 56.57; H, 4.60; N, 12.47; S, 14.33.

EXAMPLE L(3)
5-(6-Thiophen-3-yl-pyridin-2-yl)-N$^2$-(3,4,5-trimethoxy-phenyl)-thiazole-2,4-diamine

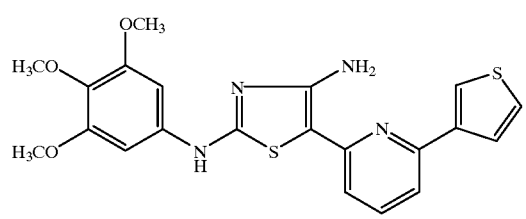

MS (FAB) [m+]/z Calcd: 440; Found: 440. Anal. Calcd: C, 57.25; H, 4.58; N, 12.72; S, 14.56. Found: C, 56.57; H, 4.60; N, 12.47; S, 14.33.

EXAMPLE M(1)

4-Benzylsulfanylmethyl-N-(4-isopropyl-phenyl)-[2,5'] bithiazolyl-2'4'-diamine

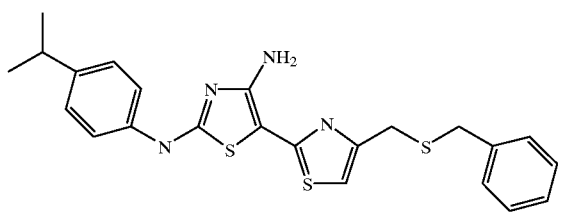

A solution of 204 mg (0.7 mmol) of 4-amino-2-(4-isopropyl-phenylamino)-thiazol-5-carbothioamide (prepared as in Example A(1), Step (ii)) and 1,3-dibromoacetone (154 mg, 0.72 mmol) was stirred in MeOH (10 ml) at room temperature for 2 hours. The resultant reaction mixture was then diluted with ethyl ether (150 ml). A yellow-brown solid was filtered off, rinsed with ethyl ether, and dried in vacuum to give a crude intermediate as brown solid (298 mg, 91% yield). Without further purification, the above intermediate (50 mg, 0.12 mmol) was dissolved in DMF (10 mL) with DIEA (17 mg, 0.14 mmol). Benzyl mercapten (17 mg, 0.14 mmol) was then added. The resultant mixture was stirred at room temperature for 2 hours. Solvent was removed under reduced pressure and the residue was re-dissolved in ethyl acetate (100 mL). The organic solution was extracted with saturated NaHCO$_3$ (3×20 ml) followed by brine. The organic layer was dried over magnesium sulfate and concentrated to furnish a brown solid. The final product was subsequently purified by preparative HPLC to provide 4-benzylsulfanylmethyl-N-(4-isopropyl-phenyl)-[2,5']bithiazolyl-2'4'-diamine (9 mg, 18% yield). $^1$H NMR (DMSO-d$_6$): δ 7.91 (s, 1H), 7.20–7.38 (m, 9H), 6.65 (s, 1H), 5.98 (s, 2H), 3.73 (s, 1H), 3.63 (s, 2H), 2.9 (heptet, J=6.9 Hz, 1H), 1.22–1.24 (d, J=6.9 Hz, 6H). FABMS (M+): 452; FABMS (MNa+): 475.

EXAMPLE N(1)

4'-Amino-2'-(4-methanesulfonyl-phenylamino)-[2,5'] bithiazoyl-4-carboxylic acid trifluoro-acetic acid salt

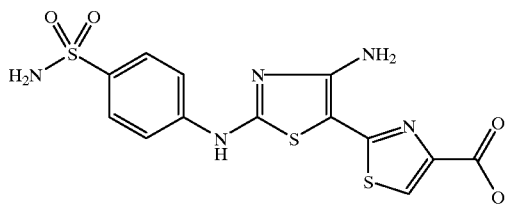

The title compound was prepared as follows: to a solution of 4-Amino-2-(4-sulfamoyl-phenylamino)-thiazol-5-carbothioic acid amide (164 mg, 0.5 mmol) in DMF, bromopyruvic acid (125 mg, 0.75 mmol) was added, and the resultant mixture was stirred at ambient temperature for 2 hours. Following removal of solvent, the residue was dissolved with ethyl acetate and washed with water and brine, then dried with MgSO$_4$. Purification of the residue by preparative HPLC provided the title compound as a yellow power in 34% yield.
$^1$H NMR (DMSO): δδ 10.08 (s, 1H), 8.04 (s, 1H), 7.88–7.78 (m, 4H), 7.31 (s, 4H). HRFABMS (MH$^+$): Calcd.: 398.0051. Found: 398.0059.

EXAMPLE N(2)

4-Amino-2'-(4-sulfamoyl-phenylamino)-[2,5']-bithiazoyl-4-carboxylic acid (2-dimethylamino-ethyl)-amide

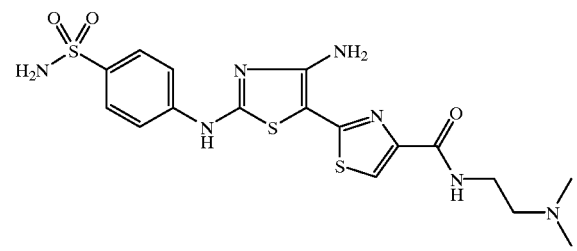

The title compound was prepared as follows: a mixture of 4'-Amino-2'-(4-methanesulfonyl-phenylamino)-[2,5'] bithiazoyl-4-carboxylic acid (64 mg, 0.13 mmol), PyBop (81 mg, 0.16 mmol), N,N-dimethylethylenediamine (28 μl, 0.25 mmol) and DIEA (65 μl, 0.38 mmol) in DMF was stirred at ambient temperature for 2 hours. The solvent was removed under reduced pressure and the residue was dissolved in ethyl acetate. The ethyl acetate solution was extracted with saturated solution of NaHCO$_3$ followed by brine, and dried with MgSO$_4$. Purification of the residue by preparative HPLC provided the title compound as a yellow power in 17% yield.
$^1$HNMR (DMSO): δδ 10.91 (s, 1H), 8.72 (t, 1H, J=12.3), 7.80 (dd, 4H, J=27.1), 7.73 (s, 1H), 7.28 (s, 2H), 7.20 (s, 2H), 2.61–2.51 (m, 4H), 2.25 (s, 6H). HRFABMS (MH$^+$): Calcd.: 468.0946. Found: 468.0955.

In a manner similar to that used to prepare Example N(2), the following Examples N(3) and N(4) were prepared.

EXAMPLE N(3)

4'-Amino-2'-(4-sulfamoyl-phenylamino)-[2,5']bithiazolyl-4-carboxylic acid methoxy-methyl-amide

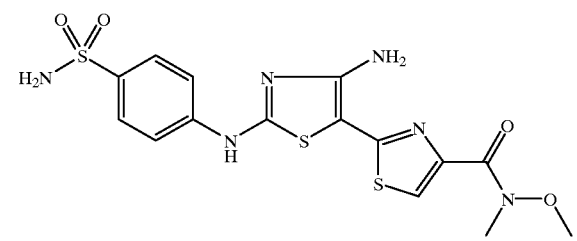

mp 195–198° C.; $^1$H NMR (CD$_3$OD): δ 9.80 (s, NH), 7.80–7.65 (m, 4H), 7.54 (s, 1H), 6.60 (s, NH$_2$), 6.32 (s, NH$_2$), 3.61 (s, 3H), 3.22 (s, 3H). FABMS (MH$^+$): 441.

EXAMPLE N(4)

4'-Amino-2'-(4-sulfamoyl-phenylamino)-[2,5']bithiazolyl-4 carboxylic acid phenylamide

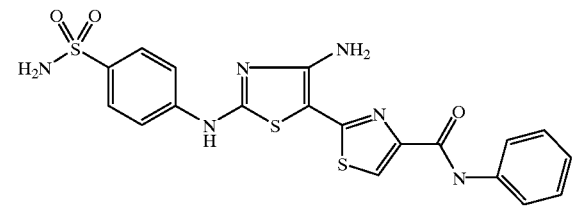

$^1$H NMR (CD$_3$OD): δ 7.91 (s, 1H), 7.88–7.71 (m, 4H), 7.40–7.22 (m, 4H), 7.17–7.09 (m, 1H). FABMS Calcd for C$_{19}$H$_{16}$N$_6$O$_3$S$_3$: 473.0524. Found: 473.0540.

EXAMPLE O(1)

N-[5-(5-{4-Amino-2-[3-(2-morpholin-4-yl-ethyl)-ureido]-thiazol-5-yl}-[1,2,4]oxadiazol-3-yl)-2,4-difluoro-phenyl]-3-methoxy-benzamide

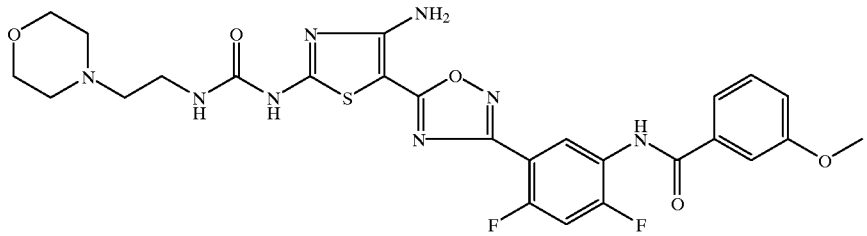

Step(i): A solution of activated carbamate (prepared in step(ii)), amine, and DMF (0.60 mL) were stirred at room temperature for 1 h. The resulting solution was concentrated in vacuo, then purified by "Chromatatron" radial chromatography (10% methanol/methylene chloride), giving 35 mg (72% yield) of the title compound as a white solid.
Anal. Calcd. for $C_{26}H_{26}F_2N_8O_5S \cdot 1.2\ H_2O$: C, 50.19; H, 4.60; N, 18.01; S, 5.15. Found: C, 50.16; H, 4.35; N, 17.95; S, 5.22. ESIMS (MH$^+$): 601.

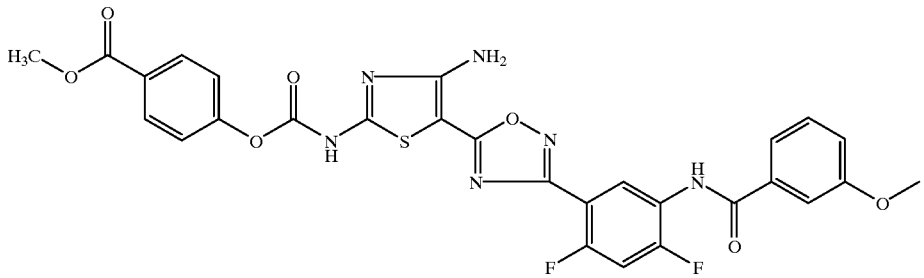

Step(ii): Preparation of the activated carbamate (4-{4-Amino-5-[3-(2,4-difluoro-5-{[1-(3-methoxy-phenyl)-methanoyl]-amino}-phenyl)-[1,2,4]oxadiazol-5-yl]-thiazol-2-ylcarbamoyloxy}-benzoic acid methyl ester). A solution of N-{5-[5-(2,4-Diamino-thiazol-5-yl)-[1,2,4]oxadiazol-3-yl]-2,4-difluoro-phenyl}-3-methoxy-benzamide (533 mg, 1.20 mmol) prepared analogously to example E(1), dissolved in anhydrous THF (20.0 mL) and anhydrous N-methylpyrolidinone (1.0 mL) at −78° C., was treated with phenyllithium (0.660 mL, 01.20 mmol), followed by p-carboxymethyl chloroformate (772 mg, 3.60 mmol) dissolved in anhydrous THF (5.0 mL), in one portion (internal temperature rose to −55° C.). After 5 minutes a second portion of phenyllithium (0.660 mL, 1.20 mmol) was added slowly. After stirring for an additional 15 minutes the reaction was quenched with acetic acid (0.30 mL), warmed to room temperature, diluted with ethyl acetate, extracted with 1:1 mixture of brine and sodium bicarbonate solution, dried with magnesium sulfate, and filtered. The resulting solution was concentrated in vacuo until only ~50 ml of solvent remained, and a white precipitate had formed. The white solid was collected by filtration, giving 446 mg (60% yield) of the activated carbamate. ESIMS (MNa$^+$): 645.

The following examples O(2) through O(32) were prepared in manner analogous to O(1).

EXAMPLE O(2)

N-{5-[5-(4-Amino-2-{3-[3-(2-oxo-pyrrolidin-1-yl)-propyl]-ureido}-thiazol-5-yl)-1,2,4]oxadiazol-3-yl]-2,4-difluoro-phenyl}-3-methoxy-benzamide

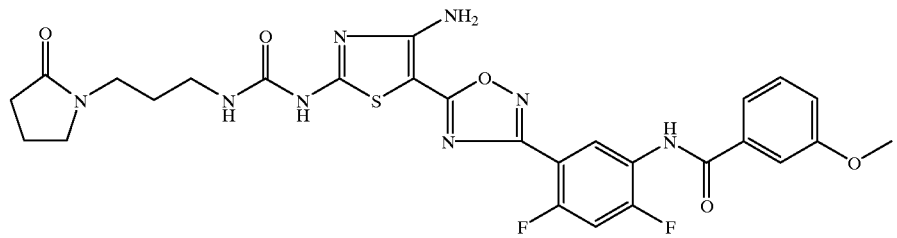

Anal. Calcd. for $C_{27}H_{26}F_2N_8O_5S \cdot 1.5\ H_2O$: C, 50.07; H, 4.57; N, 17.52; S, 5.01. Found: C, 50.60; H, 4.58; N, 17.42; S, 5.17. ESIMS (MH$^+$): 613.

EXAMPLE O(3)
N-(5-{5-[4-Amino-2-(3-carbamoylmethyl-ureido)-thiazol-5-yl]-[1,2,4]oxadiazol-3-yl}-2,4-difluoro-phenyl)-3-methoxy-benzamide

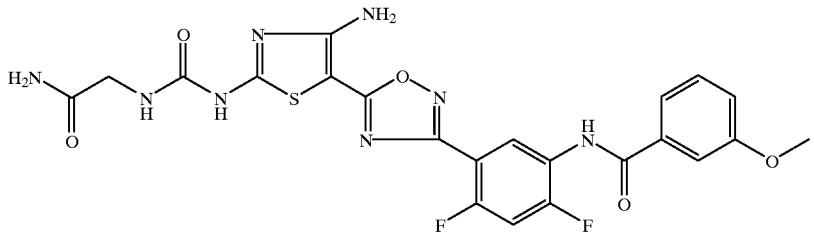

Anal. Calcd. for $C_{22}H_{18}F_2N_8O_5S \cdot 0.6\ H_2O$: C, 47.86; H, 4.05; N, 20.09; S, 5.11. Found: C, 47.92; H, 3.95; N, 20.01; S, 5.44. ESIMS (MNa$^+$): 567.

EXAMPLE O(4)
N-(5-{5-[4-Amino-2-(3-methyl-ureido)-thiazol-5-yl]-[1,2,4]oxadiazol-3-yl}-2,4-difluoro-phenyl)-3-methoxy-benzamide

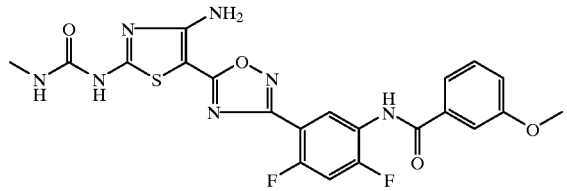

Anal. Calcd. for $C_{21}H_{17}F_2N_7O_4S \cdot (0.9\ DMF,\ 0.5\ H_2O)$: C, 49.47; H, 4.10; N, 19.23; S, 5.57. Found: C, 49.58; H, 4.24; N, 19.33; S, 5.63. ESIMS (M–H$^-$): 500.

EXAMPLE O(5)
N-[5-(5-{4-Amino-2-[3-(tetrahydro-furan-2-ylmethyl)-ureido]-thiazol-5-yl}-[1,2,4]oxadiazol-3-yl)-2,4-difluoro-phenyl]-3-methoxy-benzamide

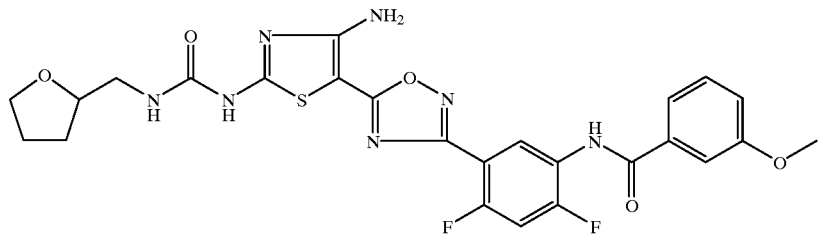

Anal. Calcd. for $C_{25}H_{23}F_2N_7O_5S \cdot 0.5\ H_2O$: C, 51.72; H, 4.17; N, 16.89; S, 5.52. Found: C, 51.61; H, 4.09; N, 16.87; S, 5.57. ESIMS (MNa$^+$): 594.

EXAMPLE O(6)
N-{5-[5-(4-Amino-2-{3-[2-(2-hydroxy-ethoxy)-ethyl]-ureido}-thiazol-5-yl)-[1,2,4]oxadiazol-3-yl]-2,4-difluoro-phenyl}-3-methoxy-benzamide

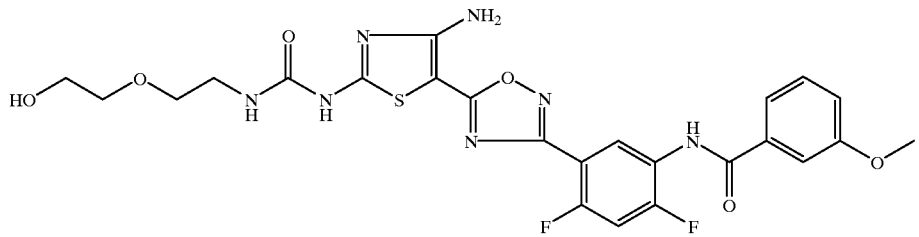

Anal. Calcd. for $C_{24}H_{23}F_2N_7O_6S \cdot 1.0\ H_2O$: C, 48.56; H, 4.25; N, 16.52; S, 5.40. Found: C, 48.67; H, 4.04; N, 16.63; S, 5.50. ESIMS (M–H$^-$): 574.

EXAMPLE O(7)
N-(5-{5-[4-Amino-2-(3-isobutyl-ureido)-thiazol-5-yl]-[1,2,4]oxadiazol-3-yl}-2,4-difluoro-phenyl)-3-methoxy-benzamide

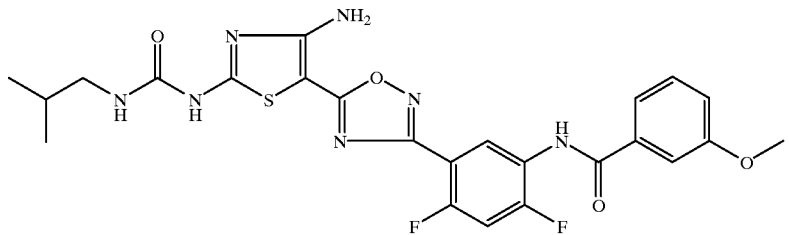

Anal. Calcd. for $C_{24}H_{23}F_2N_7O_4S \cdot 0.6\ H_2O$: C, 52.00; H, 4.40; N, 17.69; S, 5.78. Found: C, 52.02; H, 4.29; N, 17.87; S, 5.85. ESIMS (MH$^+$): 544.

EXAMPLE O(8)
N-(5-{5-[4-Amino-2-(3-pyridin-2-ylmethyl-ureido)-thiazol-5-yl]-[1,2,4]oxadiazol-3-yl}-2,4-difluoro-phenyl)-3-methoxy-benzamide

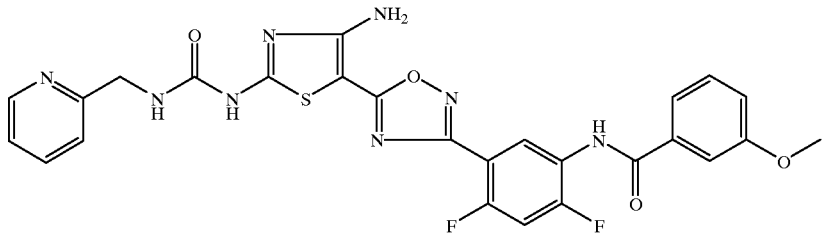

Anal. Calcd. for $C_{26}H_{20}F_2N_8O_4S \cdot 1.0\ H_2O$: C, 52.34; H, 3.72; N, 18.78; S, 5.37. Found: C, 52.24; H, 3.75; N, 18.74; S, 5.32. ESIMS (MH$^+$): 579.

EXAMPLE O(9)
N-(5-{5-[4-Amino-2-(3-pyridin-3-ylmethyl-ureido)-thiazol-5-yl]-[1,2,4]oxadiazol-3-yl}-2,4-difluoro-phenyl)-3-methoxy-benzamide

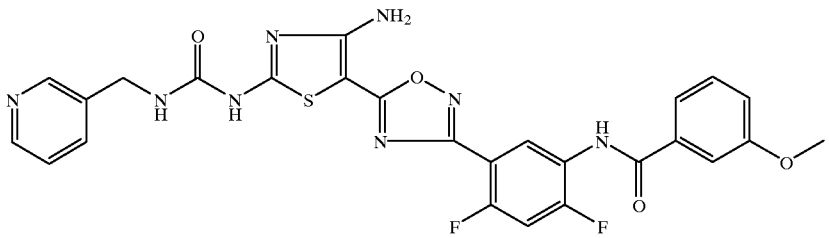

Anal. Calcd. for $C_{26}H_{20}F_2N_8O_4S \cdot 0.8\ H_2O$: C, 52.66; H, 3.67; N, 18.90; S, 5.41. Found: C, 52.57; H, 3.99; N, 18.92; S, 5.16. ESIMS (MH$^+$): 579.

EXAMPLE O(10)
N-[5-(5-{4-Amino-2-[3-(2-hydroxy-ethyl)-ureido]-thiazol-5-yl}-[1,2,4]oxadiazol-3-yl)-2,4-difluoro-phenyl]-3-methoxy-benzamide

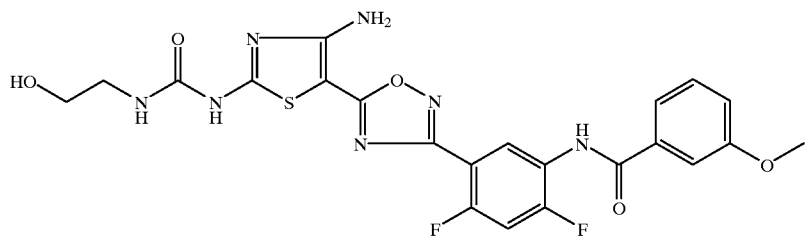

Anal. Calcd. for $C_{22}H_{19}F_2N_7O_5S$: C, 49.72; H, 3.6; N, 18.45; S, 6.03. Found: C, 49.45; H, 3.80; N, 18.30; S, 5.97. ESIMS (M–H$^-$): 530.

EXAMPLE O(11)
N-[5-(5-{4-Amino-2-[3-(trans-4-hydroxy-cyclohexyl)-ureido]-thiazol-5-yl}-[1,2,4]oxadiazol-3-yl)-2,4-difluoro-phenyl]-3-methoxy-benzamide

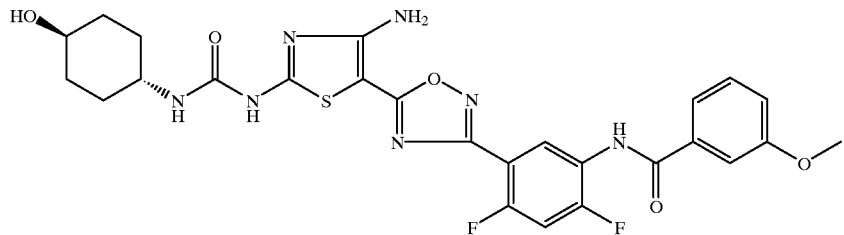

Anal. Calcd. for $C_{26}H_{25}F_2N_7O_5S \cdot 2.8\ H_2O$: C, 49.10; H, 4.85; N, 15.42; S, 5.04. Found: C, 49.06; H, 4.71; N, 15.39; S, 4.79. ESIMS (M–H$^-$): 584.

EXAMPLE O(12)
N-[3-(5-{4-Amino-2-[3-(3-morpholin-4-yl-propyl)-ureido]-thiazol-5-yl}-[1,2,4]oxadiazol-3-yl)-phenyl]-3-methyl-benzamide

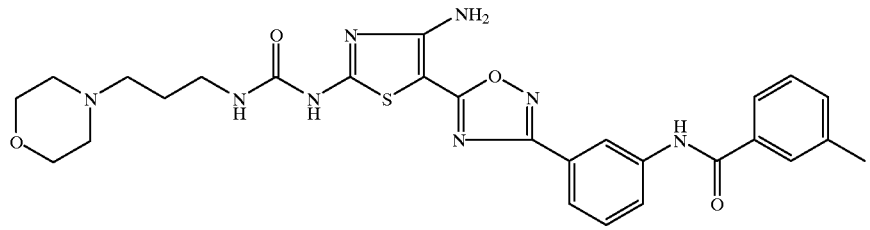

Anal. Calcd. for $C_{27}H_{30}N_8O_4S \cdot 1.5\ H_2O$: C, 54.99; H, 5.64; N, 19.00; S, 5.44. Found: C, 54.83; H, 45.49; N, 18.50; S, 15.30. ESIMS (MH$^+$): 563.

EXAMPLE O(13)
N-{5-[4'-Amino-2'-(3-benzyl-ureido)-[2,5']bithiazolyl-4-yl]-2,4-difluoro-phenyl}-3-methoxy-benzamide

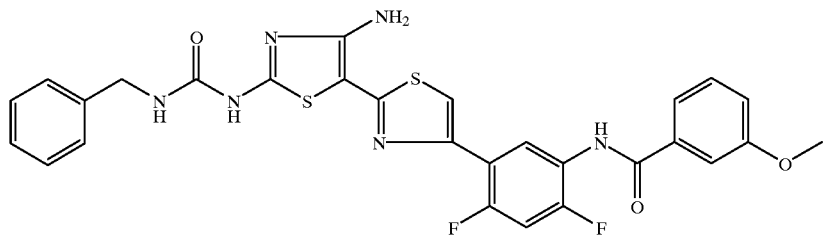

Anal. Calcd. for $C_{28}H_{22}F_2N_6O_3S_2$: C, 56.75; H, 3.74; N, 14.18; S, 10.82. Found: C, 56.70; H, 3.85; N, 14.09; S, 10.70. ESIMS (MH⁺): 593.

EXAMPLE O(14)
N-(5-{4'-Amino-2'-[3-(2-methoxy-1-methyl-ethyl)-ureido]-[2,5']bithiazolyl-4-yl}-2,4-difluoro-phenyl)-3-methoxy-benzamide

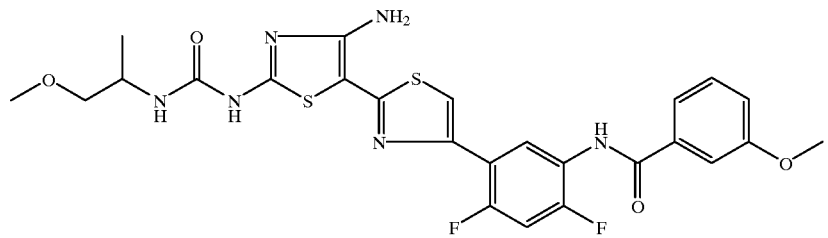

Anal. Calcd. for $C_{25}H_{24}F_2N_6O_4S_2$: C, 52.25; H, 4.21; N, 14.63; S, 11.16. Found: C, 52.06; H, 4.21; N, 14.55; S, 11.09. MALDI FTMS (MH⁺): 575.1341, Found 575.1342.

EXAMPLE O(15)
N-[5-(4'-Amino-2'-{3-[3-(2-oxo-pyrolidin-1-yl)-propyl]-ureido}-[2,5']bithiazolyl-4-yl)-2,4-difluoro-phenyl]-3-methoxy-benzamide

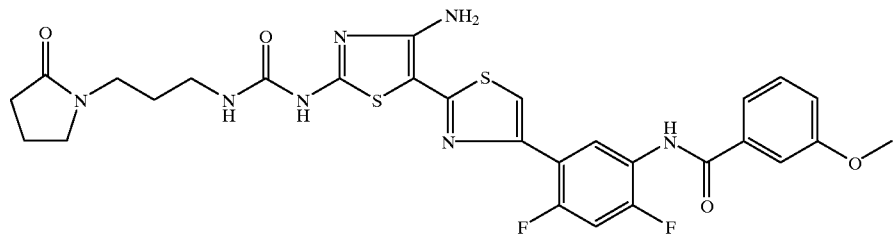

Anal. Calcd. for $C_{28}H_{27}F_2N_7O_4S_2 \cdot 1.1\ H_2O$: C, 51.94; H, 4.55; N, 15.14; S, 9.90. Found: C, 52.38; H, 4.79; N, 14.64; S, 9.48. MALDI FTMS (MNa⁺): 650.1426, Found 650.1344.

EXAMPLE O(16)
N-{5-[4'-Amino-2'-(3-pyridin-2-ylmethyl-ureido)-[2,5']bithiazolyl-4-yl]-2,4-difluoro-phenyl}-3-methoxy-benzamide

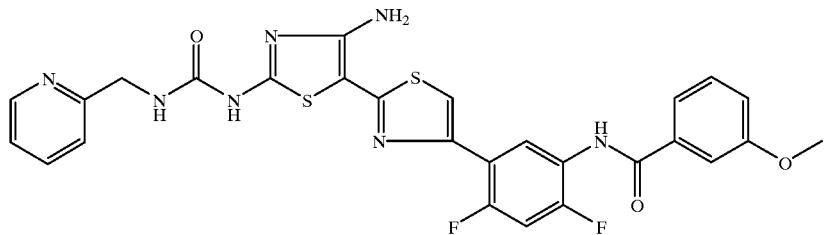

Anal. Calcd. for $C_{27}H_{21}F_2N_7O_3S_2$: C, 54.63; H, 3.57; N, 16.52; S, 10.80. Found: C, 54.44; H, 3.68; N, 16.33; S, 10.60. MALDI FTMS (MH$^+$): 594.1188, Found 594.1191.

EXAMPLE O(17)
N-{5-[4'-Amino-2'-(3-pyridin-3-ylmethyl-ureido)-[2,5']bithiazolyl-4-yl]-2,4-difluoro-phenyl}-3-methoxy-benzamide

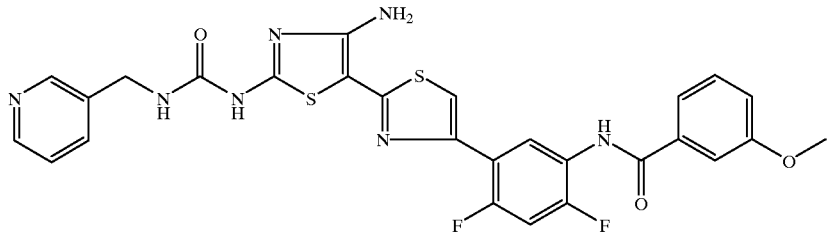

Anal. Calcd. for $C_{27}H_{21}F_2N_7O_3S_2 \cdot 0.5\ H_2O$: C, 53.81; H, 3.68; N, 16.27; S, 10.64. Found: C, 53.95; H, 3.78; N, 16.21; S, 10.68. MALDI FTMS (MH$^+$): 594.1188, Found 594.1185.

EXAMPLE O(18)
N-{5-[4'-Amino-2'-(3-pyridin-4-ylmethyl-ureido)-[2,5']bithiazolyl-4-yl]-2,4-difluoro-phenyl}-3-methoxy-benzamide

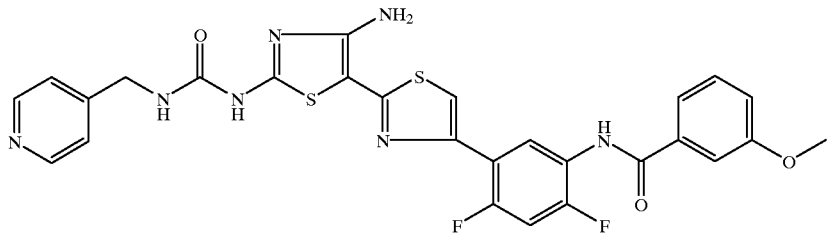

Anal. Calcd. for $C_{27}H_{21}F_2N_7O_3S_2 \cdot 0.5\ H_2O$: C, 53.81; H, 3.68; N, 16.27; S, 10.64. Found: C, 53.83; H, 3.60; N, 16.33; S, 10.80. MALDI FTMS (MH$^+$): 594.1188, Found 594.1198.

EXAMPLE O(19)

N-(5-{4'-Amino-2'-[3-((R)-2-hydroxy-propyl)-ureido]-[2,5']bithiazolyl-4-yl}-2,4-difluoro-phenyl)-3-methoxy-benzamide

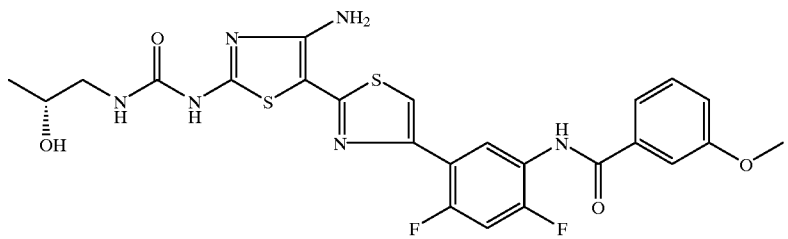

Anal. Calcd. for $C_{24}H_{22}F_2N_6O_4S_2$: C, 51.42; H, 3.96; N, 14.99; S, 11.44. Found: C, 50.95; H, 4.12; N, 14.97; S, 11.22. MALDI FTMS (MH$^+$): 561.1185, Found 561.1212.

EXAMPLE O(20)

N-(5-{4'-Amino-2'-[3-((S)-2-hydroxy-propyl)-ureido]-[2,5']bithiazolyl-4-yl}-2,4-difluoro-phenyl)-3-methoxy-benzamide

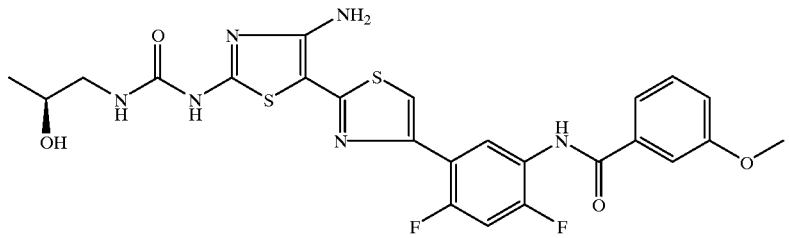

Anal. Calcd. for $C_{24}H_{22}F_2N_6O_4S_2 \cdot 1.0\ H_2O$: C, 49.82; H, 4.18; N, 14.53; S, 11.08. Found: C, 49.77; H, 3.92; N, 14.74; S, 10.96. ESIMS (MNa$^+$): 583.

EXAMPLE O(21)

N-(5-{4'-Amino-2'-[3-((R)-1-hydroxymethyl-propyl)-ureido]-[2,5']bithiazolyl-4-yl}-2,4-difluoro-phenyl)-3-methoxy-benzamide

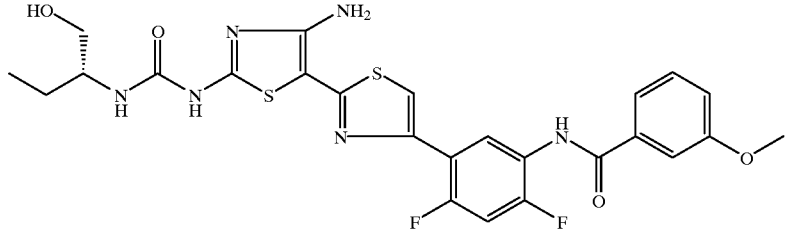

Anal. Calcd. for $C_{25}H_{24}F_2N_6O_4S_2 \cdot 0.5\ H_2O$: C, 51.45; H, 4.32; N, 14.40; S, 10.99. Found: C, 51.32; H, 4.30; N, 14.53; S, 11.06. ESIMS (MNa$^+$): 597.

EXAMPLE O(22)

N-(5-{4'-Amino-2'-[3-((S)-1-hydroxymethyl-propyl)-ureido]-[2,5']bithiazolyl-4-yl}-2,4-difluoro-phenyl)-3-methoxy-benzamide

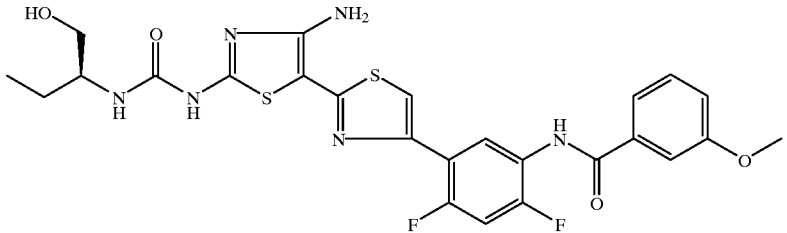

Anal. Calcd. for $C_{25}H_{24}F_2N_6O_4S_2 \cdot 0.5\ H_2O$: C, 51.45; H, 4.32; N, 14.40; S, 10.99. Found: C, 51.49; H, 4.26; N, 14.66; S, 11.16. ESIMS (MNa$^+$): 597.

EXAMPLE O(23)

N-[5-(4'-Amino-2'-{3-[(S)-1-(tetrahydro-furan-2-yl)methyl]-ureido}-[2,5']bithiazolyl-4-yl)-2,4-difluoro-phenyl]-3-methoxy-benzamide

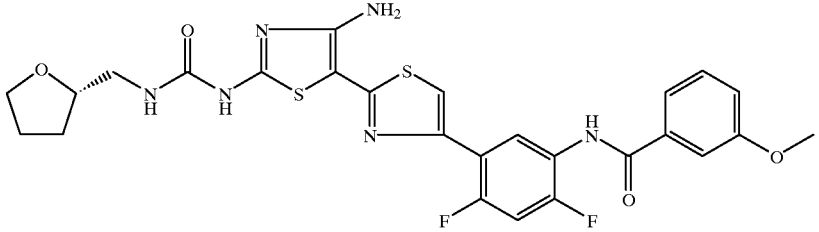

Anal. Calcd. for $C_{26}H_{24}F_2N_6O_4S_2 \cdot 0.5\ H_2O$: C, 52.43; H, 4.23; N, 14.11; S, 10.77. Found: C, 52.55; H, 4.29; N, 14.44; S, 10.53. ESIMS (M–H$^-$): 585.

EXAMPLE O(24)

N-[5-(4'-Amino-2'-{3-[(R)-1-(tetrahydro-furan-2-yl)methyl]-ureido}-[2,5']bithiazolyl-4-yl)-2,4-difluoro-phenyl]-3-methoxy-benzamide

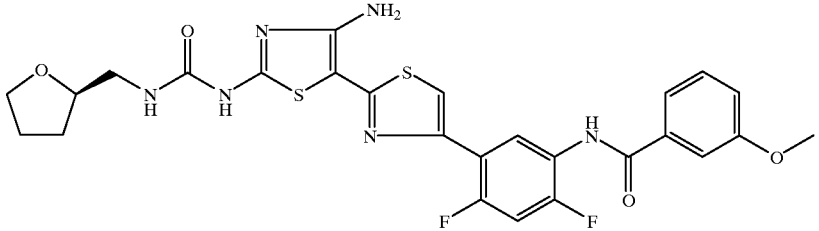

Anal. Calcd. for $C_{26}H_{24}F_2N_6O_4S_2 \cdot 0.6\ H_2O$: C, 52.27; H, 4.25; N, 14.07; S, 10.73. Found: C, 52.29; H, 4.33; N, 14.33; S, 10.55. ESIMS (M–H$^-$): 585.

EXAMPLE O(25)
N-{5-[4'-Amino-2'-(3-cyclohexylmethyl-ureido)-[2,5']bithiazolyl-4-yl]-2,4-difluoro-phenyl}-3-methoxy-benzamide

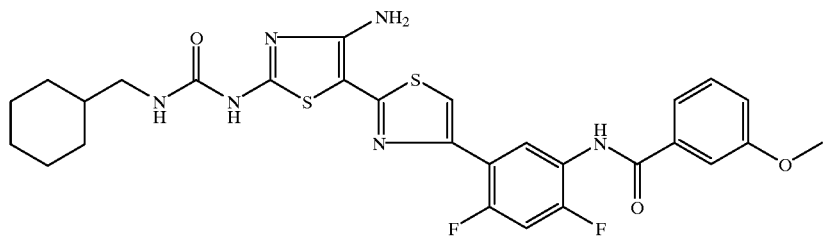

Anal. Calcd. for $C_{28}H_{28}F_2N_6O_3S_2 \cdot 0.5\ H_2O$: C, 55.34; H, 4.81; N, 13.83; S, 10.55. Found: C, 55.26; H, 4.78; N, 14.00; S, 10.56. MALDI FTMS (MH$^+$): 599.1705, Found 621.1525.

EXAMPLE O(26)
N-(5-{4'-Amino-2'-[3-(2-morpholin-4-yl-ethyl)-ureido]-[2,5']bithiazolyl-4-yl}-2,4-difluoro-phenyl)-3-methoxy-benzamide

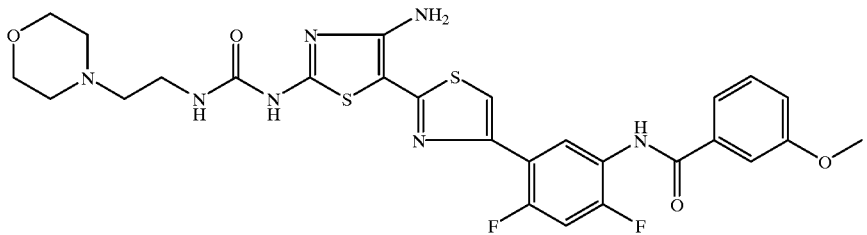

Anal. Calcd. for $C_{27}H_{27}F_2N_7O_4S_2 \cdot 1.0\ H_2O$: C, 51.17; H, 4.61; N, 15.47; S, 10.12. Found: C, 51.00; H, 4.39; N, 15.12; S, 9.75. MALDI FTMS (MH$^+$): 616.1607, Found 616.1597.

EXAMPLE O(27)
N-(5-{4'-Amino-2'-[3-(2-pyrrolidin-1-yl-ethyl)-ureido]-[2,5']bithiazolyl-4-yl}-2,4-difluoro-phenyl)-3-methoxy-benzamide

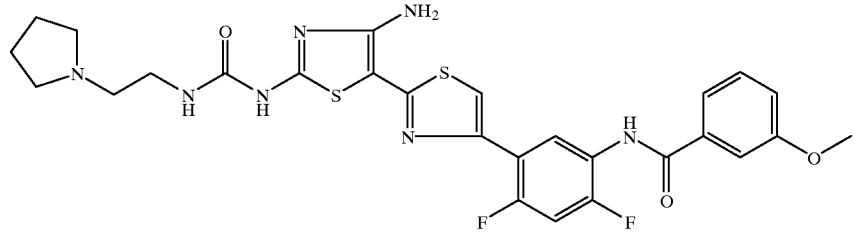

Anal. Calcd. for $C_{27}H_{27}F_2N_7O_3S_2$: C, 54.08; H, 4.54; N, 16.35; S, 10.69. Found: C, 53.93; H, 4.66; N, 16.11; S, 10.51. MALDI FTMS (MH$^+$): 600.1658, Found 600.1640.

EXAMPLE O(28)
N-[5-(4'-Amino-2'-{3-[2-(2-hydroxy-ethoxy)-ethyl]-ureido}-[2,5']bithiazolyl-4-yl)-2,4-difluoro-phenyl]-3-methoxy-benzamide

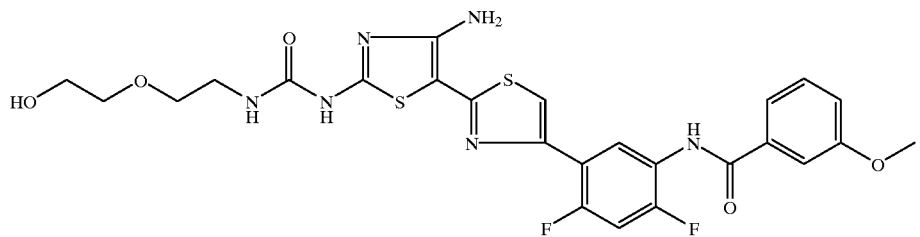

Anal. Calcd. for $C_{25}H_{24}F_2N_6O_5S_2 \cdot 1.0\ H_2O$: C, 49.33; H, 4.31; N, 13.81; S, 10.54. Found: C, 49.47; H, 4.08; N, 13.87; S, 10.49. MALDI FTMS (MH$^+$): 591.1290, Found 591.1276.

EXAMPLE O(29)
N-(5-{4'-Amino-2'-[3-(2-pyridin-2-yl-ethyl)-ureido]-[2,5']bithiazolyl-4-yl}-2,4-difluoro-phenyl)-3-methoxy-benzamide

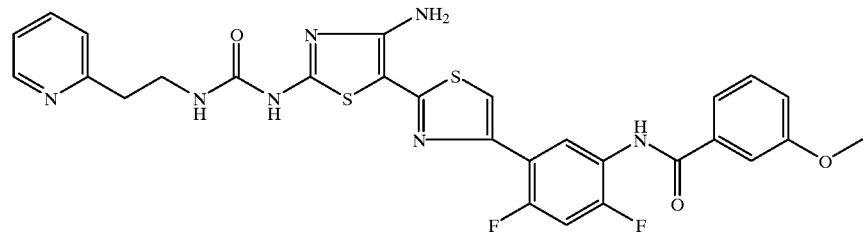

Anal. Calcd. for $C_{28}H_{23}F_2N_7O_3S_2 \cdot 1.8\ H_2O$: C, 52.54; H, 4.19; N, 15.32; S, 10.02. Found: C, 52.56; H, 4.07; N, 15.54; S, 10.03. MALDI FTMS (MH$^+$): 608.1345, Found 608.1346.

EXAMPLE O(30)
N-(5-{4'-Amino-2'-[3-(2-pyridin-4-yl-ethyl)-ureido]-[2,5']bithiazolyl-4-yl}-2,4-difluoro-phenyl)-3-methoxy-benzamide

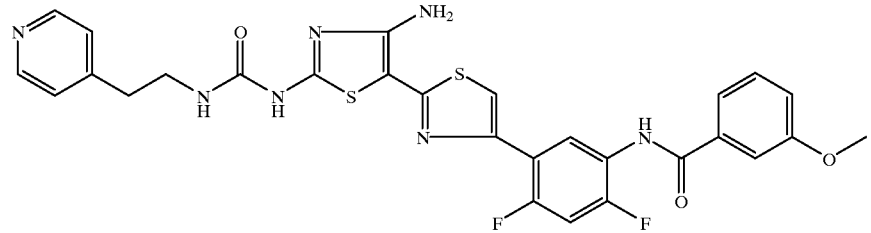

Anal. Calcd. for $C_{28}H_{23}F_2N_7O_3S_2 \cdot 1.0\ H_2O$: C, 53.75; H, 4.03; N, 15.67; S, 10.25. Found: C, 53.32; H, 4.01; N, 15.50; S, 9.90. MALDI FTMS (MH$^+$): 608.1345, Found 608.1327.

EXAMPLE O(31)
N-{3-[4'-Amino-5-methyl-2'-(3-methyl-ureido)-[2,5'] bithiazolyl-4-yl]-phenyl}-3-methoxy-benzamide

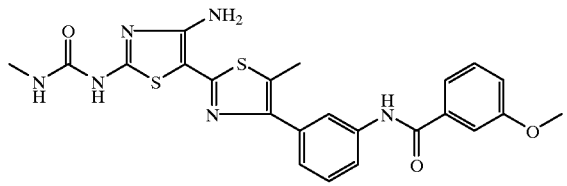

The precursor (N-[3-(2',4'-Diamino-5-methyl-[2,5'] bithiazolyl-4-yl)-phenyl]-3-methoxy-benzamide) to the activated carbamate from which this example was prepared, was synthesized analogously to example E(3) only starting with 3-aminopropiophenone rather than 3-aminoacetophenone. Anal. Calcd. for $C_{23}H_{22}N_6O_3S_2 \cdot 0.6 \, H_2O$: C, 54.66; H, 4.63; N, 16.63; S, 12.69. Found: C, 54.50; H, 4.48; N, 16.77; S, 12.70. ESIMS (MH$^+$): 495.

EXAMPLE O(32)
N-(5-{4'-Amino-2'-[3-(2-pyridin-3-yl-ethyl)-ureido]-[2,5'] bithiazolyl-4-yl}-2,4-difluoro-phenyl)-3-methoxy-benzamide

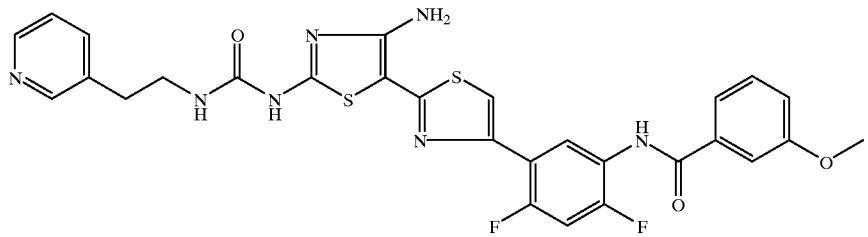

Anal. Calcd. for $C_{28}H_{23}F_2N_7O_3S_2 \cdot 0.5 \, H_2O$: C, 54.53; H, 3.92; N, 15.90; S, 10.40. Found: C, 54.35; H, 4.02; N, 16.05; S, 10.30. ESIMS (MH$^+$): 608. The exemplary compounds described above may be tested for their activity as described below.

BIOLOGICAL TESTING; ENZYME ASSAYS

The stimulation of cell proliferation by growth factors such as VEFG, FGF, and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

VEGF-R2 Construct for Assay: This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ50 contains residues 806–939 and 990–1171, and also one point mutation (E990V) within the kinase insert domain relative to wild-type VEGF-R2. Autophosphorylation of the purified construct was performed by incubation of the enzyme at a concentration of 4 μM in the presence of 3 mM ATP and 40 mM MgCl$_2$ in 100 mM Hepes, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., Biochemistry, 37, 16788–16801 (1998).

FGF-R1 Construct for Assay: The intracellular kinase domain of human FGF-R1 was expressed using the baculovirus vector expression system starting from the endogenous methionine residue 456 to glutamate 766, according to the residue numbering system of Mohammadi et al., Mol. Cell. Biol., 16, 977–989 (1996). In addition, the construct also has the following 3 amino acid substitutions: L457V, C488A, and C584S.

LCK Construct for Assay: The LCK tyrosine kinase was expressed in insect cells as an N-terminal deletion starting from amino acid residue 223 to the end of the protein at residue 509, with the following two amino acid substitutions at the N-terminus: P233M and C224D.

CHK-1 Construct for Assay: C-terminally His-tagged full-length human CHK1 (FL-CHK1) was expressed using the baculovirus/insect cell system. It contains 6 histidine residues (6×His-tag) at the C-terminus of the 476 amino acid human CHK1. The protein was purified by conventional chromatographic techniques.

CDK2/Cyclin A Construct for Assay: CDK2 was purified using published methodology (Rosenblatt et al., J. Mol. Biol., 230, 1317–1319 (1993)) from insect cells that had been infected with a baculovirus expression vector. Cyclin A was purified from E. coli cells expressing full-length recombinant cyclin A, and a truncated cyclin A construct was generated by limited proteolysis and purified as described previously (Jeffrey et al., Nature, 376, 313–320 (Jul. 27, 1995)).

CDK4/Cyclin D Construct for Assay: A complex of human CDK4 and cyclin D3, or a complex of cyclin DI and a fusion protein of human CDK4 and glutathione-S-transferase (GST-CDK4), was purified using traditional biochemical chromatographic techniques from insect cells that had been co-infected with the corresponding baculovirus expression vectors.

FAK Construct for Assay. The catalytic domain of human FAK (FAKcd409) was expressed using the baculovirus vector expression system. The 280 amino acid domain expressed comprises residues methionine 409 to glutamate 689. One amino acid substitution exists (P410T) relative to the sequence assession number L13616 published by Whithey, G. S. et al., DNA Cell Biol 9, 823–830, 1993. The protein was purified using classical chromatography techniques.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2Δ50 (indicated as FLVK-P in the tables below) were the following: 1 mM PEP; 250 μM NADH; 50 units of LDH/mL; 20 units of PK/mL; 5 mM DTT; 5.1 mM poly($E_4Y_1$); 1 mM ATP; and 25 mM MgCl$_2$ in 200 mM Hepes, pH 7.5. Assay conditions for unphosphorylated VEGF-R2Δ50 (indicated as FLVK in the tables) were the following: 1 mM PEP; 250 μM NADH; 50 units of LDH/mL; 20 units of PK/mL; 5 mM DTT; 20 mM poly($E_4Y_1$); 3 mM ATP; and 60 mM MgCl$_2$ and 2 mM MnCl$_2$ in 200 mM Hepes, pH 7.5. Assays were initiated with 5 to 40 nM of enzyme. $K_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1–17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azino-di-[3-ethylbenzathiazoline sulfonate(6)] diammonium salt (ABTS). Typical assay solutions contained: 2 μM biotinylated gastrin peptide; 5 mM DTT; 20 μM ATP; 26 mM MgCl$_2$; and 2 mM MnCl$_2$ in 200 mM Hepes, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid (H$_2$SO$_4$), followed by absorbance reading at 405 nm. $K_i$ values were determined by measuring enzyme activity in the presence of varying concentrations of test compounds. The data were analyzed using Enzyme Kinetic and Kaleidagraph software.

FGF-R Assay

The spectrophotometric assay was carried out as described above for VEGF-R2, except for the following changes in concentration: FGF-R=50 nM, ATP=2 mM, and poly(E4Y1)=15 mM.

LCK Assay

The spectrophotometric assay was carried out as described above for VEGF-R2, except for the following changes in concentration: LCK=60 nM, MgCl$_2$=0 mM, poly(E4Y1)=20 mM.

CHK1 Assay

The production of ADP from ATP that accompanies phosphoryl transfer to the synthetic substrate peptide Syntide-2 (PLARTLSVAGLPGKK) was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm ($\epsilon$340=6.22 cm$^{-1}$ mM$^{-1}$) using a HP8452 spectrophotometer. Typical reaction solutions contained: 4 mN PEP; 0.15 mM NADH; 28 units of LDH/ml; 16 units of PK/ml; 3 mM DTT; 0.125 mM Syntide-2; 0.15 mM ATP; 25 mM MgCl$_2$ in 50 mM TRIS, pH 7.5; and 400 mM NaCl. Assays were initiated with 10 nM of FL-CHK1. $K_i$ values were determined by measuring initial enzyme activity in the presence of varying concentrations of test compounds. The data were analyzed using Enzyme Kinetic and Kaleidagraph software.

CDK2/Cyclin A and CDK4/Cyclin D Assays

Cyclin-dependent kinase activity was measured by quantifying the enzyme-catalyzed, time-dependent incorporation of radioactive phosphate from [$^{32}$P]ATP into a recombinant fragment of the retinoblastoma protein. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM β-glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.2 μCi [$^{32}$P]ATP. The substrate (0.3–0.5 μg) was purified recombinant retinoblastoma protein fragment (Rb) (residues 386–928 of the native retinoblastoma protein; 62.3 kDa, containing the majority of the phosphorylation sites found in the native 106-kDa protein, as well as a tag of six histidine residues for ease of purification). Reactions were initiated with CDK2 (150 nM CDK2/Cyclin A complex) or CDK4 (50 nM CDK4/Cyclin D3 complex), incubated at 30° C., and terminated after 20 minutes by the addition of ethylenediaminetetraacetic acid EDTA) to 250 mM. The phosphorylated substrate was then captured on a nitrocellulose membrane using a 96-well filtration manifold, and unincorporated radioactivity was removed by repeated washing with 0.85% phosphoric acid. Radioactivity was quantified by exposing the dried nitrocellulose membranes to a phosphorimager. Apparent $K_i$ values were measured by assaying enzyme activity in the presence of different compound concentrations and subtracting the background radioactivity measured in the absence of enzyme. The kinetic parameters (kcat, Km for ATP) were measured for each enzyme under the usual assay conditions by determining the dependence of initial rates on ATP concentration. The data were fit to an equation for competitive inhibition using Kaleidagraph (Synergy Software), or were fit to an equation for competitive tight-binding inhibition using the software KineTic (BioKin, Ltd.). Measured $K_i$ values for known inhibitors against CDK4 and CDK2 agreed with published IC$_{50}$ values. The specific activity of CDK4 was the same whether complexed to full-length cyclin D3 or the truncated Cyclin D3 construct; both complexes also yielded very similar $K_i$ values for selected inhibitors.

FAK Assay

FAK HTS utilized the fluorescence polarization assay provided by LJL Biosystems. The kinase reaction contained: 100 mM Hepes pH 7.5, 10 mM MgCl$_2$, 1 mM DTT, 1 mM ATP, and 1 mg/ml poly Glu-Tyr (4:1). The reaction is initiated by the addition of 5 nM FAKcd409. The reaction is terminated by the addition of EDTA followed by addition of fluor-labelled peptide and anti-phosphotyrosine antibody, both provided by LJL Biosystems. Inhibition results are read on a Analyst (LJL) detector.

HUVEC Proliferation Assay

This assay determines the ability of a test compound to inhibit the growth factor-stimulated proliferation of human umbilical vein endothelial cells ("HUVEC"). HUVEC cells (passage 3-4, Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 μg/ml endothelial cell growth supplement (ECGS), and 0.1 mg/ml heparin). Exponentially-growing HUVEC cells were used in experiments thereafter. Ten to twelve thousand HUVEC cells were plated in 96-well dishes in 100 µl of rich, culture medium (described above). The cells were allowed to attach for 24 hours in this medium. The medium was then removed by aspiration and 105 µl of starvation media (F12K+1% FBS) was added to each well. After 24 hours, 15 µl of test agent dissolved in 1% DMSO in starvation medium or this vehicle alone was added into each treatment well; the final DMSO concentration was 0.1%. One hour later, 30 µl of VEGF (30 ng/ml) in starvation media was added to all wells except those containing untreated controls; the final VEGF concentration was 6 ng/ml. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595 λ was determined on a 96-well spectrophotometer plate reader.

$IC_{50}$ values were calculated by curve-fitting the response of $A^{595}$ to various concentrations of the test agent; typically, seven concentrations separated by 0.5 log were employed, with triplicate wells at each concentration. For screening compound library plates, one or two concentrations (one well per concentration) were employed, and the % inhibition was calculated by the following formula:

% inhibition=(control−test) divided by (control−starvation)

where control=$A^{595}$ when VEGF is present without test agent test=$A^{595}$ when VEGF is present with test agent starvation=$A^{595}$ when VEGF and test agent are both absent.

Cancer Cell Proliferation (MV522) Assay

To determine the whether a protein kinases inhibitor should have therapeutic usefulness in treating cancer, it is important to demonstrate the inhibitor's ability to block cellular proliferation in response to a growth factor that is involved in mediating a proliferative disorder. The protocol for assessing cellular proliferation in cancer cells is similar to that used for assessments in HUVEC cells. Two thousand lung cancer cells (line MV522, acquired from American Tissue Cultural Collection) were seeded in growth media (RPMI1640 medium supplemented with 2 mM glutamine and 10% FBS). Cells are allowed to attach for 1 day prior to addition of test agents and/or vehicles. Cells are treated simultaneously with the same test agents used in the HUVEC assay. Cellular proliferation is quantified by MTT dye reduction assay 72 hours after exposure to test agents. The total length of the assay is 4 days vs. 5 for HUVEC cells because MV522 cells are not exposed to starvation medium.

In Vivo Assay of Retinal Vascular Development in Neonatal Rats

The development of the retinal vascular in rats occurs from postnatal day 1 to postnatal day 14 (P1–P14). This process is dependent on the activity of VEGF (J. Stone, et al, J. Neurosci., 15, 4738 (1995)). Previous work has demonstrated that VEGF also acts as a survival factor for the vessels of the retina during early vascular development (Alon, et. al, Nat. Med., 1, 1024 (1995)). To assess the ability of specific compounds to inhibit the activity of VEGF in vivo, compounds were formulated in an appropriate vehicle, usually 50% polyethylene glycol, average molecular weight 400 daltons, and 50% solution of 300 mM sucrose in deionized water. Typically, two microliters (2 µl) of the drug solution was injected into the midvitreous of the eye of rat pups on postnatal day 8 or 9. Six days after the intravitreal injection, the animals were sacrificed and the retinas dissected free from the remaining ocular tissue. The isolated retinas were then subjected to a histochemical staining protocol that stains endothelial cells specifically (Lutty and McLeod, Arch. Ophthalmol., 110, 267 (1992 )), revealing the extent of vascularization within the tissue sample. The individual retinas are then flat-mount onto glass slides and examined to determine the extent of vascularization. Effective compounds inhibit the further development of the retinal vasculature and induce a regression of all but the largest vessels within the retina. The amount of vessel regression was used to assess the relative potency of the compounds after in vivo administration. Vessel regression is graded on subjective scale of one to three pluses, with one plus being detectable regression judged to be approximately 25 percent or less, two pluses being judged to be approximately 25–75% regression and three pluses give to retinas with near total regression (approximately 75% or greater). In the development model, the compound Example B(30) is one of the most effective compounds tested to date, being graded a two plus (++) when a dose of 2 µl of 5 mg/ml initial drug concentration was given.

In Vivo Assay of Retinal Vascular Development in Neonatal Rat Model of Retinopathy of Prematurity A second model of VEGF dependent retinal neovascularization was employed to evaluate the activities of this series of compounds. In this model (Penn et. al, Invest. Ophthalmol. Vis. Sci., 36, 2063, (1995)), rats pups (n=16) with their mother are placed in a computer controlled chamber that regulates the concentration of oxygen. The animals are exposed for 24 hours to a concentration of 50% oxygen followed by 24 hours at a concentration of 10% oxygen. This alternating cycle of hyperoxia followed by hypoxia is repeated 7 times after which the animals are removed to room air (P14). Compounds are administered via intravitreal injection upon removal to room air and the animals are sacrificed 6 days later (P20). The isolated retinas are then isolated, stained mounted and analyzed as detail above in the development model. The effectiveness was also graded as is described for the development model. Example D(74) is the most effective compound tested to date in this model (++).

The results of the testing of the compounds using various assays are summarized in the tables below, where a notation of "%@" indicates the percent inhibition at the stated concentration and "NI" indicates no inhibition.

TABLE 1

| Example | FLVK-P $K_i$ (nM) | FLVK $K_i$ (nM) | LCK Ki (nM) | CHK-1 $K_i$ (nM) | FGF-R $K_i$ (nM) | CDK2 Ki (nM) | CDK4 Ki (nM) | HUVEC $IC_{50}$ (nM) | MV522 $IC_{50}$ (µM) |
|---|---|---|---|---|---|---|---|---|---|
| A(36) | 36% @ 0.05 | | | | | | | | |
| A(37) | 22% @ 5 | | | | | | | | |
| A(38) | 7% @ 0.05 | | | | | | | | |

TABLE 1-continued

| Example | FLVK-P $K_i$ (nM) | FLVK $K_i$ (nM) | LCK $K_i$ (nM) | CHK-1 $K_i$ (nM) | FGF-R $K_i$ (nM) | CDK2 $K_i$ (nM) | CDK4 $K_i$ (nM) | HUVEC $IC_{50}$ (nM) | MV522 $IC_{50}$ ($\mu$M) |
|---|---|---|---|---|---|---|---|---|---|
| A(39) | 74% @ 1 | | | | | | | | |
| A(40) | 51% @ 1 | | | | | | | | |
| A(41) | 70% @ 1 | | | | | | | | |
| A(42) | 7.3 | | | | | | | | |
| A(43) | 68% @ 1 | | | | | | | | |
| A(44) | 82% @ 1 | | | | | | | | |
| A(45) | 9.7 | | | | | | | | |
| A(46) | 74% @ 1 | | | | | | | | |
| A(47) | 7.9 | | | | | | | | 260 | >10 |
| A(48) | 3.1 | | | | | | | 350 | >10 |
| A(49) | 49% @ 1 | | | | | | | | |
| A(50) | 8.9 | | | | | | | >700 | >10 |
| A(51) | 38% @ 1 | | | | | | | | |
| A(52) | 75% @ 1 | | | | | | | | |
| A(53) | 24 | | | | | | | 370 | >10 |
| A(54) | 1% @ 1 | | | | | | | | |
| A(55) | 14% @ 1 | | | | | | | | |
| A(56) | 84 | | | | | | | | |
| A(57) | 6.7 | | | | | | | | |
| A(58) | 65% @ 1 $\mu$M | | | | | | | | |
| A(59) | NI @ 5 | | | | | | | | |
| A(60) | 11% @ 5 | | | | | | | | |
| B(2) | 16.5 | | | | | | | >700 | 3.65 |
| C(1) | 300* | | | | | | | | |
| D(1) | 46 | | | | | | | | |
| D(10) | 56* | | | | | | | | |
| D(11) | 1.9 | | | | | | | | |
| D(12) | 2 | 2.6 | | | | | | 160 | >10 |
| D(13) | 120* | | | | | | | | |
| D(14) | 120* | | | | | | | | |
| D(15) | 240* | | | | | | | | |
| D(16) | 11.8 | | | | | | | | |
| D(17) | 33% @ 5 | | | | | | | | |
| D(18) | 55% @ 5 | | | | | | | | |
| D(19) | 38% @ 5 | | | | | | | | |
| D(2) | 98 | | | | | | | | |
| D(20) | 3.7 | | | | | | | 990 | >10 |
| D(21) | 60* | | | | | | | 200 | >10 |
| D(22) | 89* | | | | | | | | |
| D(23) | 150 | | | | | | | 130 | >10 |
| D(24) | 1.8 | 2 | | | | | | 110 | >10 |
| D(25) | 1 | | | | | | | 745 | >10 |
| D(26) | 38% @ 5 $\mu$M | | | | | | | | |
| D(27) | 1.8 | | | | | | | 82 | >10 |
| D(28) | 6 | | | | | | | | |
| D(29) | 1.4 | | | | | | | 32 | >10 |
| D(3) | 63 | | | | | | | >700 | >10 |
| D(30) | 2.9 | | | | | | | 48 | >10 |
| D(31) | 4.8 | | | | | | | | |
| D(32) | 3.9 | | | | | | | 59 | >10 |
| D(33) | 3.8 | 3.6 | | | | | | 120 | >10 |
| D(34) | 0.85 | | | | | | | 89 | 9 |
| D(35) | 1.8 | | | | | | | 42 | >10 |
| D(36) | 2 | | | | | | | 43 | >10 |
| D(37) | 3.4 | | | | | | | 150 | >10 |
| D(38) | 0.93 | | | | | | | 40 | >10 |
| D(39) | 1.4 | | | | | | | 62 | >10 |
| D(4) | 7.6* | | | | | | | 240 | >10 |
| D(40) | 1.1 | 1.4 | | | | | | 39 | >10 |
| D(41) | 1.9 | | | | | | | 37 | >10 |
| D(42) | 0.34 | 0.77 | | | | | | 53 | >10 |
| D(43) | 2.9 | | | | | | | 241 | >10 |
| D(44) | 5.4 | 2.1 | | | | | | 373 | >10 |
| D(45) | 43% @ 1 $\mu$M | | | | | | | 235 | 0.65 |
| D(46) | 17.1 | | | | | | | 123 | >10 |
| D(47) | 1.1 | 0.34 | | | | | | 13 | >10 |
| D(48) | 4.1 | | | | | | | 40 | >10 |
| D(49) | 1.6 | | | | | | | 15 | >10 |
| D(5) | 63* | | | | | | | | |
| D(50) | 1.4 | | | | | | | 17 | >10 |
| D(51) | 32* | 0.62 | | | | | | 40 | >10 |

TABLE 1-continued

| Example | FLVK-P $K_i$ (nM) | FLVK $K_i$ (nM) | LCK $K_i$ (nM) | CHK-1 $K_i$ (nM) | FGF-R $K_i$ (nM) | CDK2 $K_i$ (nM) | CDK4 $K_i$ (nM) | HUVEC $IC_{50}$ (nM) | MV522 $IC_{50}$ ($\mu$M) |
|---|---|---|---|---|---|---|---|---|---|
| D(52) | 27% @ 50 | | | | | | | | |
| D(53) | 2.5 | | | | | | | | |
| D(54) | 6.3 | | | | | | | | |
| D(55) | 6.3 | | | | | | | | |
| D(56) | 0.81 | | | | | | | | |
| D(57) | 18 | | | | | | | | |
| D(6) | 38% @ 5; 25* | | | | | | | | |
| D(7) | 120* | | | | | | | | |
| D(8) | 29* | | | | | | | | |
| D(9) | 47* | | | | | | | | |
| E(2) | 390 | 38 | | | | | | | |
| F(1) | 0.91 | 1.4 | | | | | | 29 | |
| F(2) | 3.9 | 4.71 | | | | | | 86 | |
| F(3) | 80 | | | | | | | | |
| F(4) | 33% @ 50 | | | | | | | | |
| F(5) | 31% @ 50 | | | | | | | | |
| F(6) | 34% @ 50 | | | | | | | | |
| F(7) | 114 | | | | | | | | |
| F(8) | 1.9 | | | | | | | | 22 | |
| F(9) | 7.8 | 9.6 | 12% at 1 $\mu$M | | | | | 21 | >10 |

Notes: *= determined with ELISA assay rather than spectrophotometric assay.

TABLE 2

| Example | FLVK-P $K_i$ ($\mu$M) | LCK $K_i$ ($\mu$M) | CHK-1 $K_i$ ($\mu$M) | FGF-R $K_i$ ($\mu$M) | CDK2 $K_i$ ($\mu$M) | CDK4 $K_i$ ($\mu$M) | HUVEC $IC_{50}$ ($\mu$M) | MV522 $IC_{50}$ ($\mu$M) |
|---|---|---|---|---|---|---|---|---|
| A(1) | 1.4* | | NI @ 20 | | | 4.6 | | |
| A(10) | 0.028 | | | 45% @ 5 | 13.4 | 9.1 | | |
| A(11) | NI @ 1000 | | | | NI @ 100 | 33% @ 100 | | |
| A(12) | 0.034 | | | 190 | 6.7 | 2.7 | | |
| A(13) | 0.81* | | 11% @ 5 | | | | | |
| A(14) | 1.9* | | | | 3.1 | 7.0 | | |
| A(15) | 25* | | | | 2.7 | 7.8 | | |
| A(16) | 0.022* | | | | 0.22 | 0.98 | | |
| A(17) | 0.003 | 21% @ 1 | | 2.4 | 2.1 | 29 | >1.0 | >10 |
| A(18) | | | | 38% @ 5 | | | | |
| A(19) | 0.004 | | | 0.39 | | | | |
| A(2) | 2.9* | | | | 1.8 | 7.3 | | |
| A(20) | 0.007 | 24% @ 5 | | 420 | 0.71 | 66 | 0.58 | 0.49 |
| A(21) | 8.8* | | | | 8.21 | 45 | | |
| A(22) | 0.021 | | 54% @ 5 | | | | | |
| A(23) | 0.039 | 34% @ 5 | | 47% @ 5 | | | | |
| A(24) | 5.5* | | | | 3.4 | 64% @ 10 | | |
| A(25) | 0.10* | | 0.29 | | | | | |
| A(26) | 0.014 | | | 52% @ 5 | | | >1.0 | 7.5 |
| A(27) | 38% @ 100* | | | | 3.2 | 31 | | |
| A(28) | 131* | | | | 13 | 24 | | |
| A(29) | 0.078 | 10% @ 5 | | | 6.4 | 13 | >1 | >10 |
| A(3) | 64* | | | | 2.5 | 8.4 | | |
| A(30) | 0.11 | | | | 4.8 | 22 | | |
| A(31) | 31% @ 5 | | | | | | | |

TABLE 2-continued

| Example | FLVK-P $K_i$ ($\mu$M) | LCK $K_i$ ($\mu$M) | CHK-1 $K_i$ ($\mu$M) | FGF-R $K_i$ ($\mu$M) | CDK2 $K_i$ ($\mu$M) | CDK4 $K_i$ ($\mu$M) | HUVEC $IC_{50}$ ($\mu$M) | MV522 $IC_{50}$ ($\mu$M) |
|---|---|---|---|---|---|---|---|---|
| A(32) | 21% @ 5 | | | | | | | |
| A(33) | 22% @ 5 | | | | | | | |
| A(34) | 43% @ 5 | | | | | | | |
| A(35) | 390* | | | | | | | |
| A(4) | | | | | 57% @ 10 | 42% @ 10 | | |
| A(5) | | | | | 27% @ 10 | 30% @ 10 | | |
| A(6) | | | | | 36% @ 10 | 54% @ 10 | | |
| A(61) | 24% @ 1 | | | | 2.7 | | | |
| A(62) | | | | | 0.53 | 4.4 | | |
| A(63) | | | | | 2.0 | 20 | | |
| A(64) | | | | | 0.52 | | | |
| A(65) | | | | | 0.15 | 2.1 | | |
| A(66) | | | | | 1.1 | NI @ 1 | | |
| A(67) | 0.11 | | | | 0.015 | 0.67 | | |
| A(68) | | | | | 0.13 | 4.5 | | |
| A(69) | | | | | 4 | 7.2 | | |
| A(7) | | | | | 25% @ 10 | 28% @ 10 | | |
| A(70) | | | | | NI @ 100 | NI @ 100 | | |
| A(71) | | | | | 29 | 190 | | |
| A(72) | | | | | 0.16 | 48% @ 5 $\mu$M | | |
| A(73) | | | | | 36% @ 100 $\mu$M | NI @ 100 $\mu$M | | |
| A(8) | 0.058* | | | | 0.80 | 0.42 | | |
| A(9) | 1.9* | | | | 29% @ 100 | NI @ 100 | | |
| B(3) | NI @ 300 | | | | | | | |
| B(4) | 0.2 | | | | | | | |
| G(9) | | | | | | | | |
| C(2) | 49% @ 1 | | | | | | | |
| C(3) | | | | | 2.7 | 4.6 | | |
| D(2) | 98 | | | | | | | |
| D(3) | 0.063 | | | | | | | |
| E(4) | | | | | 8.8 | 21 | | |
| G(1) | 57* | | | | | 50 | | |
| G(2) | 18% @ 100* | | | | | 5.7 | | |
| G(3) | 13% @ 20* | | | | | 6.2 | | |
| G(4) | 42% @ 300* | | NI @ 100 | | | 11.4 | | |
| G(5) | NI @ 1000* | | | | | | | |
| G(6) | NI @ 300 $\mu$M | | | | | 100 | | |
| G(7) | 1.6* | | | | 21% @ 10 | NI @ 10 | | |
| G(8) | | | | | 18 | 31% @ 100 | | |
| H(1) | 3.6* | | | | 0.65 | 3.8 | | |
| H(2) | | | | | 10.4 | 11 | | |
| H(3) | 6.1* | | | | 8.8 | 1.7 | | |
| H(4) | | | | | 2.6 | 2.1 | | |
| H(5) | | | | | 29% @ 100 | NI @ 100 | | |
| H(6) | | | | | 0.2 | 1.2 | | |
| I(1) | >100 | | | | | | | 61 |
| I(10) | 15% @ 5 | | | | | | | |
| I(11) | 0.53 | | | | | | | |
| I(12) | 71% @ 20 | | | | | | | |
| I(13) | 1.25* | | | | | | | |
| I(14) | 1.17* | | | | | | | |

TABLE 2-continued

| Example | FLVK-P $K_i$ (μM) | LCK $K_i$ (μM) | CHK-1 $K_i$ (μM) | FGF-R $K_i$ (μM) | CDK2 $K_i$ (μM) | CDK4 $K_i$ (μM) | HUVEC $IC_{50}$ (μM) | MV522 $IC_{50}$ (μM) |
|---|---|---|---|---|---|---|---|---|
| I(15) | 73* | | | | | | | |
| I(16) | 178* | | | | | | | |
| I(17) | 35* | | | | | | | |
| I(18) | 2.7* | | | | | | | |
| I(19) | 34* | | | | | | | |
| I(20) | 46% @ 100 μM | | | | | | | |
| I(2) | NI @ 600* | | | | | NI @ 100 | | |
| I(3) | 40% @ 300* | | | | | NI @ 100 | | |
| I(4) | NI @ 100* | | | | | NI @ 100 | | |
| I(5) | 0.77* | | NI @ 40 | | | 47% @ 100 | | |
| I(6) | 0.1 | | NI @ 40 | 22 | | | | |
| I(7) | 5.2* | | | | | | | |
| I(8) | 12% @ 5 | | | | | | | |
| I(9) | 0.083 | | | | | | | |
| J(1) | 64* | | | | | NI @ 100 | | |
| J(2) | 53* | | | | | 29% @ 100 | | |
| K(1) | 0.006 | 42% @ 1 | | | 0.62 | 6.7 | 0.95 | 5.4 |
| L(1) | NI @ 1000* | | | | | | | |
| L(3) | NI @ 300 μM | | | | | | | |
| L(2) | NI @ 300* | | | | | | | |
| M(1) | | | | | NI @ 100 | NI @ 100 | | |

Note: *= determined with ELISA assay rather than spectrophotometric assay

TABLE 3

| Example | FLVK-P $K_i$ (nM) | FLVK Ki (nM) | LCK $K_i$ (nM) (% inh @ 1 uM) | CHK1 $K_i$ (nM) | FGF-P $K_i$ (nM) (% inh @ 1 uM) | CDK2 $K_i$ (nM) | CDK4 $K_i$ (nM) | HUVEC $IC_{50}$ (nM) | MV522 $IC_{50}$ (nM) |
|---|---|---|---|---|---|---|---|---|---|
| D(67) | | Slow binder | 1 | | 13 | | | 4.1 | >10 |
| D(70) | 91% @ 50 nM | 3.5 | 61 | | 59 | | | 5.4 | >10 |
| B(9) | | 0.36 | 91 | | 78 | | | | |
| B(34) | | 88% @ 50 nM | | | | | | | |
| B(8) | | 0.1 | | | | | | | |
| B(27) | | 0.3 | | | | | | | |
| B(10) | | 0.13 | | | | | | | |
| B(11) | | 0.7 | | | | | | | |
| B(30) | | 0.085 | | | | | | | |
| B(29) | | 0.9 | | | | | | | |
| B(28) | | 3 | | | | | | | |
| B(32) | | 1.8 | | | | | | | |
| B(31) | | 5.1 | | | | | | | |
| B(33) | | 82% | | | | | | | |
| B(26) | | 2.8 | | | | | | | |
| O(31) | | 0.23 | | | | | | | |
| N(1) | 24% @ 1 μM | | | NI @ 25 μM | | 2700 | | | |
| N(2) | | | | | | 120 | 1300 | | |
| N(3) | | | | | | 100 | 1100 | | |
| N(4) | | | | | | 158 | 480 | | |
| D(66) | | 1 | 15 | | 55 | | | 4.2 | >10 |
| O(4) | 87% @ 50 nM | 0.19 | 3 | | 9 | | | 0.64 | |

TABLE 3-continued

| Example | FLVK-P $K_i$ (nM) | FLVK $K_i$ (nM) | LCK $K_i$ (nM) (% inh @ 1 uM) | CHK1 $K_i$ (nM) | FGF-P $K_i$ (nM) (% inh @ 1 uM) | CDK2 $K_i$ (nM) | CDK4 $K_i$ (nM) | HUVEC $IC_{50}$ (nM) | MV522 $IC_{50}$ (nM) |
|---|---|---|---|---|---|---|---|---|---|
| O(10) | | 94 | | | | | | 6.7 | |
| O(3) | | 0.57 | | | | | | | |
| O(2) | | 0.33 | 7 | | 28 | | | 0.58, 1.9 | |
| O(1) | | 0.28 | | | | | | | |
| O(5) | | 0.22 | | | | | | | |
| O(6) | | 0.15 | | | | | | | |
| O(7) | | 0.16 | | | | | | 5.2 | |
| O(8) | | 0.21 | | | | | | | |
| O(9) | | 0.42 | | | | | | 4.3 | |
| O(11) | | 0.45 | | | | | | 14 | |
| O(14) | | Slow binder | 0 | | 10 | | | 16 | |
| O(24) | | 22% @ 50 nM | | | | | | | |
| O(23) | | 29% @ 50 nM | | | | | | | |
| O(22) | | 1.5 | | | | | | | |
| O(21) | 61% @ 50 nM | 1.1 | | | | | | | |
| O(20) | | Slow binder | | | | | | | |
| O(19) | | Slow binder | | | | | | | |
| O(18) | | Slow binder | | | | | | | |
| O(17) | | Slow binder | | | | | | | |
| O(16) | | 11% @ 50 nM | | | | | | | |
| O(15) | | 0.5 | 2 | | 28 | | | | |
| O(13) | | Slow binder | | | | | | 140 | |
| O(30) | | 39% @ binder | | | | | | | |
| O(30) | | 39% @ 50 nM | | | | | | | |
| O(29) | | Slow binder | | | | | | | |
| O(32) | | Slow binder | | | | | | | |
| O(28) | | 0.29 | | | | | | | |
| O(27) | | 1.7 | | | | | | | |
| O(26) | | 1.4 | | | | | | | |
| O(25) | | 28% @ 50 nM | | | | | | | |
| D(65) | | 1 | 9.3 91 | | 37 | | | 4.3 | 2.1 |
| D(73) | | 1.2 | 41 | | 56 | | | 6 | 4.45 |
| D(72) | | 0.9 | 35 | NI | 49 | NI | NI | 4.7 | >10 |
| D(74) | 91% @ 50 nM | Slow binder | 92 | | 61 | | | 5.2 | 2.9/13 |
| B(36) | | 0.56 | 72 | | 23 | | | | |
| B(35) | | 0.26 | 34 | | 39 | | | | |
| B(7) | | 61% @ 50 nM | | | | | | | |
| D(63) | | 51% @ 50 nM | | | | | | >10000 | |
| D(64) | | 1.4 | 3.2 9.4 | | 84 | | | 10–100 | 2 |
| D(75) | | Slow binder | 1.1 97 | | 64 | | | 7.8 | 0.75/2.0 |
| D(76) | | 2.7 | | | | | | >1000 | |
| F(10) | | 0.14 | 42 | | 47 | | | 8.5 | 0.27/ 0.74 |
| B(14) | 13% @ 50 nM | 0.76 | 10 | | 46 | | | 11 | >10 |
| B(12) | | 1.6 | 29 | | 52 | | | 15 | 3.6 |
| D(69) | | 0.5 | 79 | | 78 | | | 15 | 2.3 |
| F(11) | | 0.26 | 15 | | 25 | | | 12 | 9.6/>10 |
| B(16) | | 3% @ 50 nM | | | | | | | |
| B(18) | | 0.9 | NI | | 8% | | | 10 | 1.9 |
| B(20) | | 80% | | | | | | | |

TABLE 3-continued

| Example | FLVK-P $K_i$ (nM) | FLVK Ki (nM) | LCK $K_i$ (nM) (% inh @ 1 uM) | CHK1 $K_i$ (nM) | FGF-P $K_i$ (nM) (% inh @ 1 uM) | CDK2 $K_i$ (nM) | CDK4 $K_i$ (nM) | HUVEC $IC_{50}$ (nM) | MV522 $IC_{50}$ (nM) |
|---|---|---|---|---|---|---|---|---|---|
| O(12) | | 0.19 | 21 | | 33 | | | 45 | 44 |
| F(13) | | 0.25 | 29 | | 25 | | | 16 | |
| F(14) | | 0.36 | | | | | | 150 | |
| F(12) | | 2.2 | | | | | | >300 | |
| B(6) | | 0.61 | | | | | | 56 | |
| D(61) | | Slow binder | 4 | | 9 | | | 165 | >10 |
| D(77) | | 2.6 | | | | | | | |
| D(78) | 9% @ 1 μM | | | | | | | | |
| D(59) | | 2.8 | 44 | | 54 | | | >100 | 3.1 |
| D(60) | | 1.4 | 11 | | 10 | | | >100 | |
| D(68) | | 0.69 | | | | | | >100 | |
| D(71) | | 4.1 | | | | | | | |
| D(58) | | 1.4 | 29 | | 23 | | | >100 | >10 |
| B(17) | | 3.4 | | | | | | 63 | 1.3 |
| B(23) | | 1.7 | | | | | | | |
| B(24) | | 2.1 | | | | | | | |
| B(21) | | 10% @ 50 nM | | | | | | | |
| B(22) | | 54% @ 50 nM | | | | | | >1000 | |
| B(19) | | 36% @ 50 nM | | | | | | | |
| B(25) | | 29 | | | | | | | |
| B(39) | | 6.3 | | | | | | >100 | |
| B(40) | 31% @ 1 μM | | | | | | | | |
| B(41) | | 0% @ 50 nM | | | | | | | |
| B(42) | | 12% @ 50 nM | | | | | | | |
| B(43) | | 11% @ 50 nM | | | | | | | |
| B(37) | | 36% @ 50 nM | | | | | | >1000 | |
| B(38) | | 13% @ 50 nM | | | | | | >700 | |
| C(8) | | 21% @ 50 nM | | | | | | >700 | |
| C(7) | | 17 | | | | | | 300 | |
| B(13) | | 1.3 | | | | | | 300 | |
| B(15) | | 1.7 | | | | | | 100 | |
| C(5) | | 15% @ 50 nM | | | | | | | |
| D(62) | | 20% @ 50 nM | | | | | | 500 | |
| C(6) | | 33 | | | | | | 300 | |
| C(9) | | 8 | | | | | | 300 | |
| C(4) | | 3% @ 50 nM | | | | | | | |
| B(5) | | 2.3 | | | | | | | |
| F(15) | | 5% @ 50 nM | | | | | | | |
| F(16) | | | | | | 480 | 35% @ 5 μM | | |

CHK1 High-throughput screening results shown in Table 4

TABLE 4

| Example | % inhibition @ 20 μM |
|---|---|
| A4 | −10.2 |
| A4 | 17.9 |
| A5 | −16.1 |
| A5 | 25.3 |
| A6 | −10.2 |
| A6 | 25.4 |
| A7 | −16.6 |
| A7 | 19.3 |
| A8 | −6.2 |
| A8 | 57.4 |
| H3 | 16.9 |

TABLE 4-continued

| Example | % inhibition @ 20 μM |
|---|---|
| H3 | 10.3 |
| H4 | 0.9 |
| H2 | −1.7 |
| A16 | 35.4 |
| A21 | −7.2 |
| H5 | 13.4 |
| A70 | 3.8 |
| G8 | −4 |
| G8 | −4.8 |
| G8 | −3 |
| G8 | −3 |
| C3 | −3.7 |
| C3 | 2.9 |
| C3 | −3.7 |
| C3 | −3.7 |
| A69 | 4.8 |
| A69 | 2.7 |
| A69 | 3.8 |
| A69 | 3.8 |
| A63 | 3.8 |
| A63 | 5.4 |
| A63 | 9.8 |
| A64 | 1.1 |
| A64 | 7.2 |
| A64 | 8.3 |
| A66 | 3.6 |
| A66 | 6.6 |
| A66 | 9.1 |
| A68 | −0.7 |
| A68 | −4.4 |
| A68 | 6.1 |
| A62 | 7.4 |
| A62 | 12.2 |
| H6 | 17.4 |
| H6 | 15.2 |
| H6 | 6.5 |
| A67 | 15.3 |
| A67 | 6.9 |
| A67 | 4.2 |
| A65 | 3.2 |
| A65 | 2.5 |
| A65 | 8.2 |
| E4 | 5 |
| E4 | 6.4 |
| B5 | 10.7 |
| B5 | 1 |
| B5 | 9.7 |
| F16 | 4.3 |
| F16 | 7.6 |
| A73 | 14.3 |
| A73 | 14.4 |
| A73 | 7.3 |
| N3 | 5.2 |
| N3 | 2 |
| N3 | 5.8 |
| J2 | 16 |
| J1 | 20.8 |
| I3 | 20.1 |
| I4 | 19.4 |
| I2 | 16.1 |
| I5 | 3.3 |
| I6 | 9.6 |
| A24 | 13.3 |
| I7 | 4.1 |
| I7 | −3.1 |
| I12 | 5.3 |
| I12 | −0.6 |
| A1 | 36.6 |
| A1 | 49.8 |
| A2 | 2.6 |
| A2 | 7.6 |
| A3 | 2.8 |
| A3 | −1.9 |
| A15 | −4.1 |
| A15 | −1.2 |

TABLE 4-continued

| Example | % inhibition @ 20 μM |
|---|---|
| I13 | 11.3 |
| I14 | 11.9 |
| I15 | −1.5 |
| I15 | 14.8 |
| I19 | −1.3 |
| I19 | −2.7 |
| I16 | 13.7 |
| A28 | 0.4 |
| A28 | 9.3 |
| I(20) | −9.4 |
| I(20) | 6.5 |
| A27 | −5.5 |
| A27 | 2 |
| J18 | 12 |
| A9 | −8.2 |
| A9 | 4.9 |
| A10 | −5.9 |
| A10 | 36.2 |
| A11 | −7 |
| A11 | 12.2 |
| A12 | −7 |
| A12 | 24.7 |
| A17 | 10.8 |
| A17 | 41.4 |
| A23 | −7.2 |
| A23 | 4.2 |
| C1 | 12.4 |
| A18 | 60.8 |
| D2 | 0.8 |
| D2 | −5 |
| D3 | 8.6 |
| D3 | 6.7 |
| A20 | 62.7 |
| D4 | 9.3 |
| D5 | 1.3 |
| D5 | −5.3 |
| D6 | 6.1 |
| D6 | 18.6 |
| A13 | 5 |
| A19 | 78.5 |
| D7 | 10.1 |
| D7 | 14.3 |
| D8 | 6.6 |
| D8 | −5.7 |
| D9 | 3.7 |
| D9 | 4.3 |
| D10 | 4 |
| D10 | −1.5 |
| D12 | 11 |
| D13 | 5.5 |
| D13 | 0.8 |
| D14 | 12.3 |
| D14 | 0 |
| D15 | 8.9 |
| D15 | 1.2 |
| D16 | 4.1 |
| A22 | 7.5 |
| A25 | 19.7 |
| A26 | 42.5 |
| D17 | 5.3 |
| D17 | 19 |
| D18 | 6.4 |
| D18 | 12.1 |
| D19 | 9 |
| D19 | 4.2 |
| D20 | 13.4 |
| A31 | 2.5 |
| I10 | 16.1 |
| I9 | 6.9 |
| I11 | −5.7 |
| A32 | −3.8 |
| A33 | 9.6 |
| A33 | −3.8 |
| A34 | 4.6 |
| A34 | −3.4 |

TABLE 4-continued

| Example | % inhibition @ 20 μM |
|---|---|
| A35 | 9.9 |
| A35 | −2.1 |
| D21 | −0.7 |
| D22 | 1.8 |
| D23 | 2.9 |
| D24 | 5.4 |
| K1 | 34.1 |
| B4 | 6.7 |
| A29 | 7.1 |
| D25 | −8.7 |
| D26 | 44.7 |
| A30 | 3.4 |
| A36 | 2.8 |
| A37 | 16 |
| D27 | 5.1 |
| D27 | 12.2 |
| D28 | 6.7 |
| D28 | 26.9 |
| D29 | 4.3 |
| D29 | 19 |
| D30 | 4.2 |
| D30 | 16.4 |
| D31 | 0.8 |
| D31 | 8.8 |
| D32 | 1.7 |
| D32 | 13.8 |
| A38 | 9.1 |
| A38 | 9.8 |
| A39 | 2.2 |
| A40 | 1 |
| A41 | 3.8 |
| A53 | 4 |
| A56 | −2.9 |
| A58 | −7.2 |
| A55 | 0.1 |
| A52 | 2 |
| A42 | −0.1 |
| A43 | −3 |
| A44 | −7.1 |
| A45 | −1 |
| A46 | 0.9 |
| A57 | −6.1 |
| A48 | 1.3 |
| D33 | −0.3 |
| D34 | −0.3 |
| D35 | 4.5 |
| D36 | 2.5 |
| D37 | 4.2 |
| D38 | 8.4 |
| D39 | −1.4 |
| D40 | 17.7 |
| D41 | 12.6 |
| F9 | 15.3 |
| A49 | 14.1 |
| D42 | 1.8 |
| A50 | 30.1 |
| B2 | 5.9 |
| D44 | 0 |
| D45 | 2.4 |
| D46 | 3.9 |
| D47 | 1 |
| D48 | 8.5 |
| D49 | 4.9 |
| D50 | 5.6 |
| D51 | 3.8 |
| D52 | 25.9 |
| B40 | 8 |
| D78 | 9.4 |
| F2 | 3.5 |
| F1 | 3.4 |
| F4 | 10.3 |
| F5 | 10.5 |
| F6 | 8.4 |
| D53 | 5.1 |
| F8 | 55.8 |

TABLE 4-continued

| Example | % inhibition @ 20 μM |
|---|---|
| F8 | 21.1 |
| F8 | 3.4 |
| F8 | 1.8 |
| F8 | 1.9 |
| D56 | 6.5 |
| F7 | 7.3 |
| D55 | 7.3 |
| D11 | 13.3 |
| B5 | 4.3 |
| C4 | 16.9 |
| D72 | 5.1 |
| D73 | 5.3 |
| D63 | 7.4 |
| B12 | 3.1 |
| C7 | 35.6 |
| D64 | 6.4 |
| D65 | 4.9 |
| B13 | 3 |
| C8 | 12.4 |
| D66 | 3.8 |
| D67 | 5.6 |
| D58 | 4 |
| D58 | −1.7 |
| D58 | 0.1 |
| C9 | 8.6 |
| C9 | 6.5 |
| C9 | 15.1 |
| D60 | 6.7 |
| D60 | −4.1 |
| D60 | 3.7 |
| D68 | 10.2 |
| D68 | 7 |
| D68 | 14.1 |
| F12 | 10.3 |
| F12 | 6.3 |
| F12 | 13.2 |
| B41 | 8.6 |
| B41 | 7.3 |
| B41 | 12.9 |
| C5 | 4.7 |
| C5 | 2 |
| C5 | 3.7 |
| F13 | 9 |
| F13 | 11.3 |
| F13 | 12.9 |
| B14 | 8 |
| B14 | 1.5 |
| B14 | 2.8 |
| C9 | 14.8 |
| C9 | 5.5 |
| C9 | 16.5 |
| F14 | 14 |
| F14 | 10.2 |
| F14 | 18.1 |
| B15 | 9 |
| B15 | 4.1 |
| B15 | 9.1 |
| B6 | 4.6 |
| B6 | −2.1 |
| B6 | −1.3 |
| C6 | 24.5 |
| C6 | 5.4 |
| C6 | 4.4 |
| D74 | 11.3 |
| D74 | 3.1 |
| D74 | 14.3 |
| D75 | 9.3 |
| D75 | 4.9 |
| D75 | 18.8 |
| B42 | 4.7 |
| B42 | 0.4 |
| B42 | 9.5 |
| B43 | 8.1 |
| B43 | 2.8 |
| B43 | 11.8 |

TABLE 4-continued

| Example | % inhibition @ 20 μM |
|---|---|
| B16 | 82.8 |
| B16 | 78.9 |
| B16 | 55.4 |
| B16 | 38.6 |
| B16 | 29.1 |
| B16 | 77.5 |
| B16 | 82 |
| O3 | 17.1 |
| O3 | 24.5 |
| B21 | 4.5 |
| B21 | 20.6 |
| B35 | 4.4 |
| B35 | 14.1 |
| B36 | 6.2 |
| B36 | 15.1 |
| B25 | 3 |
| B25 | 10.3 |
| B26 | 7.5 |
| B26 | 13.3 |
| B27 | −1.4 |
| B27 | 1.3 |

FAK High-throughput screening results shown in Table 5

TABLE 5

Inhibition of FAK at 10 uM compound In HTS Delphia assay

| Example | % inhibition of FAK |
|---|---|
| A4 | 6 |
| A5 | 10 |
| A6 | 0 |
| A7 | 2 |
| A8 | 17 |
| H3 | 19 |
| H4 | 6 |
| H2 | 18 |
| A16 | 36 |
| A21 | 26 |
| H5 | 42 |
| H5 | 17 |
| H5 | 3 |
| H5 | 3 |
| A70 | 11 |
| J2 | −7 |
| J1 | −4 |
| I3 | 3 |
| I4 | −5 |
| I2 | −6 |
| I5 | −2 |
| I6 | 12 |
| A24 | 7 |
| I7 | −1 |
| I12 | −3 |
| A1 | 5 |
| A2 | 8 |
| A3 | −9 |
| A15 | 0 |
| I15 | 3 |
| I19 | 57 |
| I19 | 7 |
| I19 | 5 |
| A28 | 4 |
| I20 | −2 |
| A27 | 2 |
| A9 | 4 |
| A10 | −4 |
| A11 | 15 |

TABLE 5-continued

Inhibition of FAK at 10 uM compound In HTS Delphia assay

| Example | |
|---|---|
| A12 | 8 |
| A17 | −2 |
| A23 | 4 |
| C1 | −2 |
| A18 | 29 |
| D1 | −3 |
| D2 | 26 |
| D3 | 20 |
| A20 | 20 |
| D4 | 17 |
| D5 | 7 |
| D6 | 23 |
| A13 | 12 |
| A19 | 37 |
| D7 | 23 |
| D8 | 8 |
| D9 | 22 |
| D10 | 4 |
| D12 | 29 |
| D13 | 12 |
| D14 | 23 |
| D15 | 17 |
| D16 | 17 |
| A22 | 13 |
| A25 | 57 |
| A25 | 90 |
| A25 | 88 |
| A25 | 88 |
| A26 | 17 |
| D17 | 24 |
| D18 | 14 |
| D19 | 7 |
| D20 | 25 |
| A31 | 27 |
| I8 | 12 |
| I8 | 12 |
| I9 | 26 |
| I11 | −18 |
| A32 | −3 |
| A33 | −17 |
| A34 | −13 |
| A35 | −10 |
| D21 | −1 |
| D22 | 2 |
| D23 | −12 |
| D24 | −4 |
| K1 | 17 |
| B4 | 49 |
| B4 | 36 |
| B4 | 11 |
| B4 | 46 |
| B4 | 32 |
| A29 | −8 |
| D25 | 6 |
| D26 | 51 |
| D26 | 19 |
| A30 | −16 |
| A36 | −6 |
| A37 | −2 |
| A38 | 83 |
| A38 | 23 |
| A38 | 12 |
| A39 | −10 |
| A40 | −6 |
| A41 | 97 |
| A41 | 18 |
| A41 | 12 |
| A53 | −10 |
| A56 | −7 |
| A58 | −9 |
| A55 | 59 |
| A55 | 11 |
| A55 | 16 |
| A52 | 9 |

TABLE 5-continued

Inhibition of FAK at 10 uM compound
In HTS Delphia assay

| Example | % inhibition |
|---|---|
| A42 | −15 |
| A43 | −19 |
| A44 | −15 |
| A45 | −13 |
| A46 | −14 |
| A57 | −18 |
| A48 | −2 |
| D33 | −7 |
| D34 | −9 |
| D35 | −19 |
| D36 | 1 |
| D37 | −6 |
| D38 | −14 |
| D39 | −21 |
| D40 | −6 |
| D41 | −19 |
| F9 | −13 |
| A49 | −13 |
| D42 | −5 |
| A50 | −14 |
| B2 | −17 |
| D44 | −9 |
| D45 | −9 |
| D46 | −14 |
| D47 | −19 |

| Example | % inhibition |
|---|---|
| A4 | −7 |
| A4 | −10 |
| A5 | −8 |
| A5 | −10 |
| A6 | −15 |
| A6 | −16 |
| A7 | −10 |
| A7 | −9 |
| A8 | −12 |
| A8 | −14 |
| H3 | −11 |
| H3 | −9 |
| H4 | −2 |
| H4 | 1 |
| H2 | 0 |
| H2 | 5 |
| A16 | 94 |
| A16 | 96 |
| A21 | 4 |
| A21 | −1 |
| H5 | 4 |
| H5 | 2 |
| A70 | −11 |
| A70 | 2 |
| G8 | −16 |
| G8 | −30 |
| C3 | −19 |
| C3 | 0 |
| A69 | 40 |
| A69 | 15 |
| A63 | −6 |
| A63 | −24 |
| A63 | −22 |
| A63 | −23 |
| A64 | −20 |
| A64 | −34 |
| A66 | −38 |
| A66 | −39 |
| A68 | −18 |
| A68 | −18 |
| A62 | 7 |
| A62 | 6 |
| H6 | −13 |
| H6 | −30 |
| A67 | −29 |
| A67 | −33 |
| A65 | −31 |

TABLE 5-continued

Inhibition of FAK at 10 uM compound
In HTS Delphia assay

| Example | % inhibition |
|---|---|
| A65 | −39 |
| E4 | 9 |
| E4 | 17 |
| B5 | −4 |
| B5 | −13 |
| F16 | −13 |
| F16 | −16 |
| A73 | −23 |
| A73 | −30 |
| N3 | −12 |
| N3 | −17 |
| J2 | −2 |
| J2 | −10 |
| J1 | −8 |
| J1 | −13 |
| I3 | 4 |
| I3 | −5 |
| I4 | 11 |
| I4 | −1 |
| I2 | 19 |
| I2 | 6 |
| I5 | 6 |
| I5 | 0 |
| I6 | 6 |
| I6 | 15 |
| A24 | −4 |
| A24 | −13 |
| B3 | 30 |
| B3 | 26 |
| I7 | 9 |
| I7 | 19 |
| I12 | −7 |
| I12 | −7 |
| A1 | −4 |
| A1 | 82 |
| A2 | −9 |
| A2 | 5 |
| A3 | −9 |
| A3 | 3 |
| A15 | −9 |
| A15 | −7 |
| I13 | −2 |
| I13 | −7 |
| I14 | −24 |
| I14 | −23 |
| I15 | −7 |
| I15 | −11 |
| I19 | −5 |
| I19 | 4 |
| I16 | −3 |
| I16 | −1 |
| A28 | −14 |
| A28 | −8 |
| I20 | 9 |
| I20 | 7 |
| A27 | −14 |
| A27 | −11 |
| J18 | 3 |
| J18 | −8 |
| A9 | −6 |
| A9 | −5 |
| A10 | −2 |
| A10 | −5 |
| A11 | −8 |
| A11 | −10 |
| A12 | −16 |
| A12 | −16 |
| A17 | 33 |
| A17 | 9 |
| A23 | −5 |
| A23 | −6 |
| C1 | 8 |
| C1 | 11 |
| A18 | 25 |

TABLE 5-continued

Inhibition of FAK at 10 uM compound
In HTS Delphia assay

| Example | |
|---|---|
| A18 | 32 |
| D1 | 2 |
| D1 | 13 |
| D2 | -3 |
| D2 | 7 |
| D3 | -4 |
| D3 | 0 |
| A20 | 46 |
| A20 | 56 |
| D4 | -3 |
| D4 | -5 |
| D5 | -1 |
| D5 | 17 |
| D6 | -2 |
| D6 | -3 |
| A13 | 7 |
| A13 | 27 |
| A19 | 76 |
| A19 | 86 |
| D7 | -6 |
| D7 | -1 |
| D8 | -5 |
| D8 | 12 |
| D9 | -8 |
| D9 | -10 |
| D10 | -5 |
| D10 | 5 |
| D12 | -7 |
| D12 | -10 |
| D13 | -8 |
| D13 | -1 |
| D14 | -9 |
| D14 | -10 |
| D15 | -3 |
| D15 | -6 |
| D16 | -2 |
| D16 | 4 |
| A22 | 35 |
| A22 | 38 |
| A25 | 60 |
| A25 | 47 |
| A26 | 72 |
| A26 | 72 |
| D17 | -10 |
| D17 | -10 |
| D18 | -6 |
| D18 | -9 |
| D19 | -4 |
| D19 | -10 |
| D20 | -6 |
| D20 | -10 |
| A31 | -6 |
| A31 | -7 |
| I10 | 8 |
| I10 | -1 |
| I8 | 9 |
| I8 | -1 |
| I9 | 45 |
| I9 | 35 |
| I11 | 30 |
| I11 | 25 |
| A32 | 8 |
| A32 | 11 |
| A33 | 2 |
| A33 | 4 |
| A34 | -3 |
| A34 | -8 |
| A35 | -5 |
| A35 | -9 |
| D21 | 0 |
| D21 | 10 |
| D22 | -6 |
| D22 | 24 |
| D23 | -6 |

TABLE 5-continued

Inhibition of FAK at 10 uM compound
In HTS Delphia assay

| Example | |
|---|---|
| D23 | 1 |
| D24 | -4 |
| D24 | -7 |
| K1 | 92 |
| K1 | 96 |
| B4 | 56 |
| B4 | 43 |
| A29 | -6 |
| A29 | -11 |
| D25 | -9 |
| D25 | 1 |
| D26 | -2 |
| D26 | 0 |
| A30 | -3 |
| A30 | 9 |
| A36 | -11 |
| A36 | -15 |
| A37 | 34 |
| A37 | 37 |
| D27 | 79 |
| D27 | 86 |
| D28 | -15 |
| D28 | -7 |
| D29 | -2 |
| D29 | -9 |
| D30 | -24 |
| D30 | -18 |
| D31 | -11 |
| D31 | 0 |
| D32 | -20 |
| D32 | -13 |
| H3 | -6 |
| H3 | -9 |
| A39 | 2 |
| A39 | 7 |
| A40 | -6 |
| A40 | -6 |
| A41 | -6 |
| A41 | -9 |
| A53 | -8 |
| A53 | -10 |
| A56 | 8 |
| A56 | 3 |
| A58 | 6 |
| A58 | 0 |
| A55 | -3 |
| A55 | -7 |
| A52 | 1 |
| A52 | -6 |
| A42 | -1 |
| A42 | -8 |
| A43 | 6 |
| A43 | -2 |
| A44 | -5 |
| A44 | -10 |
| A45 | -4 |
| A45 | -6 |
| A46 | -2 |
| A46 | -9 |
| A57 | 2 |
| A57 | -7 |
| A48 | -8 |
| A48 | -8 |
| D33 | -3 |
| D33 | -7 |
| D34 | -1 |
| D34 | -5 |
| D35 | 8 |
| D35 | 4 |
| D36 | 19 |
| D36 | 6 |
| D37 | -5 |
| D37 | -8 |
| D38 | 2 |

TABLE 5-continued

Inhibition of FAK at 10 uM compound
In HTS Delphia assay

| Example | |
|---|---|
| D38 | −7 |
| D39 | 22 |
| D39 | 8 |
| D40 | −2 |
| D40 | −10 |
| D41 | 0 |
| D41 | −7 |
| F9 | 24 |
| F9 | 14 |
| A49 | −7 |
| A49 | −10 |
| D42 | 1 |
| D42 | −10 |
| A50 | 8 |
| A50 | 2 |
| B2 | 13 |
| B2 | 2 |
| D44 | 58 |
| D44 | 56 |
| D45 | 17 |
| D45 | 10 |
| D46 | 27 |
| D46 | 19 |
| D47 | 51 |
| D47 | 46 |
| D48 | 22 |
| D48 | 24 |
| D49 | 75 |
| D50 | 42 |
| D50 | 44 |
| D51 | 16 |
| D52 | −26 |
| D52 | −13 |
| B40 | −26 |
| B40 | −29 |
| D78 | −22 |
| D78 | −15 |
| F2 | −18 |
| F2 | −15 |
| F1 | 19 |
| F1 | 25 |
| F4 | −10 |
| F4 | −15 |
| F5 | −16 |
| F5 | −10 |
| F6 | −14 |
| F6 | 1 |
| D53 | −15 |
| D53 | −2 |
| F8 | 81 |
| F8 | 82 |
| D56 | 73 |
| D56 | 71 |
| F7 | −2 |
| F7 | −21 |
| D55 | −14 |
| D55 | −35 |
| D11 | −25 |
| D11 | −41 |
| B5 | 34 |
| B5 | 33 |
| C4 | −5 |
| C4 | 9 |
| D72 | 65 |
| D72 | 69 |
| D73 | 69 |
| D73 | 73 |
| D63 | −130 |
| D63 | −126 |
| B12 | 43 |
| B12 | 44 |
| C7 | 55 |

TABLE 5-continued

Inhibition of FAK at 10 uM compound
In HTS Delphia assay

| Example | |
|---|---|
| C7 | 57 |
| D64 | 92 |
| D64 | 93 |
| D65 | 94 |
| D65 | 93 |
| B13 | 30 |
| B13 | 36 |
| C8 | 33 |
| C8 | 35 |
| D66 | 79 |
| D67 | 73 |
| D67 | 75 |
| D58 | −14 |
| D58 | −12 |
| C9 | −19 |
| C9 | −16 |
| C60 | −11 |
| C60 | −9 |
| C68 | −8 |
| C68 | −7 |
| F12 | −9 |
| F12 | −14 |
| B41 | −28 |
| B41 | −26 |
| C5 | −6 |
| C5 | −11 |
| F13 | 54 |
| F13 | 56 |
| B14 | −11 |
| B14 | −17 |
| C9 | 19 |
| C9 | 18 |
| F14 | 2 |
| F14 | −2 |
| B15 | 5 |
| B15 | −2 |
| B6 | 11 |
| B6 | 10 |
| C6 | 19 |
| C6 | 11 |
| D74 | 96 |
| D74 | 94 |
| D75 | 92 |
| D75 | 91 |
| B42 | −7 |
| B42 | −11 |
| B43 | −16 |
| B43 | −17 |
| O3 | 31 |
| O3 | 42 |
| B21 | −3 |
| B21 | 2 |
| B35 | 96 |
| B36 | 91 |
| B36 | 93 |
| B25 | −6 |
| B25 | 0 |
| B26 | 76 |
| B27 | 91 |
| B27 | 94 |

Synthetic Protocol for Combinatorial Examples in Tables A–D

The four library building blocks 2-(4-aminosulfonylphenyl)amino,4-aminoithiazole-5-carbothioamide, 2-(4-dimethylaminophenyl)amino,4-aminoithiazole-5-carbothioamide, 2-(3,4,5-trimethoxylaminosulfonylphenyl)amino,4-aminoithiazole-5-carbothioamide and 2-(4-isopropylphenyl)amino,4- aminoithiazole-5-carbothioamide were synthesized in a manner similar to that of step (i) and (ii) in Example A above.

All the compounds in Table A–D were synthesized by the chemistry similar to that used to prepare Example A(1) except: A stock solution of corresponding 4 above carbothioamides in 10% DMF/methanol was distributed into a 96 deep well plate so that each well contained 5 μMoles of material. Then, 5 μmoles of 63 α-halid ketones were added to individual wells of each plate. After the reaction plates were shaken at room temperature for 16 hours, approximately 10 mg of Merrifield resin and 10 mg of N-(2-mercaptoethyl)aminomethyl polystyrene resin were added to each well. The reaction plates were shaken for another 2 hours. The reaction mixture was then filtered and the filtrates of each reaction well were collected individually into a receiving 96-well plate. The compounds were obtained after the removal of solvent.

TABLE A

| EXAMPLES | VEGF[a] | CHK1[b] | CDK2[c] | CDK4[d] |
|---|---|---|---|---|
| (structure) | 34 | 47.7 | −10.3 | 65.4 |
| (structure) | 3 | 9.2 | 11.6 | −1 |
| (structure) | 57 | 46.3 | 7.3 | 33.1 |
| (structure) | 26 | 32 | −0.2 | 18.3 |
| (structure) | 24 | 49.5 | −4.8 | 35.1 |

TABLE A-continued

| EXAMPLES | VEGF[a] | CHK1[b] | CDK2[c] | CDK4[d] |
|---|---|---|---|---|
| (structure) | 38 | 23 | 12.4 | 31.3 |
| (structure) | −2 | 20 | −3.5 | −5.1 |
| (structure) | 19 | 3.7 | −2.1 | 1.9 |
| (structure) | −5 | 9.9 | 4.9 | −19.9 |
| (structure) | 18 | 11.2 | 0.1 | −6.9 |
| (structure) | 3 | 6.1 | 12.2 | 17 |

TABLE A-continued

| EXAMPLES | VEGF[a] | CHK1[b] | CDK2[c] | CDK4[d] |
|---|---|---|---|---|
| (structure) | 41 | 15.3 | −13 | 3 |
| (structure) | 27 | 2.7 | 23.2 | −4 |
| (structure) | 25 | 36.6 | 1.9 | 11.6 |
| (structure) | −8 | 15.2 | −14.4 | −5.6 |
| (structure) | 3 | 11.7 | −4.4 | −17.8 |
| (structure) | −2 | 18.7 | 20.4 | −4.7 |
| (structure) | 18 | 10.3 | 15.6 | −0.3 |

TABLE A-continued

| EXAMPLES | VEGF[a] | CHK1[b] | CDK2[c] | CDK4[d] |
|---|---|---|---|---|
| (structure) | 32 | 31.3 | 3.8 | 23.7 |
| (structure) | 26 | 17.9 | 13.6 | 19.5 |
| (structure) | 22 | 32.9 | 5.4 | −16 |
| (structure) | 53 | 48.3 | 35 | 32.3 |
| (structure) | −4 | 22.3 | 14.6 | 2.2 |
| (structure) | 53 | 31.3 | 14.3 | 24.5 |

TABLE A-continued

| EXAMPLES | VEGF[a] | CHK1[b] | CDK2[c] | CDK4[d] |
|---|---|---|---|---|
| (structure) | 26 | 16.5 | −5 | −27.6 |
| (structure) | −6 | 8.8 | 6.6 | −14.9 |
| (structure) | 1 | 12.1 | 7.3 | −31.7 |
| (structure) | 66 | 48.3 | 3 | 17.5 |
| (structure) | 38 | 27.9 | 28.4 | 7.8 |
| (structure) | 50 | 48.8 | 10.3 | 32.3 |
| (structure) | 47 | 12 | −1.2 | −7.3 |

TABLE A-continued
| EXAMPLES | VEGF[a] | CHK1[b] | CDK2[c] | CDK4[d] |
|---|---|---|---|---|
| 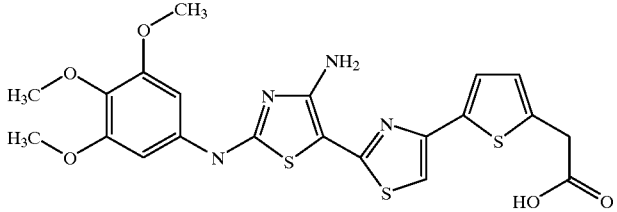 | 59 | 41.9 | 26.7 | 26.4 |
| 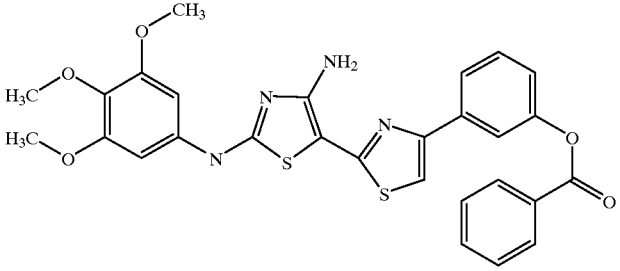 | 22 | 23.9 | −12.3 | −14.7 |
| 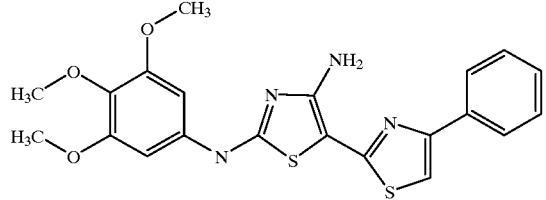 | 23 | 21.1 | −0.2 | −40.1 |
| 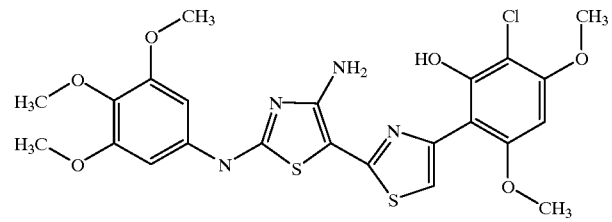 | 49 | 56 | 11.8 | 36.4 |
| 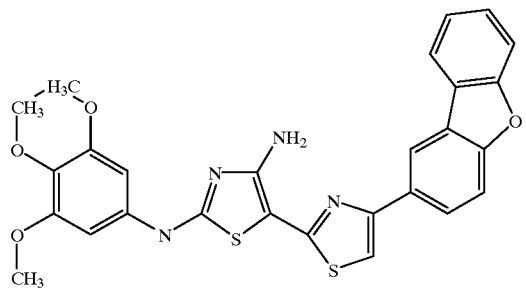 | 34 | 34.1 | 19 | 13.7 |
| 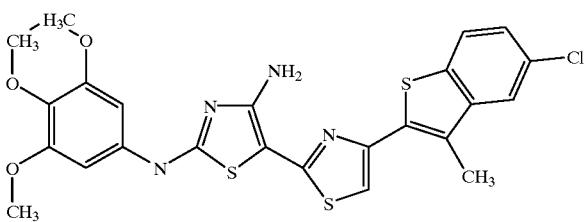 | 56 | 48.7 | 7.3 | 37.1 |

TABLE A-continued

| EXAMPLES | VEGF[a] | CHK1[b] | CDK2[c] | CDK4[d] |
|---|---|---|---|---|
| (structure) | 38 | 29.4 | 1.7 | 11.7 |
| (structure) | 52 | 38.1 | 12 | 31 |
| (structure) | 17 | 22.4 | 4.2 | −3.4 |
| (structure) | −1 | 8.5 | 13.9 | −17.7 |
| (structure) | 20 | 31.9 | −7.8 | −14.6 |
| (structure) | 37 | 0.5 | 4.6 | −21.1 |

TABLE A-continued

| EXAMPLES | VEGF[a] | CHK1[b] | CDK2[c] | CDK4[d] |
|---|---|---|---|---|
| (structure) | −3 | 10.4 | 13.8 | −9 |
| (structure) | 11 | 21.6 | −2.7 | 20.2 |
| (structure) | 16 | 4.7 | 23.1 | −24 |
| (structure) | −11 | 25.3 | 5.3 | −0.1 |
| (structure) | 46 | 14.1 | −1 | −18.7 |
| (structure) | 34 | 21.2 | −0.4 | −48.1 |

TABLE A-continued
| EXAMPLES | VEGF[a] | CHK1[b] | CDK2[c] | CDK4[d] |
|---|---|---|---|---|
| 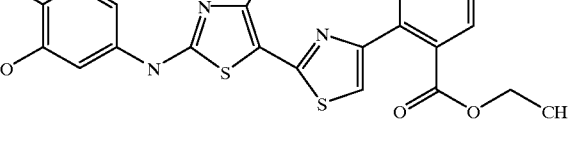 | 35 | 41.4 | 4.4 | 22.8 |
| 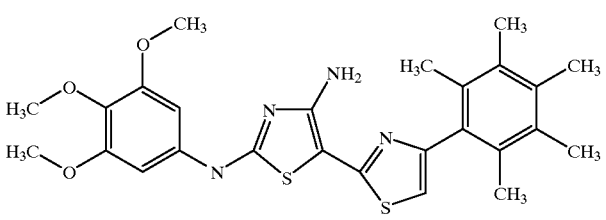 | 51 | 48.3 | 19.8 | 50.6 |
|  | 14 | 2.7 | 11.2 | −19.9 |
| 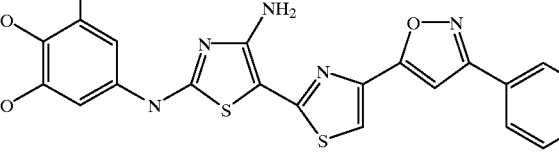 | 27 | 30.9 | −7.5 | 8.2 |
| 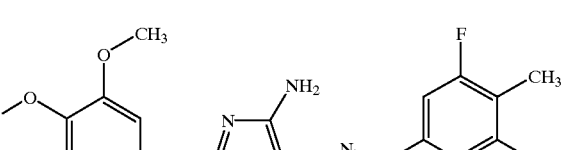 | −3 | 0.9 | 17.5 | −10.4 |
| 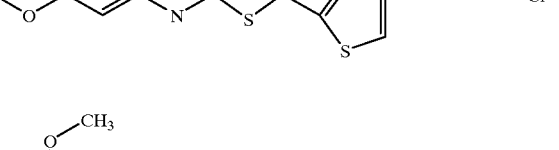 | −13 | 8.9 | 11.3 | −34.4 |

TABLE A-continued

| EXAMPLES | VEGF[a] | CHK1[b] | CDK2[c] | CDK4[d] |
|---|---|---|---|---|
| (structure) | 50 | −7.4 | 1.6 | −8.4 |
| (structure) | 26 | 26.2 | −6 | 4.7 |
| (structure) | 60 | 32.5 | −12.1 | 28.7 |
| (structure) | −5 | 1.3 | 6.3 | −4.5 |
| (structure) | 41 | 13.2 | 9.1 | 11.5 |
| (structure) | 15 | 6.4 | 3.9 | 29.3 |

TABLE A-continued

| EXAMPLES | VEGF[a] | CHK1[b] | CDK2[c] | CDK4[d] |
|---|---|---|---|---|
| (structure: 3,4,5-trimethoxyphenyl-NH-thiazole(NH2)-thiazole-chlorobenzofuran) | 3 | 25.4 | −6 | −6.5 |
| (structure: 3,4,5-trimethoxyphenyl-NH-thiazole(NH2)-thiazole-bromophenyl) | 19 | 13.5 | 15.6 | −10.5 |

TABLE B

| EXAMPLES | VEGF[a] | CHK1[b] | CDK2[c] | CDK4[d] |
|---|---|---|---|---|
| (structure: sulfamoylphenyl-NH-thiazole(NH2)-thiazole-dihydroxyphenyl) | 49 | 28.5 | 55.9 | 57.2 |
| (structure: sulfamoylphenyl-NH-thiazole(NH2)-thiazole-naphthyl) | 12 | 7.8 | 25.5 | −8.9 |
| (structure: sulfamoylphenyl-NH-thiazole(NH2)-thiazole-methylthiophene) | 34 | 26.6 | 68.2 | 59.6 |
| (structure: sulfamoylphenyl-NH-thiazole(NH2)-thiazole-bromochlorothiophene) | 6 | 7.9 | 60.5 | 56.4 |

TABLE B-continued

| EXAMPLES | VEGF[a] | CHK1[b] | CDK2[c] | CDK4[d] |
|---|---|---|---|---|
| (structure: sulfamoyl-phenyl-aminothiazole-thiazole-(4-chloro-3-nitrophenyl)) | −2 | 13.1 | 17.6 | −28.2 |
| (structure: sulfamoyl-phenyl-aminothiazole-thiazole-furan-(2,4-dichlorophenyl)) | −2 | 3.3 | 21.4 | 25 |
| (structure: sulfamoyl-phenyl-aminothiazole-thiazole-(2-methoxyphenyl)) | 21 | 18.7 | 18.9 | 16 |
| (structure: sulfamoyl-phenyl-aminothiazole-thiazole-(4-methylphenyl)) | 33 | −2.1 | 20.5 | −9.6 |
| (structure: sulfamoyl-phenyl-aminothiazole-thiazole-(2,4-dimethoxyphenyl)) | 3 | −3.9 | 12.5 | −1.2 |
| (structure: sulfamoyl-phenyl-aminothiazole-thiazole-(4-chlorophenyl)) | 27 | 4.4 | 18.5 | 10.9 |

TABLE B-continued

| EXAMPLES | VEGF[a] | CHK1[b] | CDK2[c] | CDK4[d] |
|---|---|---|---|---|
| (structure) | 8 | −2.3 | 28.4 | 41.2 |
| (structure) | 48 | 6.9 | 10.7 | 9.3 |
| (structure) | 3 | 1.1 | 29.8 | −13 |
| (structure) | 47 | 25.6 | 55.4 | 57.8 |
| (structure) | 3 | 11 | 27.7 | −16.3 |
| (structure) | 2 | 15.9 | 8.3 | −28 |
| (structure) | −3 | 12.3 | 11.2 | −11.3 |

TABLE B-continued
| EXAMPLES | VEGF[a] | CHK1[b] | CDK2[c] | CDK4[d] |
|---|---|---|---|---|
| 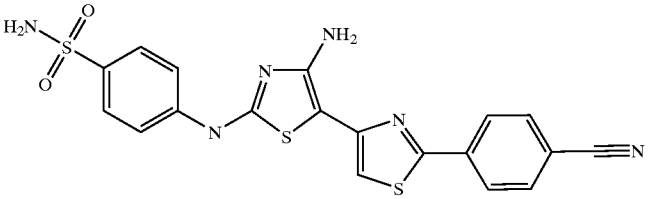 | 13 | 3.7 | 13.3 | 16.3 |
| 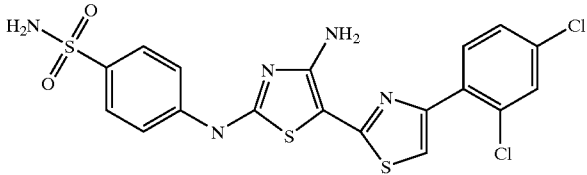 | 32 | 14.7 | 63 | 79.2 |
| 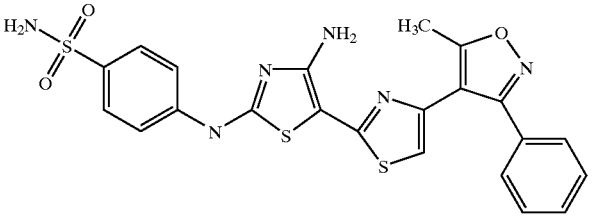 | −2 | 2.9 | −4.5 | −3.9 |
| 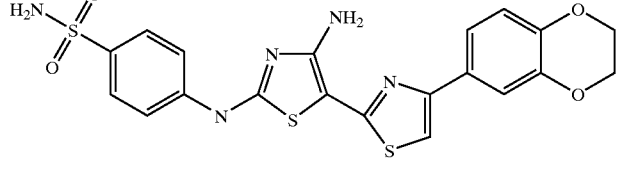 | 29 | 20.1 | 21.4 | 31.8 |
| 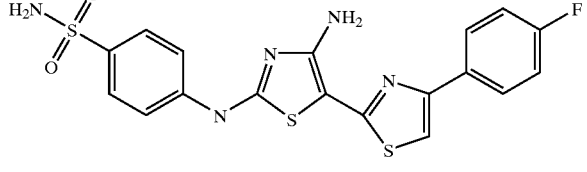 | 43 | 33.7 | 74.7 | 61.2 |
| 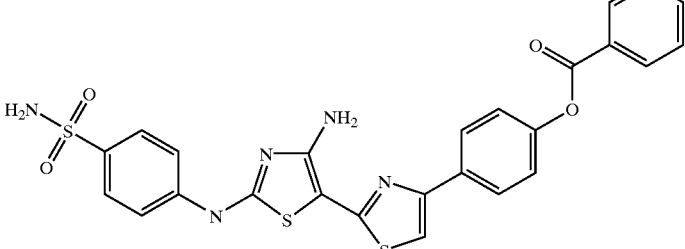 | 8 | 4.4 | 20.7 | −27 |
| 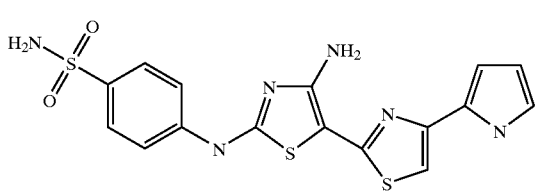 | 13 | 13.6 | 14.6 | 39.7 |

TABLE B-continued

| EXAMPLES | VEGF[a] | CHK1[b] | CDK2[c] | CDK4[d] |
|---|---|---|---|---|
| (structure) | 38 | 17.5 | 12.4 | −5.3 |
| (structure) | 30 | 10.8 | 17.8 | −28.6 |
| (structure) | 9 | 11.7 | 1.3 | −3.1 |
| (structure) | 56 | 18.7 | 57.9 | 51.3 |
| (structure) | 25 | 13.4 | 40.7 | 46 |
| (structure) | 11 | 19.8 | 66.8 | 58 |
| (structure) | 50 | 0.2 | 19.6 | −13.5 |

TABLE B-continued
| EXAMPLES | VEGF[a] | CHK1[b] | CDK2[c] | CDK4[d] |
|---|---|---|---|---|
| 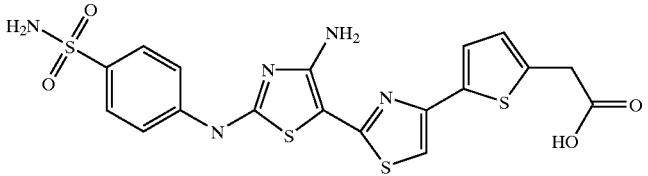 | 11 | 11.3 | 51.6 | 65 |
| 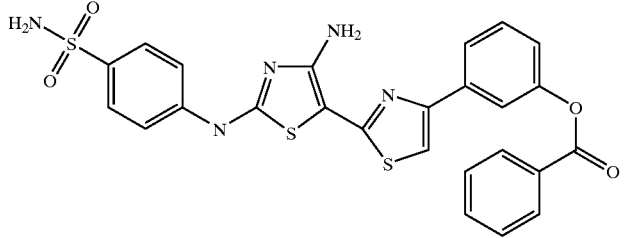 | 43 | 6.8 | 37.2 | −1.9 |
| 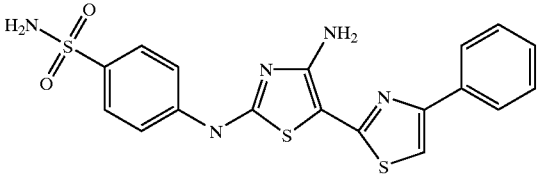 | 23 | 11.2 | 8.2 | −33.4 |
| 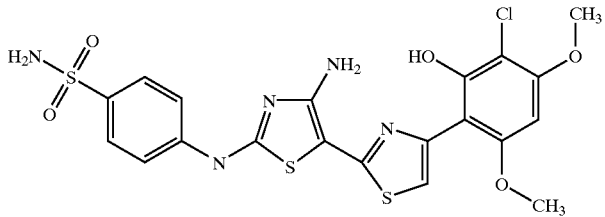 | 29 | 25.6 | 69.5 | 62.5 |
| 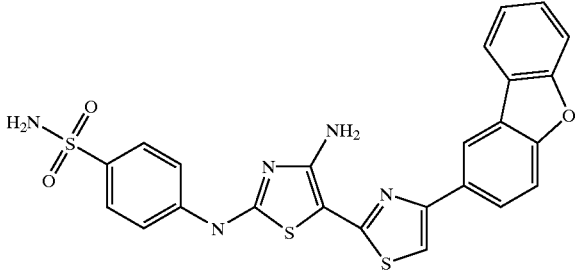 | 18 | 18.3 | 45.7 | 57.5 |
| 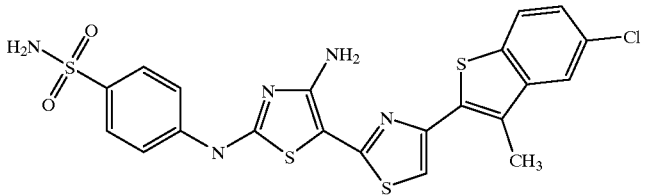 | 23 | 28.4 | 67 | 59.9 |

TABLE B-continued

| EXAMPLES | VEGF[a] | CHK1[b] | CDK2[c] | CDK4[d] |
|---|---|---|---|---|
| (structure) | 11 | 10.7 | 54.2 | 40.9 |
| (structure) | 19 | 9.7 | 56 | 70.6 |
| (structure) | −2 | 13.1 | 35.9 | 31.8 |
| (structure) | 2 | 4.2 | 4.5 | −3.6 |
| (structure) | 7 | 15.3 | 56.6 | 42.2 |
| (structure) | 9 | −1.6 | 29 | 2.3 |
| (structure) | −2 | 1.3 | 14.1 | −3.5 |

TABLE B-continued

| EXAMPLES | VEGF[a] | CHK1[b] | CDK2[c] | CDK4[d] |
|---|---|---|---|---|
| (structure) | 3 | 9.7 | 61.4 | 53.4 |
| (structure) | 3 | 5.6 | 9.2 | −0.3 |
| (structure) | −9 | 17.5 | 25 | 17 |
| (structure) | 34 | 12.3 | 60.8 | 43.3 |
| (structure) | 23 | 15.2 | 5.9 | −4.2 |
| (structure) | 9 | 11.4 | 52.6 | 53.3 |
| (structure) | 33 | 29 | 77.2 | 64.1 |

TABLE B-continued

| EXAMPLES | VEGF[a] | CHK1[b] | CDK2[c] | CDK4[d] |
|---|---|---|---|---|
| (sulfonamide-phenyl-NH-thiazole(NH2)-thiazole-isoxazole-phenyl) | −1 | −1.2 | 12 | −0.5 |
| (sulfonamide-phenyl-NH-thiazole(NH2)-thiazole-(3-Cl,5-F,4-CH3-phenyl)) | 5 | 21.1 | 68 | 75 |
| (sulfonamide-phenyl-NH-thiazole(NH2)-thiazole-isoxazole-(3,4-diCl-phenyl)) | −5 | 0.5 | 16.1 | −31.3 |
| (sulfonamide-phenyl-NH-thiazole(NH2)-thiazole-(4-pentyl-phenyl)) | −13 | 10.8 | −9.9 | −7.2 |
| (sulfonamide-phenyl-NH-thiazole(NH2)-thiazole-(2-OAc-phenyl)) | 33 | −7.3 | 25.4 | −4.8 |
| (sulfonamide-phenyl-NH-thiazole(NH2)-thiazole-(2,6-diCl-4-CF3-phenyl)) | 9 | 21.7 | 53.9 | 58 |
| (sulfonamide-phenyl-NH-thiazole(NH2)-thiazole-(2,4-diF-phenyl)) | 40 | 21.6 | 74.1 | 58.2 |

TABLE B-continued

| EXAMPLES | VEGF[a] | CHK1[b] | CDK2[c] | CDK4[d] |
|---|---|---|---|---|
| (structure: sulfonamide-phenyl-NH-aminothiazole-thiazole-phenyl-N(CH2CH3)2) | 10 | 6.1 | 34.8 | 29.3 |
| (structure: sulfonamide-phenyl-NH-aminothiazole-thiazole-benzothiophene) | 10 | 0.4 | 48.9 | 44.1 |
| (structure: sulfonamide-phenyl-NH-aminothiazole-thiazole-N-methylpyrrole with trichloroacetyl) | −4 | 3.3 | 23.2 | 14 |
| (structure: sulfonamide-phenyl-NH-aminothiazole-thiazole-chlorobenzofuran) | −4 | 13.6 | 16.6 | −15 |
| (structure: sulfonamide-phenyl-NH-aminothiazole-thiazole-(3-bromophenyl)) | 15 | 16.4 | 17.6 | −0.3 |

TABLE C

| EXAMPLES | VEGF[a] | CHK1[b] | CDK2[c] | CDK4[d] |
|---|---|---|---|---|
| (structure: isopropylphenyl-NH-aminothiazole-thiazole-(3,4-dihydroxyphenyl)) | 28 | 31.6 | 23.8 | 62.7 |

TABLE C-continued

| EXAMPLES | VEGF[a] | CHK1[b] | CDK2[c] | CDK4[d] |
|---|---|---|---|---|
| (structure) | −2 | 10.7 | 17.2 | 51.2 |
| (structure) | 50 | 27.4 | 17.5 | 76.5 |
| (structure) | 25 | 9.2 | 26 | 84.7 |
| (structure) | 7 | 23.5 | 14.2 | 71.5 |
| (structure) | 3 | −7.9 | 15.1 | 49.7 |
| (structure) | −13 | 15.6 | 6.3 | 53.3 |
| (structure) | −2 | 0.8 | 14.2 | 55.9 |

TABLE C-continued

| EXAMPLES | VEGF[a] | CHK1[b] | CDK2[c] | CDK4[d] |
|---|---|---|---|---|
| (structure) | −10 | 1.8 | −22.6 | 38.2 |
| (structure) | −2 | −0.2 | 10.8 | 53.1 |
| (structure) | 12 | −5.2 | 12.2 | 79.4 |
| (structure) | 19 | 4.7 | 27.8 | 60.9 |
| (structure) | 9 | −5.7 | 15 | 28.7 |
| (structure) | 16 | 32.2 | 17.7 | 63 |
| (structure) | −4 | 6 | 17.8 | 35.6 |

TABLE C-continued

| EXAMPLES | VEGF[a] | CHK1[b] | CDK2[c] | CDK4[d] |
|---|---|---|---|---|
| (structure) | −7 | 9 | 11.7 | 9.1 |
| (structure) | −9 | 3.2 | 9.6 | 0.7 |
| (structure) | 7 | 7.1 | 5.9 | 58.4 |
| (structure) | 23 | 21.4 | 25.7 | 81.4 |
| (structure) | 5 | −0.9 | 11.1 | 49.8 |
| (structure) | 14 | 23.8 | 22 | 50.6 |
| (structure) | 48 | 39.8 | 16.1 | 80.7 |

TABLE C-continued

| EXAMPLES | VEGF[a] | CHK1[b] | CDK2[c] | CDK4[d] |
|---|---|---|---|---|
| (structure: isopropylphenyl-NH-thiazole(NH2)-thiazole-phenyl-O-C(O)-phenyl) | −4 | 7.5 | 73 | 45.9 |
| (structure: isopropylphenyl-NH-thiazole(NH2)-thiazole-pyrrole) | 22 | 17.6 | 19 | 53.3 |
| (structure: isopropylphenyl-NH-thiazole(NH2)-thiazole-3,4-difluorophenyl) | 5 | 10.9 | 21.2 | 39.5 |
| (structure: isopropylphenyl-NH-thiazole(NH2)-thiazole-3-nitrophenyl) | −2 | 7.2 | 24.7 | 35.3 |
| (structure: isopropylphenyl-NH-thiazole(NH2)-thiazole-3,4-dichlorophenyl) | −4 | 0.3 | 10.4 | −7.9 |
| (structure: isopropylphenyl-NH-thiazole(NH2)-thiazole-4-hydroxyphenyl) | 49 | 25 | 10.5 | 77 |
| (structure: isopropylphenyl-NH-thiazole(NH2)-thiazole-3,5-dimethyl-4-hydroxyphenyl) | 45 | 5.1 | 14.1 | 74.6 |

TABLE C-continued
| EXAMPLES | VEGF[a] | CHK1[b] | CDK2[c] | CDK4[d] |
|---|---|---|---|---|
| 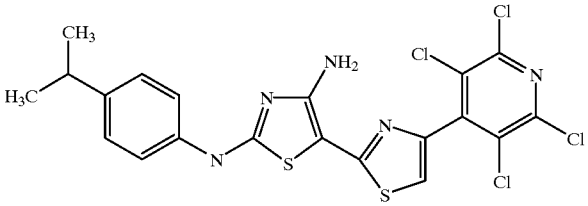 | 30 | 19.3 | 12.5 | 72.7 |
|  | 14 | −2.5 | 23.3 | 50 |
| 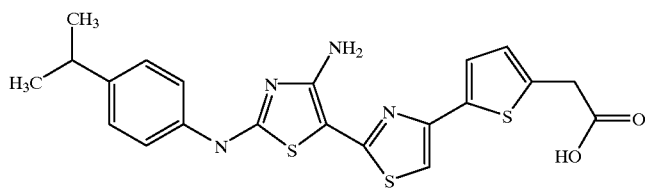 | 33 | 13 | 21.8 | 61.8 |
| 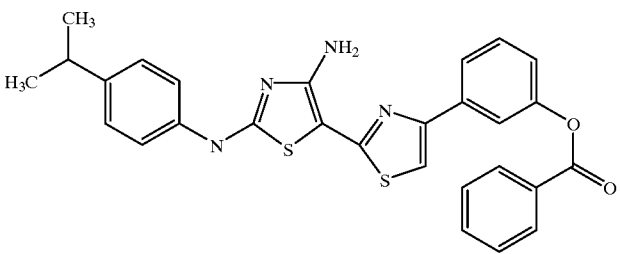 | 5 | 8.8 | 21.7 | 48 |
| 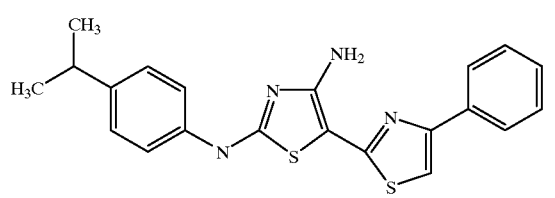 | −4 | 4 | 23.3 | −42.5 |
| 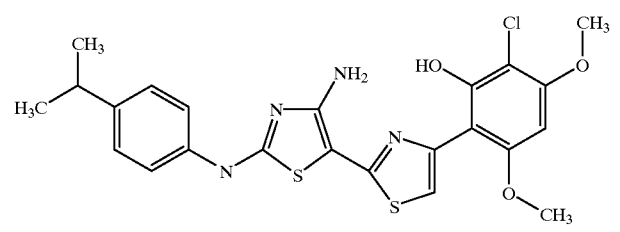 | 51 | 38.9 | 31.8 | 72.8 |

TABLE C-continued

| EXAMPLES | VEGF[a] | CHK1[b] | CDK2[c] | CDK4[d] |
|---|---|---|---|---|
| (structure) | 39 | 18.9 | −4.3 | 75.5 |
| (structure) | 47 | 32.3 | 38.6 | 79.6 |
| (structure) | 12 | 14.2 | 38.3 | 79 |
| (structure) | 42 | 17.8 | 31 | 79.9 |
| (structure) | 19 | 11.6 | 5.2 | 74.4 |
| (structure) | −4 | 3.7 | 8.7 | 48.3 |
| (structure) | 21 | 20.9 | 29.1 | 59.5 |

TABLE C-continued
| EXAMPLES | VEGF[a] | CHK1[b] | CDK2[c] | CDK4[d] |
|---|---|---|---|---|
| 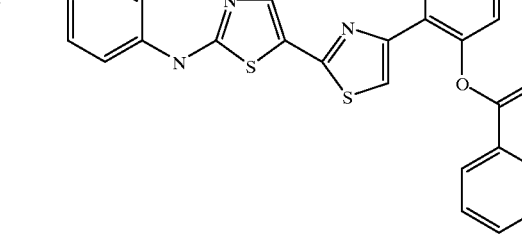 | 7 | −4.2 | 4.8 | 56.1 |
| 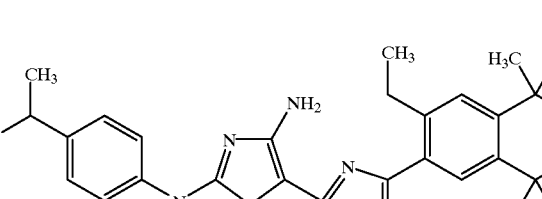 | 13 | 6.5 | 6.2 | 61.4 |
|  | 15 | 14.1 | 26 | 85.1 |
| 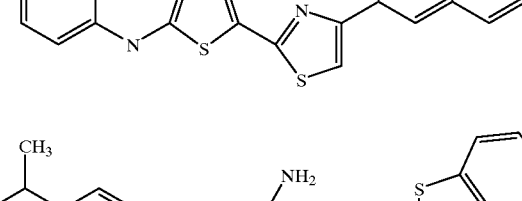 | 5 | −4.7 | 4 | 2.4 |
| 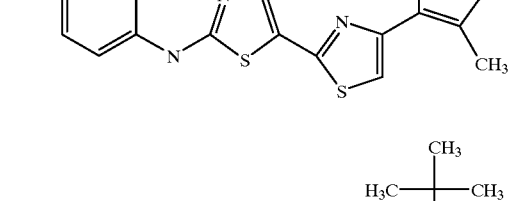 | −6 | 7.9 | 20.9 | 46.8 |
| 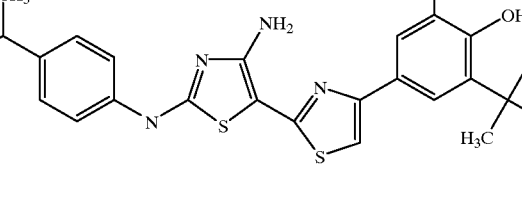 | 22 | 0.2 | 18.5 | 59.4 |

TABLE C-continued

| EXAMPLES | VEGF[a] | CHK1[b] | CDK2[c] | CDK4[d] |
|---|---|---|---|---|
| (isopropylphenyl-NH-thiazole(NH2)-thiazole-3-methoxyphenyl) | 10 | 3.8 | 16 | 49.3 |
| (isopropylphenyl-NH-thiazole(NH2)-thiazole-phenyl-C(O)OEt) | 26 | 26 | 29.2 | 81.6 |
| (isopropylphenyl-NH-thiazole(NH2)-thiazole-pentamethylphenyl) | 59 | 34.9 | 39.9 | 84.7 |
| (isopropylphenyl-NH-thiazole(NH2)-thiazole-isoxazole-phenyl) | 13 | −4.7 | 2.4 | 50.4 |
| (isopropylphenyl-NH-thiazole(NH2)-thiazole-(F,CH3,Cl-phenyl)) | 18 | 22.8 | 28.2 | 88.6 |
| (isopropylphenyl-NH-thiazole(NH2)-thiazole-isoxazole-(3,4-dichlorophenyl)) | −5 | −9 | 18.5 | −26.5 |

TABLE C-continued
| EXAMPLES | VEGF[a] | CHK1[b] | CDK2[c] | CDK4[d] |
|---|---|---|---|---|
| 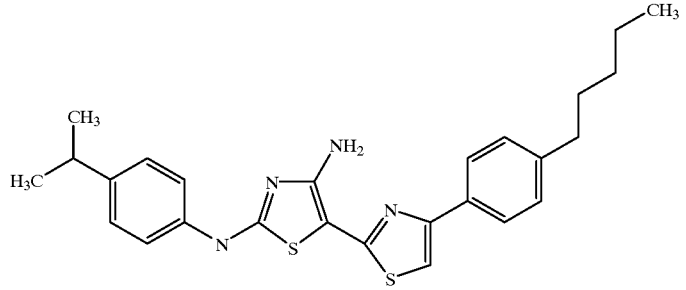 | −14 | 0.7 | 3.6 | 10.3 |
| 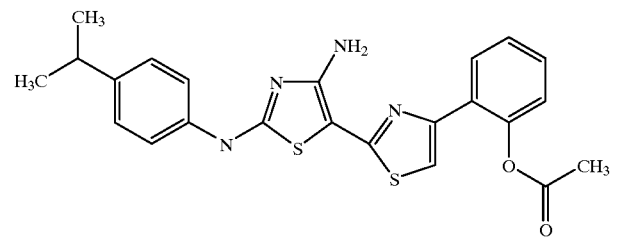 | 14 | −12.8 | 6.6 | 44.3 |
| 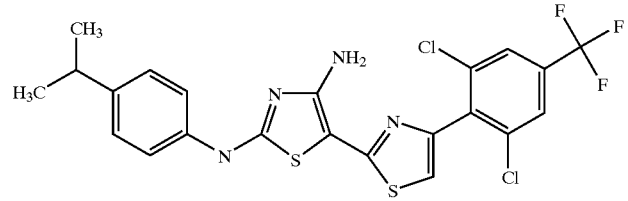 | 31 | 14.8 | 26 | 86.2 |
| 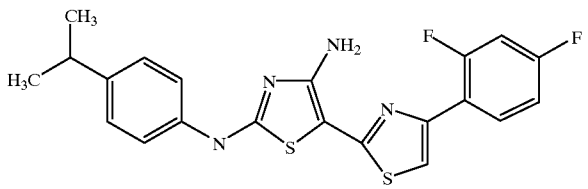 | 46 | 19.7 | 30.6 | 91.5 |
| 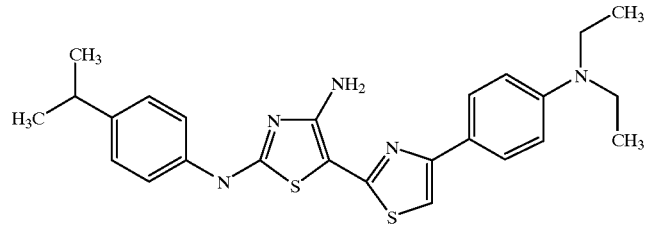 | 9 | −5.3 | 12.2 | 73 |
| 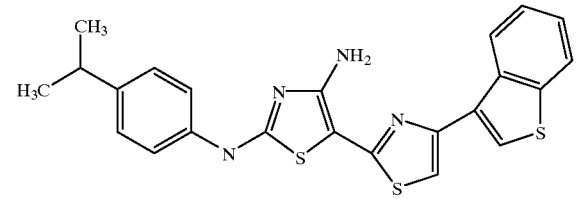 | 25 | −4.3 | 9.3 | 72 |

TABLE C-continued

| EXAMPLES | VEGF[a] | CHK1[b] | CDK2[c] | CDK4[d] |
|---|---|---|---|---|
| (isopropylphenyl-aminothiazole-thiazole-trichloroacetyl-N-methylpyrrole) | −3 | 0.7 | 10.1 | 37.8 |
| (isopropylphenyl-aminothiazole-thiazole-chlorobenzofuran) | −11 | 3.4 | 17 | 33.2 |
| (isopropylphenyl-aminothiazole-thiazole-bromophenyl) | 5 | 12 | 14.6 | 48.1 |

TABLE D

| EXAMPLES | VEGF[a] | CHK1[b] | CDK2[c] | CDK4[d] |
|---|---|---|---|---|
| (dimethylaminophenyl-aminothiazole-thiazole-dihydroxyphenyl) | 34 | 46.5 | 16.8 | 53 |
| (dimethylaminophenyl-aminothiazole-thiazole-naphthyl) | 5 | 19.6 | 26.9 | 45.5 |
| (dimethylaminophenyl-aminothiazole-thiazole-dimethylthienyl) | 32 | 43.9 | 24 | 64.1 |

TABLE D-continued

| EXAMPLES | VEGF[a] | CHK1[b] | CDK2[c] | CDK4[d] |
|---|---|---|---|---|
| (4-bromo-5-chloro-thiophene derivative) | 18 | 22.8 | 17.6 | 69.1 |
| (4-chloro-3-nitrophenyl derivative) | −2 | 16 | 4.1 | 59.8 |
| (2,4-dichlorophenyl-furan derivative) | 5 | −7.6 | 17.7 | 35.6 |
| (2-methoxyphenyl derivative) | 0 | 14.8 | −6.4 | 8.7 |
| (4-methylphenyl derivative) | 16 | 15.2 | 17.7 | 61.6 |
| (2,4-dimethoxyphenyl derivative) | 1 | 3.1 | 6.7 | 35.4 |
| (4-chlorophenyl derivative) | 10 | 2.5 | 11.2 | 36.5 |

TABLE D-continued

| EXAMPLES | VEGF[a] | CHK1[b] | CDK2[c] | CDK4[d] |
|---|---|---|---|---|
| (structure: 4-dimethylaminophenyl-NH-thiazole(NH2)-thiazole-2,5-dimethoxyphenyl) | 13 | 14.1 | 15.6 | 68.7 |
| (structure: 4-dimethylaminophenyl-NH-thiazole(NH2)-thiazole-4-methoxyphenyl) | 13 | 2.7 | 6.1 | 19.1 |
| (structure: 4-dimethylaminophenyl-NH-thiazole(NH2)-thiazole-isoxazole-CO2Et) | 9 | −4.5 | 13.4 | 33.7 |
| (structure: 4-dimethylaminophenyl-NH-thiazole(NH2)-thiazole-2-nitrophenyl) | 17 | 39.5 | 8.3 | 46.2 |
| (structure: 4-dimethylaminophenyl-NH-thiazole(NH2)-thiazole-4-nitrophenyl) | 8 | 17.8 | 22.1 | 50.4 |
| (structure: 4-dimethylaminophenyl-NH-thiazole(NH2)-thiazole-4-chloro-3-methylphenyl) | 2 | 16.6 | 11.7 | 15.2 |

TABLE D-continued
| EXAMPLES | VEGF[a] | CHK1[b] | CDK2[c] | CDK4[d] |
|---|---|---|---|---|
| 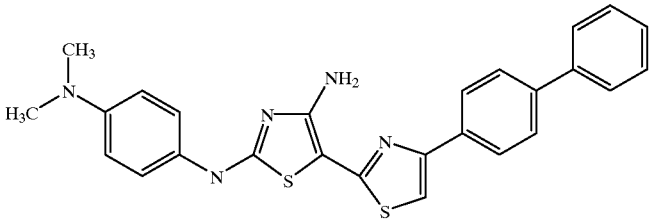 | −12 | 5 | 14.5 | −12.6 |
| 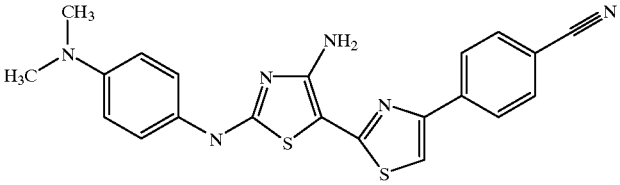 | 11 | 8.2 | 14.3 | 36.4 |
| 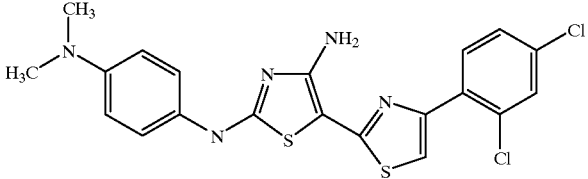 | 19 | 26.9 | 17.3 | 76.1 |
| 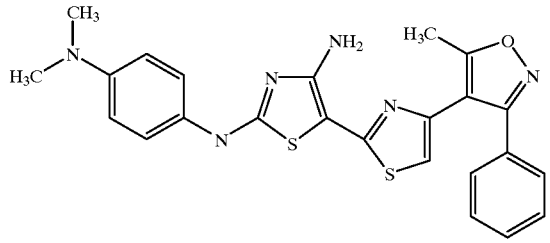 | 25 | 8.1 | 8.3 | 59.8 |
| 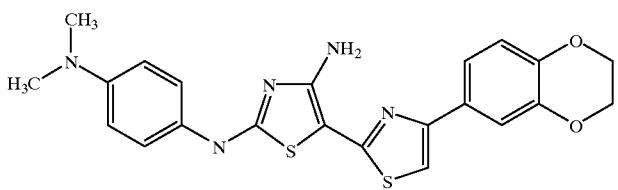 | 16 | 40.8 | 5 | 56.5 |
| 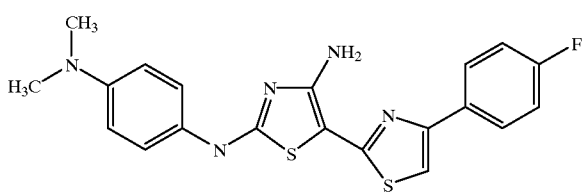 | 41 | 41.7 | 34.8 | 56 |

TABLE D-continued

| EXAMPLES | VEGF[a] | CHK1[b] | CDK2[c] | CDK4[d] |
|---|---|---|---|---|
| (structure) | −4 | 5.5 | 8.7 | 49.4 |
| (structure) | 28 | 32.5 | 31.7 | 63.6 |
| (structure) | 8 | 4.2 | 3.3 | 8.1 |
| (structure) | 6 | 13.8 | 17.1 | 27 |
| (structure) | 0 | 5.1 | 9.2 | −6.5 |
| (structure) | 46 | 47.1 | 26.6 | 66.8 |
| (structure) | 24 | 27.2 | 29.8 | 52.4 |

TABLE D-continued
| EXAMPLES | VEGF[a] | CHK1[b] | CDK2[c] | CDK4[d] |
|---|---|---|---|---|
| 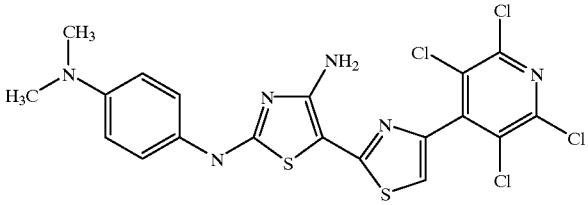 | 35 | 41.4 | 33.3 | 64.4 |
| 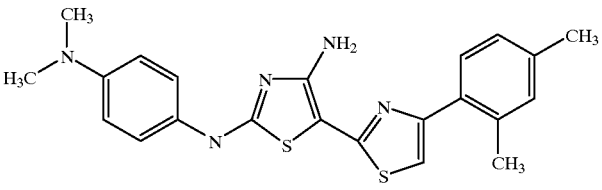 | 21 | −0.9 | 16.1 | 23.3 |
| 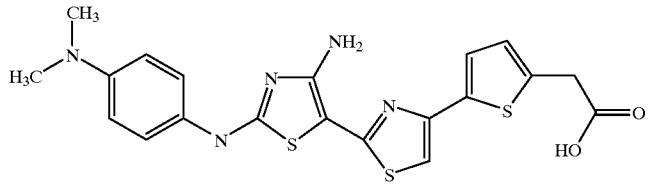 | 28 | 38.1 | 6.3 | 69.4 |
| 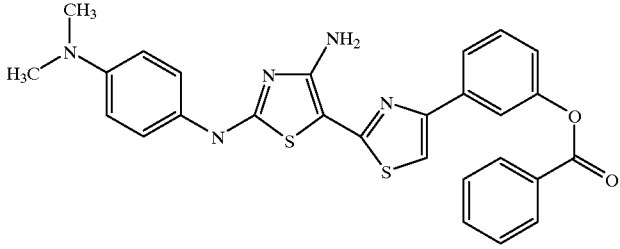 | 16 | 23.3 | 0.6 | 57.5 |
| 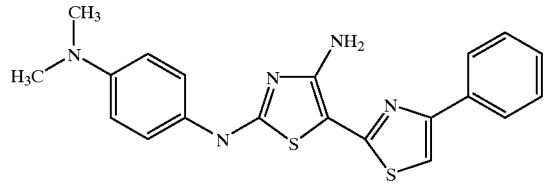 | 17 | 13.1 | 17.2 | −48.3 |
| 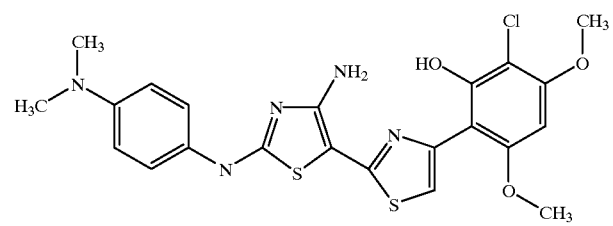 | 36 | 41.1 | 24.1 | 69.3 |

TABLE D-continued

| EXAMPLES | VEGF[a] | CHK1[b] | CDK2[c] | CDK4[d] |
|---|---|---|---|---|
| (structure) | 27 | 29.3 | 38.3 | 63.5 |
| (structure) | 31 | 41.9 | 17.1 | 64.3 |
| (structure) | 23 | 34.8 | 29.8 | 83 |
| (structure) | 29 | 26.8 | 37.3 | 65.1 |
| (structure) | 18 | 32.9 | 3.1 | 74.4 |
| (structure) | 5 | 13.1 | 33.4 | 60.3 |
| (structure) | 20 | 32.7 | −2.5 | 43.7 |

TABLE D-continued

| EXAMPLES | VEGF[a] | CHK1[b] | CDK2[c] | CDK4[d] |
|---|---|---|---|---|
| (structure) | 23 | 9.8 | 27.1 | 48.5 |
| (structure) | 17 | 18.8 | 20.5 | 70.9 |
| (structure) | 14 | 26 | 24.6 | 81.8 |
| (structure) | 26 | 3.2 | 23.3 | 12.1 |
| (structure) | 6 | 37.1 | 18.3 | 73.2 |
| (structure) | 30 | 17.5 | 19.7 | 65.1 |

TABLE D-continued

| EXAMPLES | VEGF[a] | CHK1[b] | CDK2[c] | CDK4[d] |
|---|---|---|---|---|
| (structure: dimethylamino-phenyl-NH-thiazole(NH2)-thiazole-3-methoxyphenyl) | 10 | 7.8 | 16.3 | −20.3 |
| (structure: dimethylamino-phenyl-NH-thiazole(NH2)-thiazole-phenyl-CO2Et) | 25 | 38.5 | 19.8 | 45.9 |
| (structure: dimethylamino-phenyl-NH-thiazole(NH2)-thiazole-pentamethylphenyl) | 33 | 37 | 33.9 | 62.7 |
| (structure: dimethylamino-phenyl-NH-thiazole(NH2)-thiazole-(3-phenyl-isoxazol-5-yl)) | 5 | 0.8 | 24 | 29.6 |
| (structure: dimethylamino-phenyl-NH-thiazole(NH2)-thiazole-(3-chloro-5-fluoro-4-methylphenyl)) | 9 | 27 | 8.2 | 76.5 |
| (structure: dimethylamino-phenyl-NH-thiazole(NH2)-thiazole-(3-(3,4-dichlorophenyl)isoxazol-5-yl)) | 1 | −2.8 | 12.6 | −17.5 |

TABLE D-continued

| EXAMPLES | VEGF[a] | CHK1[b] | CDK2[c] | CDK4[d] |
|---|---|---|---|---|
| (structure) | −8 | 9.5 | −6 | 36.2 |
| (structure) | 24 | −4.6 | 27.8 | 48.5 |
| (structure) | 26 | 37.5 | 29.1 | 82.6 |
| (structure) | 34 | 25.2 | 20.3 | 64.3 |
| (structure) | 16 | 17.4 | 14.6 | 57.8 |
| (structure) | 22 | 12.6 | 23.5 | 57.7 |

TABLE D-continued

| EXAMPLES | VEGF[a] | CHK1[b] | CDK2[c] | CDK4[d] |
|---|---|---|---|---|
| 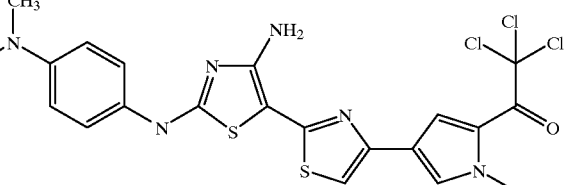 | 3 | 5.2 | 36.7 | 45.2 |
| 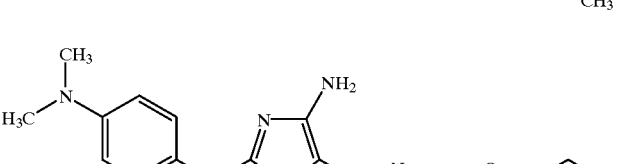 | −3 | 7.6 | 16.9 | 29.6 |
| 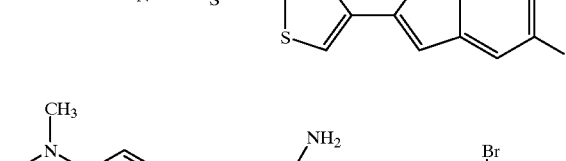 | 17 | 14.2 | 29 | 30.1 |

[a] % inhibition at 20 μM
[b] % Inhibition at 20 μM
[c] % Inhibition at 1.0 μM
[d] % Inhibition at 1.0 μM Combinatorial procedure for the synthesis of Urea functionalized thiazole derivatives and inhibition of HUVEC Profileration

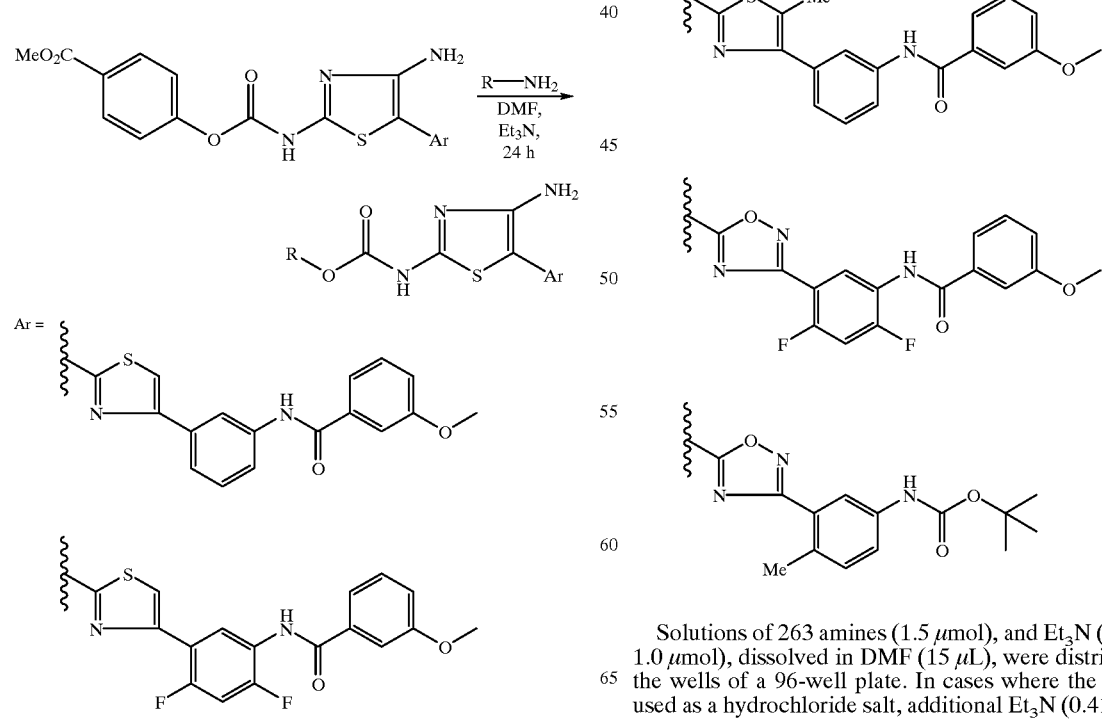

Solutions of 263 amines (1.5 μmol), and Et₃N (0.1393 μL, 1.0 μmol), dissolved in DMF (15 μL), were distributed in to the wells of a 96-well plate. In cases where the amine was used as a hydrochloride salt, additional Et₃N (0.4179 μL, 3.0 μmol) was added to liberate the free base. Each of the wells was treated with a solution of p-carboxy phenol carbamate (0.5395 mg, 1.0 μmol) dissolved in DMF (30 μL), then agitated for 24 h at room temperature. The crude reaction mixtures were concentrated using a GeneVac™ apparatus, and then diluted with DMSO to a final concentration of 10 mM, yielding the examples shown in Table E.

TABLE E

Inhibition of HUVEC Proliferation

| MOLSTRUCTURE | % inhibition @ 10 nM | % inhibition @ 50 nM |
|---|---|---|
| | 28 | 62 |
| | 7 | 126 |
| | −5 | 33 |
| | −38 | 39 |
| | −13 | 29 |
| | −3 | 3 |
| | 19 | 83 |

TABLE E-continued

Inhibition of HUVEC Proliferation

| MOLSTRUCTURE | % inhibition @ 10 nM | % inhibition @ 50 nM |
| --- | --- | --- |
| (structure) | 25 | 18 |
| (structure) | 46 | 87 |
| (structure) | 28 | 123 |
| (structure) | 39 | 0 |
| (structure) | 22 | 25 |
| (structure) | −11 | 114 |
| (structure) | −18 | 55 |

TABLE E-continued
Inhibition of HUVEC Proliferation
| MOLSTRUCTURE | % inhibition @ 10 nM | % inhibition @ 50 nM |
|---|---|---|
| 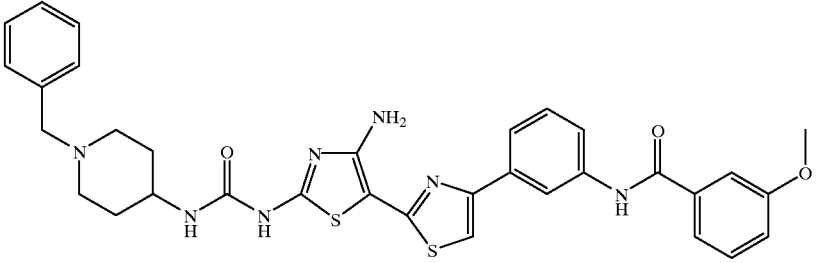 | −22 | 23 |
| 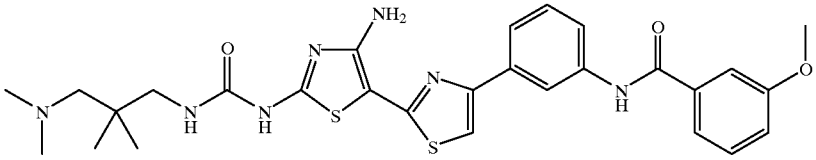 | −25 | 36 |
| 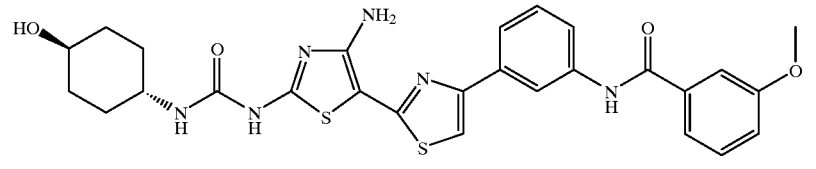 | −6 | 21 |
| 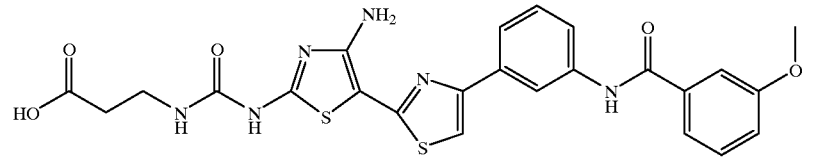 | −1 | 8 |
| 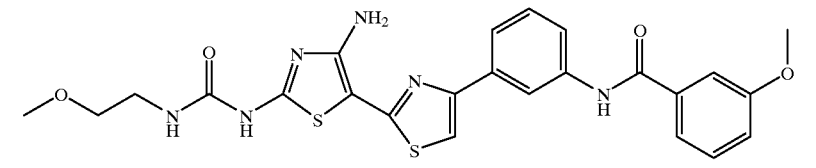 | 35 | 32 |
| 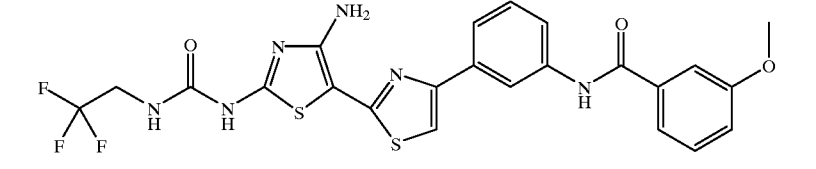 | 20 | 15 |
| 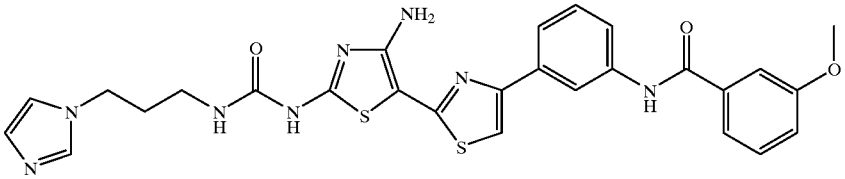 | 9 | 39 |

TABLE E-continued

Inhibition of HUVEC Proliferation

| MOLSTRUCTURE | % inhibition @ 10 nM | % inhibition @ 50 nM |
|---|---|---|
| | 34 | 49 |
| | 1 | 10 |
| | 19 | 67 |
| | −8 | 38 |
| | −17 | 52 |
| | 4 | 35 |
| | 5 | 24 |

TABLE E-continued
Inhibition of HUVEC Proliferation
| MOLSTRUCTURE | % inhibition @ 10 nM | % inhibition @ 50 nM |
|---|---|---|
| 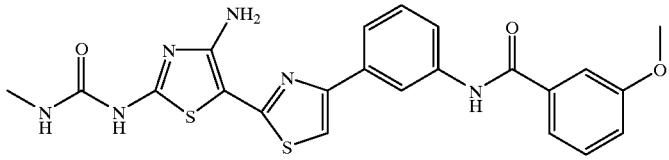 | 15 | 115 |
| 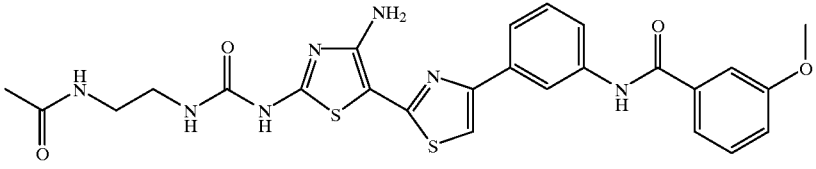 | 20 | 77 |
| 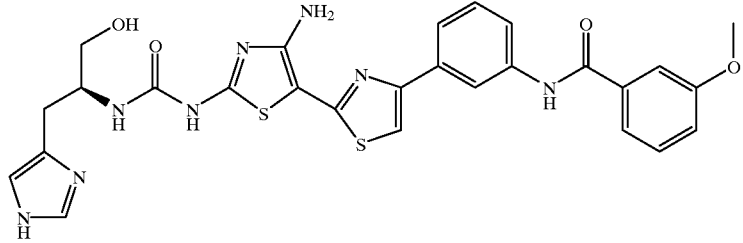 | 16 | 19 |
| 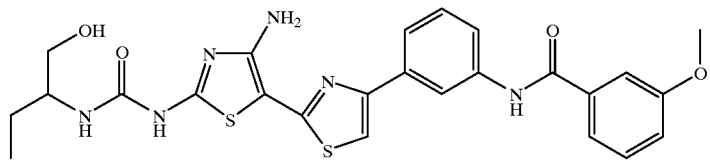 | 13 | 62 |
| 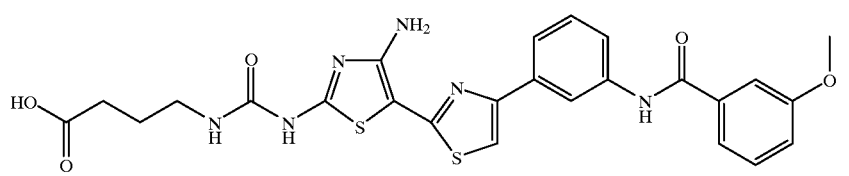 | 23 | 24 |
| 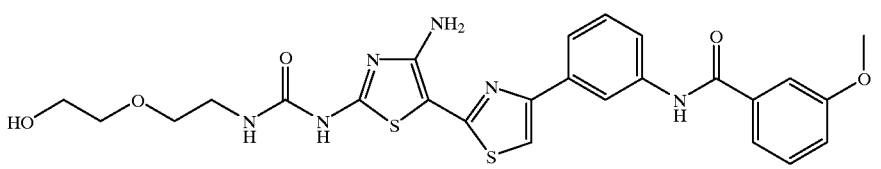 | 13 | 92 |
| 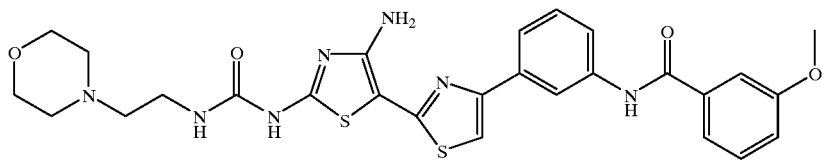 | 1 | 121 |

TABLE E-continued

Inhibition of HUVEC Proliferation

| MOLSTRUCTURE | % inhibition @ 10 nM | % inhibition @ 50 nM |
|---|---|---|
| | 4 | 39 |
| | −2 | 128 |
| | 7 | 17 |
| | 8 | 42 |
| | −5 | 103 |
| | 3 | 105 |
| | −2 | 116 |

TABLE E-continued
Inhibition of HUVEC Proliferation
| MOLSTRUCTURE | % inhibition @ 10 nM | % inhibition @ 50 nM |
|---|---|---|
| 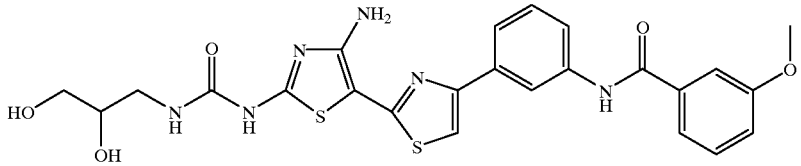 | −3 | 42 |
| 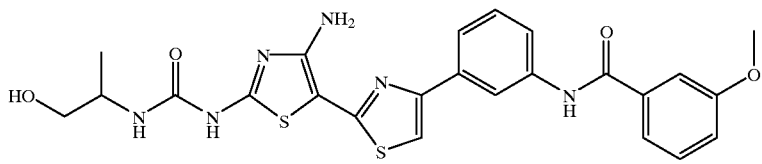 | −3 | 42 |
| 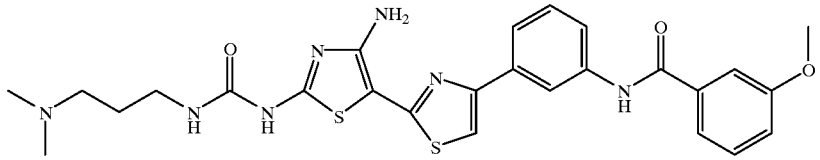 | −8 | 15 |
| 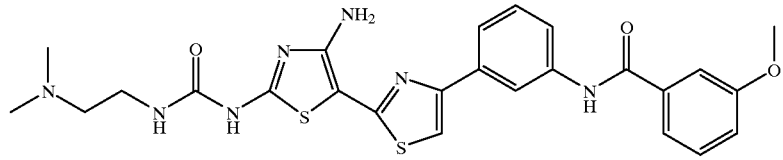 | −11 | 46 |
| 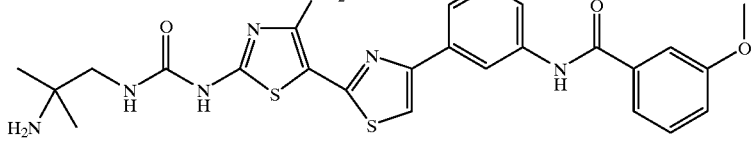 | 14 | 3 |
| 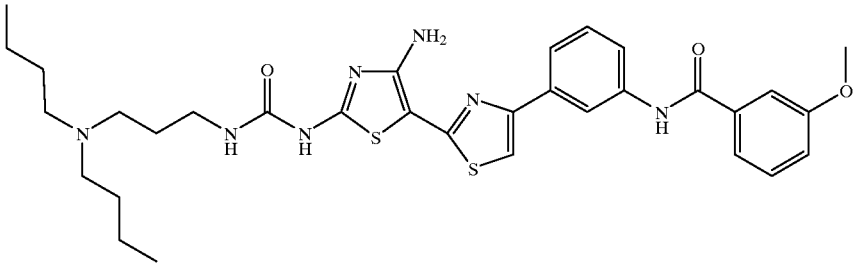 | −5 | 62 |
| 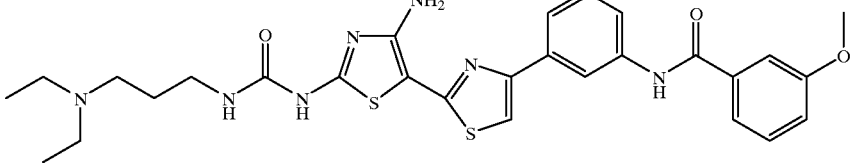 | −7 | 45 |

TABLE E-continued
Inhibition of HUVEC Proliferation
| MOLSTRUCTURE | % inhibition @ 10 nM | % inhibition @ 50 nM |
| --- | --- | --- |
| 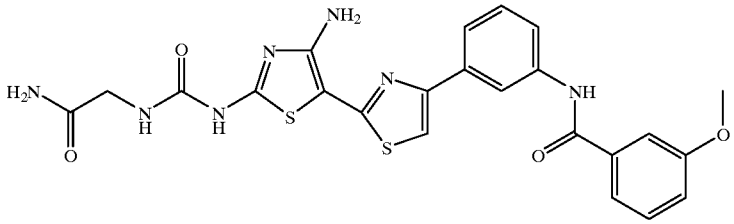 | 12 | 25 |
| 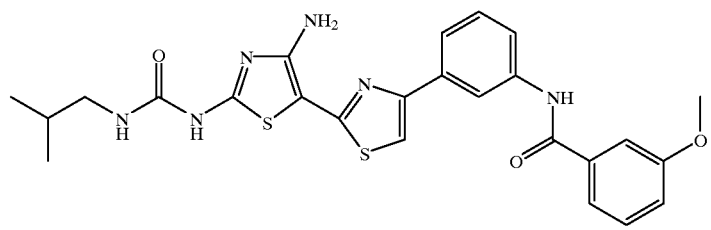 | −1 | −23 |
| 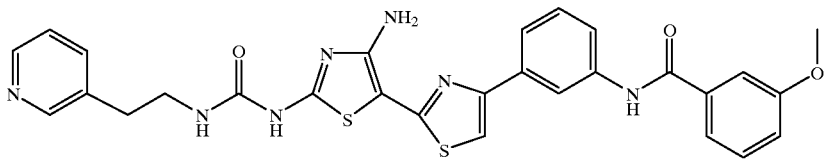 | 35 | 97 |
| 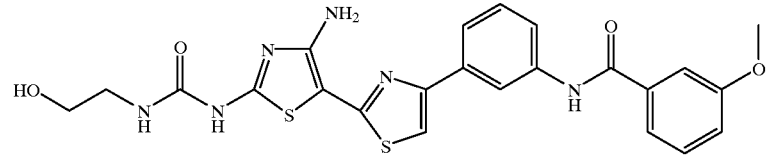 | 38 | No data |
| 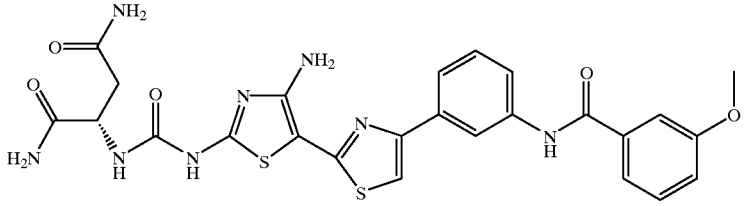 | 19 | 23 |
| 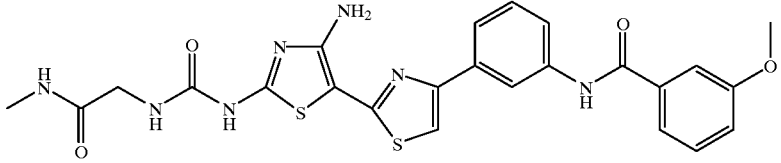 | 42 | 23 |
| 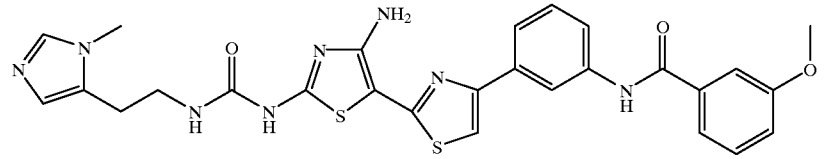 | −15 | 15 |

TABLE E-continued

Inhibition of HUVEC Proliferation

| MOLSTRUCTURE | % inhibition @ 10 nM | % inhibition @ 50 nM |
| --- | --- | --- |
| | −29 | 108 |
| | 12 | 28 |
| | 1 | 101 |
| | 2 | 22 |
| | −9 | 67 |
| | 0 | 35 |
| | 30 | 1 |
| | 7 | 68 |

TABLE E-continued

Inhibition of HUVEC Proliferation

| MOLSTRUCTURE | % inhibition @ 10 nM | % inhibition @ 50 nM |
|---|---|---|
| | −2 | 71 |
| | 32 | 24 |
| | −22 | −3 |
| | 2 | 117 |
| | 15 | 49 |
| | 9 | 86 |
| | −34 | 7 |
| | −3 | 3 |

TABLE E-continued
Inhibition of HUVEC Proliferation
| MOLSTRUCTURE | % inhibition @ 10 nM | % inhibition @ 50 nM |
|---|---|---|
| 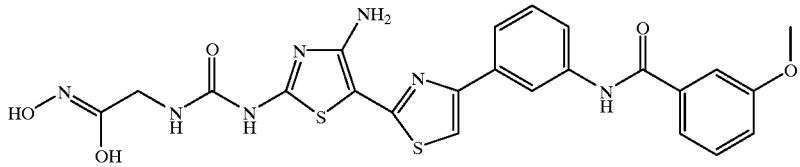 | −1 | 37 |
| 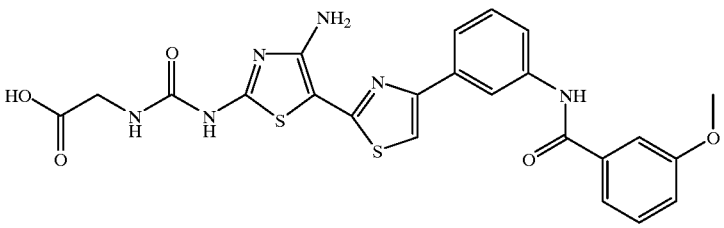 | 42 | 52 |
| 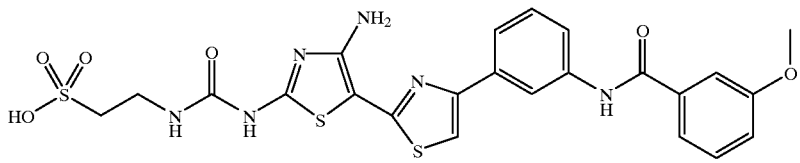 | 45 | 46 |
| 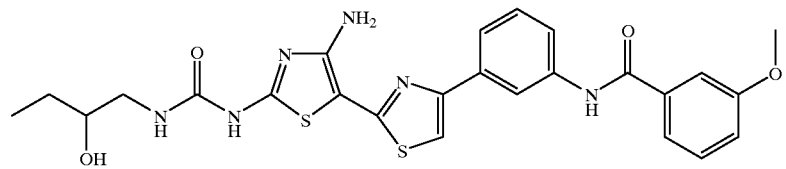 | 30 | 135 |
| 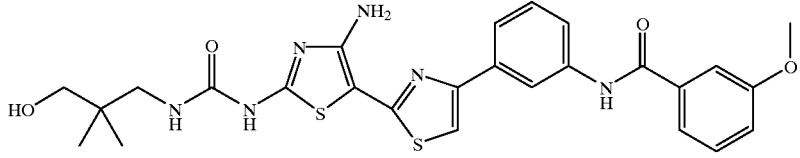 | 7 | 88 |
| 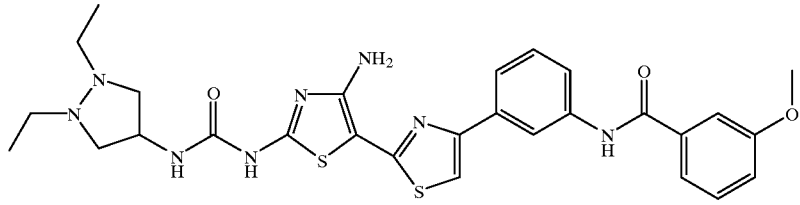 | −24 | 45 |
| 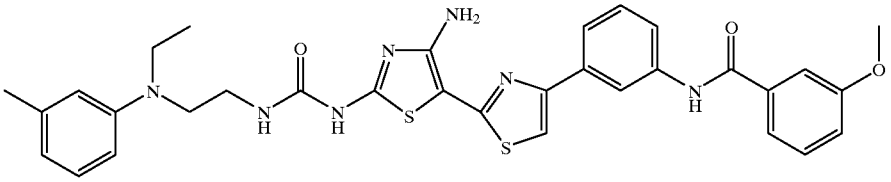 | −10 | 125 |

TABLE E-continued
Inhibition of HUVEC Proliferation
| MOLSTRUCTURE | % inhibition @ 10 nM | % inhibition @ 50 nM |
|---|---|---|
| 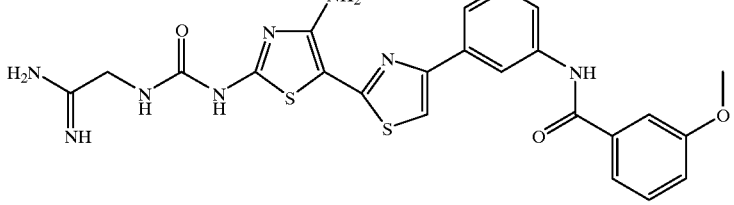 | 27 | 46 |
| 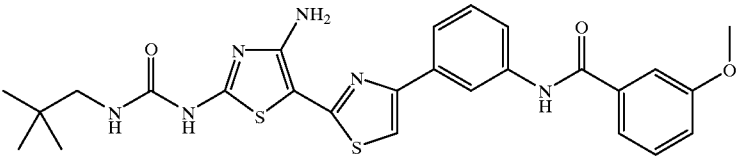 | 44 | 34 |
| 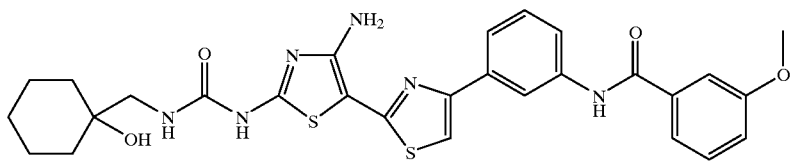 | 4 | 2 |
| 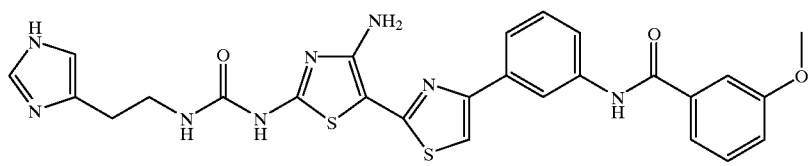 | 1 | −43 |
| 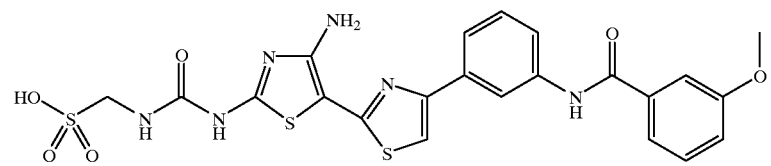 | −8 | 8 |
| 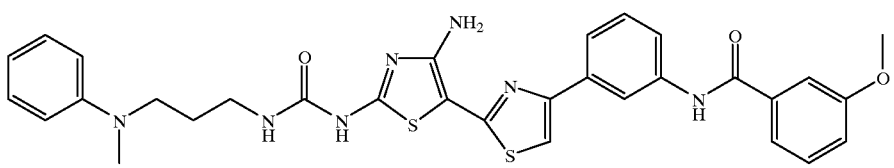 | 17 | 98 |
| 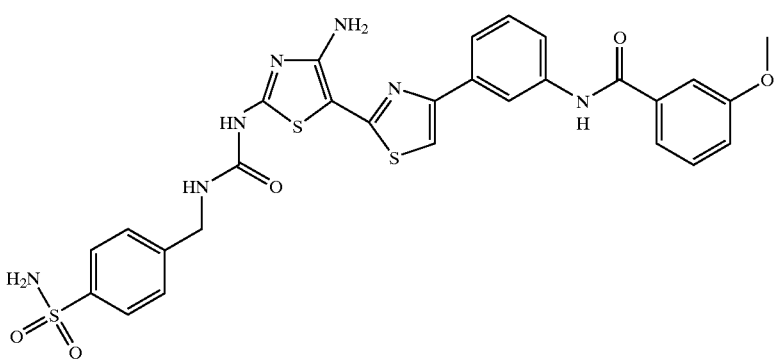 | 26 | 36 |

TABLE E-continued
Inhibition of HUVEC Proliferation
| MOLSTRUCTURE | % inhibition @ 10 nM | % inhibition @ 50 nM |
|---|---|---|
| 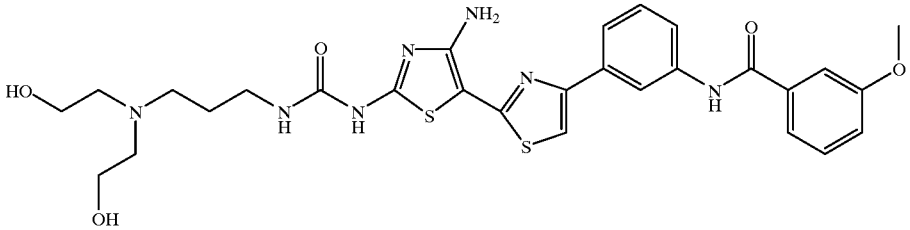 | 2 | 65 |
| 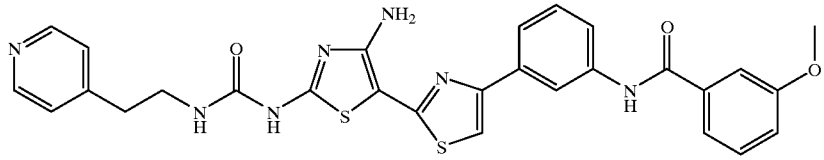 | −5 | 97 |
Inhibition of HUVEC Proliferation
| MOLSTRUCTURE | % inhibition @ 50 nM |
|---|---|
| 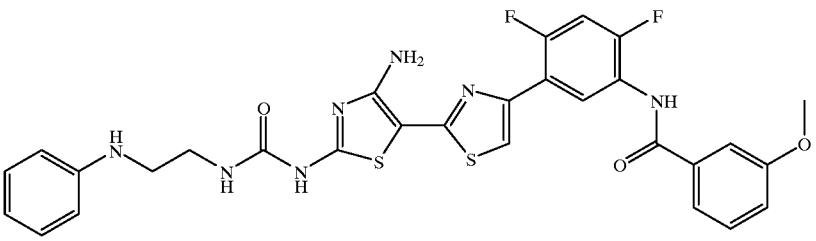 | 60 |
| 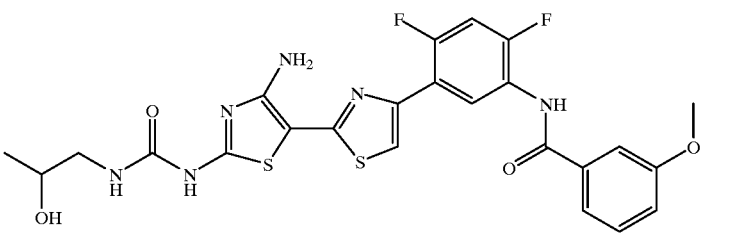 | 111 |
| 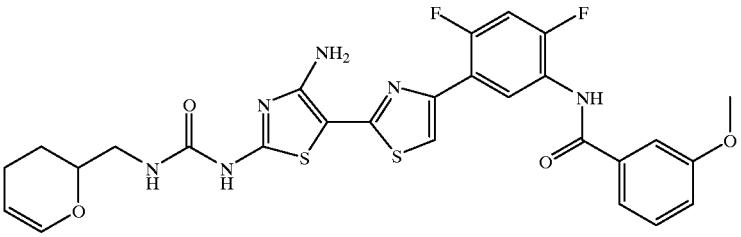 | 42 |

-continued
| Inhibition of HUVEC Proliferation | |
|---|---|
| MOLSTRUCTURE | % inhibition @ 50 nM |
| 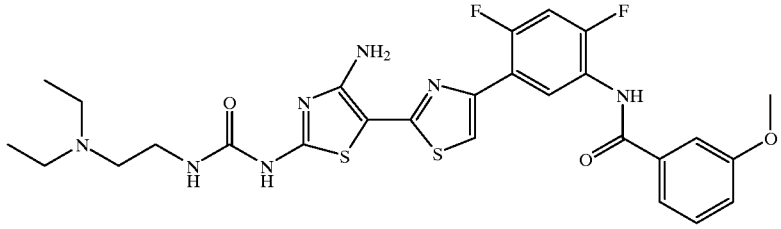 | 40 |
| 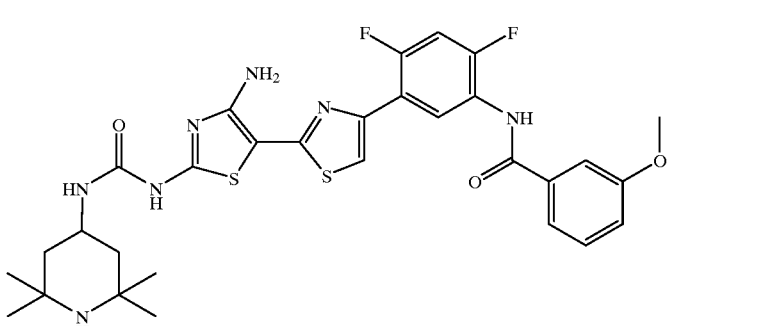 | 89 |
| 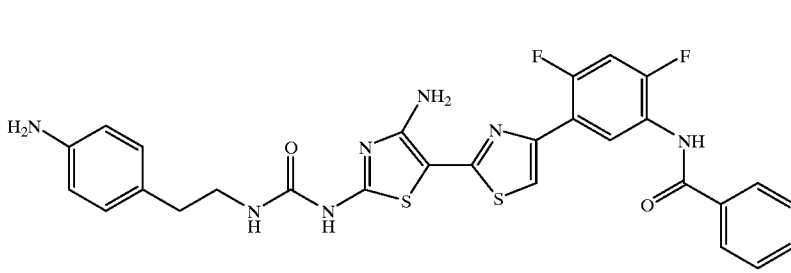 | 65 |
| 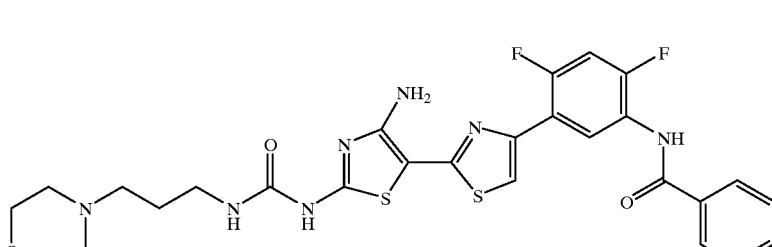 | 81 |
| 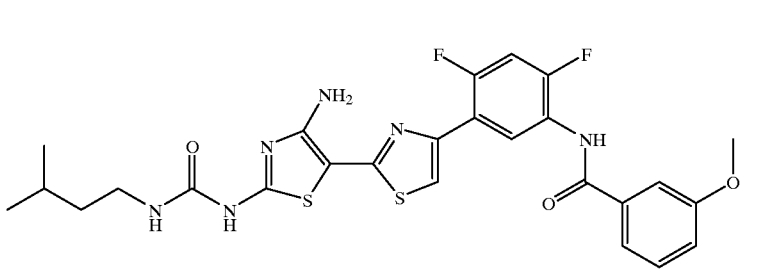 | 55 |

-continued

Inhibition of HUVEC Proliferation

| MOLSTRUCTURE | % inhibition @ 50 nM |
|---|---|
| | 92 |
| | 105 |
| | 27 |
| | 74 |
| | 93 |
| | 86 |

-continued
Inhibition of HUVEC Proliferation
| MOLSTRUCTURE | % inhibition @ 50 nM |
|---|---|
| 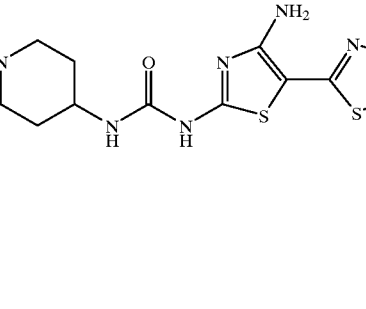 | 66 |
| 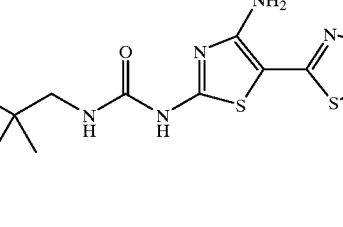 | 75 |
| 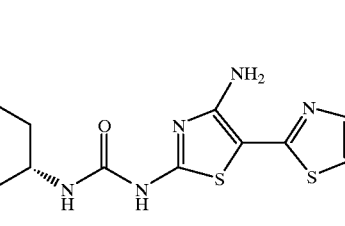 | 81 |
| 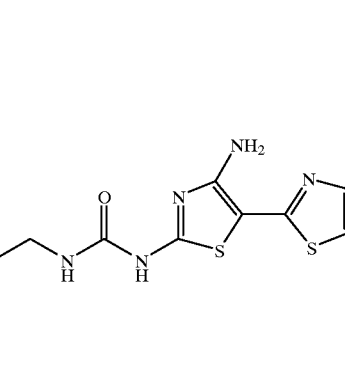 | 66 |
| 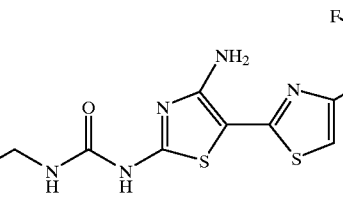 | 21 |

-continued

Inhibition of HUVEC Proliferation

| MOLSTRUCTURE | % inhibition @ 50 nM |
|---|---|
| *structure* | 2 |
| *structure* | 6 |
| *structure* | 25 |
| *structure* | 24 |
| *structure* | 39 |

-continued
Inhibition of HUVEC Proliferation
| MOLSTRUCTURE | % inhibition @ 50 nM |
|---|---|
| 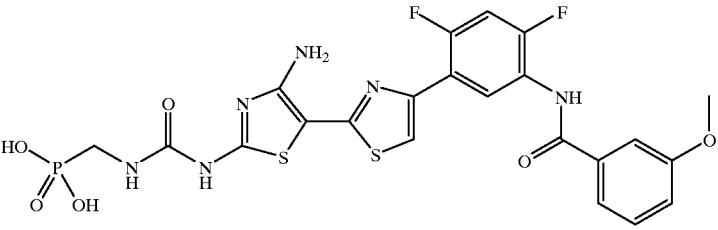 | 48 |
| 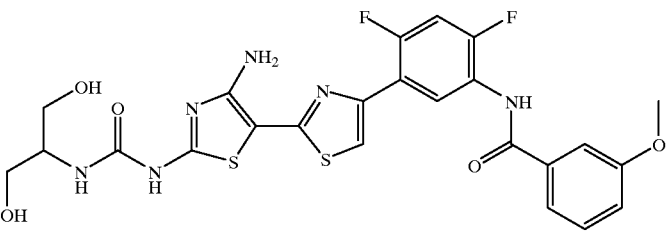 | 76 |
| 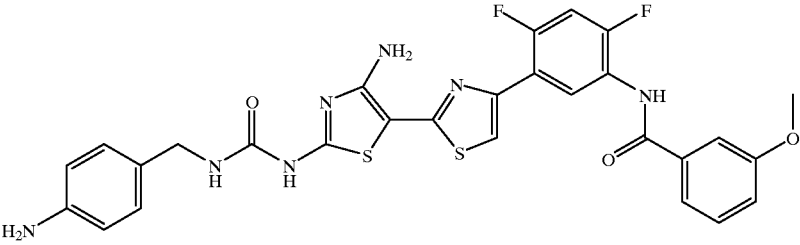 | 83 |
| 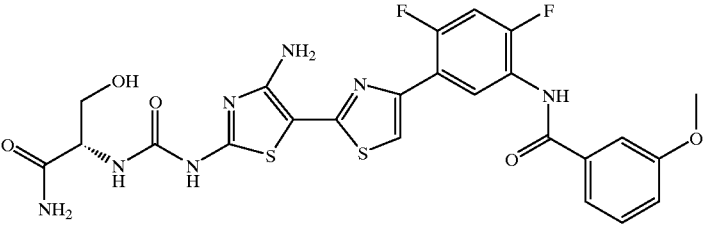 | 69 |
| 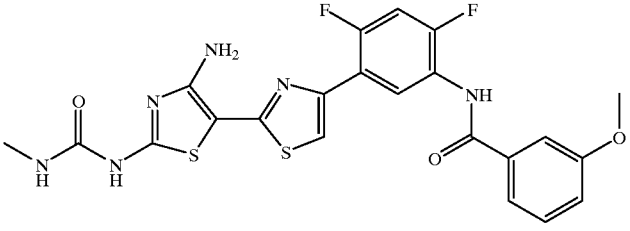 | 99 |
| 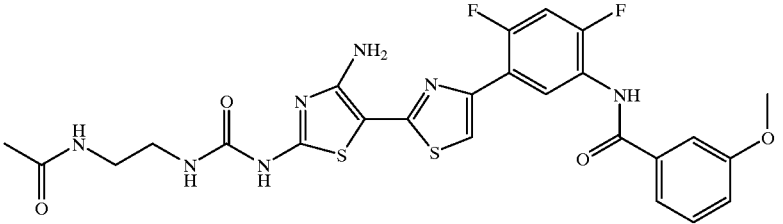 | 105 |

-continued

| Inhibition of HUVEC Proliferation | |
|---|---|
| MOLSTRUCTURE | % inhibition @ 50 nM |
| | 47 |
| | 108 |
| | 40 |
| | 98 |
| | 96 |

-continued
Inhibition of HUVEC Proliferation
| MOLSTRUCTURE | % inhibition @ 50 nM |
|---|---|
| 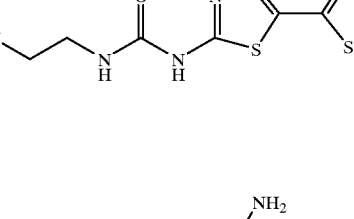 | 46 |
| 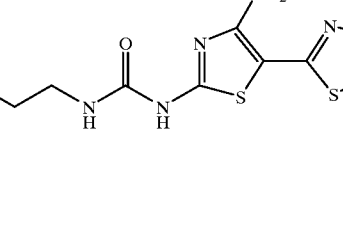 | 105 |
| 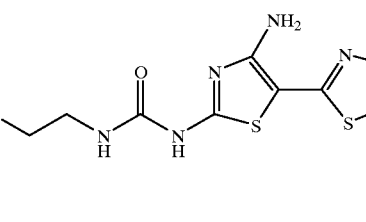 | 93 |
| 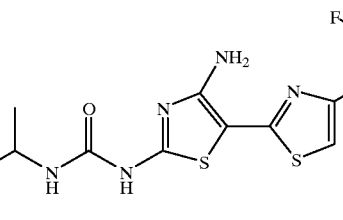 | 93 |
| 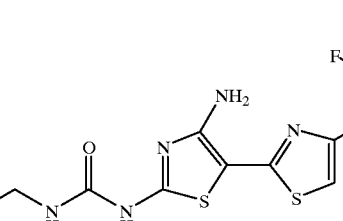 | 118 |
| 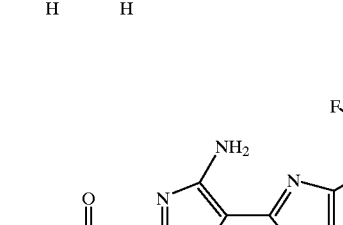 | 102 |

-continued

Inhibition of HUVEC Proliferation

| MOLSTRUCTURE | % inhibition @ 50 nM |
|---|---|
| | 95 |
| | 74 |
| | 98 |
| | 72 |
| | 63 |
| | 73 |

-continued

Inhibition of HUVEC Proliferation

| MOLSTRUCTURE | % inhibition @ 50 nM |
|---|---|
| (structure) | 81 |
| (structure) | 89 |
| (structure) | 48 |
| (structure) | 38 |
| (structure) | 100 |

-continued
Inhibition of HUVEC Proliferation
| MOLSTRUCTURE | % inhibition @ 50 nM |
|---|---|
| 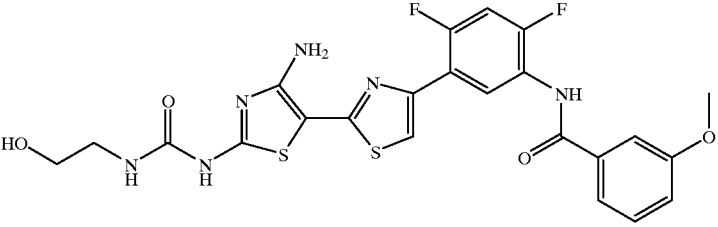 | 110 |
| 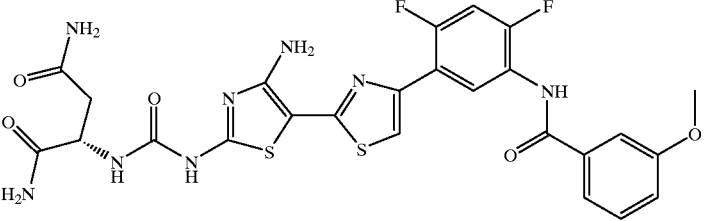 | 32 |
| 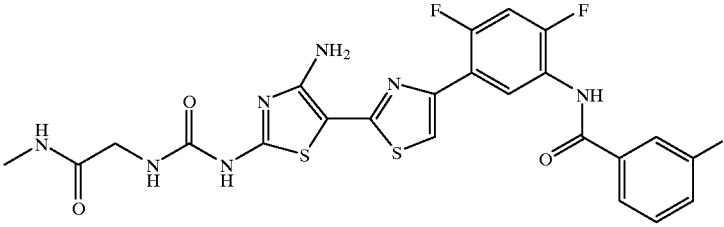 | 73 |
| 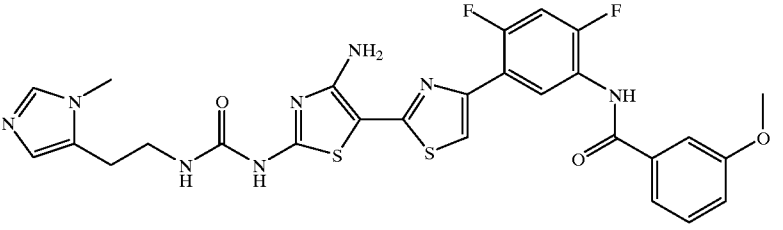 | 58 |
| 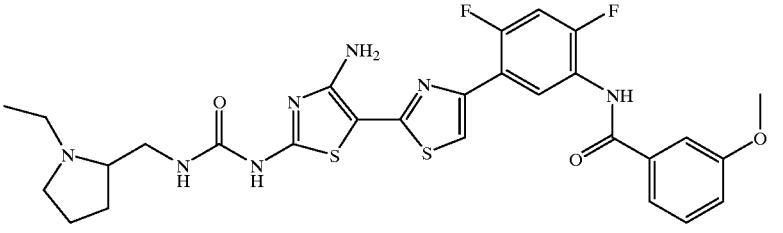 | 85 |
| 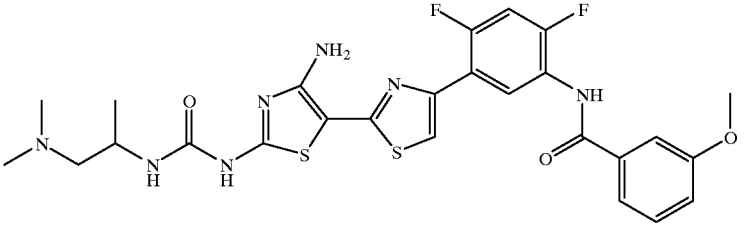 | 64 |

-continued
Inhibition of HUVEC Proliferation
| MOLSTRUCTURE | % inhibition @ 50 nM |
|---|---|
| 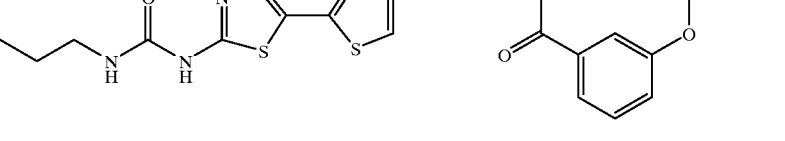 | 92 |
| 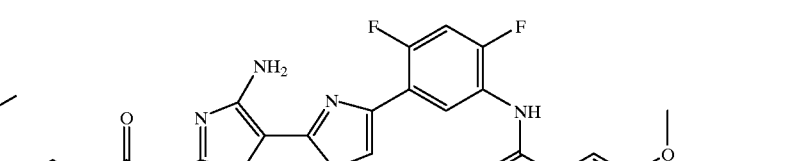 | 82 |
| 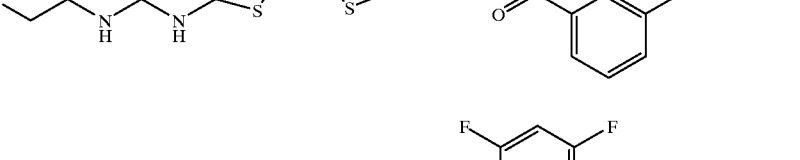 | 95 |
| 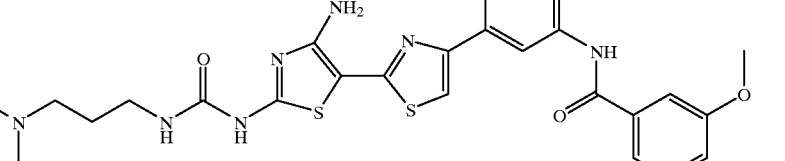 | 78 |
| 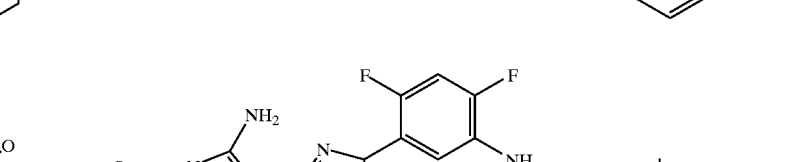 | 48 |
| 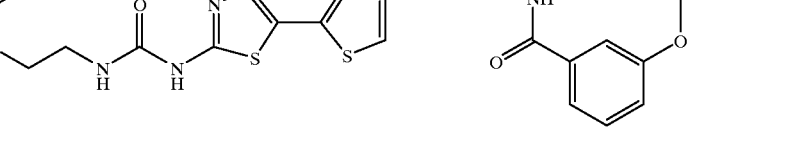 | 84 |

-continued

Inhibition of HUVEC Proliferation

| MOLSTRUCTURE | % inhibition @ 50 nM |
|---|---|
| | 30 |
| | 83 |
| | 22 |
| | 86 |
| | 89 |
| | 100 |

-continued
| Inhibition of HUVEC Proliferation | |
|---|---|
| MOLSTRUCTURE | % inhibition @ 50 nM |
| 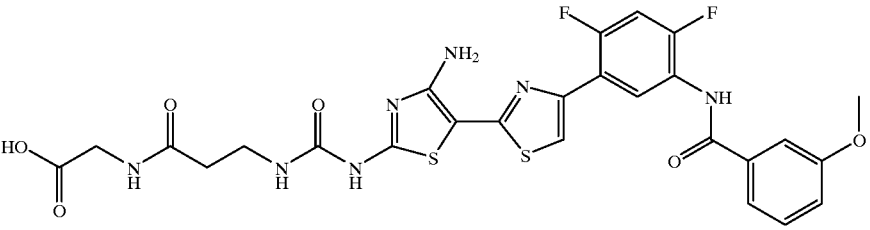 | 57 |
| 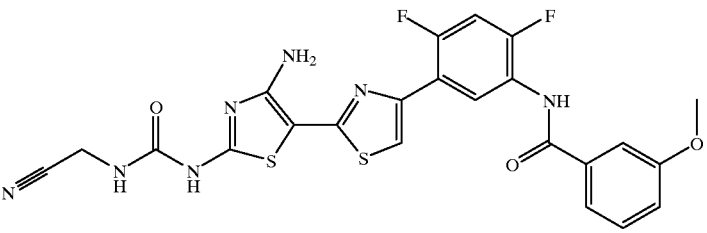 | 71 |
| 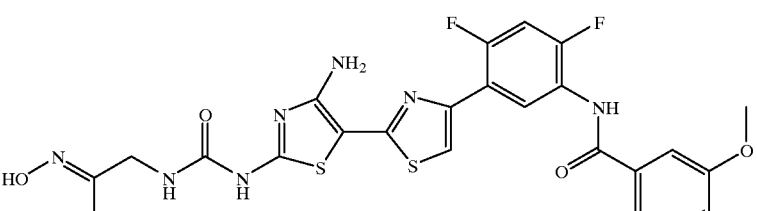 | 19 |
| 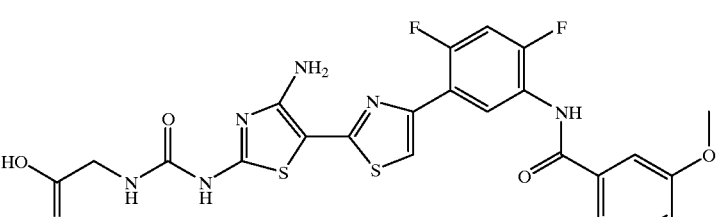 | 23 |
| 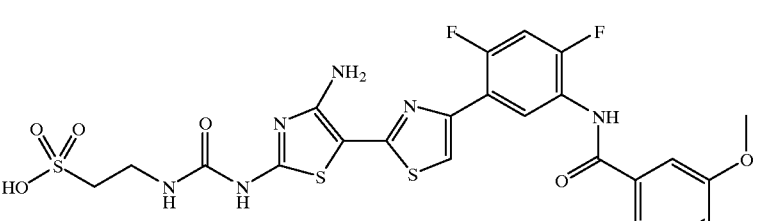 | 27 |
| 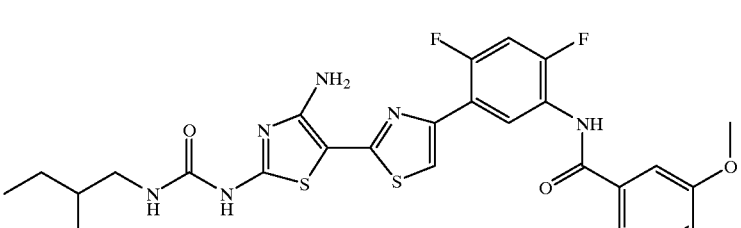 | 104 |

-continued
Inhibition of HUVEC Proliferation
| MOLSTRUCTURE | % inhibition @ 50 nM |
|---|---|
| 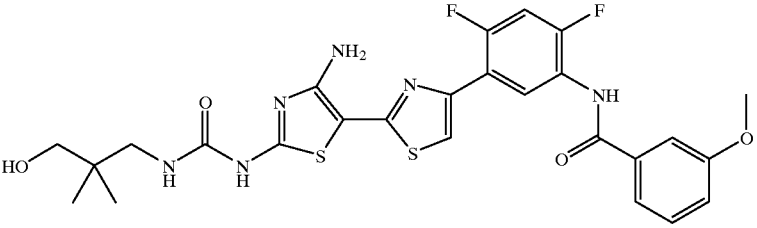 | 120 |
| 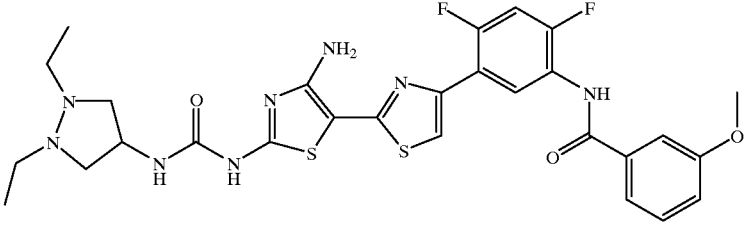 | 82 |
| 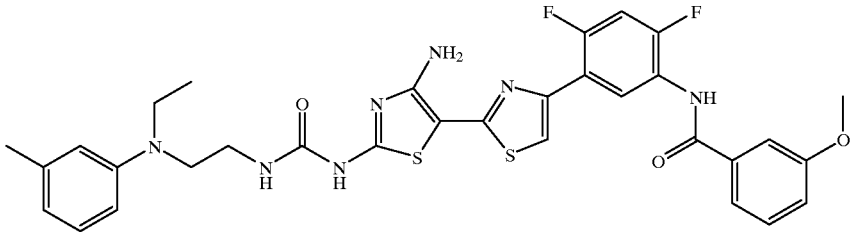 | 18 |
| 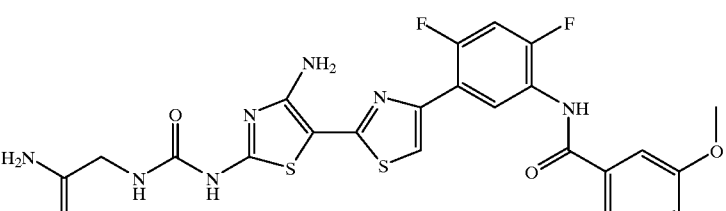 | 17 |
| 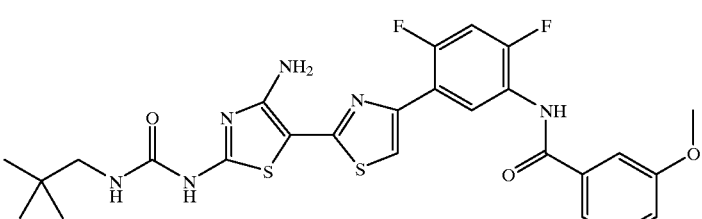 | 43 |

-continued

Inhibition of HUVEC Proliferation

| MOLSTRUCTURE | % inhibition @ 50 nM |
|---|---|
| | 72 |
| | 55 |
| | 0 |
| | 45 |

-continued

Inhibition of HUVEC Proliferation

| MOLSTRUCTURE | % inhibition @ 50 nM |
|---|---|
| (structure) | 77 |
| (structure) | 51 |
| (structure) | 98 |

Inhibition of HUVEC Proliferation

| MOLSTRUCTURE | Inhibition @ 50 nM |
|---|---|
| (structure) | 89 |

-continued
Inhibition of HUVEC Proliferation
| MOLSTRUCTURE | Inhibition @ 50 nM |
|---|---|
| 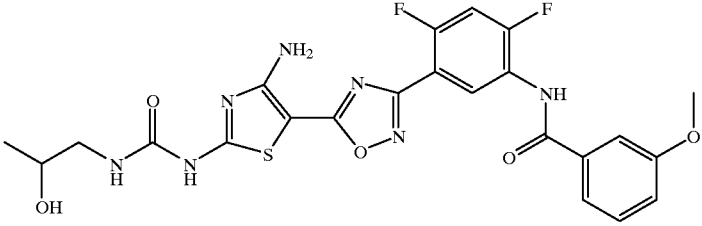 | 78 |
| 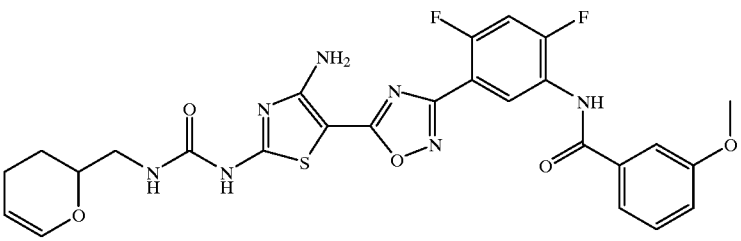 | 93 |
| 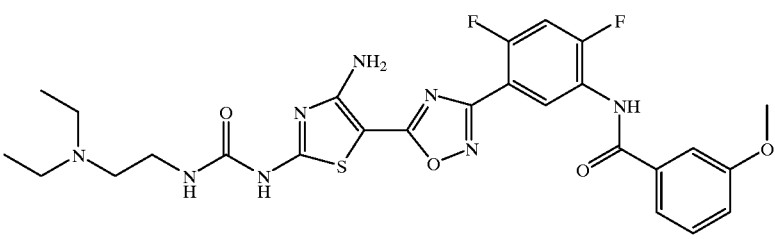 | 82 |
| 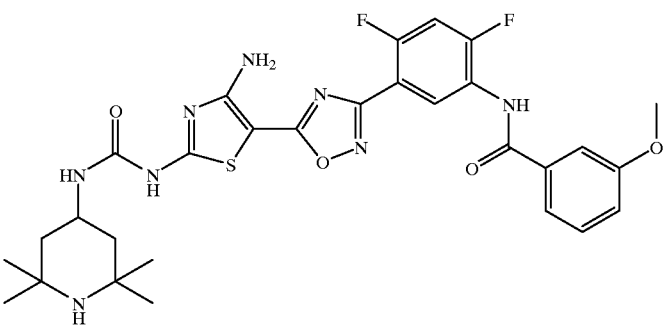 | 99 |
| 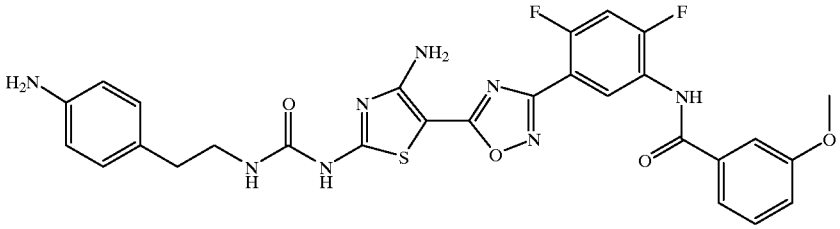 | 88 |

-continued

Inhibition of HUVEC Proliferation

| MOLSTRUCTURE | Inhibition @ 50 nM |
|---|---|
| | 80 |
| | 96 |
| | 107 |
| | 106 |
| | 104 |
| | 78 |

-continued
| Inhibition of HUVEC Proliferation | |
|---|---|
| MOLSTRUCTURE | Inhibition @ 50 nM |
| 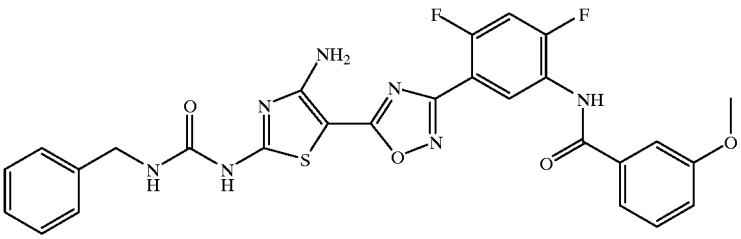 | 61 |
| 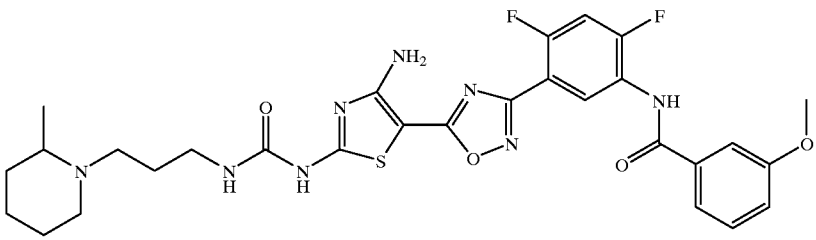 | 96 |
| 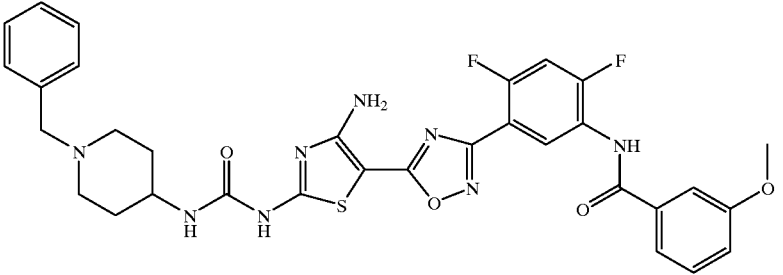 | 82 |
| 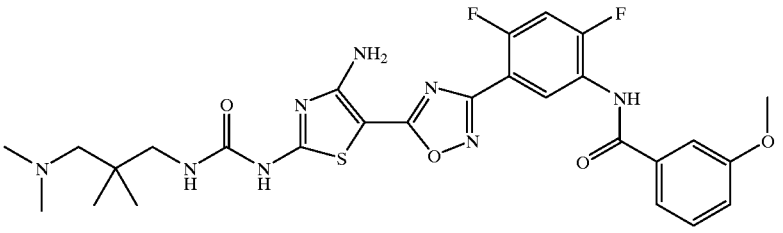 | 77 |
| 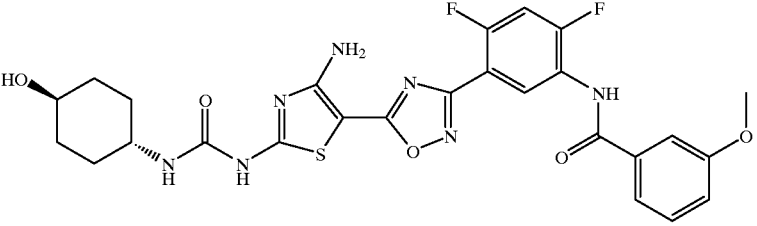 | 92 |

Inhibition of HUVEC Proliferation

| MOLSTRUCTURE | Inhibition @ 50 nM |
|---|---|
| [structure] | 56 |
| [structure] | 53 |
| [structure] | 89 |
| [structure] | 87 |
| [structure] | 83 |
| [structure] | 42 |

-continued
Inhibition of HUVEC Proliferation
| MOLSTRUCTURE | Inhibition @ 50 nM |
|---|---|
| 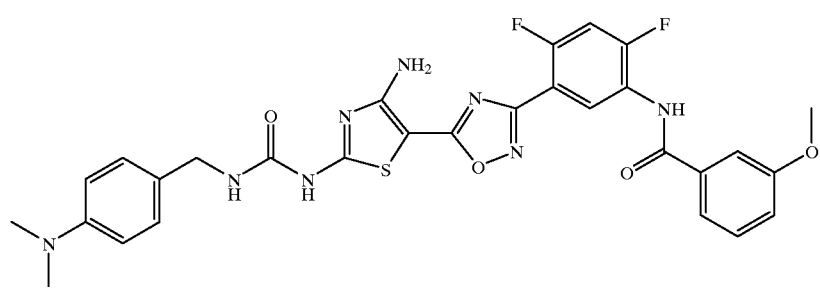 | 48 |
| 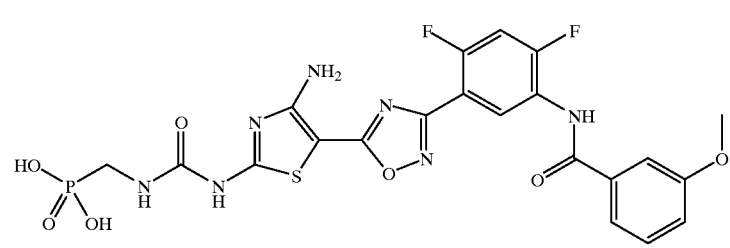 | 4 |
| 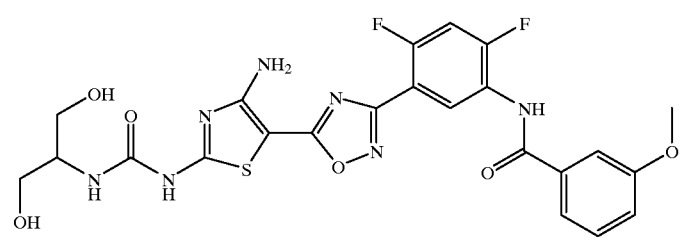 | 31 |
| 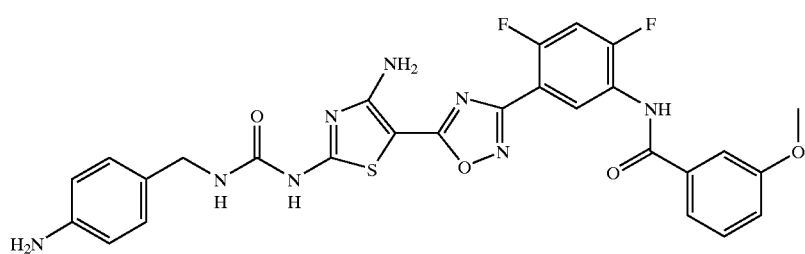 | 82 |
| 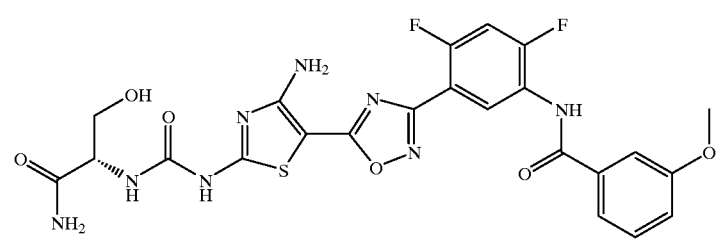 | 59 |

-continued
Inhibition of HUVEC Proliferation
| MOLSTRUCTURE | Inhibition @ 50 nM |
|---|---|
| 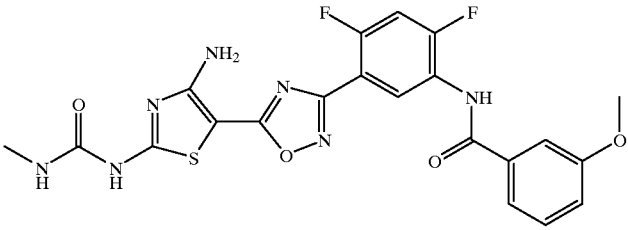 | 105 |
| 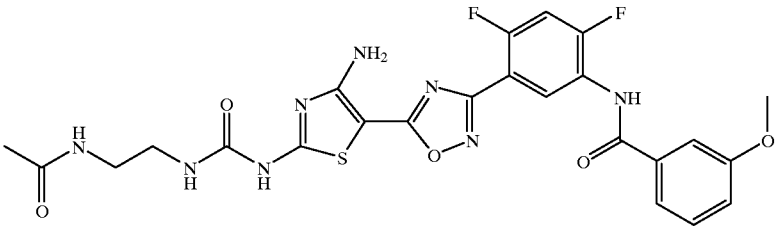 | 75 |
| 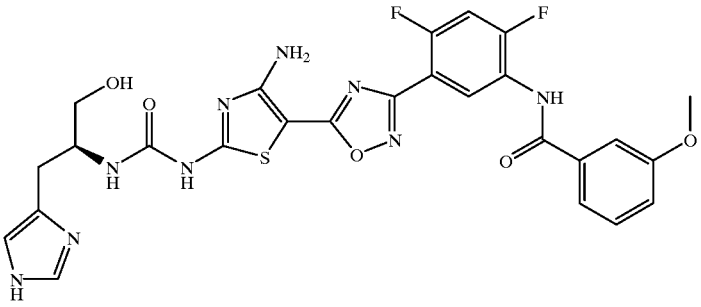 | 77 |
| 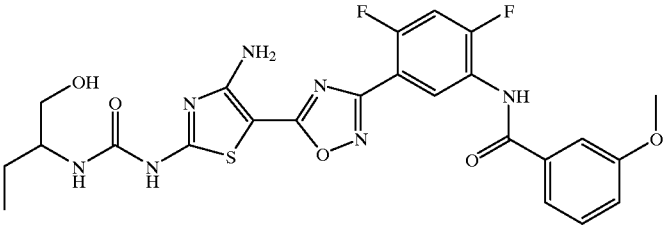 | 81 |
| 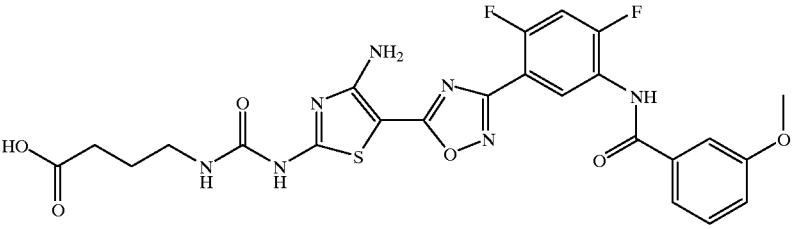 | 96 |

-continued
Inhibition of HUVEC Proliferation
| MOLSTRUCTURE | Inhibition @ 50 nM |
|---|---|
| 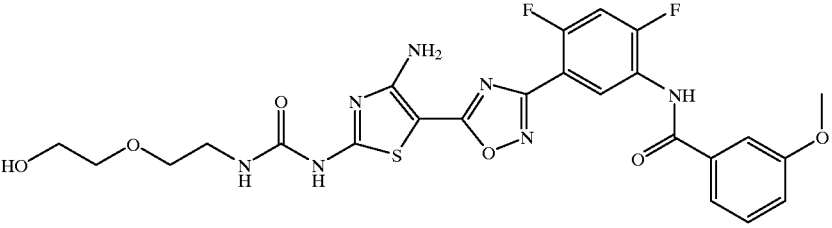 | 98 |
| 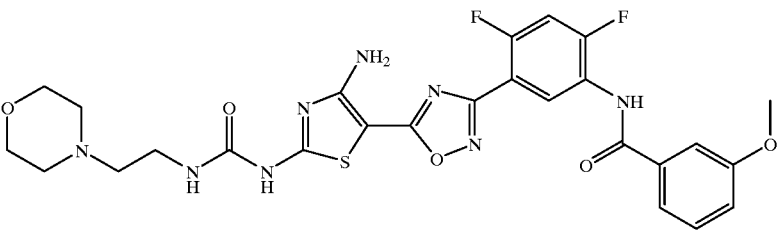 | 106 |
| 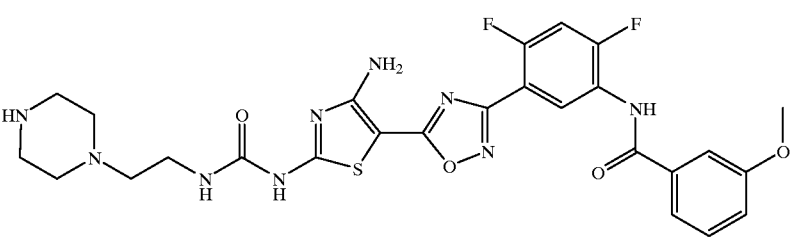 | 76 |
| 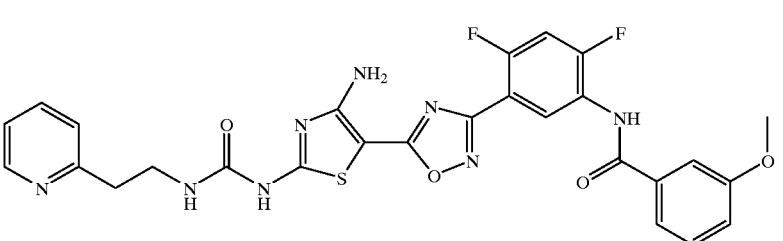 | 78 |
| 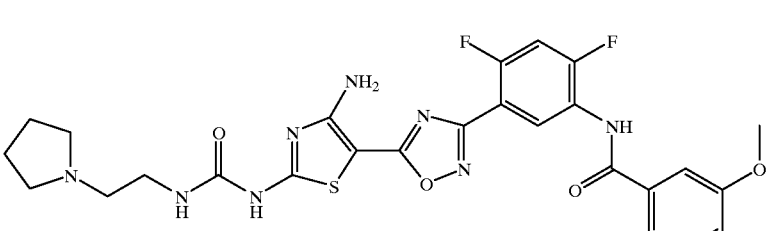 | 79 |
| 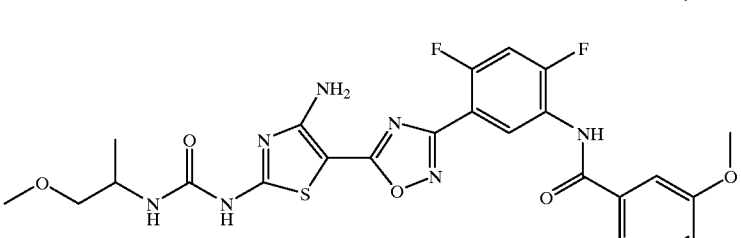 | 80 |

-continued

Inhibition of HUVEC Proliferation

| MOLSTRUCTURE | Inhibition @ 50 nM |
|---|---|
| | 112 |
| | 98 |
| | 87 |
| | 45 |
| | 77 |
| | 87 |

-continued
Inhibition of HUVEC Proliferation
| MOLSTRUCTURE | Inhibition @ 50 nM |
|---|---|
| 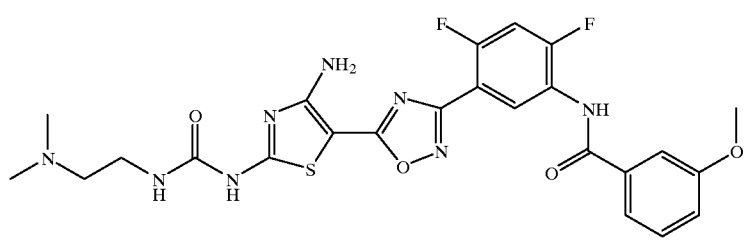 | 69 |
| 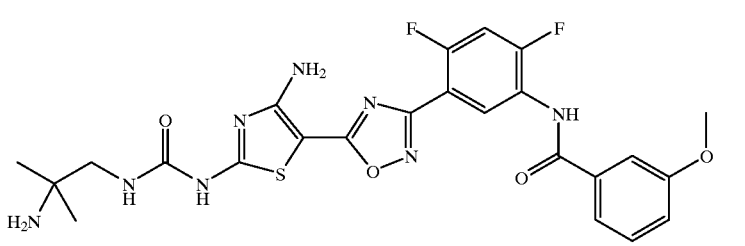 | 14 |
| 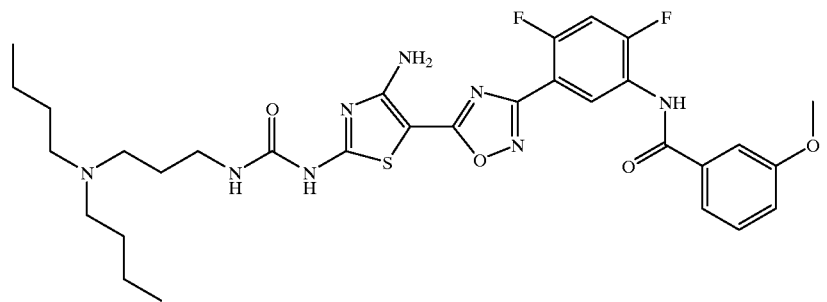 | 80 |
| 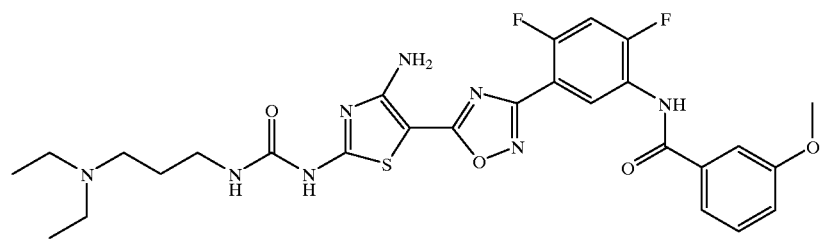 | 85 |
| 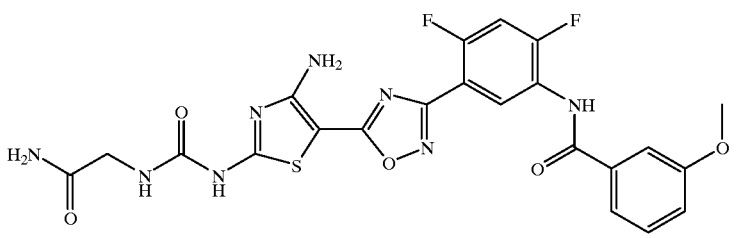 | 30 |

-continued

Inhibition of HUVEC Proliferation

| MOLSTRUCTURE | Inhibition @ 50 nM |
|---|---|
| [structure] | 20 |
| [structure] | 38 |
| [structure] | 19 |
| [structure] | 86 |
| [structure] | 51 |
| [structure] | 10 |

-continued

Inhibition of HUVEC Proliferation

| MOLSTRUCTURE | Inhibition @ 50 nM |
|---|---|
| (structure) | 12 |
| (structure) | 27 |
| (structure) | 75 |
| (structure) | −6 |
| (structure) | 72 |
| (structure) | −2 |

-continued
Inhibition of HUVEC Proliferation
| MOLSTRUCTURE | Inhibition @ 50 nM |
|---|---|
| 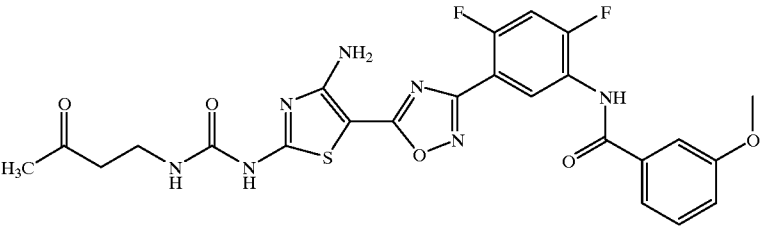 | 6 |
| 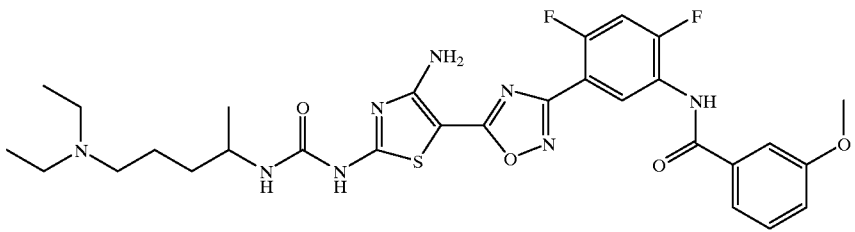 | 7 |
| 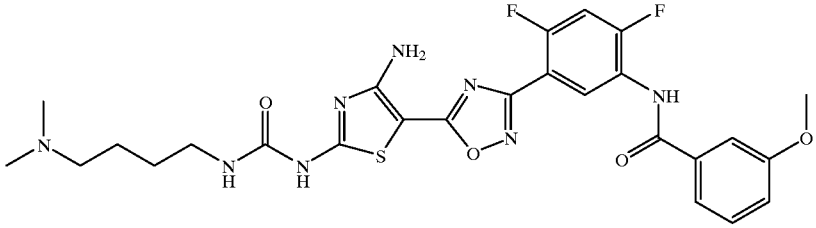 | −3 |
| 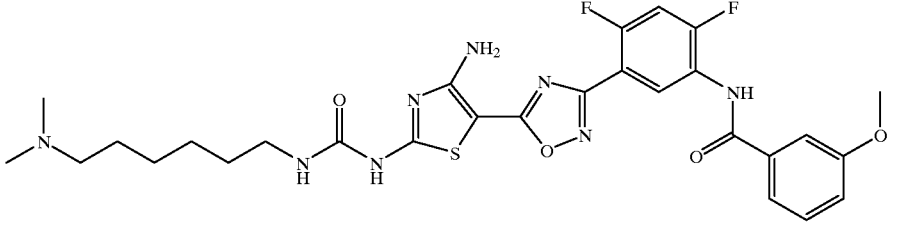 | −6 |
| 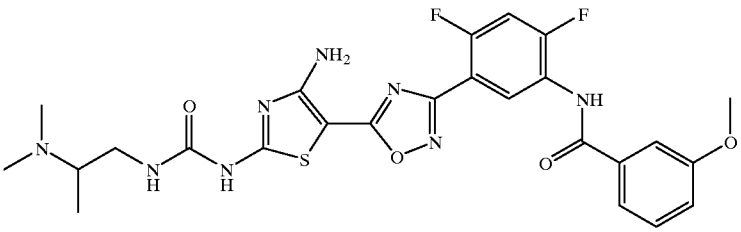 | −25 |
| 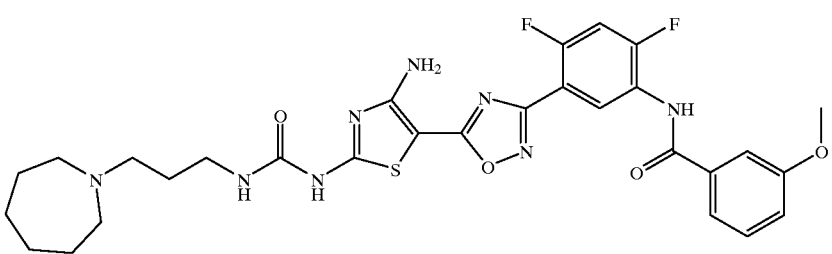 | 21 |

-continued

Inhibition of HUVEC Proliferation

| MOLSTRUCTURE | Inhibition @ 50 nM |
|---|---|
| (structure) | −20 |
| (structure) | −7 |
| (structure) | 49 |
| (structure) | 12 |
| (structure) | −12 |
| (structure) | 73 |

-continued
Inhibition of HUVEC Proliferation
| MOLSTRUCTURE | Inhibition @ 50 nM |
|---|---|
| 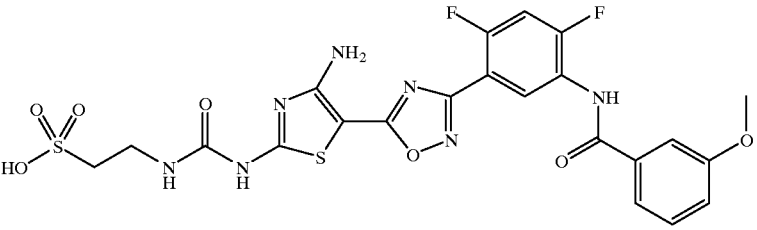 | 88 |
| 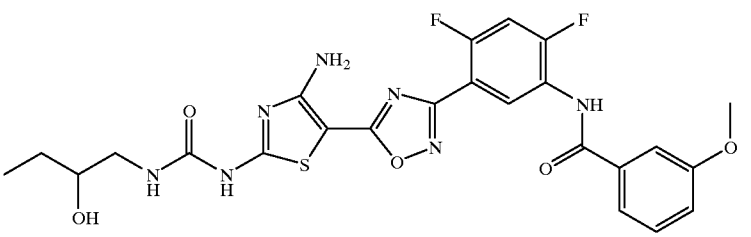 | 93 |
| 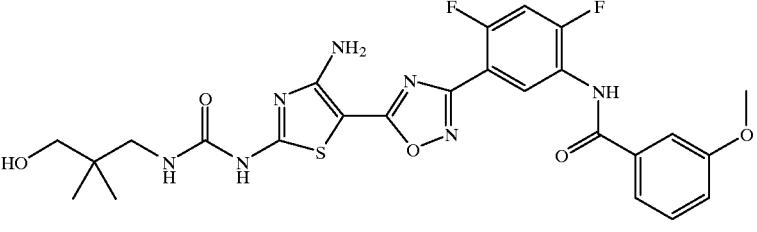 | 104 |
| 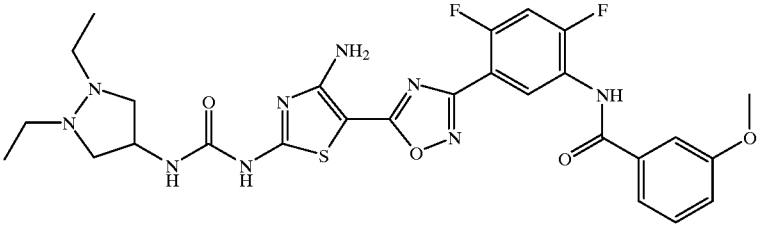 | 92 |
| 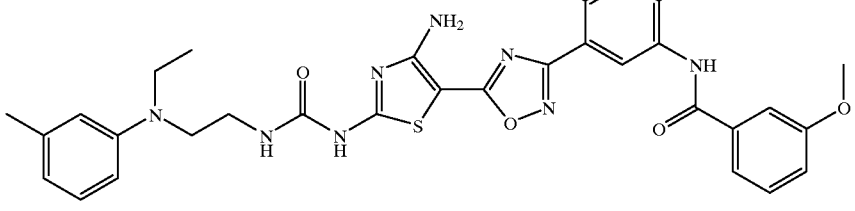 | 67 |
| 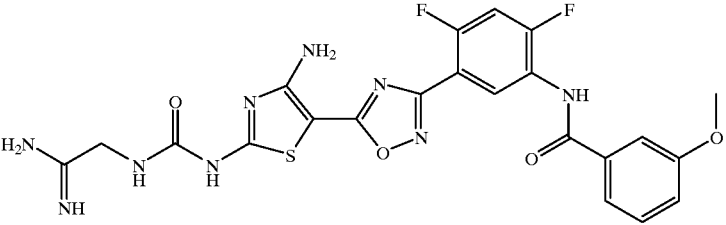 | 65 |

-continued
Inhibition of HUVEC Proliferation
| MOLSTRUCTURE | Inhibition @ 50 nM |
|---|---|
| 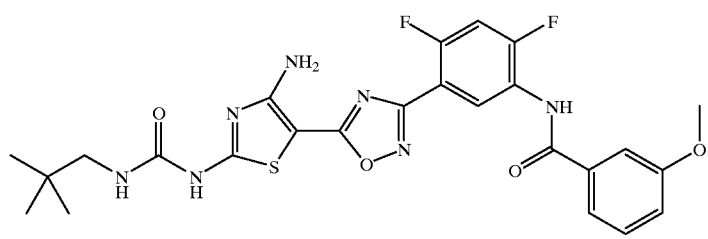 | 55 |
| 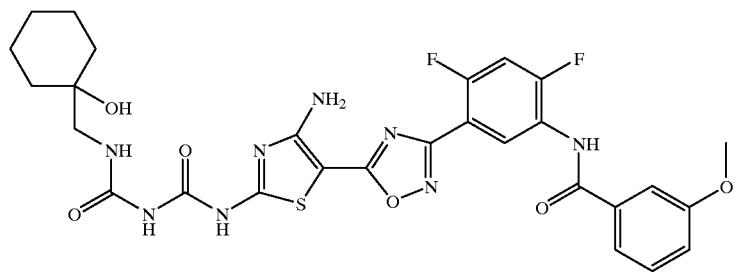 | 99 |
| 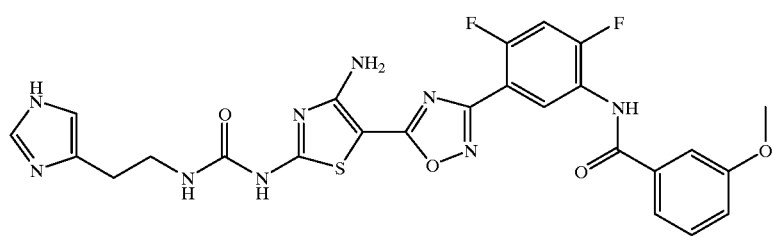 | 72 |
| 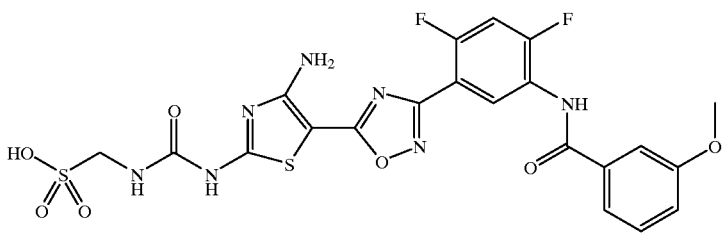 | 30 |

-continued

Inhibition of HUVEC Proliferation

| MOLSTRUCTURE | Inhibition @ 50 nM |
|---|---|
| (structure) | 84 |
| (structure) | 82 |
| (structure) | 84 |
| (structure) | 99 |

Combinatorial Procedure for Examples in Table I 0.1 M Solutions of the acid, the amine template, o-(7-azabenzotriazol-1-yl)-N,N,N',N'-tetra-methyluronium hexafluorophosphate and triethylamine were prepared separately in anhydrous DMF. To each tube in an array of 8×11 culture tubes (10×75 mm) was added 110 μL (0.011 mmol) of a different acid. To this was added 100 μL (0.01 mmol) of the amine solution, 110 μL (0.011 mmol) of the triethylamine solution followed by 110 μL (0.011 mmol) of the o-(7-azabenzotriazol-1-yl)-N,N,N',N'-tetra-methyluronium hexafluorophosphate solution. The reactions were stirred in a heating block at 60° C. for 6 h. The reaction mixtures were transferred to a 1 mL 96-well plate using a liquid handler. The solvents were removed using the SpeedVac™ apparatus and the crude reaction mixtures were redissolved in DMSO to give a final theoretical concentration of 10 mM. Screening results are shown in Table I.

TABLE I

| MOL>MOLSTRUCTURE | % inhibition @ 150 nM |
|---|---|
| [structure] | 8 |
| [structure] | 7 |

TABLE I-continued
| MOL>MOLSTRUCTURE | % inhibition @ 150 nM |
|---|---|
| 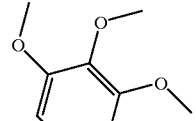 | 40 |
| 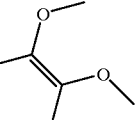 | 33 |
| 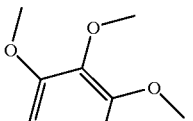 | −14 |

TABLE I-continued
| MOL>MOLSTRUCTURE | % inhibition @ 150 nM |
|---|---|
| 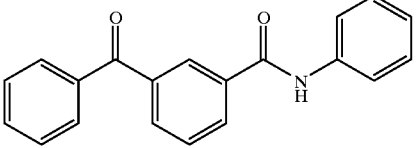 | −18 |
| 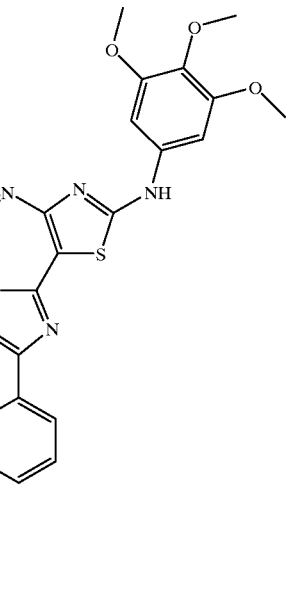 | −24 |
| 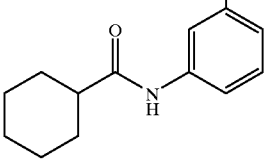 | −32 |

TABLE I-continued
| MOL>MOLSTRUCTURE | % inhibition @ 150 nM |
|---|---|
| 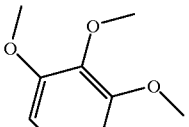 | 3 |
| 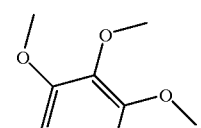 | 0 |
| 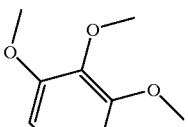 | 8 |

TABLE I-continued

| MOL>MOLSTRUCTURE | % inhibition @ 150 nM |
|---|---|
| | 36 |
| | 10 |
| | 7 |

TABLE I-continued
| MOL>MOLSTRUCTURE | % inhibition @ 150 nM |
|---|---|
| 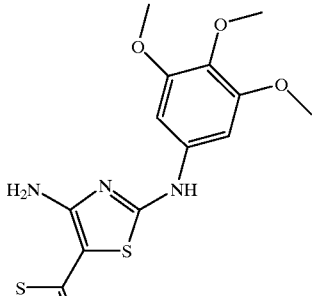 | 15 |
| 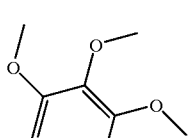 | −4 |
| 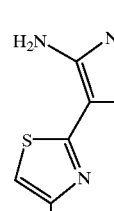 | −4 |

TABLE I-continued
| MOL>MOLSTRUCTURE | % inhibition @ 150 nM |
|---|---|
| 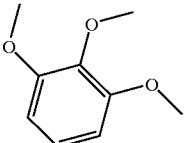 | −26 |
| 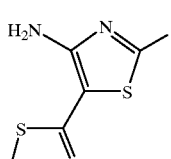 | 4 |
| 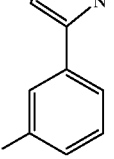 | 20 |

TABLE I-continued
| MOL>MOLSTRUCTURE | % inhibition @ 150 nM |
|---|---|
| 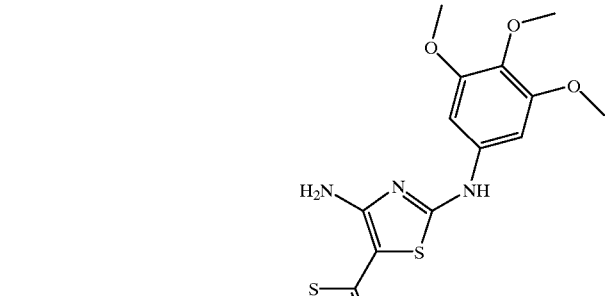 | −7 |
| 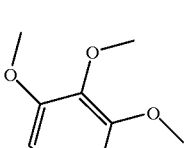 | 6 |
| 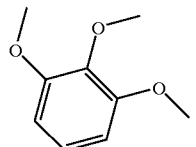 | 53 |

TABLE I-continued

| MOL>MOLSTRUCTURE | % inhibition @ 150 nM |
|---|---|
| *(structure)* | 22 |
| *(structure)* | 15 |
| *(structure)* | 3 |

TABLE I-continued

| MOL>MOLSTRUCTURE | % inhibition @ 150 nM |
|---|---|
| | 10 |
| | −4 |
| | −34 |

TABLE I-continued

| MOL>MOLSTRUCTURE | % inhibition @ 150 nM |
|---|---|
| (structure) | 3 |
| (structure) | 6 |
| (structure) | −10 |

TABLE I-continued

| MOL>MOLSTRUCTURE | % inhibition @ 150 nM |
|---|---|
| (structure) | 11 |
| (structure) | 5 |
| (structure) | 11 |

TABLE I-continued

| MOL>MOLSTRUCTURE | % inhibition @ 150 nM |
|---|---|
| | 29 |
| | 39 |
| | −3 |

TABLE I-continued

| MOL>MOLSTRUCTURE | % inhibition @ 150 nM |
|---|---|
| | 0 |
| | 15 |
| | 15 |

TABLE I-continued

| MOL>MOLSTRUCTURE | % inhibition @ 150 nM |
|---|---|
| [structure] | 5 |
| [structure] | 4 |
| [structure] | 2 |

TABLE I-continued

| MOL>MOLSTRUCTURE | % inhibition @ 150 nM |
|---|---|
| *[structure]* | 5 |
| *[structure]* | 0 |
| *[structure]* | −8 |

TABLE I-continued
| MOL>MOLSTRUCTURE | % inhibition @ 150 nM |
|---|---|
| 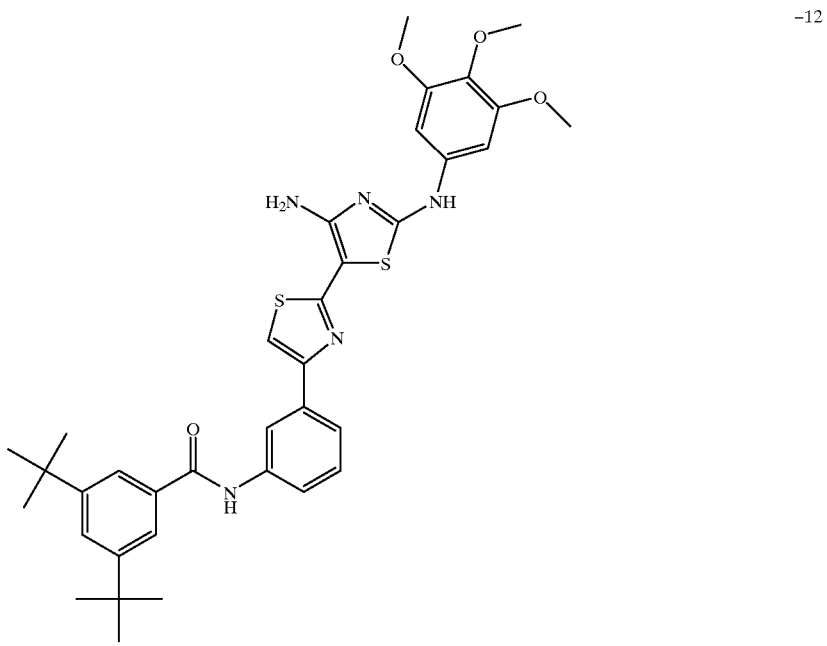 | −12 |
| 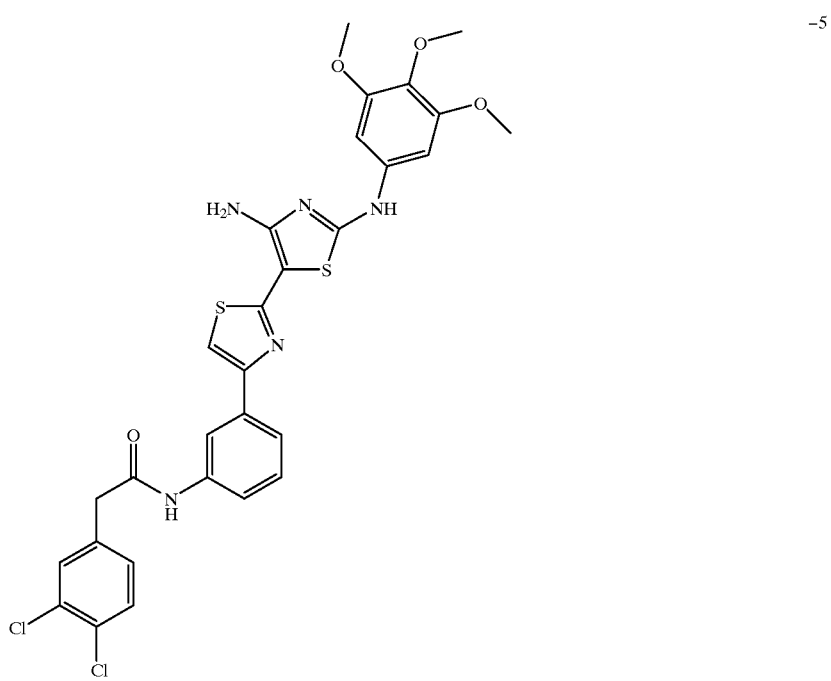 | −5 |

TABLE I-continued
| MOL>MOLSTRUCTURE | % inhibition @ 150 nM |
|---|---|
| 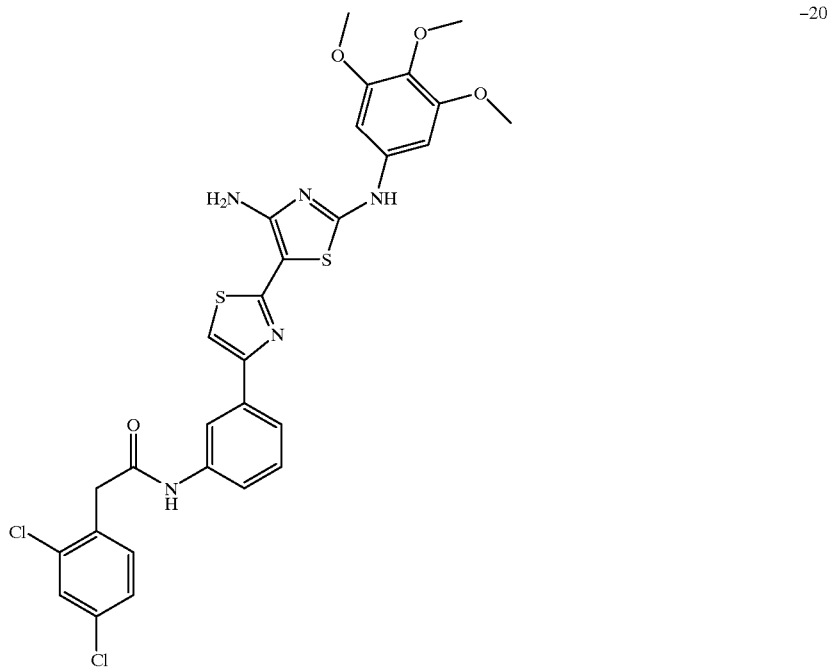 | −20 |
| 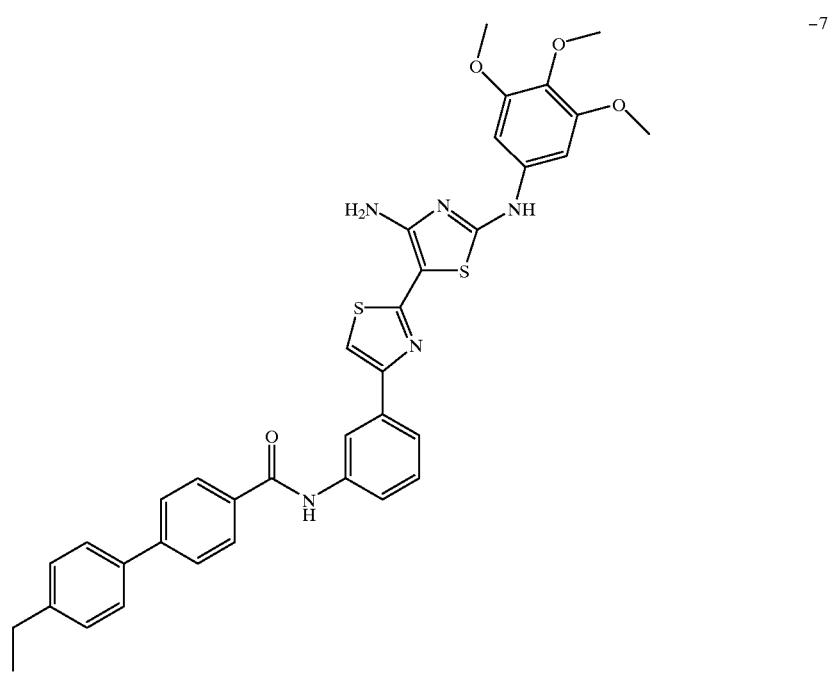 | −7 |

TABLE I-continued
| MOL>MOLSTRUCTURE | % inhibition @ 150 nM |
|---|---|
| 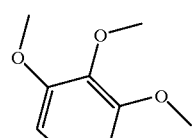 | −8 |
| 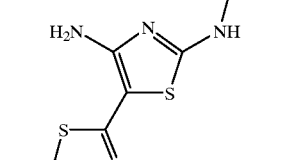 | 19 |
| 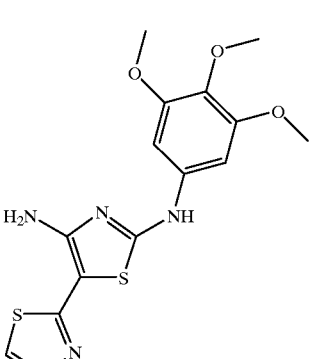 | 1 |

TABLE I-continued
| MOL>MOLSTRUCTURE | % inhibition @ 150 nM |
|---|---|
| 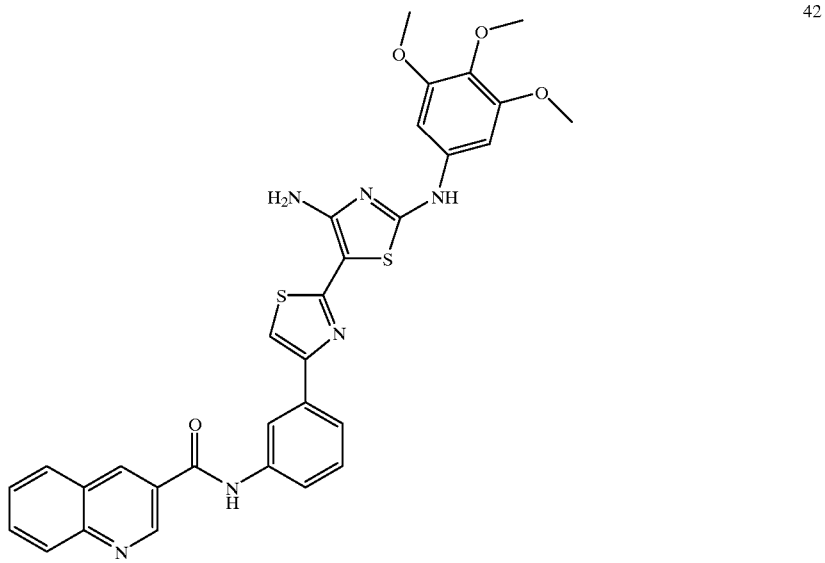 | 42 |
| 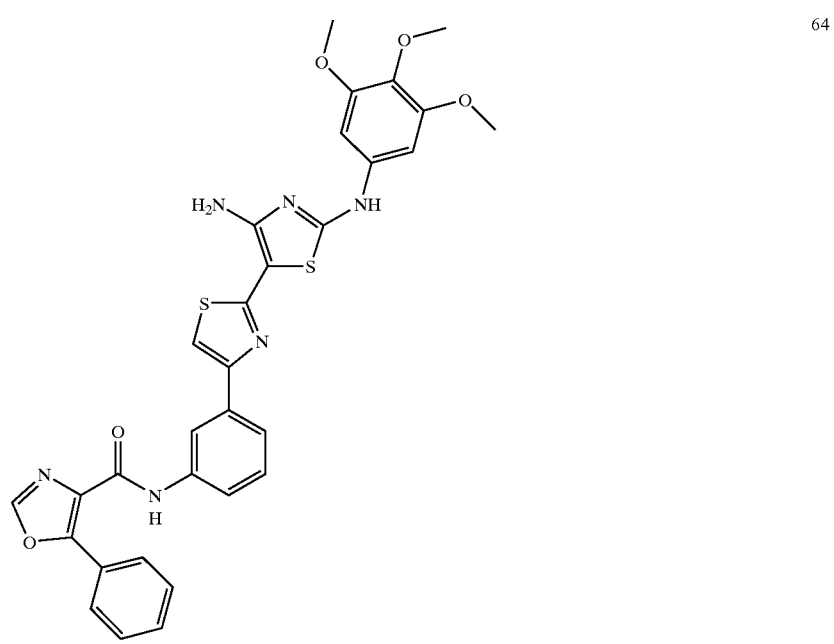 | 64 |

TABLE I-continued
| MOL>MOLSTRUCTURE | % inhibition @ 150 nM |
|---|---|
| 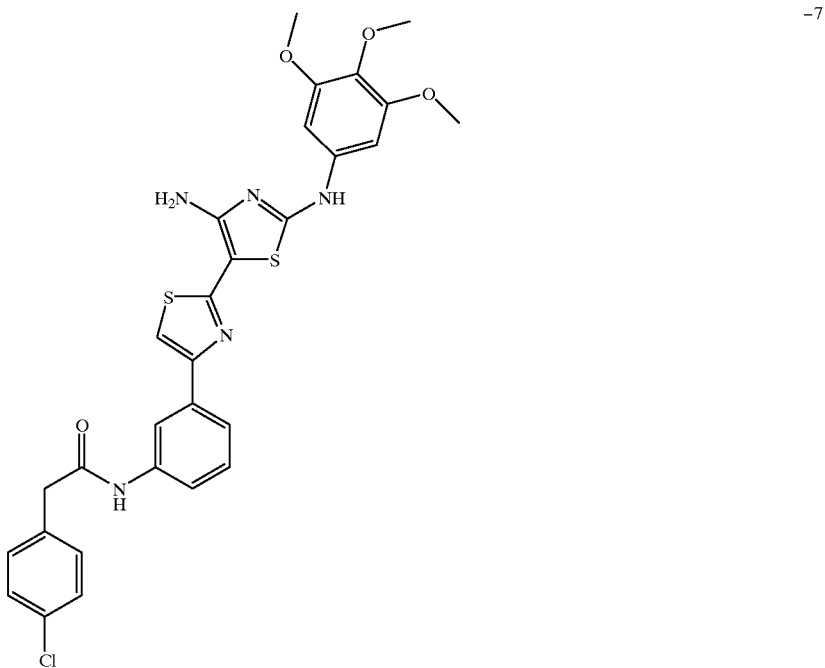 | −7 |
| 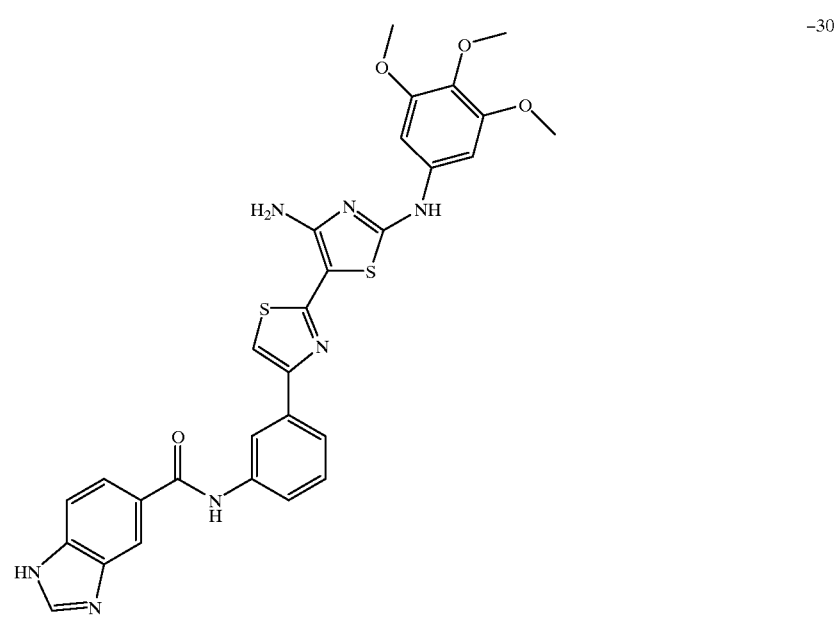 | −30 |

TABLE I-continued
| MOL>MOLSTRUCTURE | % inhibition @ 150 nM |
|---|---|
| 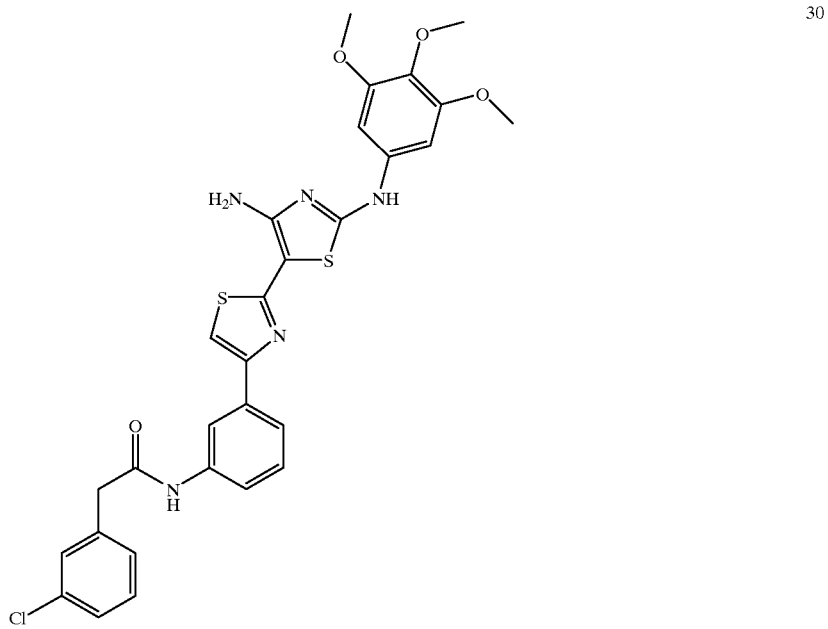 | 30 |
| 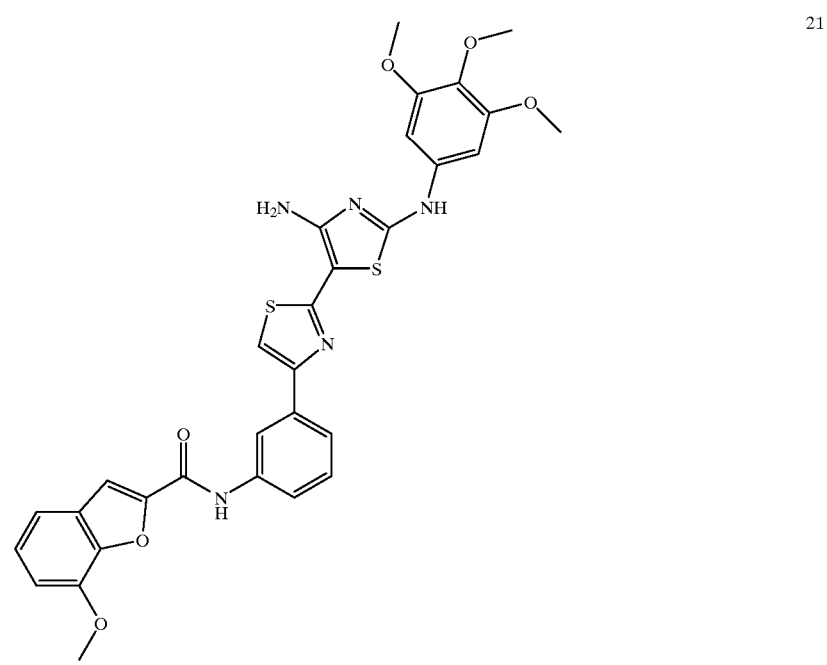 | 21 |

TABLE I-continued
| MOL>MOLSTRUCTURE | % inhibition @ 150 nM |
|---|---|
| 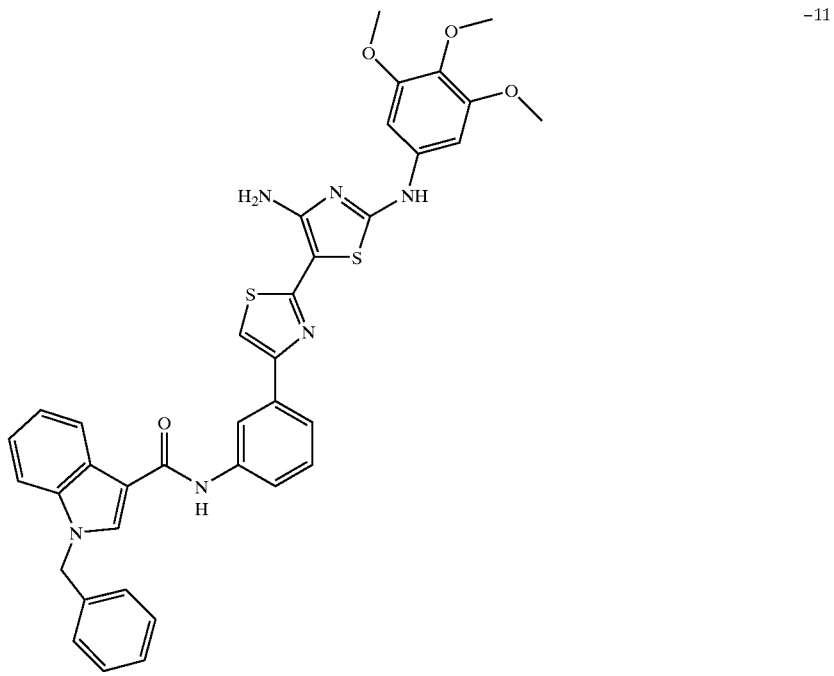 | −11 |
| 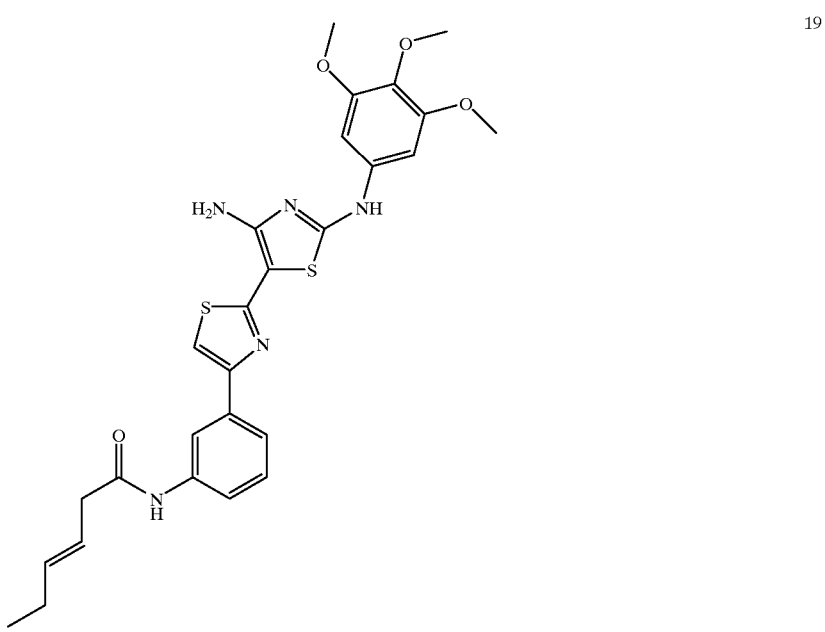 | 19 |

TABLE I-continued
| MOL>MOLSTRUCTURE | % inhibition @ 150 nM |
|---|---|
| 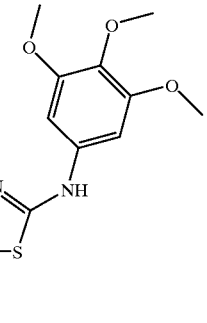 | 25 |
| 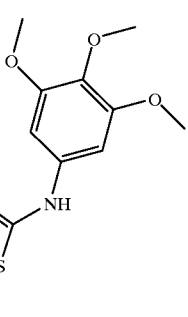 | 26 |
| 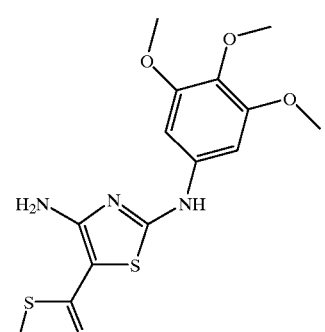 | 17 |

TABLE I-continued

| MOL>MOLSTRUCTURE | % inhibition @ 150 nM |
|---|---|
| [chemical structure] | 14 |
| [chemical structure] | 0 |
| [chemical structure] | 1 |

TABLE I-continued
| MOL>MOLSTRUCTURE | % inhibition @ 150 nM |
|---|---|
| 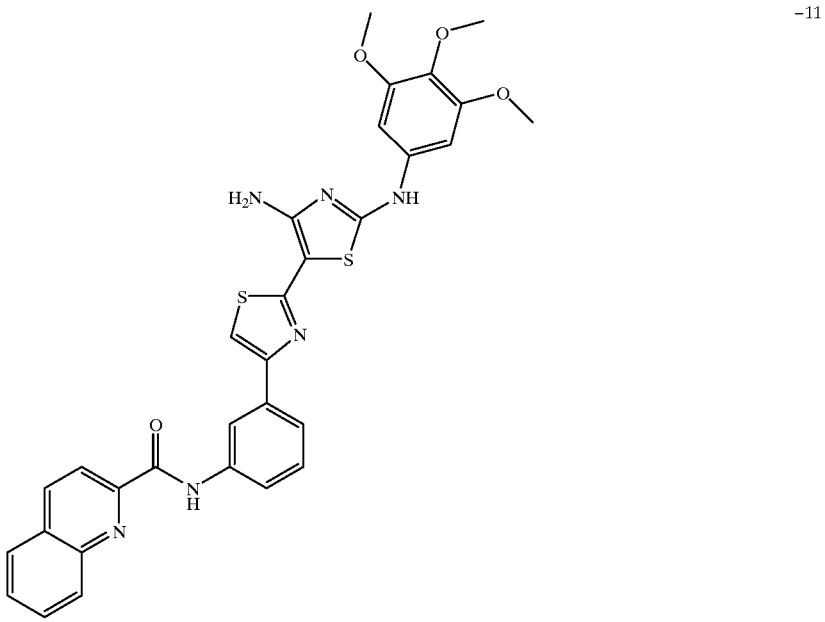 | −11 |
| 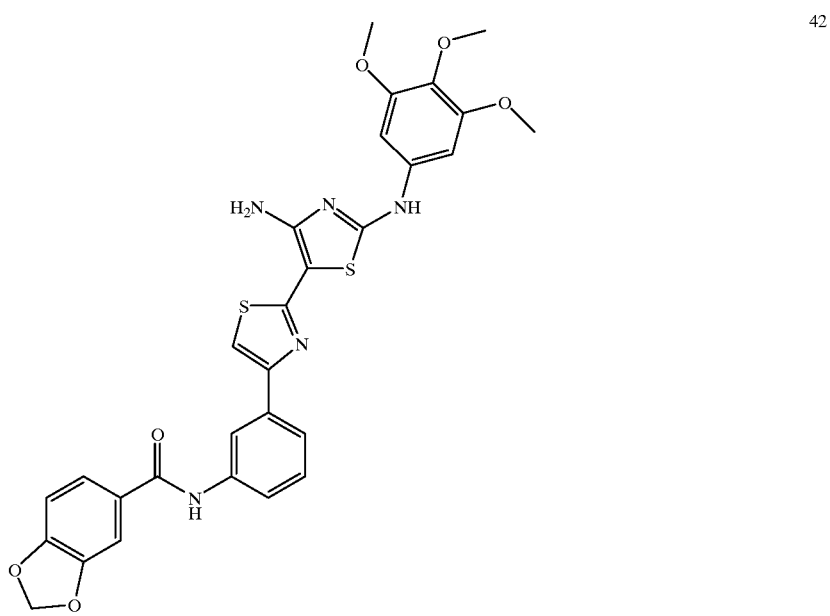 | 42 |

TABLE I-continued

| MOL>MOLSTRUCTURE | % inhibition @ 150 nM |
|---|---|
|  | −14 |
|  | 7 |
|  | 3 |

TABLE I-continued

| MOL>MOLSTRUCTURE | % inhibition @ 150 nM |
|---|---|
| | 29 |
| | 32 |
| | −13 |

TABLE I-continued

| MOL>MOLSTRUCTURE | % inhibition @ 150 nM |
|---|---|
| (structure) | 13 |
| (structure) | 0 |
| (structure) | −3 |

TABLE I-continued

| MOL>MOLSTRUCTURE | % inhibition @ 150 nM |
|---|---|
| (structure) | 7 |
| (structure) | 59 |
| (structure) | 27 |

TABLE I-continued

| MOL>MOLSTRUCTURE | % inhibition @ 150 nM |
|---|---|
| (structure) | 38 |
| (structure) | 26 |
| (structure) | 46 |

TABLE I-continued

| MOL>MOLSTRUCTURE | % inhibition @ 150 nM |
|---|---|
| | 23 |
| | 39 |
| | 34 |

TABLE I-continued

| MOL>MOLSTRUCTURE | % inhibition @ 150 nM |
|---|---|
| | 56 |
| | 34 |
| | 34 |

TABLE I-continued

| MOL>MOLSTRUCTURE | % inhibition @ 150 nM |
|---|---|
| | 31 |
| | 20 |
| | 23 |

TABLE I-continued
| MOL>MOLSTRUCTURE | % inhibition @ 150 nM |
|---|---|
| 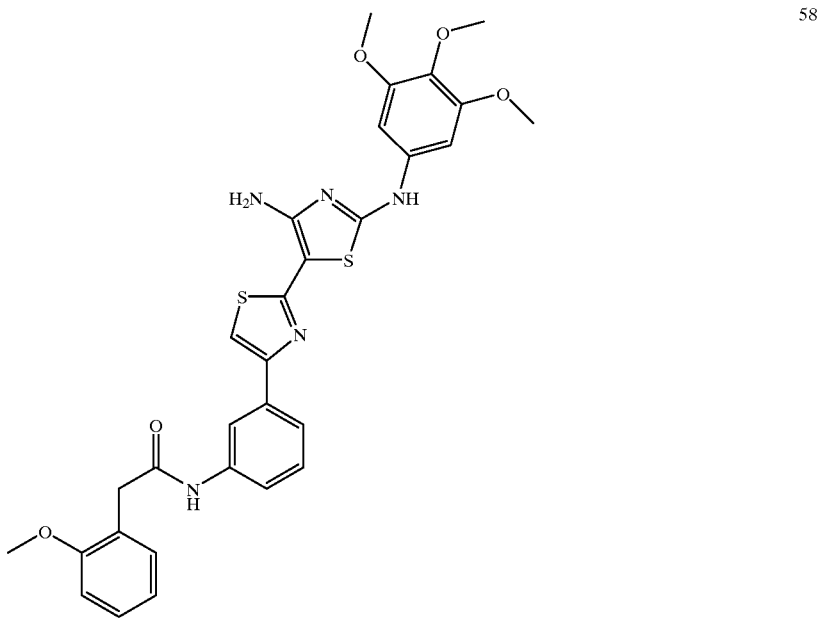 | 58 |
| 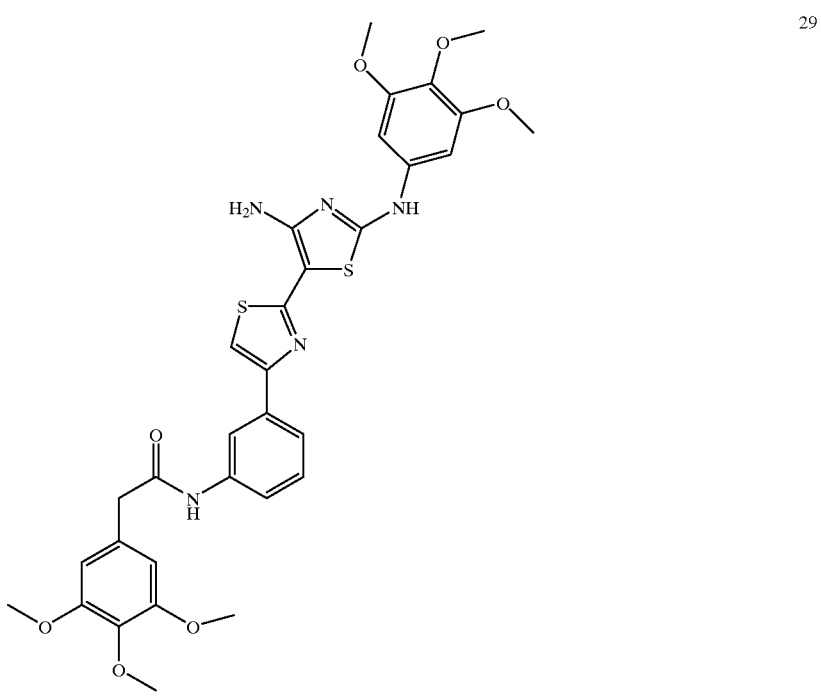 | 29 |

TABLE I-continued
| MOL>MOLSTRUCTURE | % inhibition @ 150 nM |
|---|---|
| 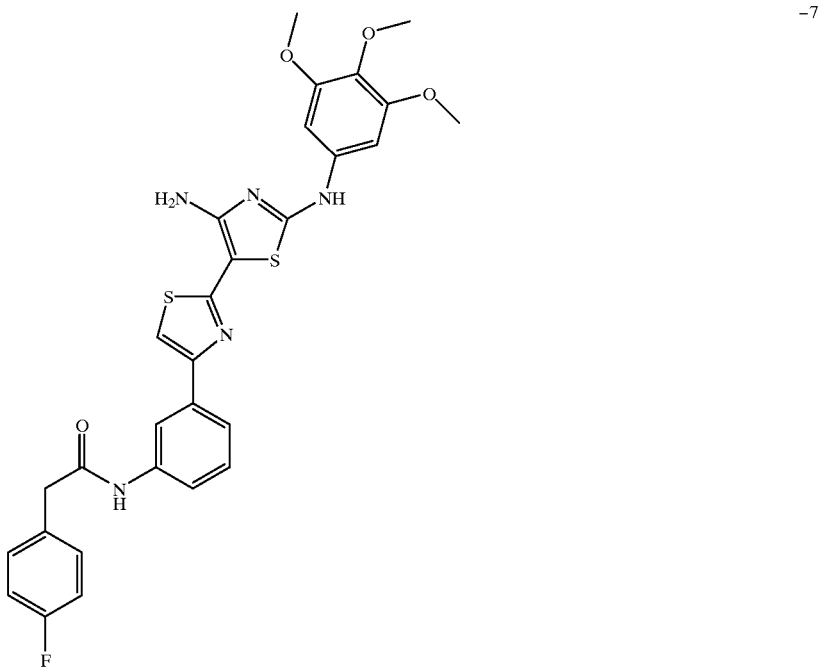 | -7 |
| 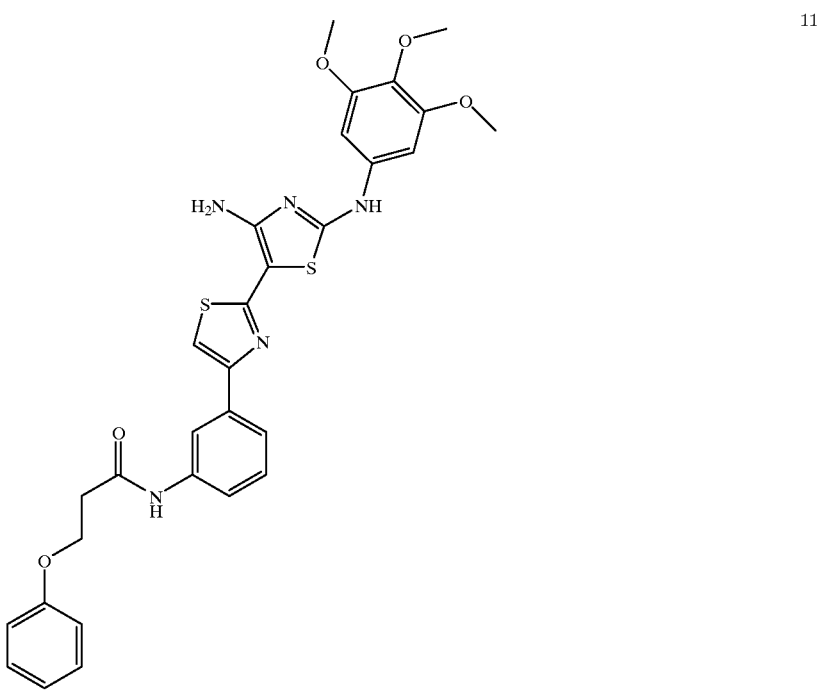 | 11 |

TABLE I-continued
| MOL>MOLSTRUCTURE | % inhibition @ 150 nM |
|---|---|
| 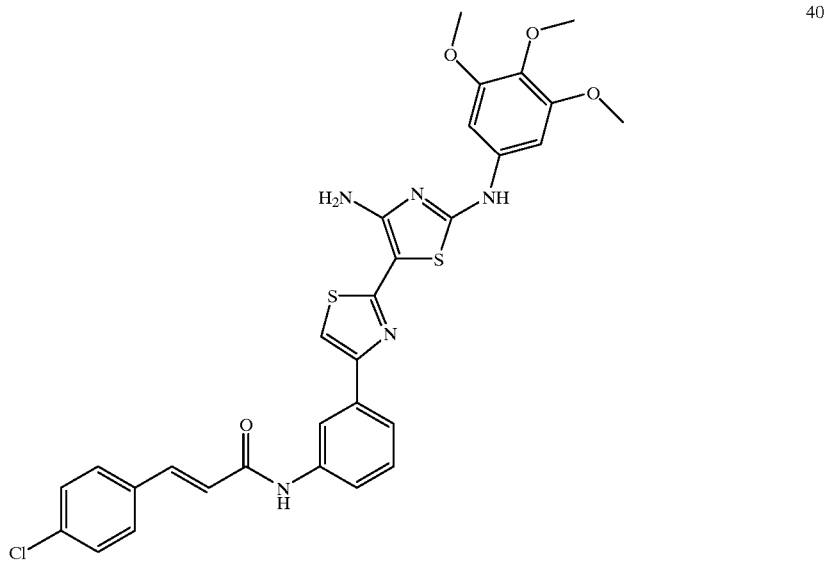 | 40 |
| 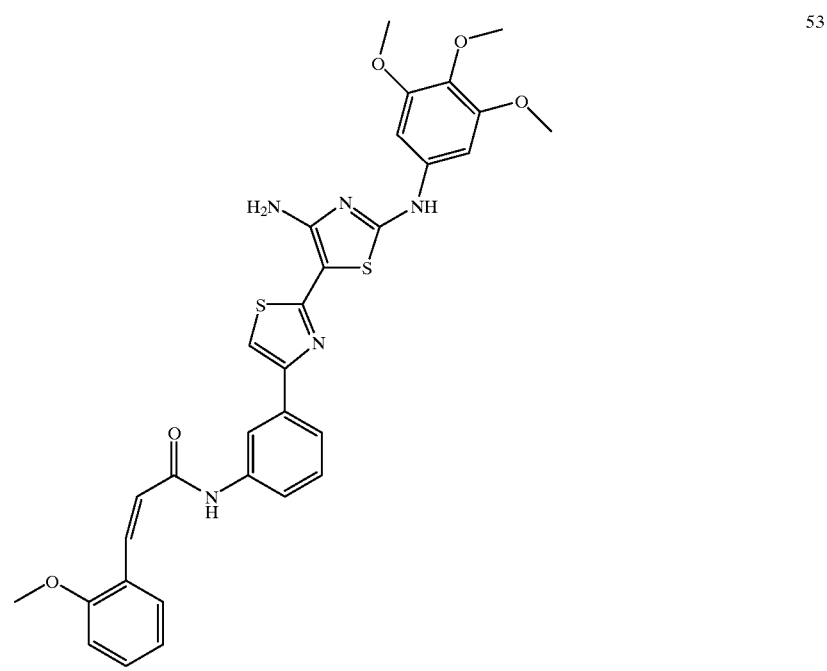 | 53 |

TABLE I-continued
| MOL>MOLSTRUCTURE | % inhibition @ 150 nM |
|---|---|
| 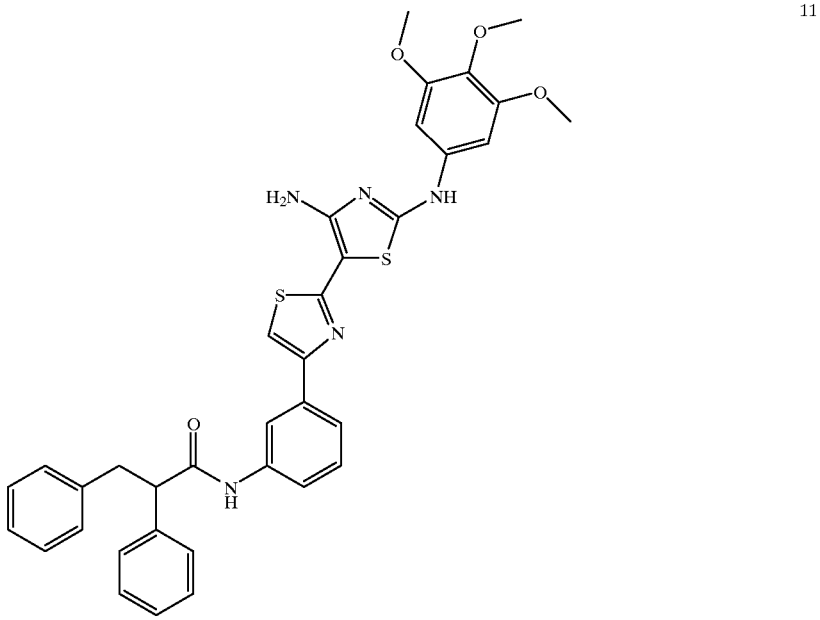 | 11 |
| 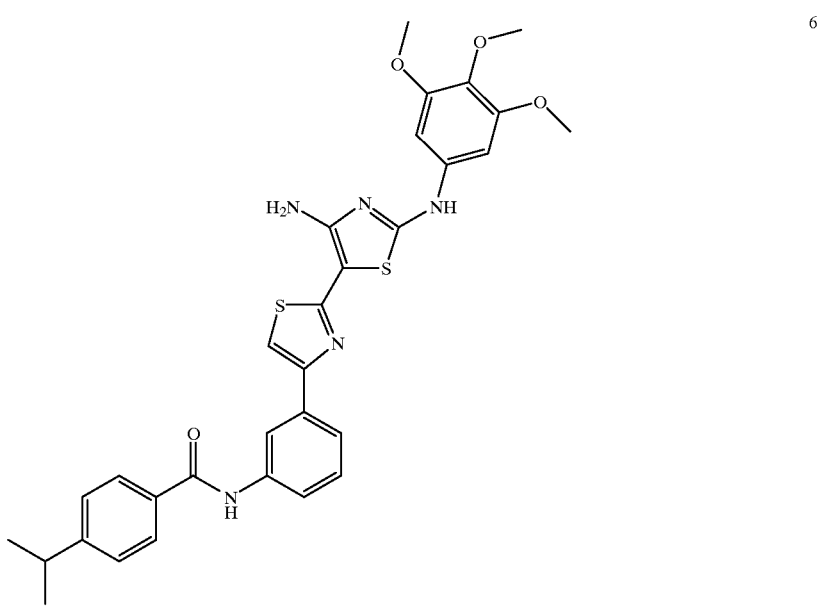 | 6 |

TABLE I-continued
| MOL>MOLSTRUCTURE | % inhibition @ 150 nM |
|---|---|
| 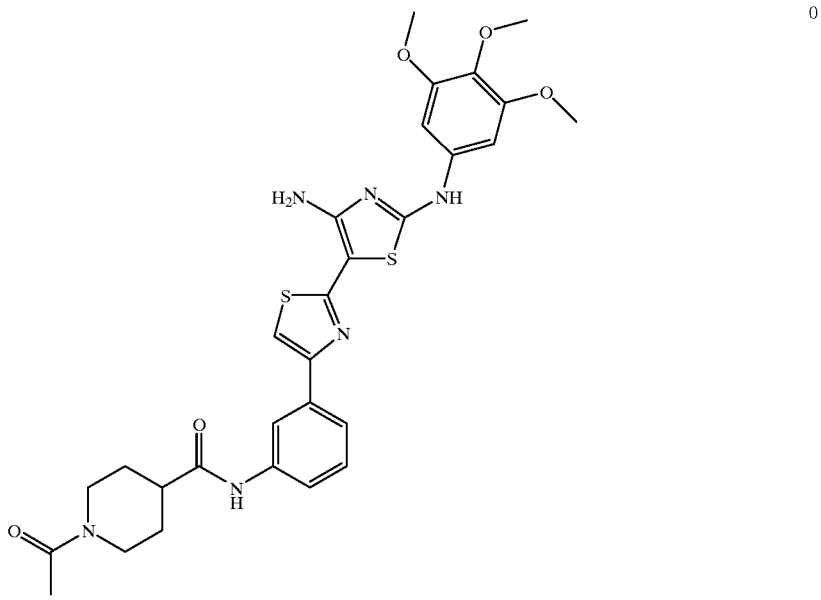 | 0 |
| 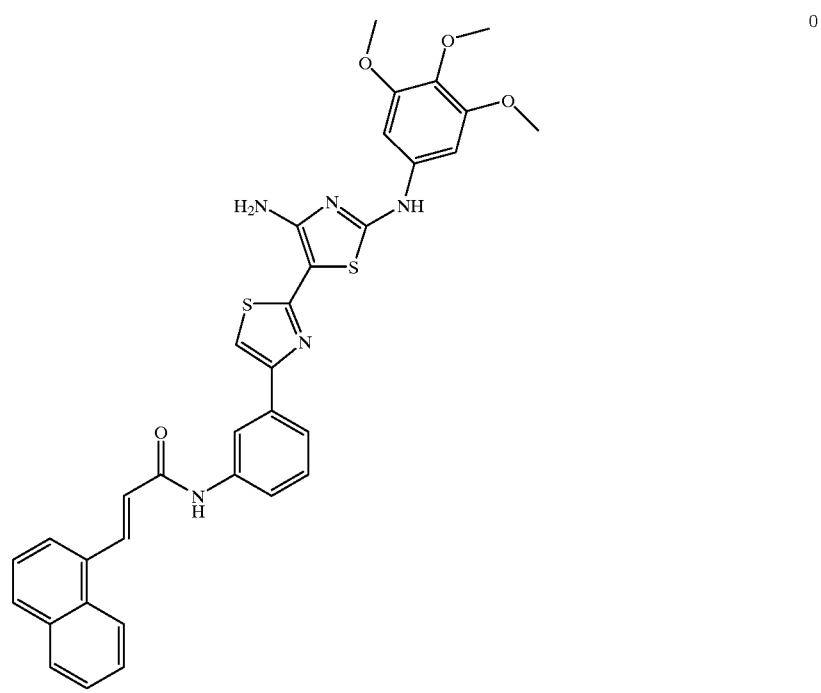 | 0 |

TABLE I-continued
| MOL>MOLSTRUCTURE | % inhibition @ 150 nM |
|---|---|
| 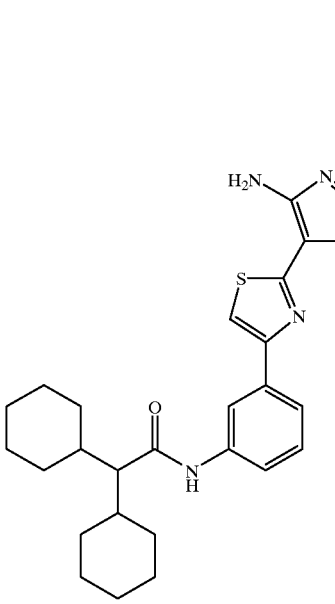 | 0 |
|  | 0 |
| 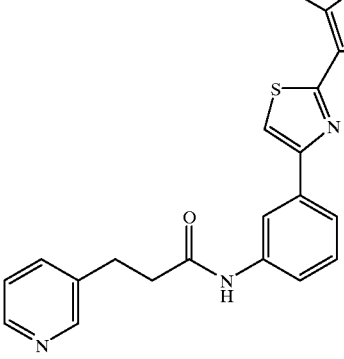 | 0 |

TABLE I-continued

| MOL>MOLSTRUCTURE | % inhibition @ 150 nM |
|---|---|
| | 0 |
| | 0 |
| | 0 |

TABLE I-continued
| MOL>MOLSTRUCTURE | % inhibition @ 150 nM |
|---|---|
| 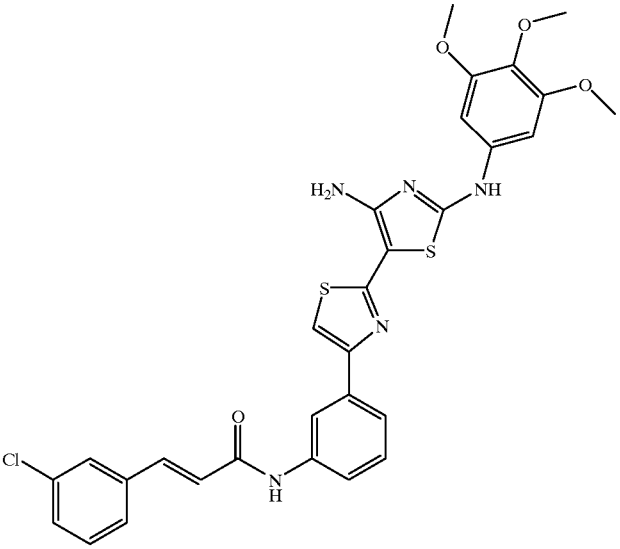 | 0 |
| 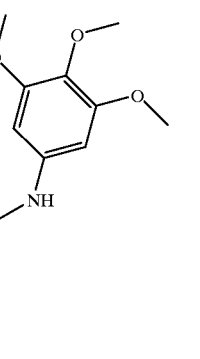 | 0 |
| 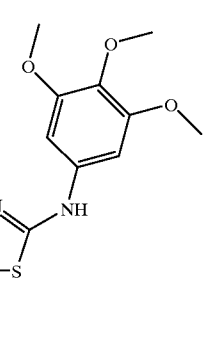 | 0 |

TABLE I-continued
| MOL>MOLSTRUCTURE | % inhibition @ 150 nM |
|---|---|
| 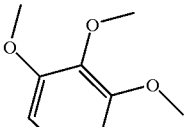 | 0 |
| 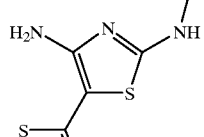 | 0 |
| 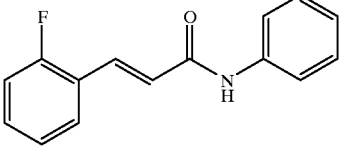 | 0 |

TABLE I-continued
| MOL>MOLSTRUCTURE | % inhibition @ 150 nM |
|---|---|
| 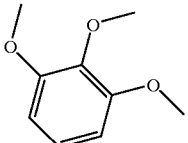 | 0 |
| 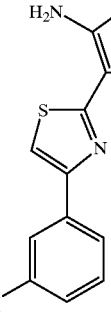 | 0 |
| 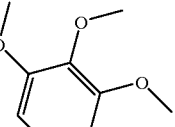 | 0 |

TABLE I-continued
| MOL>MOLSTRUCTURE | % inhibition @ 150 nM |
|---|---|
| 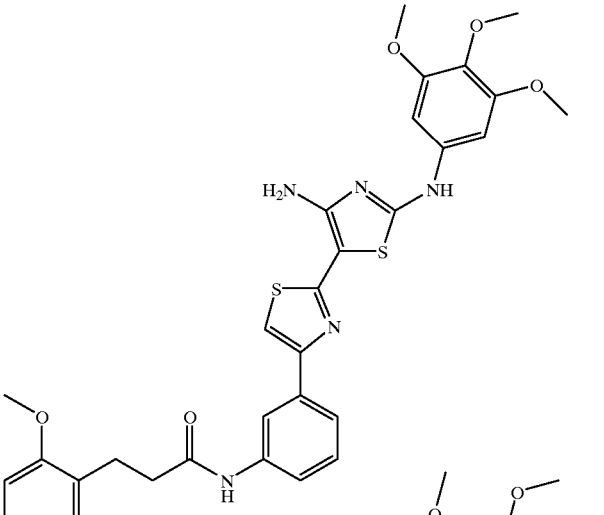 | 0 |
| 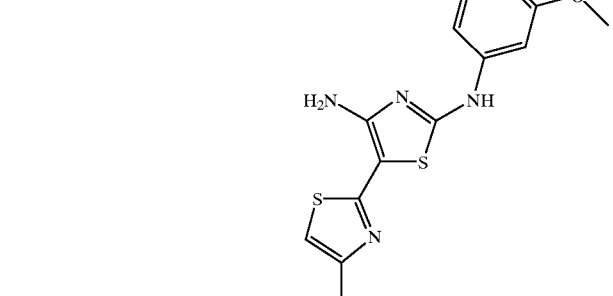 | 0 |
| 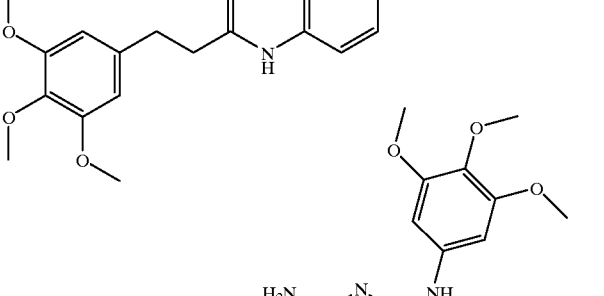 | 0 |

TABLE I-continued
| MOL>MOLSTRUCTURE | % inhibition @ 150 nM |
|---|---|
| 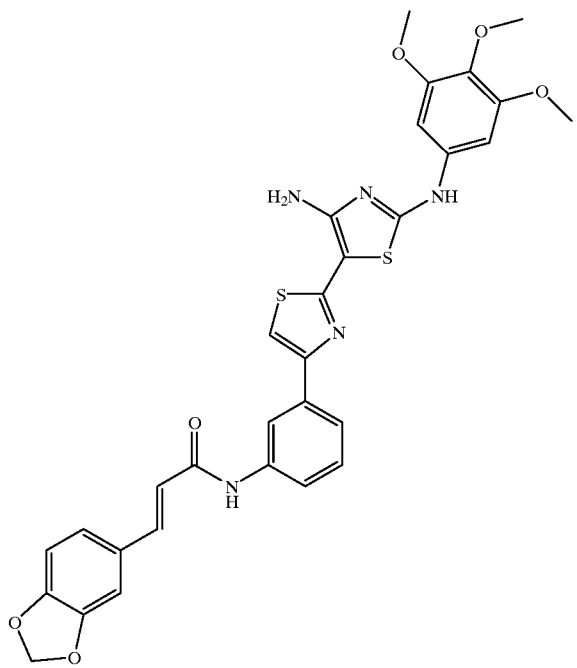 | 0 |
| | 0 |

TABLE I-continued
| MOL>MOLSTRUCTURE | % inhibition @ 150 nM |
|---|---|
| 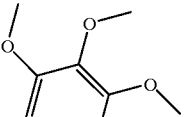 | 0 |
| 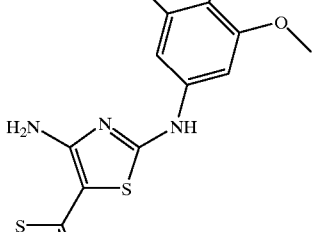 | 0 |
| 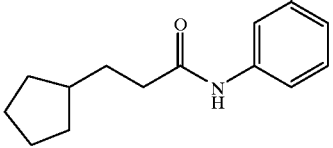 | 85 |

TABLE I-continued

| MOL>MOLSTRUCTURE | % inhibition @ 150 nM |
|---|---|
| (structure) | 20 |
| (structure) | 38 |
| (structure) | 19 |

TABLE I-continued

| MOL>MOLSTRUCTURE | % inhibition @ 150 nM |
|---|---|
| | 86 |
| | 51 |
| | 10 |

TABLE I-continued

| MOL>MOLSTRUCTURE | % inhibition @ 150 nM |
|---|---|
| *structure* | 12 |
| *structure* | 27 |
| *structure* | 75 |

TABLE I-continued
| MOL>MOLSTRUCTURE | % inhibition @ 150 nM |
|---|---|
| 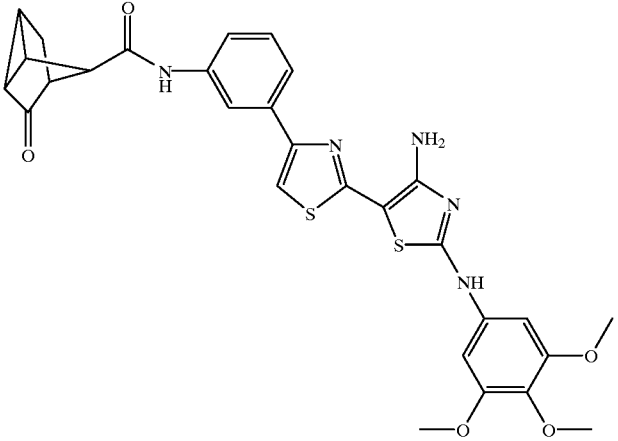 | −6 |
| 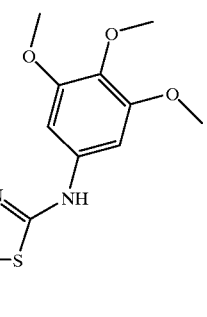 | 72 |
| 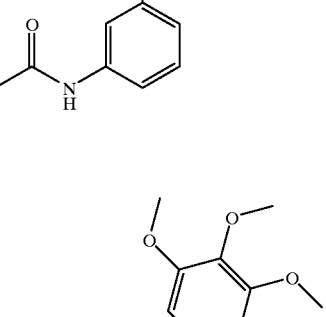 | −2 |

TABLE I-continued
| MOL>MOLSTRUCTURE | % inhibition @ 150 nM |
|---|---|
| 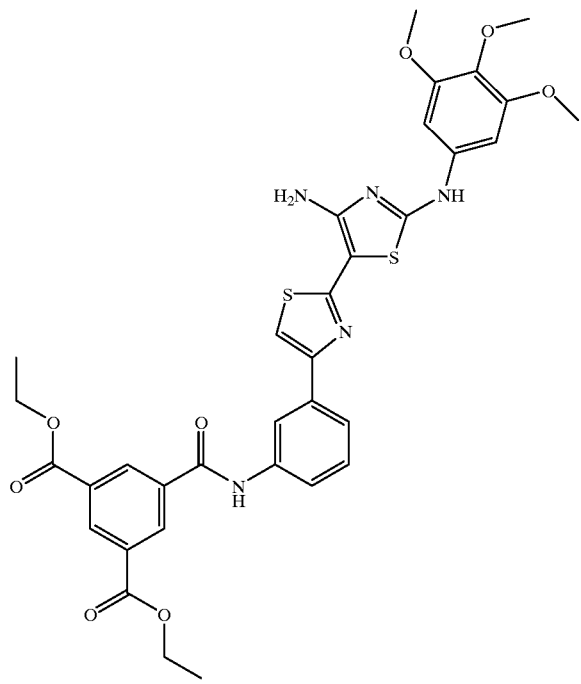 | 6 |
| 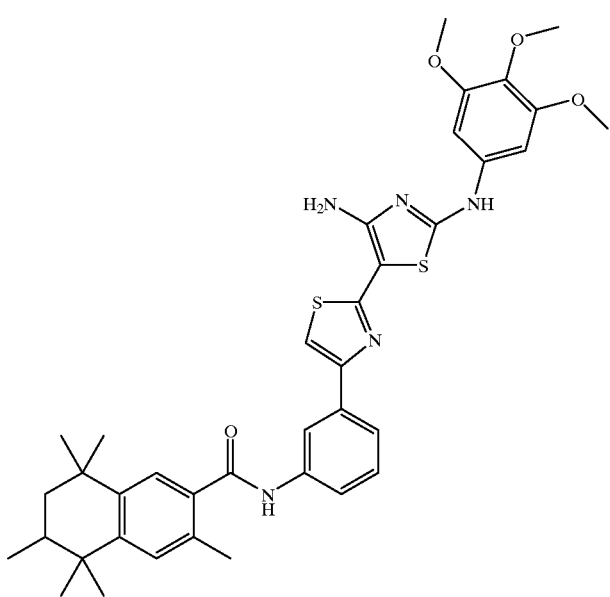 | 7 |

TABLE I-continued
| MOL>MOLSTRUCTURE | % inhibition @ 150 nM |
|---|---|
| 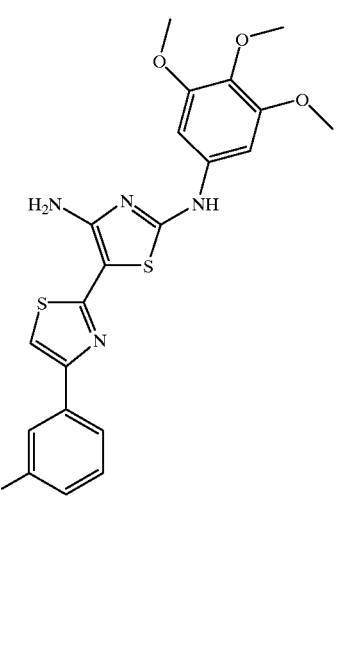 | −3 |
| 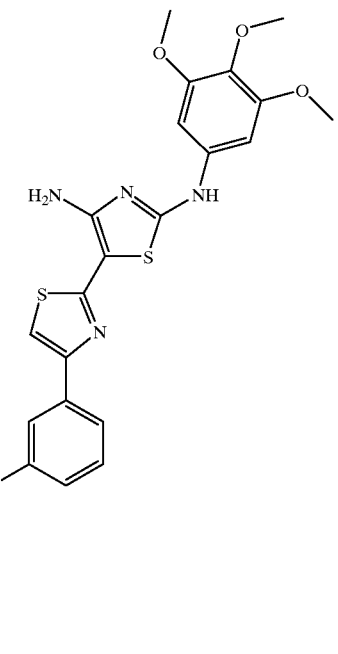 | −6 |

TABLE I-continued

| MOL>MOLSTRUCTURE | % inhibition @ 150 nM |
|---|---|
| [structure] | −25 |
| [structure] | 21 |
| [structure] | −20 |

TABLE I-continued
| MOL>MOLSTRUCTURE | % inhibition @ 150 nM |
|---|---|
| 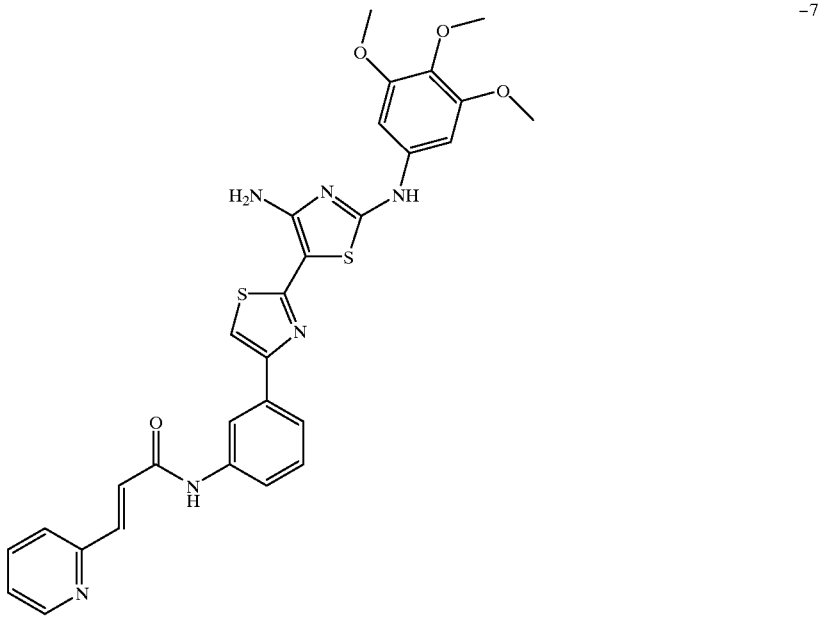 | −7 |
| 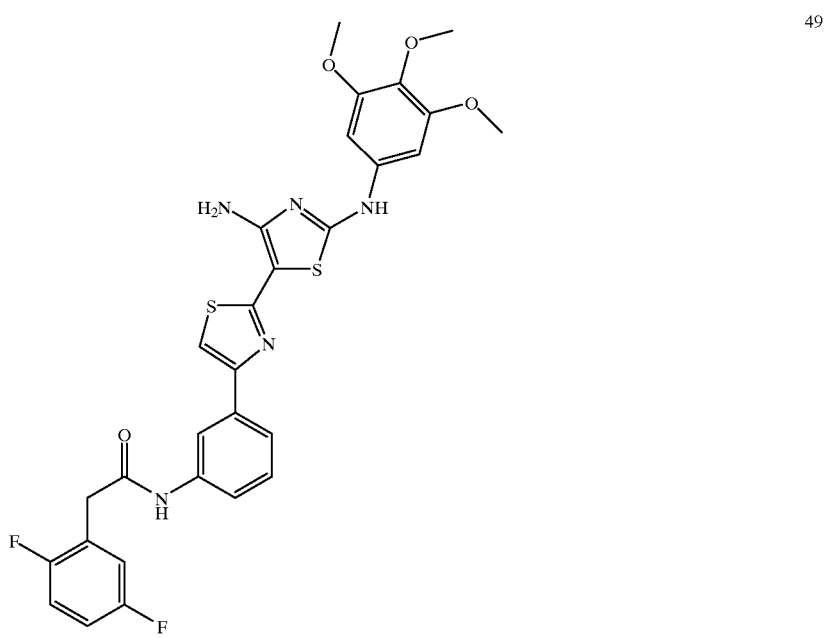 | 49 |

TABLE I-continued
| MOL>MOLSTRUCTURE | % inhibition @ 150 nM |
|---|---|
| 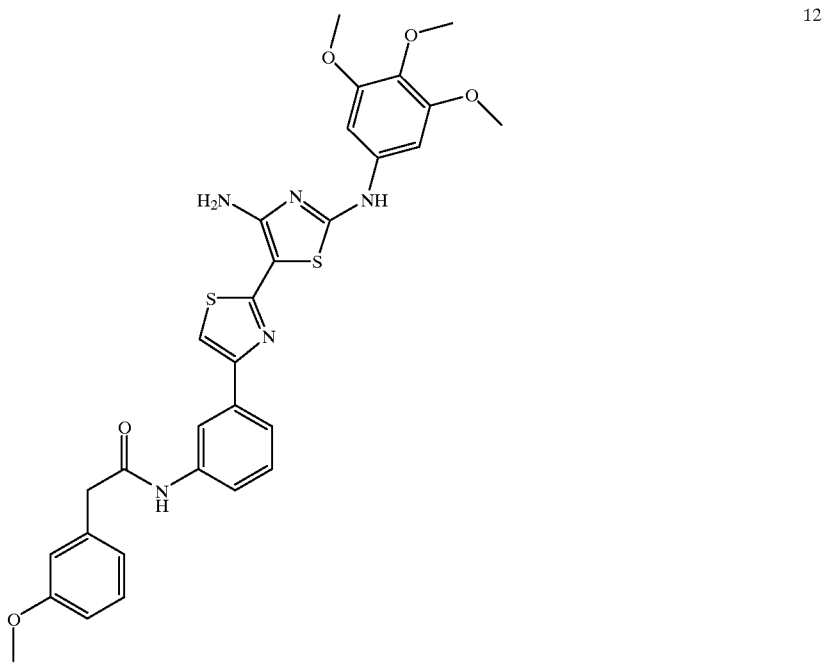 | 12 |
| 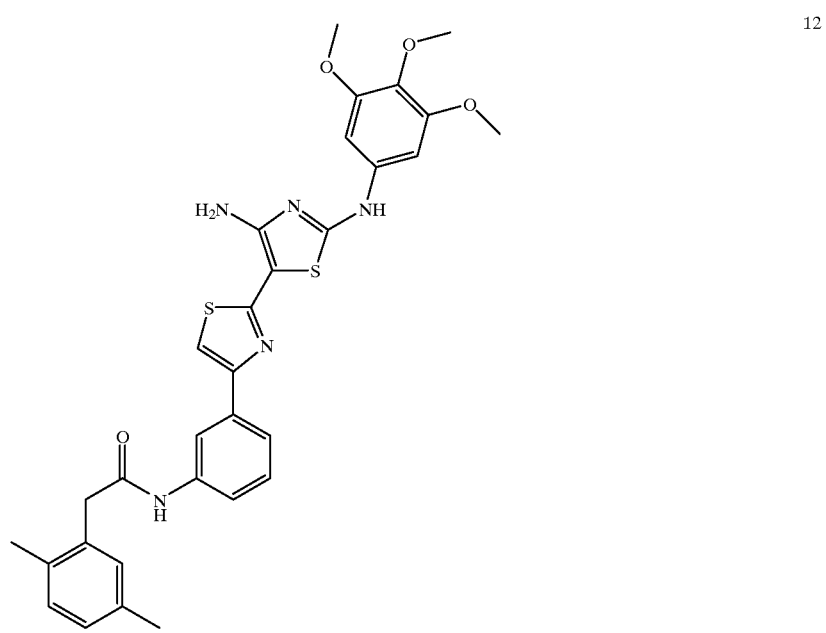 | 12 |

TABLE I-continued
| MOL>MOLSTRUCTURE | % inhibition @ 150 nM |
|---|---|
| 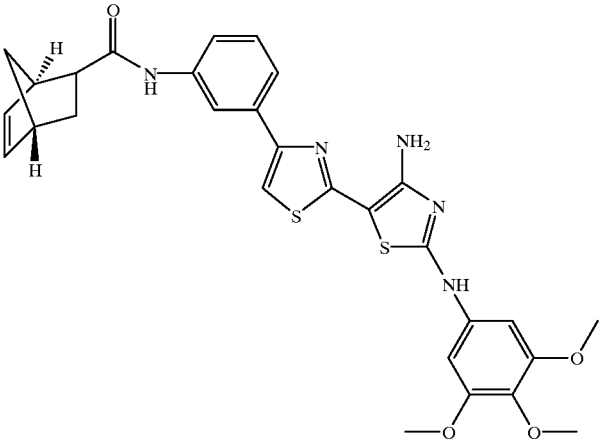 | 37 |
| 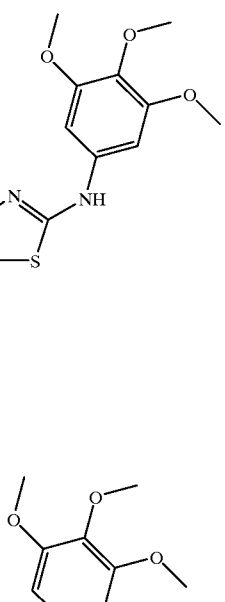 | 42 |
|  | 20 |

TABLE I-continued

| MOL>MOLSTRUCTURE | % inhibition @ 150 nM |
|---|---|
| (structure) | 15 |
| (structure) | 51 |
| (structure) | 25 |

TABLE I-continued
| MOL>MOLSTRUCTURE | % inhibition @ 150 nM |
|---|---|
| 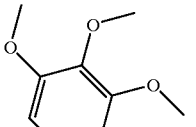 | 56 |
| 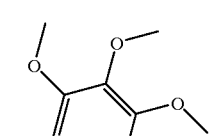 | 108 |
| 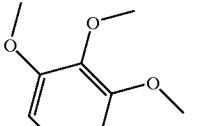 | 78 |

TABLE I-continued
| MOL>MOLSTRUCTURE | % inhibition @ 150 nM |
|---|---|
| 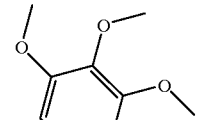 | 16 |
| 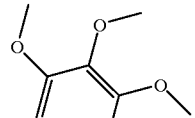 | 26 |
| 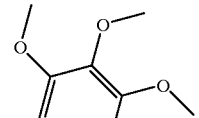 | 17 |

TABLE I-continued

| MOL>MOLSTRUCTURE | % inhibition @ 150 nM |
|---|---|
| 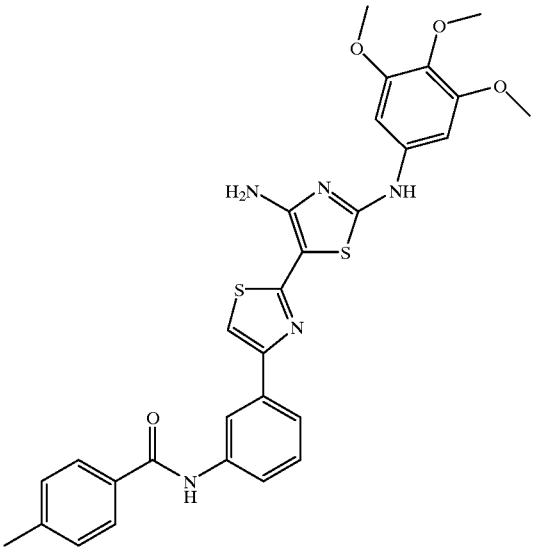 | 66 |
| 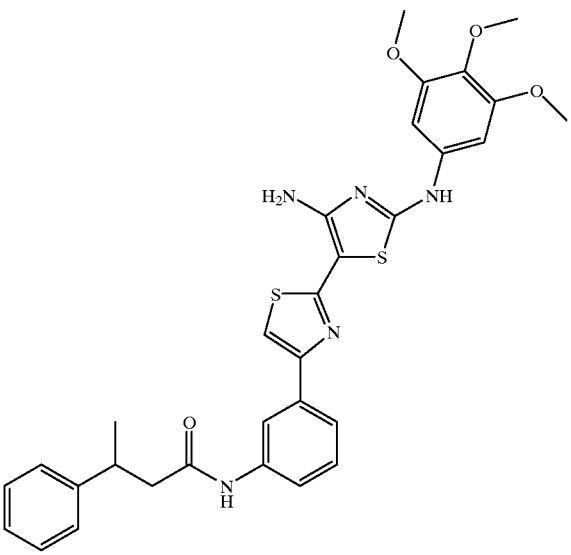 | 26 |

Combinatorial Procedure for Examples in Table II 0.1 M solutions of the acid, the amine template, o-(7-azabenzotriazol-1-yl)-N,N,N',N'-tetra-methyluronium hexafluorophosphate and triethylamine were prepared separately in anhydrous DMF. To each tube in an array of 8×11 culture tubes (10×75 mm) was added 105 μL (0.0105 mmol) of a different acid. To this was added 100 μL (0.01 mmol) of the amine solution, 105 μL (0.0105 mmol) of the triethylamine solution followed by 105 μL (0.0105 mmol) of the o-(7-azabenzotriazol-1-yl)-N,N,N',N'-tetra-methyluronium hexafluorophosphate solution. The reactions were stirred in a heating block at 50° C. for 3 h. The reaction mixtures were transferred to a 1 mL 96-well plate using a liquid handler. The solvents were removed using the SpeedVac™ apparatus and the crude reaction mixtures were redissolved in DMSO to give a final theoretical concentration of 10 mM. Screening results are shown in Table II.

TABLE II
| STRUCTURE | % inhibition @ 10 nM | % inhibition @ 1 nM |
|---|---|---|
| 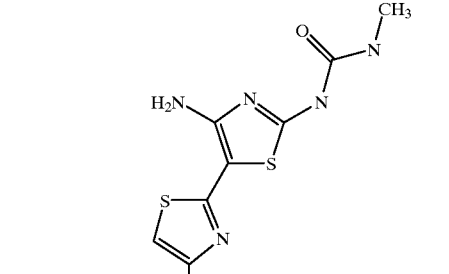 | −40 | −8 |
| 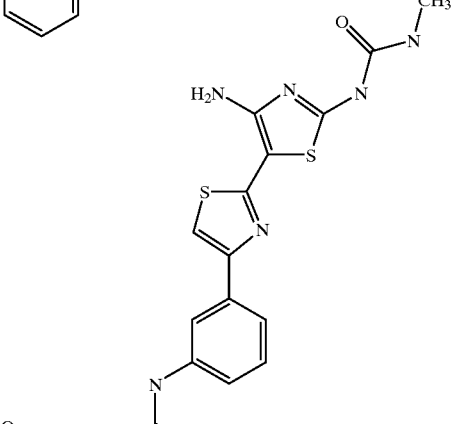 | −14 | −5 |
| 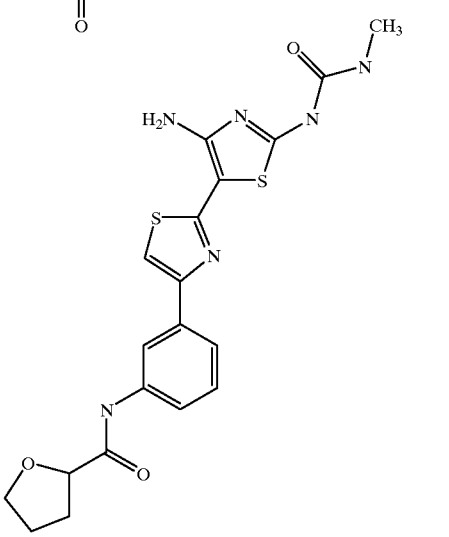 | −33 | 183 |

TABLE II-continued
| STRUCTURE | % inhibition @ 10 nM | % inhibition @ 1 nM |
|---|---|---|
| 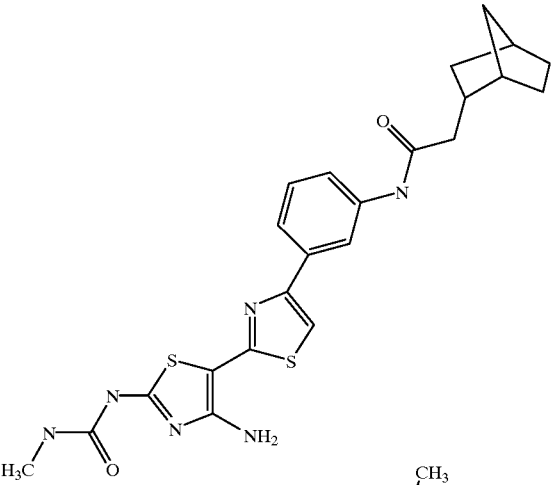 | 93 | 0 |
| 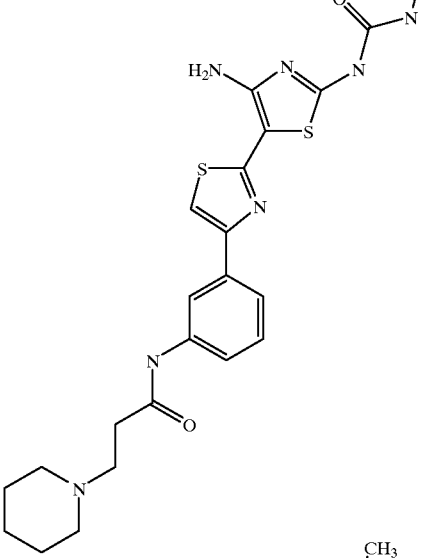 | −26 | 1 |
| 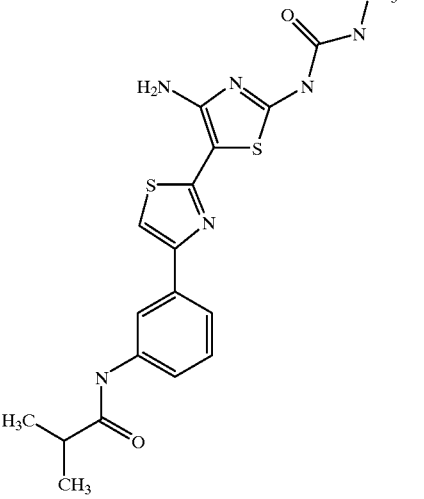 | −45 | 10 |

TABLE II-continued
| STRUCTURE | % inhibition @ 10 nM | % inhibition @ 1 nM |
|---|---|---|
| 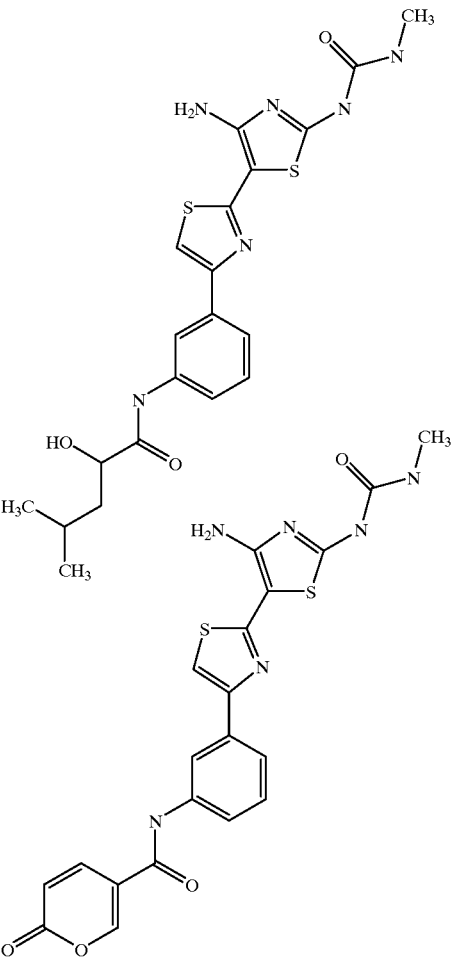 | 2 | −18 |
| 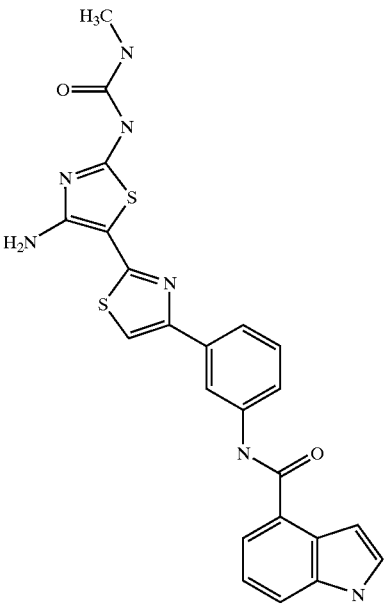 | 30 | −4 |
| 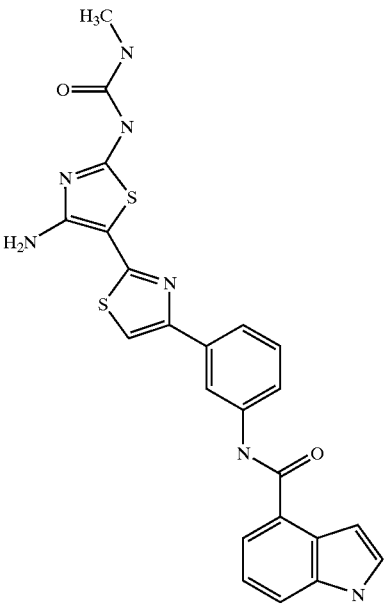 | 2 | −3 |

TABLE II-continued

| STRUCTURE | % inhibition @ 10 nM | % inhibition @ 1 nM |
|---|---|---|
| (structure) | 2 | −4 |
| (structure) | −14 | 1 |
| (structure) | −40 | −12 |

TABLE II-continued
| STRUCTURE | % inhibition @ 10 nM | % inhibition @ 1 nM |
|---|---|---|
| 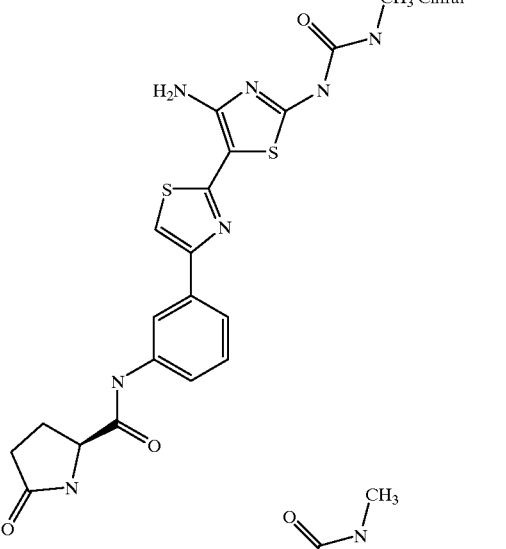 | −21 | −2 |
| 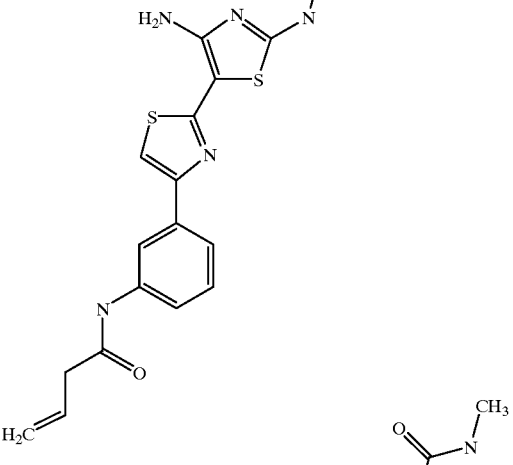 | −13 | 8 |
| 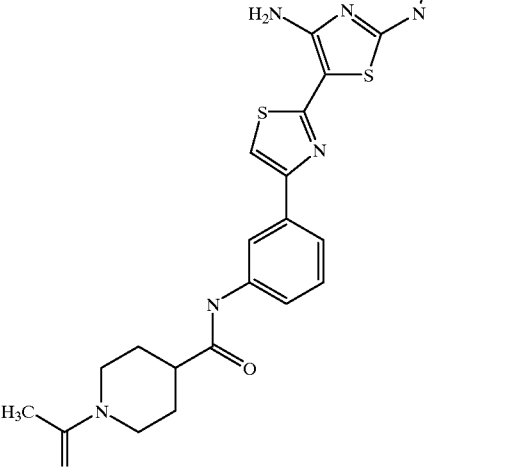 | −15 | 23 |

TABLE II-continued

| STRUCTURE | % inhibition @ 10 nM | % inhibition @ 1 nM |
|---|---|---|
| 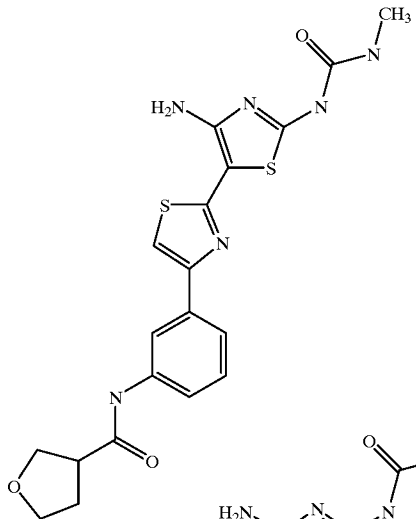 | −8 | −5 |
| 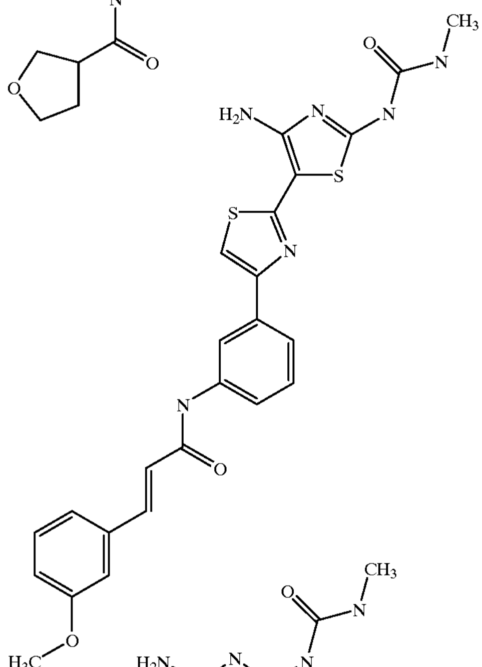 | −12 | −1 |
| 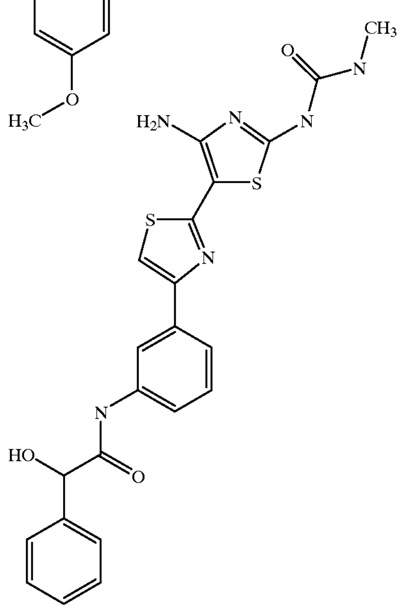 | −11 | −14 |

TABLE II-continued

| STRUCTURE | % inhibition @ 10 nM | % inhibition @ 1 nM |
|---|---|---|
| (structure 1) | 25 | 8 |
| (structure 2) | 16 | 32 |
| (structure 3) | 12 | −17 |

TABLE II-continued

| STRUCTURE | % inhibition @ 10 nM | % inhibition @ 1 nM |
|---|---|---|
| [structure] | 2 | −20 |
| [structure] | −27 | −7 |

TABLE II-continued
| STRUCTURE | % inhibition @ 10 nM | % inhibition @ 1 nM |
|---|---|---|
| 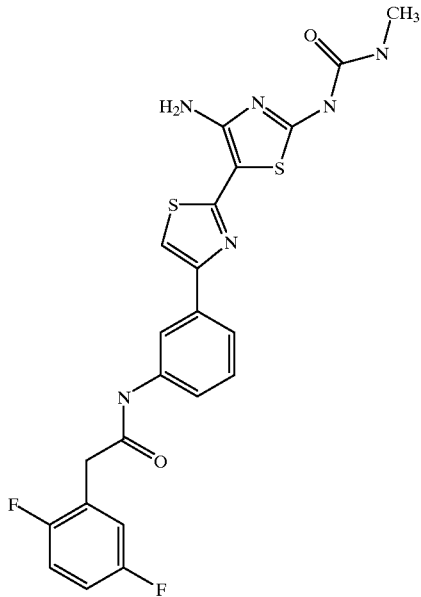 | 4 | −1 |
| 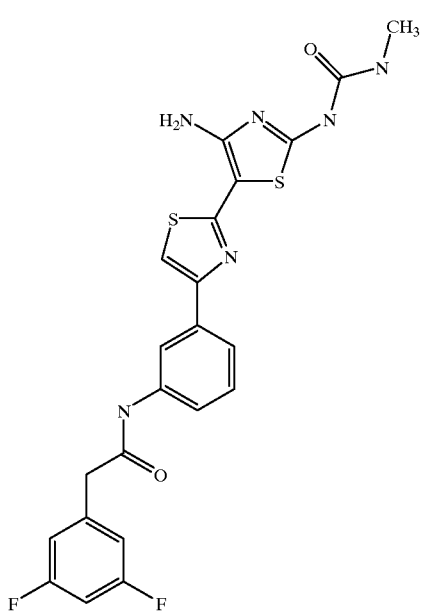 | −10 | −5 |

TABLE II-continued

| STRUCTURE | % inhibition @ 10 nM | % inhibition @ 1 nM |
|---|---|---|
| (structure) | −31 | 25 |
| (structure) | −18 | 4 |
| (structure) |  | 2 |

TABLE II-continued

| STRUCTURE | % inhibition @ 10 nM | % inhibition @ 1 nM |
|---|---|---|
| (structure 1) | 91 | 2 |
| (structure 2) | 10 | 14 |
| (structure 3) | 11 | 3 |

TABLE II-continued

| STRUCTURE | % inhibition @ 10 nM | % inhibition @ 1 nM |
|---|---|---|
| (structure) | 5 | 6 |
| (structure) | −6 | −8 |

TABLE II-continued

| STRUCTURE | % inhibition @ 10 nM | % inhibition @ 1 nM |
| --- | --- | --- |
| (structure) | −25 | 18 |
| (structure) | 13 | −2 |
| (structure) | −10 | 2 |

TABLE II-continued

| STRUCTURE | % inhibition @ 10 nM | % inhibition @ 1 nM |
|---|---|---|
| (structure) | −22 | 32 |
| (structure) | 39 | 10 |
| (structure) | −13 | 25 |

TABLE II-continued
| STRUCTURE | % inhibition @ 10 nM | % inhibition @ 1 nM |
|---|---|---|
| 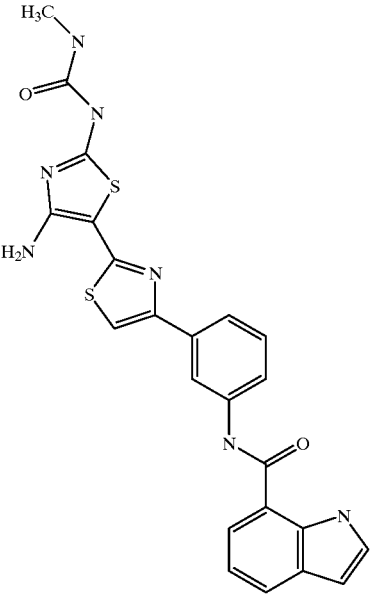 | 60 | −11 |
| 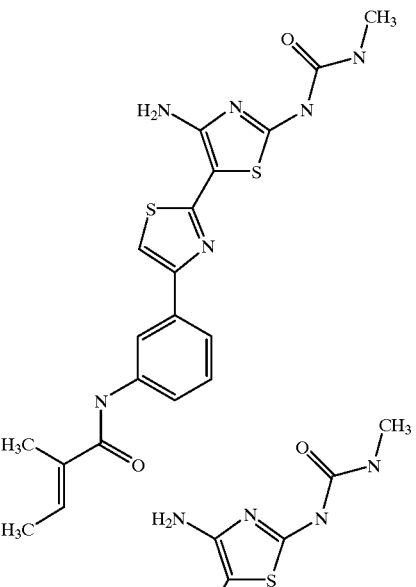 | 17 | 5 |
| 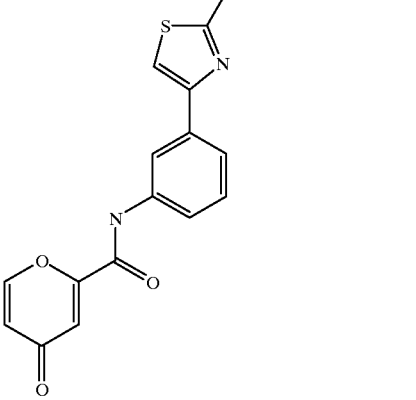 | 27 | 47 |

TABLE II-continued

| STRUCTURE | % inhibition @ 10 nM | % inhibition @ 1 nM |
|---|---|---|
| (structure) | 0 | 10 |
| (structure) | 67 | −12 |
| (structure) | −2 | −3 |

TABLE II-continued

| STRUCTURE | % inhibition @ 10 nM | % inhibition @ 1 nM |
|---|---|---|
| (structure) | 21 | 11 |
| (structure) | 29 | −1 |
| (structure) | −6 | 16 |

TABLE II-continued

| STRUCTURE | % inhibition @ 10 nM | % inhibition @ 1 nM |
|---|---|---|
| (structure) | −10 | 6 |
| (structure) | 106 | 0 |
| (structure) | −15 | 4 |

TABLE II-continued
| STRUCTURE | % inhibition @ 10 nM | % inhibition @ 1 nM |
|---|---|---|
| 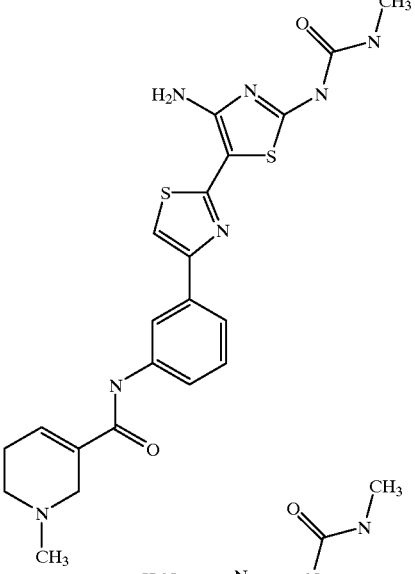 | 43 | 2 |
| 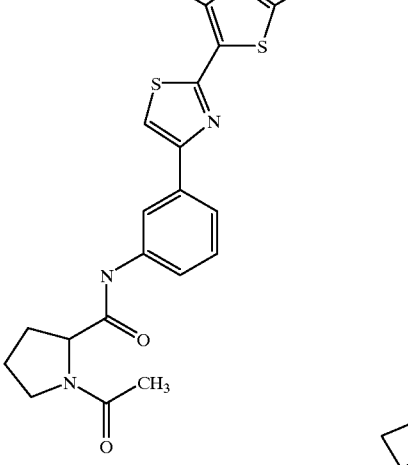 | 27 | 3 |
| 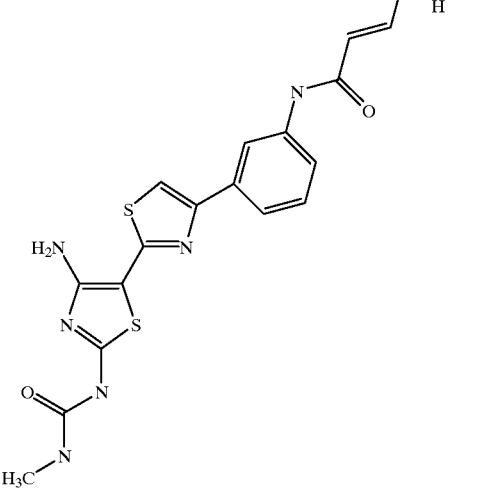 | 50 | 11 |

TABLE II-continued

| STRUCTURE | % inhibition @ 10 nM | % inhibition @ 1 nM |
|---|---|---|
| (structure) | 9 | −8 |
| (structure, Chiral) | −11 | −11 |

TABLE II-continued
| STRUCTURE | % inhibition @ 10 nM | % inhibition @ 1 nM |
|---|---|---|
| 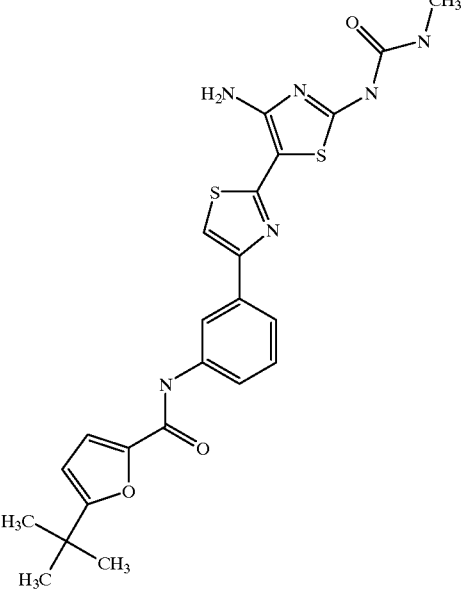 | 69 | 2 |
| 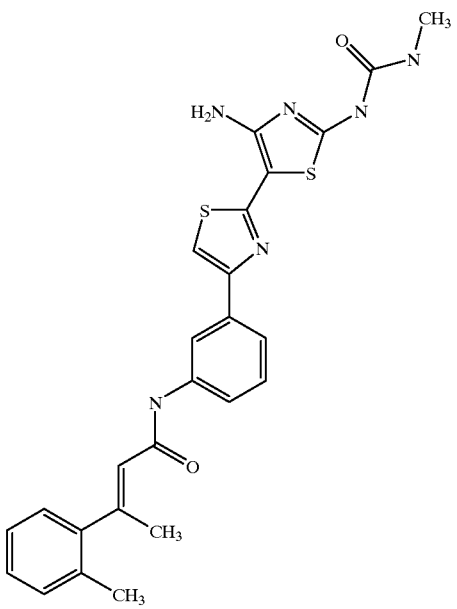 | 20 | −2 |

TABLE II-continued
| STRUCTURE | % inhibition @ 10 nM | % inhibition @ 1 nM |
|---|---|---|
| 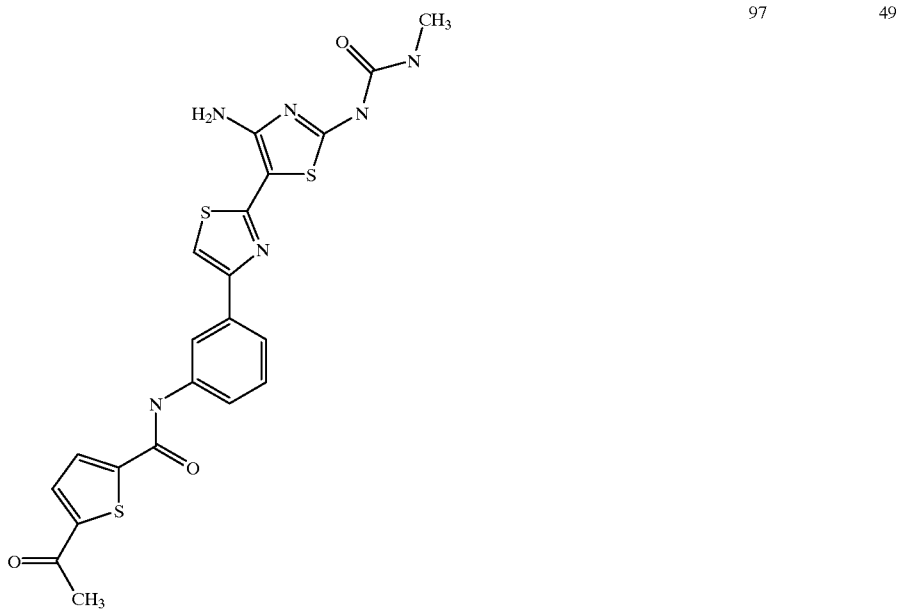 | 97 | 49 |
| 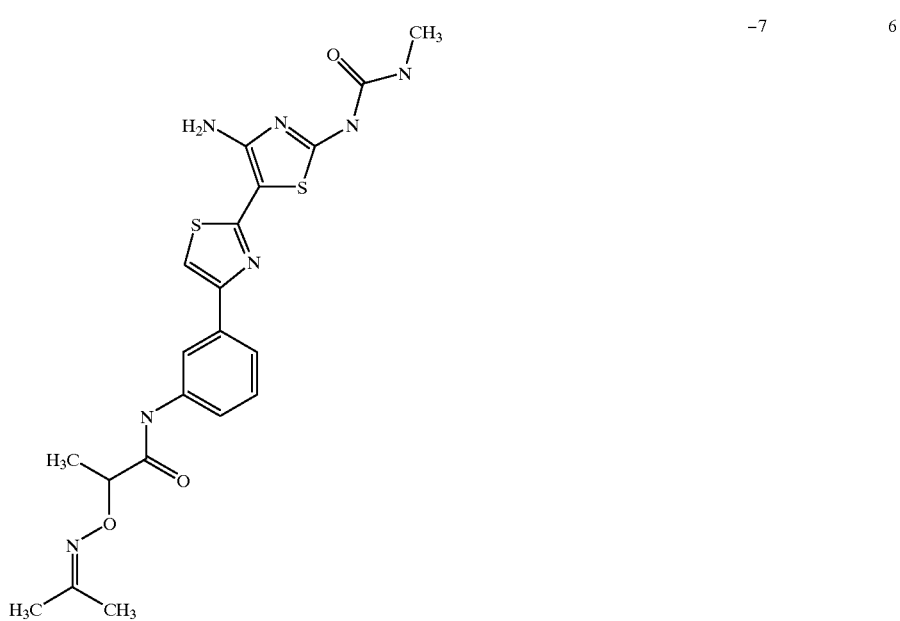 | −7 | 6 |

TABLE II-continued
| STRUCTURE | % inhibition @ 10 nM | % inhibition @ 1 nM |
|---|---|---|
| 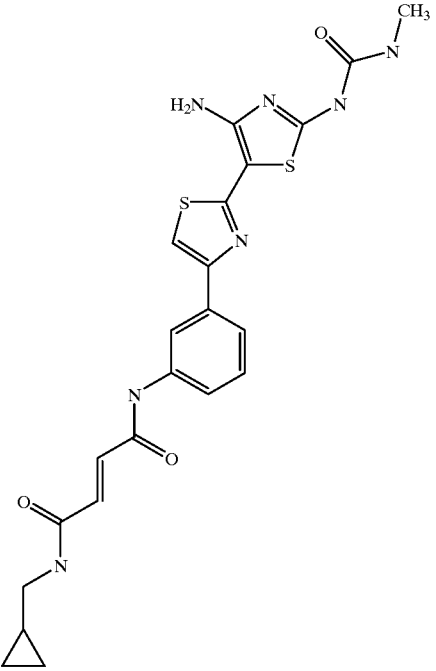 | 1 | 10 |
| 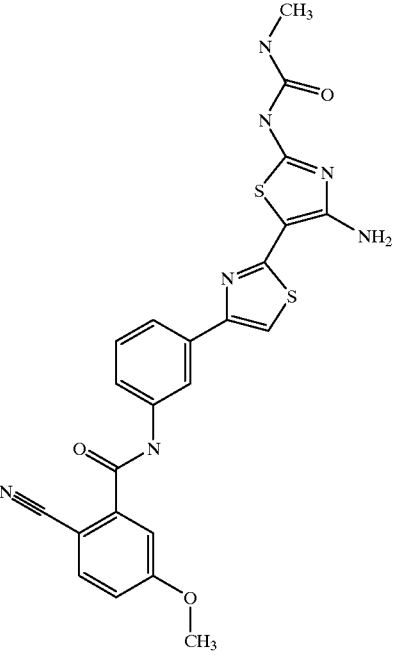 | −1 | −18 |

TABLE II-continued
| STRUCTURE | % inhibition @ 10 nM | % inhibition @ 1 nM |
|---|---|---|
| 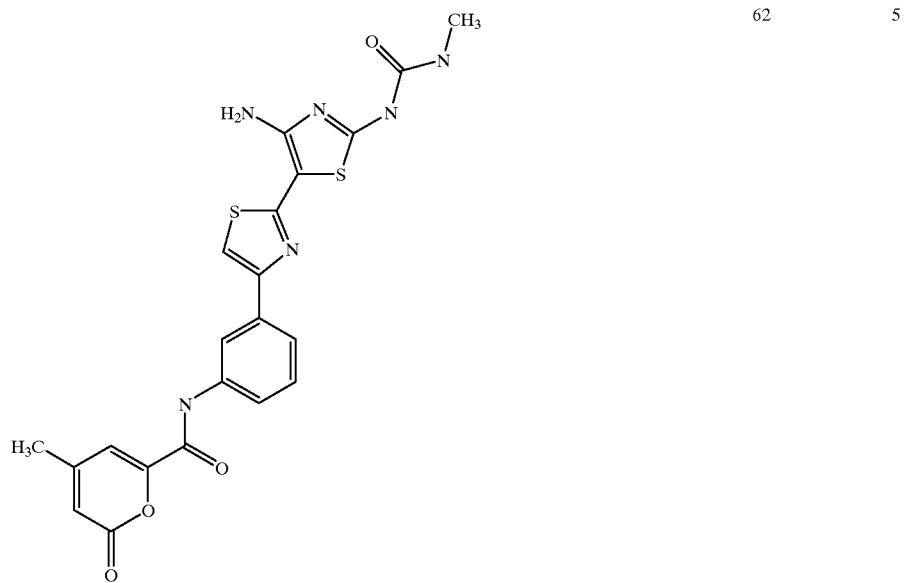 | 62 | 5 |
| 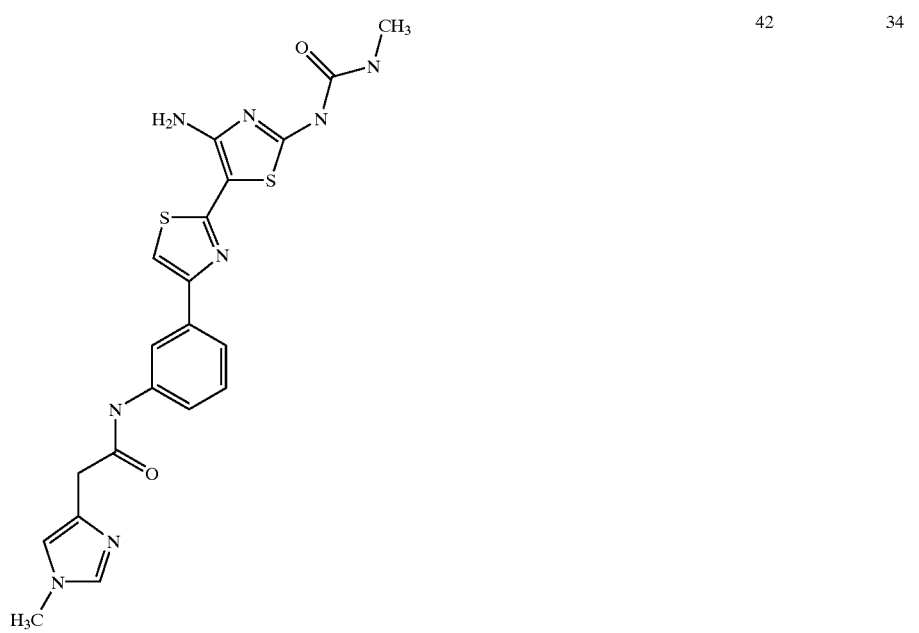 | 42 | 34 |

TABLE II-continued
| STRUCTURE | % inhibition @ 10 nM | % inhibition @ 1 nM |
|---|---|---|
| 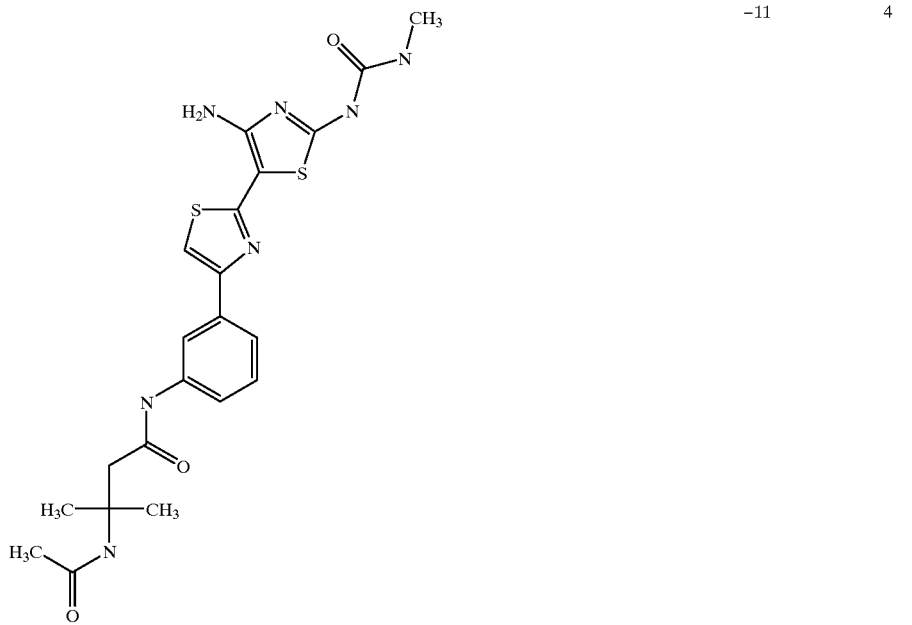 | −11 | 4 |
| 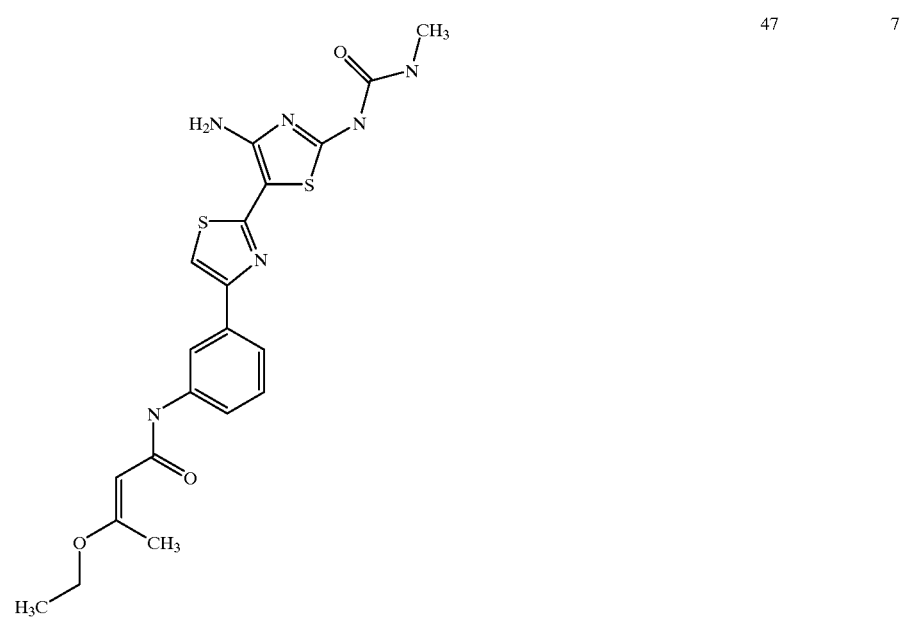 | 47 | 7 |

TABLE II-continued

| STRUCTURE | % inhibition @ 10 nM | % inhibition @ 1 nM |
|---|---|---|
| 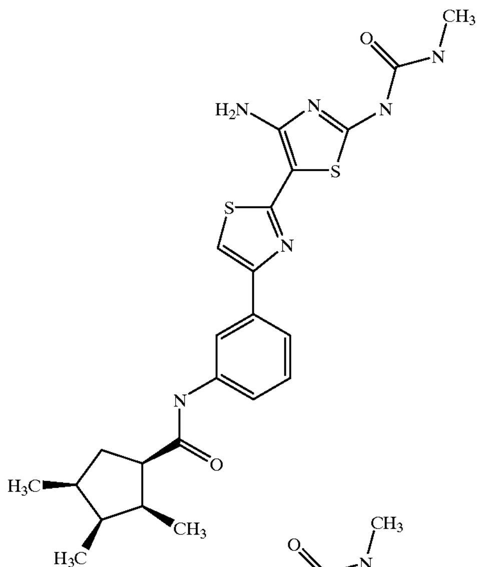 | −21 | −11 |
| 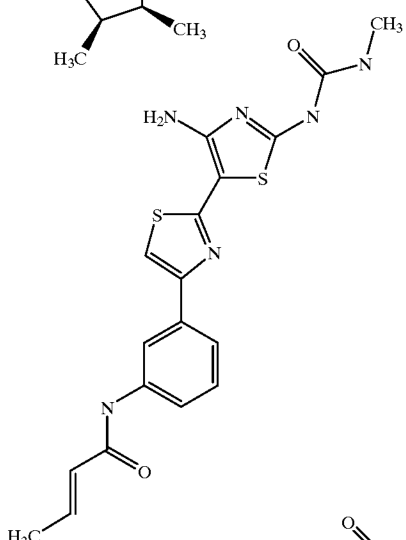 | −7 | −1 |
| 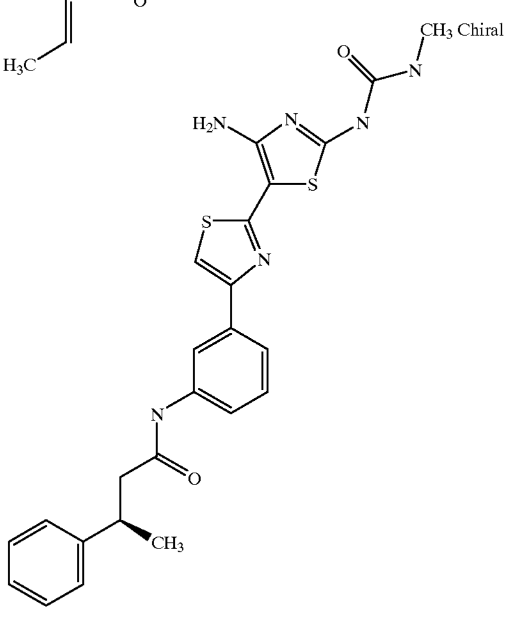 | −9 | 4 |

TABLE II-continued

| STRUCTURE | % inhibition @ 10 nM | % inhibition @ 1 nM |
|---|---|---|
| (structure) | 82 | 29 |
| (structure) | 19 | 17 |
| (structure) | 18 | 11 |

TABLE II-continued
| STRUCTURE | % inhibition @ 10 nM | % inhibition @ 1 nM |
|---|---|---|
| 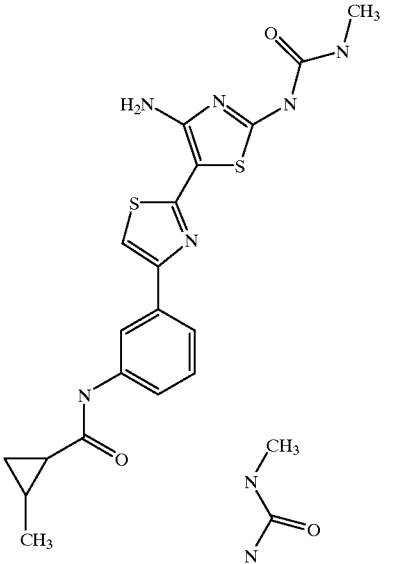 | 0 | −12 |
| 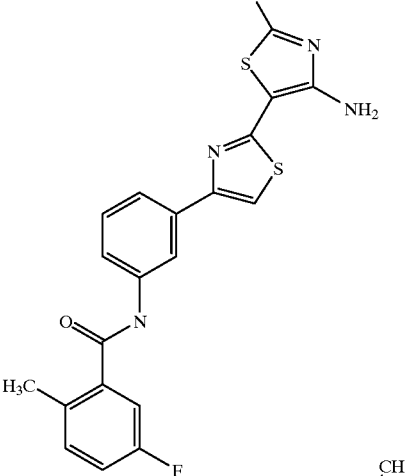 | 78 | −1 |
| 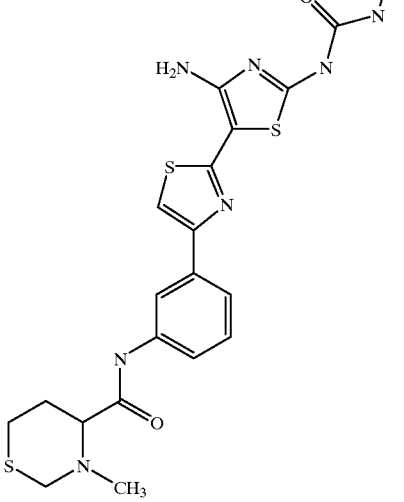 | 62 | 1 |

TABLE II-continued

| STRUCTURE | % inhibition @ 10 nM | % inhibition @ 1 nM |
|---|---|---|
| 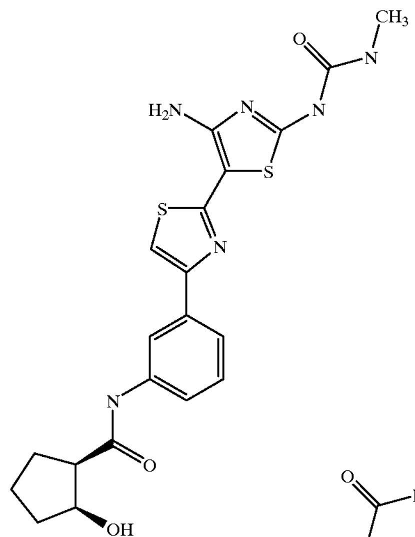 | 13 | 15 |
| 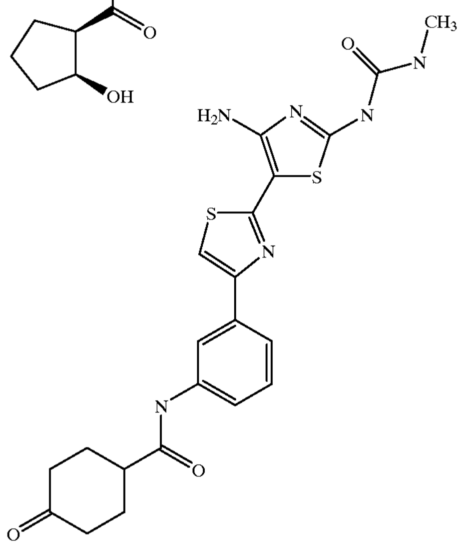 | 12 | −2 |
| 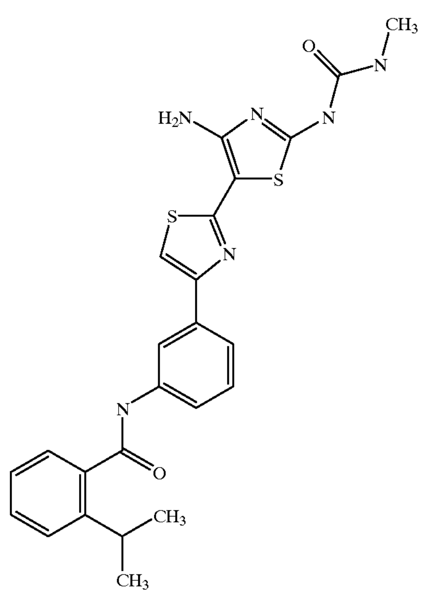 | 26 | −9 |

TABLE II-continued

| STRUCTURE | % inhibition @ 10 nM | % inhibition @ 1 nM |
|---|---|---|
| (structure) | 4 | 16 |
| (structure) | 41 | 17 |
| (structure) | 29 | 32 |

TABLE II-continued

| STRUCTURE | % inhibition @ 10 nM | % inhibition @ 1 nM |
|---|---|---|
| (structure) | −4 | 21 |
| (structure) | 71 | 7 |
| (structure) | 46 | −34 |

TABLE II-continued
| STRUCTURE | % inhibition @ 10 nM | % inhibition @ 1 nM |
|---|---|---|
| 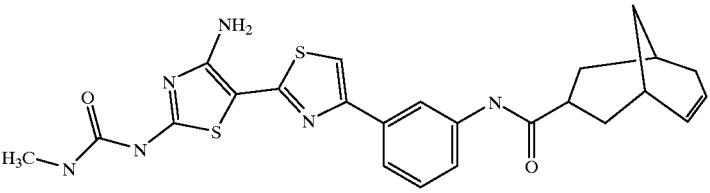 | 55 | 1 |
| 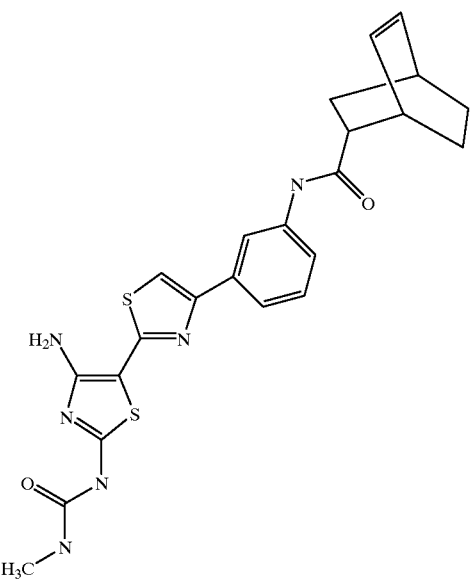 | 45 | 54 |
| 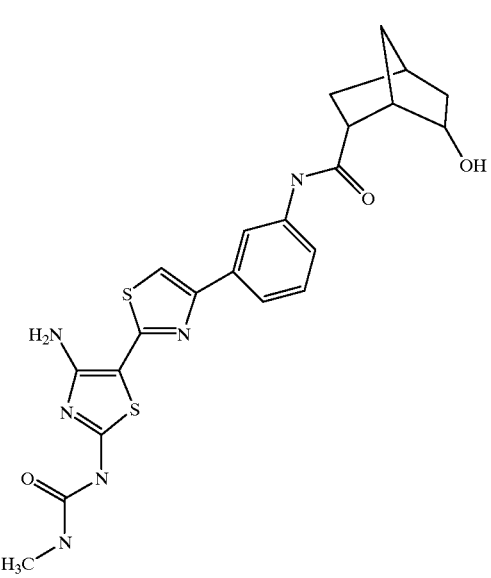 | 19 | 20 |

TABLE II-continued
| STRUCTURE | % inhibition @ 10 nM | % inhibition @ 1 nM |
|---|---|---|
| 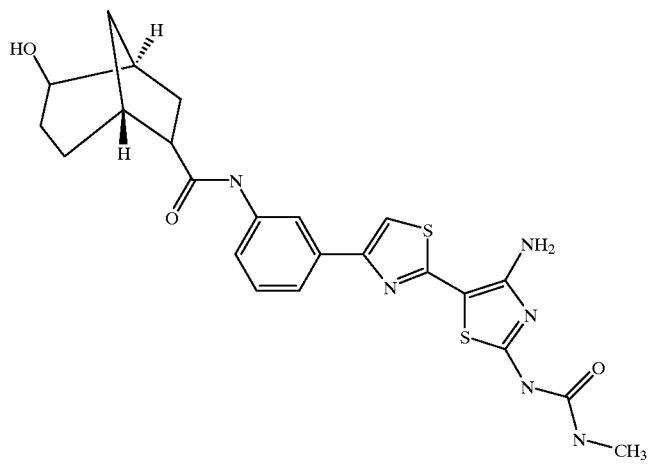 | 21 | 14 |
| STRUCTURE | % inhibition @ 10 nM | % inhibition @ 1 nM |
|---|---|---|
| 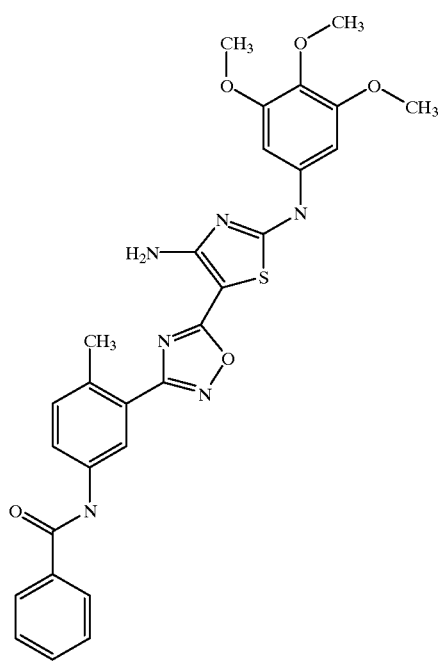 | 111 | 25 |

-continued
| STRUCTURE | % inhibition @ 10 nM | % inhibition @ 1 nM |
|---|---|---|
| 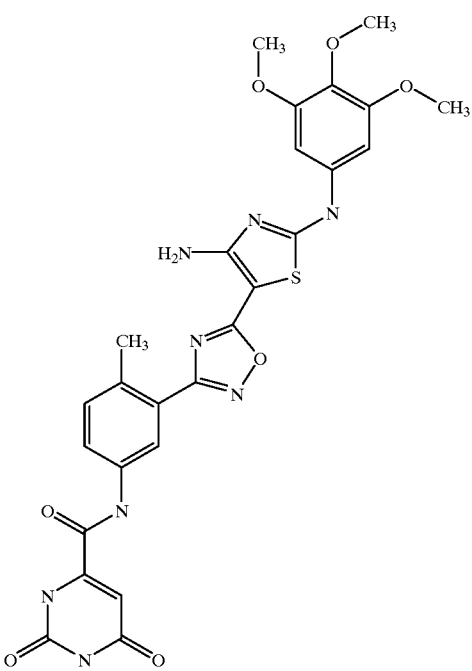 | 4 | −4 |
| 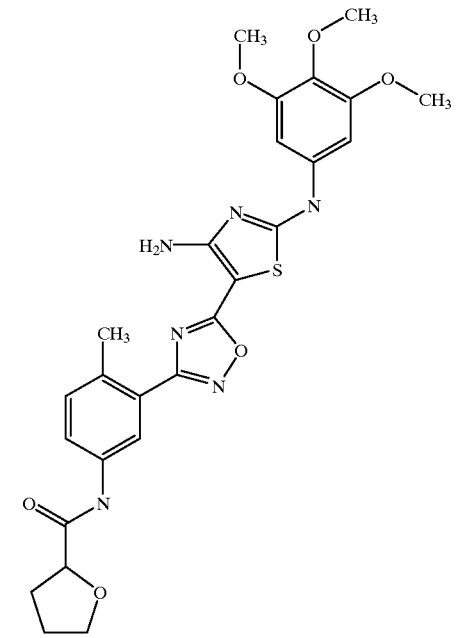 | 21 | 7 |

-continued
| STRUCTURE | % inhibition @ 10 nM | % inhibition @ 1 nM |
|---|---|---|
| 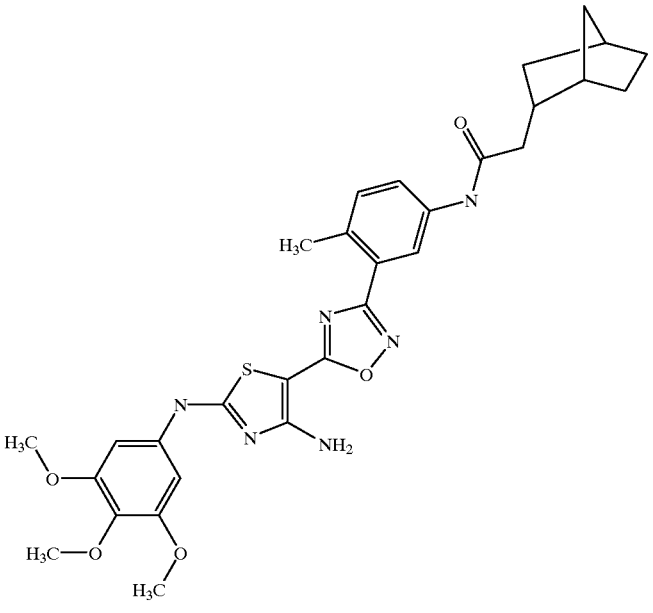 | 47 | −7 |
| 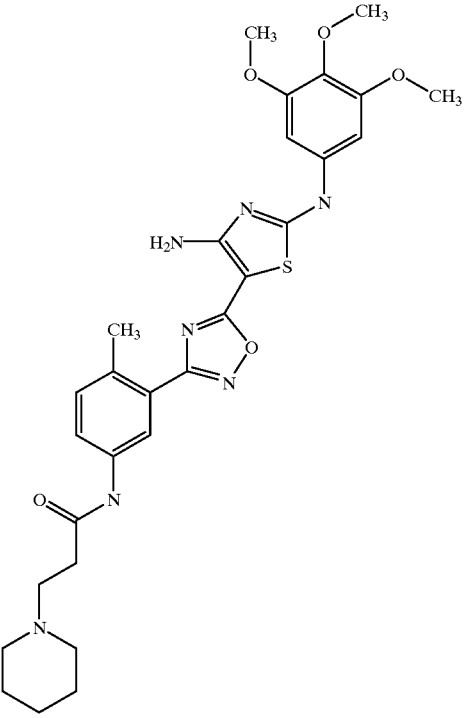 | 28 | 3 |

-continued
| STRUCTURE | % inhibition @ 10 nM | % inhibition @ 1 nM |
|---|---|---|
| 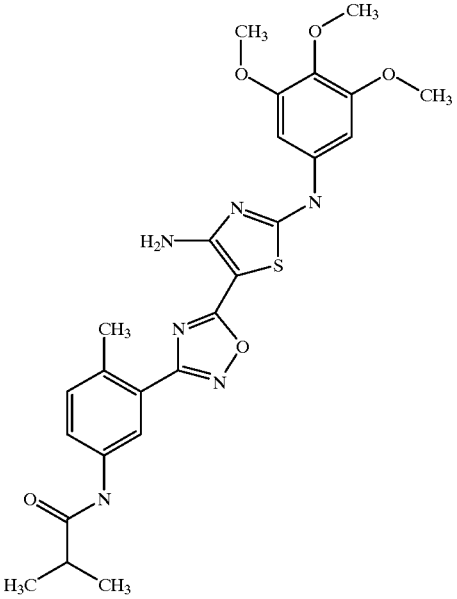 | 1 | 6 |
| 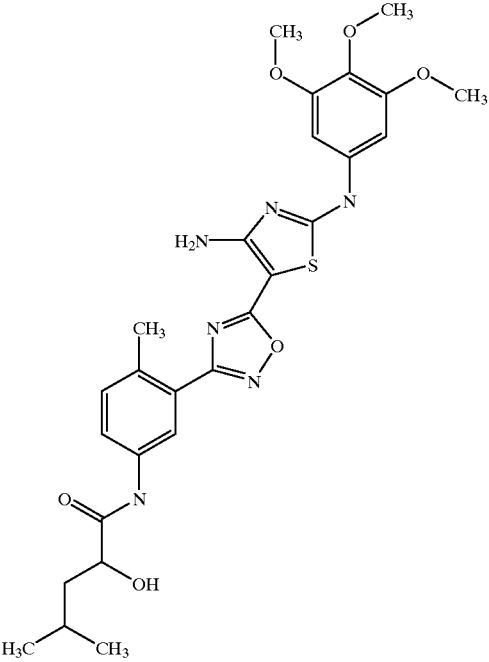 | 69 | 5 |

-continued
| STRUCTURE | % inhibition @ 10 nM | % inhibition @ 1 nM |
|---|---|---|
| 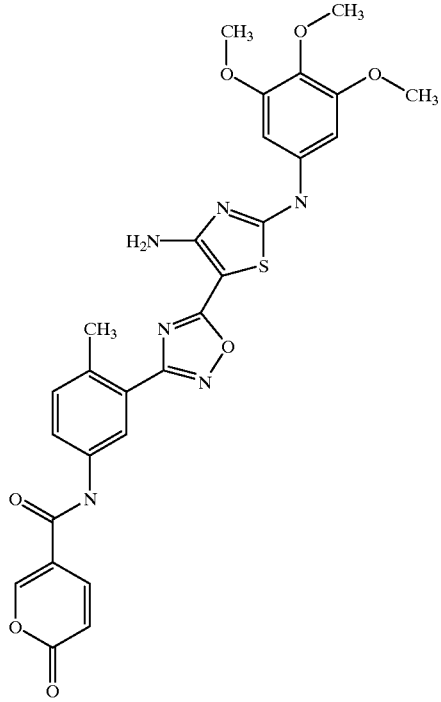 | 51 | 30 |
| 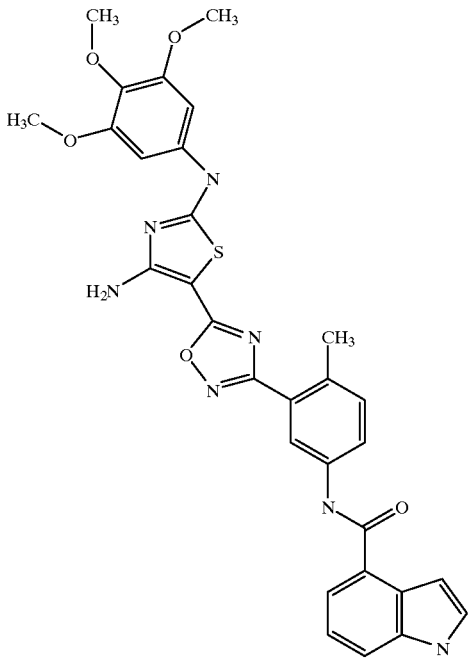 | 72 | 13 |

-continued
| STRUCTURE | % inhibition @ 10 nM | % inhibition @ 1 nM |
|---|---|---|
| 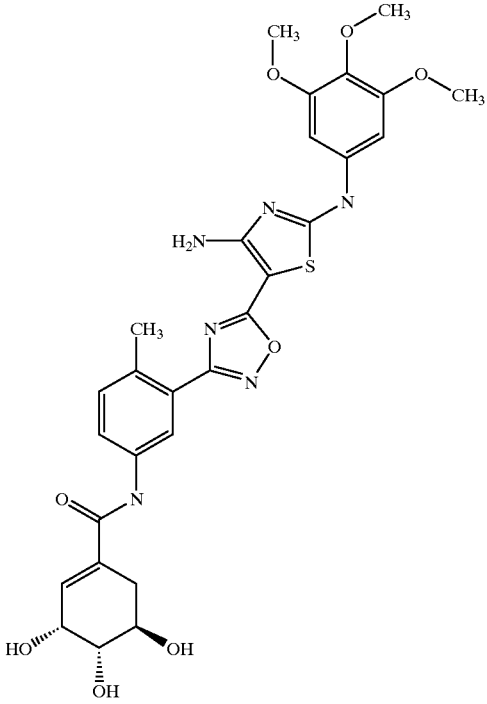 Chiral | 6 | 4 |
| 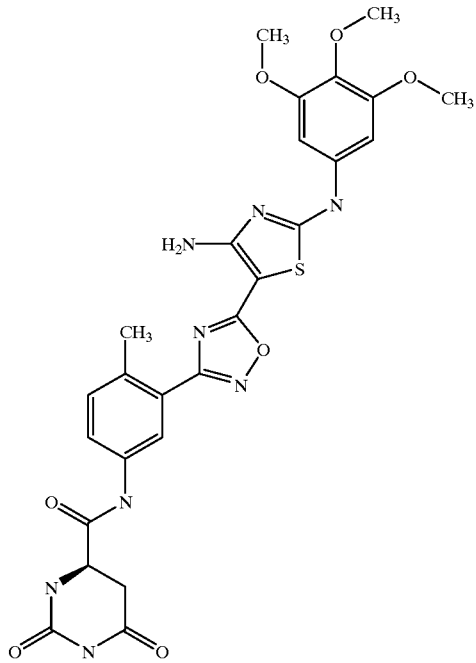 Chiral | 2 | 25 |

-continued
| STRUCTURE | % inhibition @ 10 nM | % inhibition @ 1 nM |
|---|---|---|
| 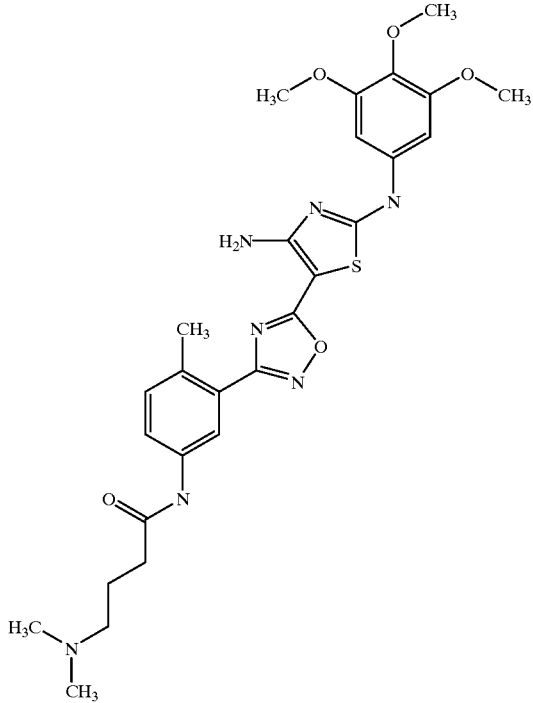 | 16 | 5 |
| 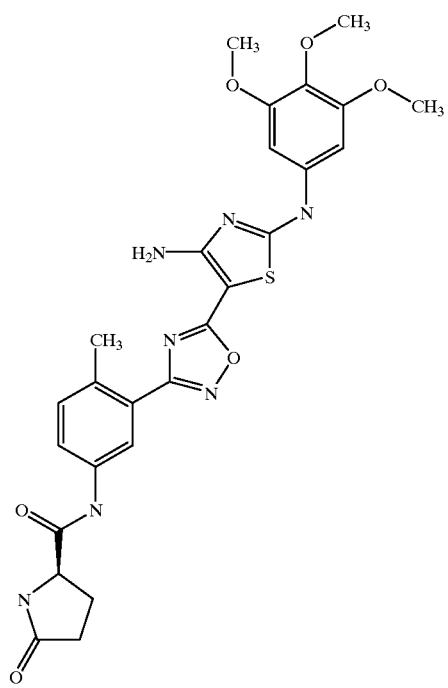 Chiral | 13 | −4 |

-continued
| STRUCTURE | % inhibition @ 10 nM | % inhibition @ 1 nM |
|---|---|---|
| 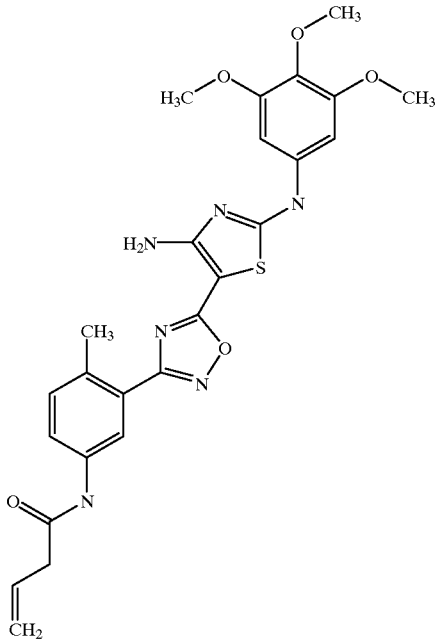 | 72 | 35 |
| 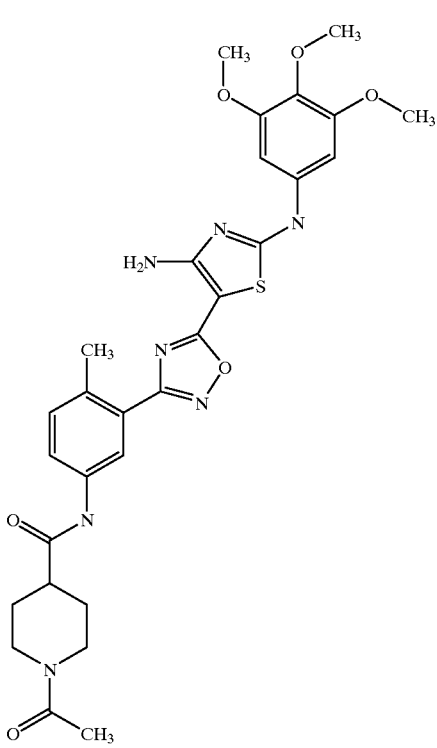 | 16 | −4 |

-continued
| STRUCTURE | % inhibition @ 10 nM | % inhibition @ 1 nM |
|---|---|---|
| 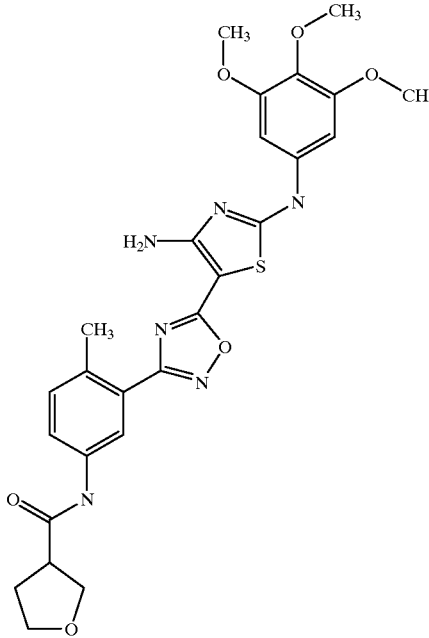 | 6 | 16 |
| 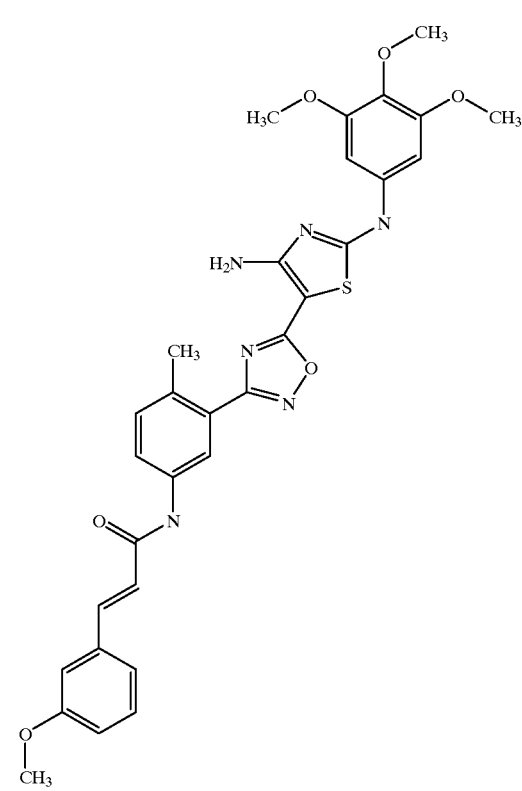 | 40 | −5 |

-continued
| STRUCTURE | % inhibition @ 10 nM | % inhibition @ 1 nM |
|---|---|---|
| 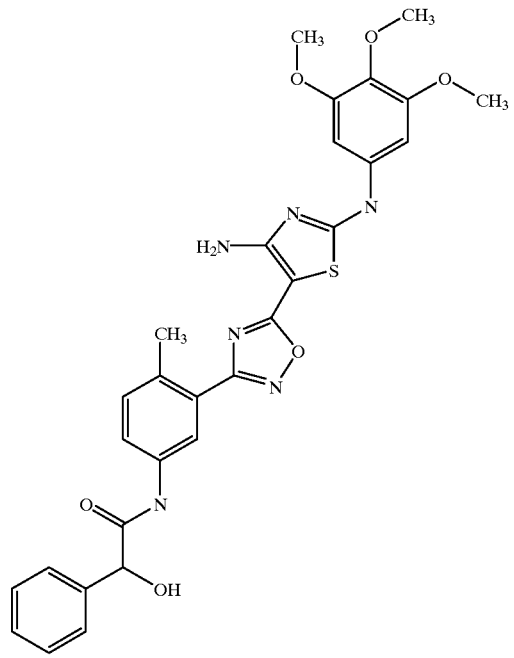 | 40 | −1 |
| 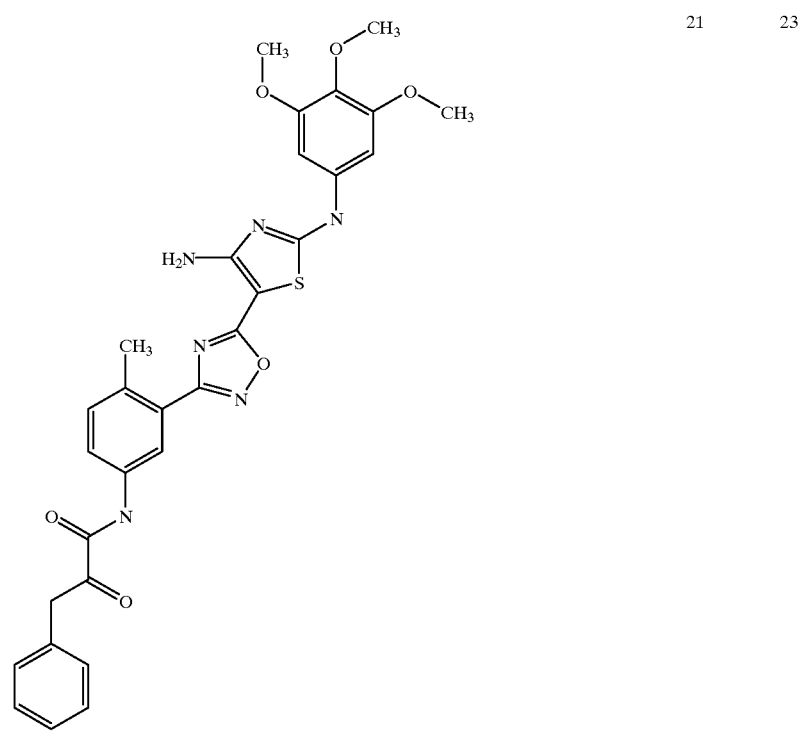 | 21 | 23 |

-continued
| STRUCTURE | % inhibition @ 10 nM | % inhibition @ 1 nM |
|---|---|---|
| 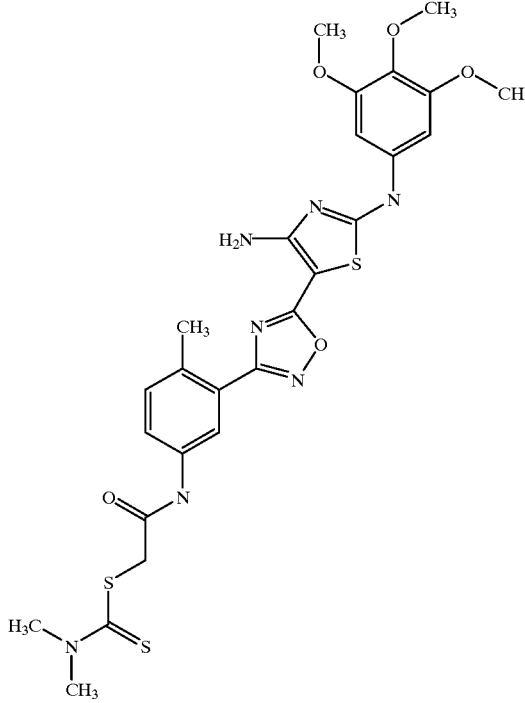 | −7 | 6 |
| 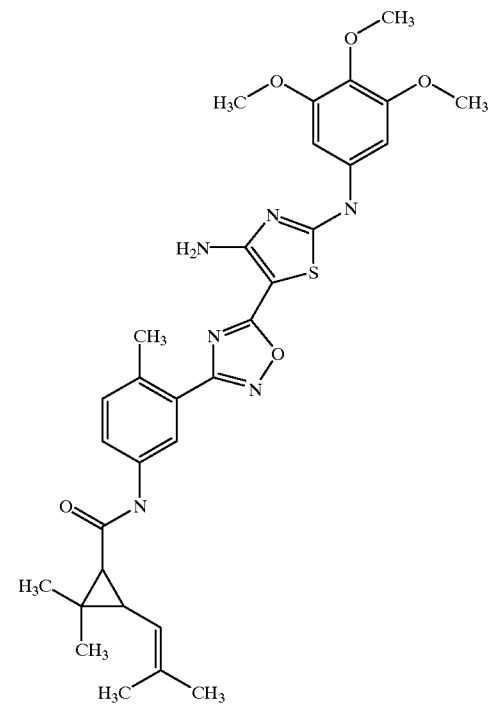 | −11 | 8 |

-continued

| STRUCTURE | % inhibition @ 10 nM | % inhibition @ 1 nM |
|---|---|---|
| [structure] | 23 | 1 |
| [structure] | 21 | −4 |

-continued
| STRUCTURE | % inhibition @ 10 nM | % inhibition @ 1 nM |
|---|---|---|
| 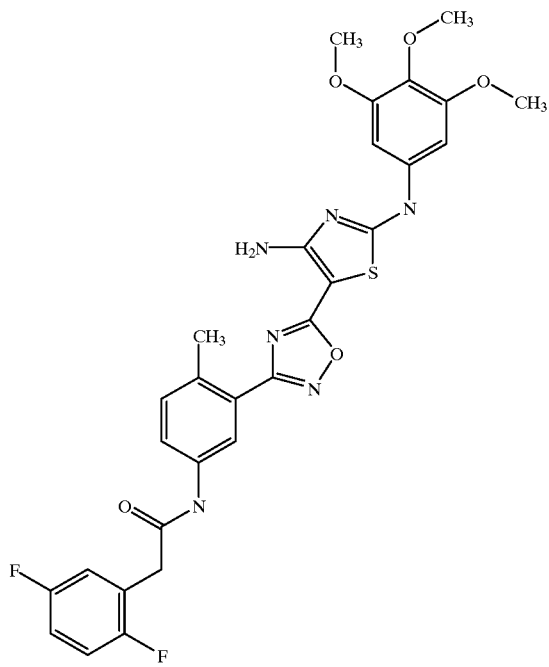 | 59 | −7 |
| 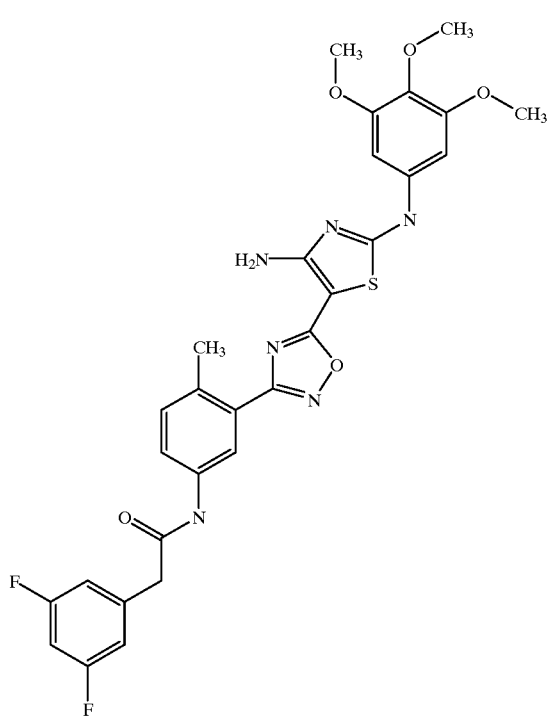 | 67 | 4 |

| STRUCTURE | % inhibition @ 10 nM | % inhibition @ 1 nM |
|---|---|---|
| 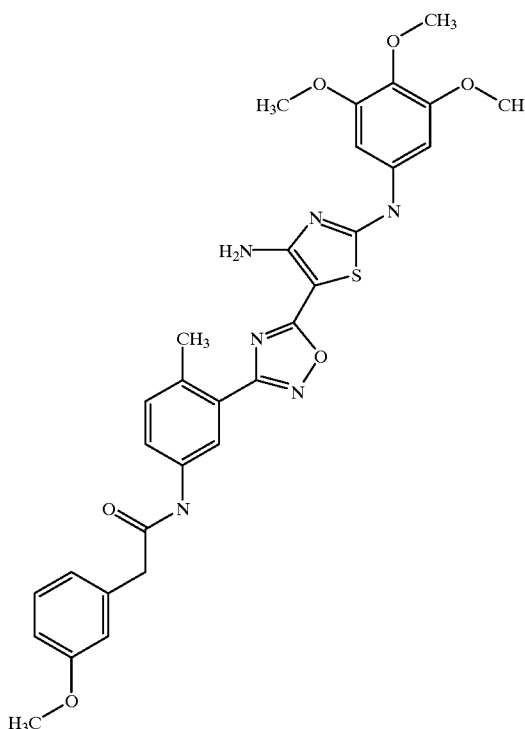 | 35 | 12 |
| 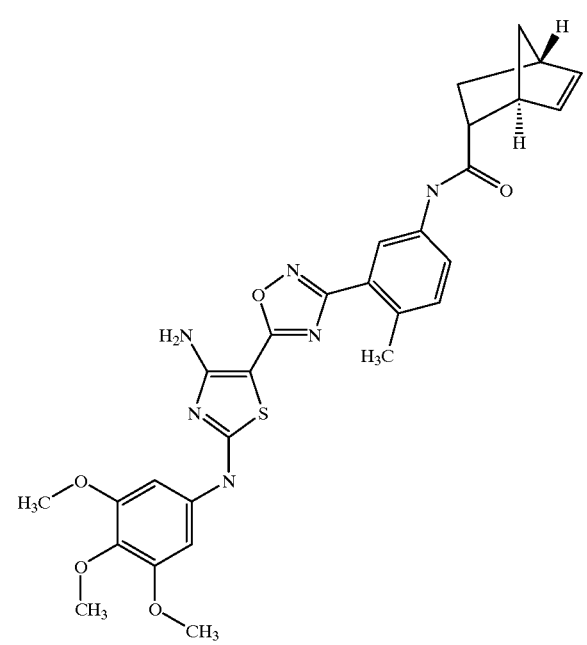 | 33 | −2 |

-continued
| STRUCTURE | % inhibition @ 10 nM | % inhibition @ 1 nM |
|---|---|---|
| 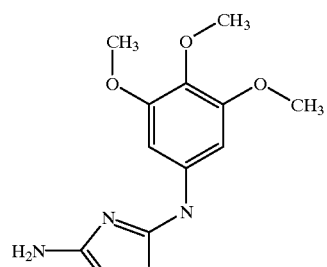 | 23 | −18 |
| 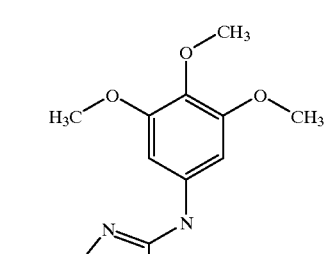 | 94 | 35 |

| STRUCTURE | % inhibition @ 10 nM | % inhibition @ 1 nM |
|---|---|---|
| 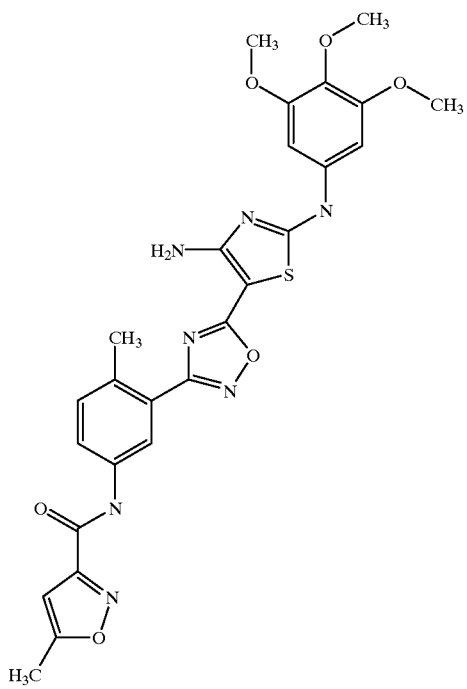 | 15 | 12 |
| 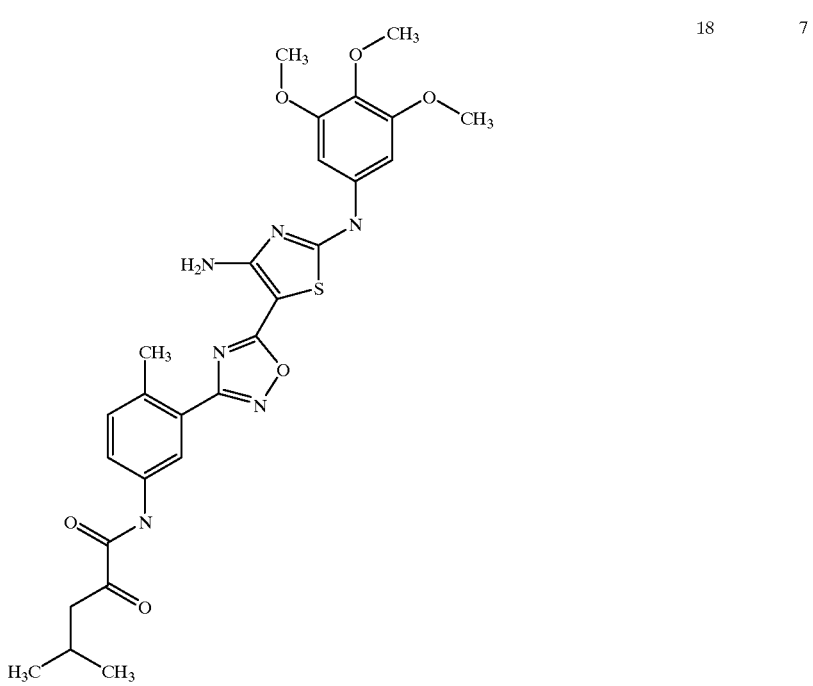 | 18 | 7 |

| STRUCTURE | % inhibition @ 10 nM | % inhibition @ 1 nM |
|---|---|---|
| 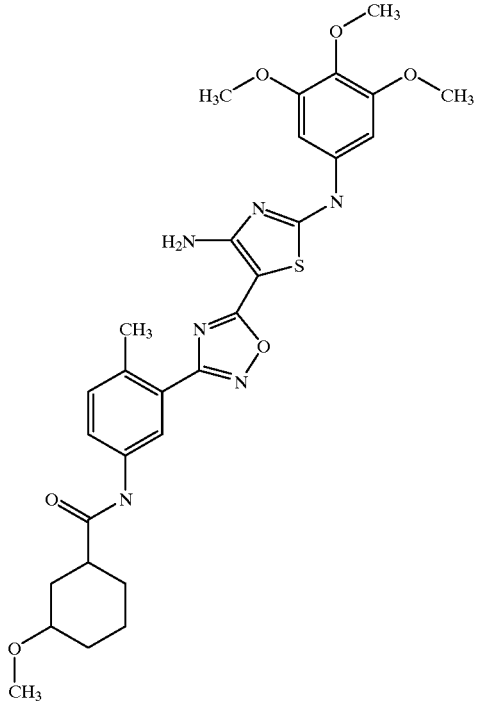 | 19 | −4 |
| 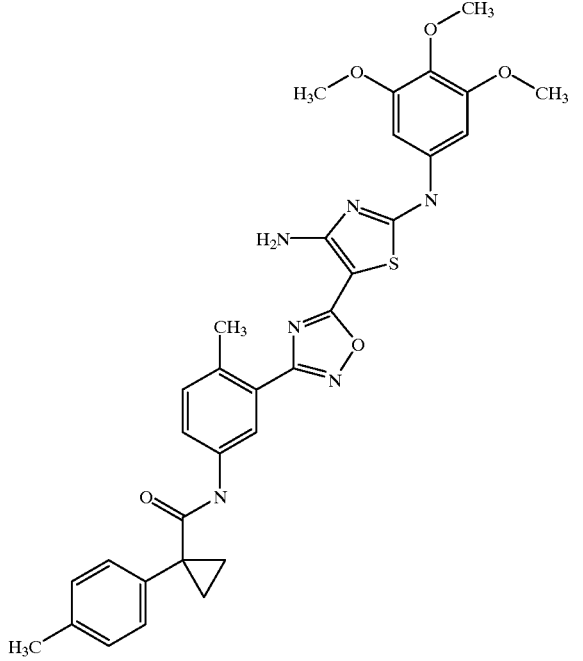 | −8 | 10 |

-continued
| STRUCTURE | % inhibition @ 10 nM | % inhibition @ 1 nM |
|---|---|---|
| 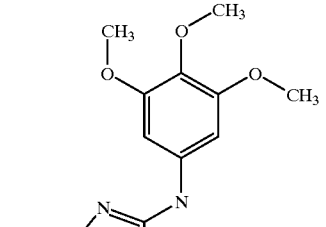 | 1 | −17 |
| 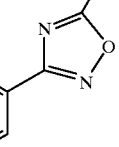 | 99 | 25 |

-continued
| STRUCTURE | % inhibition @ 10 nM | % inhibition @ 1 nM |
|---|---|---|
| 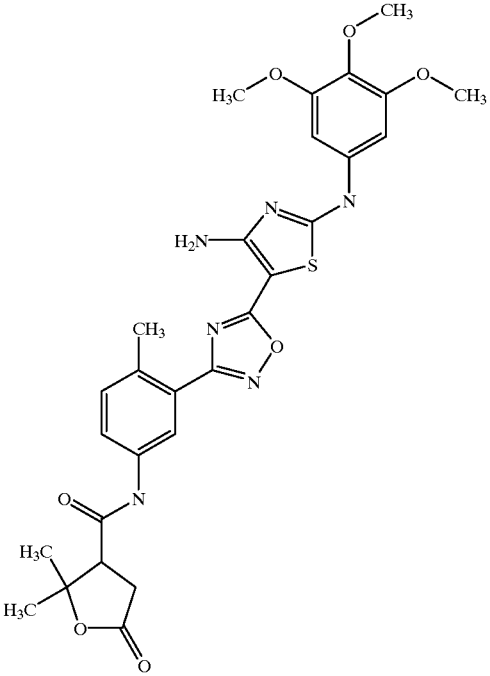 | 12 | −9 |
| 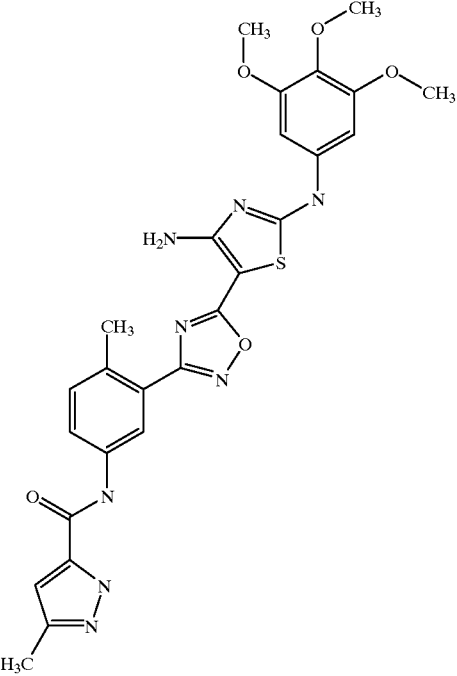 | 99 | −1 |

-continued
| STRUCTURE | % inhibition @ 10 nM | % inhibition @ 1 nM |
|---|---|---|
| 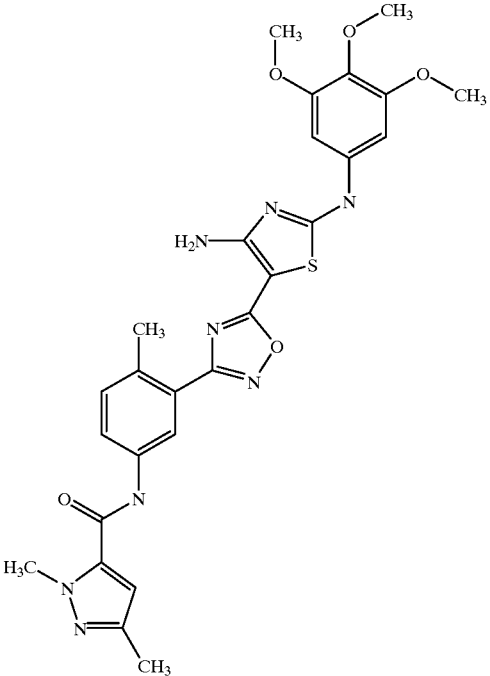 | 109 | −23 |
| 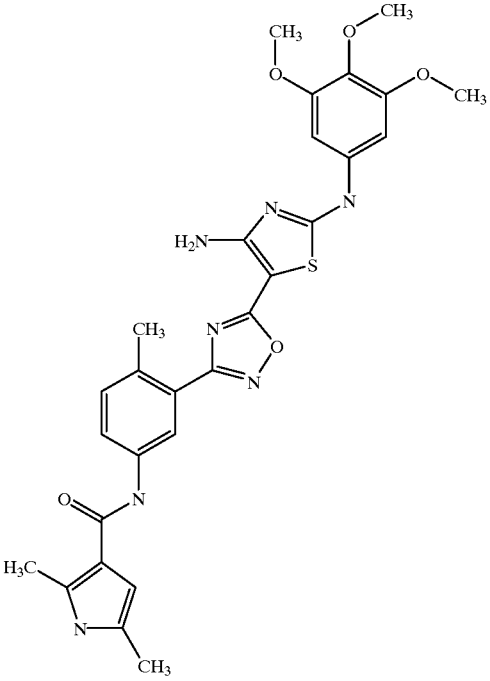 | 16 | −36 |

-continued
| STRUCTURE | % inhibition @ 10 nM | % inhibition @ 1 nM |
|---|---|---|
| 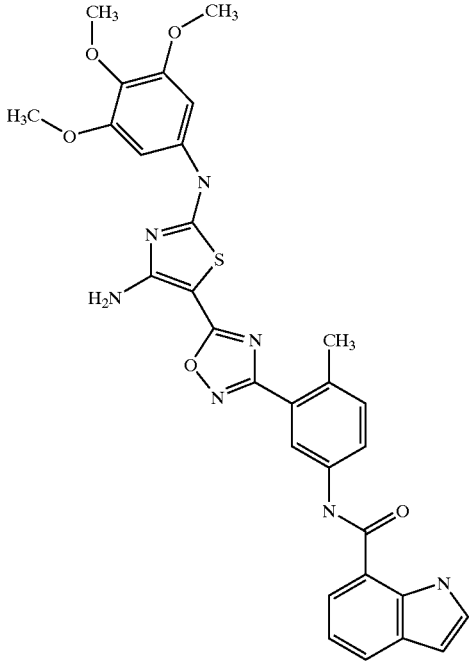 | 41 | 34 |
| 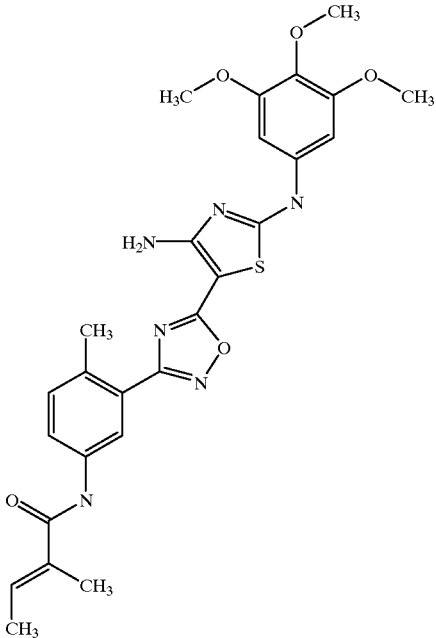 | 123 | 60 |

-continued
| STRUCTURE | % inhibition @ 10 nM | % inhibition @ 1 nM |
|---|---|---|
| 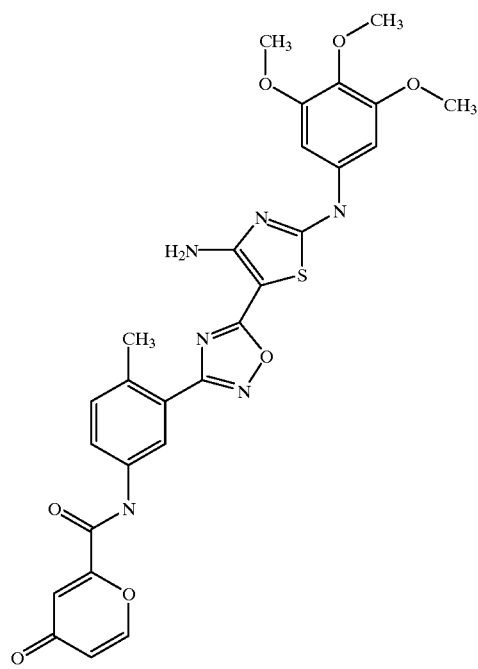 | 37 | 19 |
| 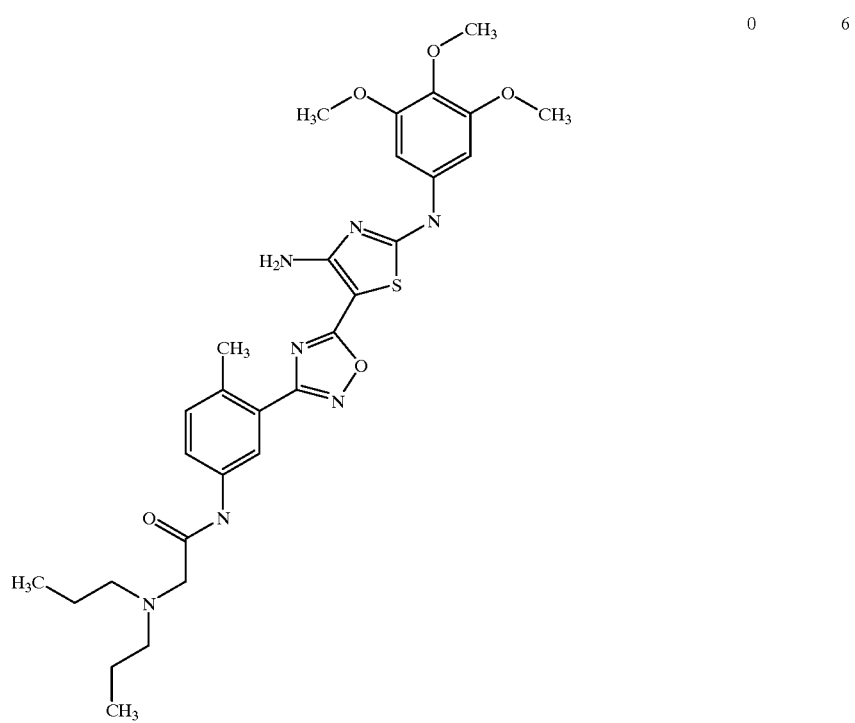 | 0 | 6 |

| STRUCTURE | % inhibition @ 10 nM | % inhibition @ 1 nM |
|---|---|---|
| 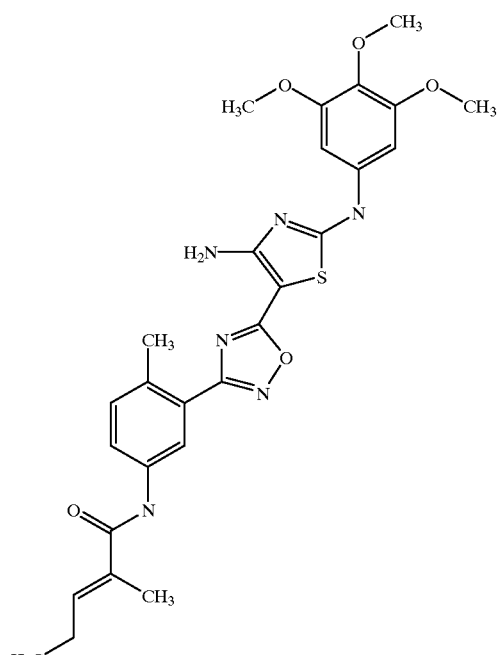 | 74 | 32 |
| 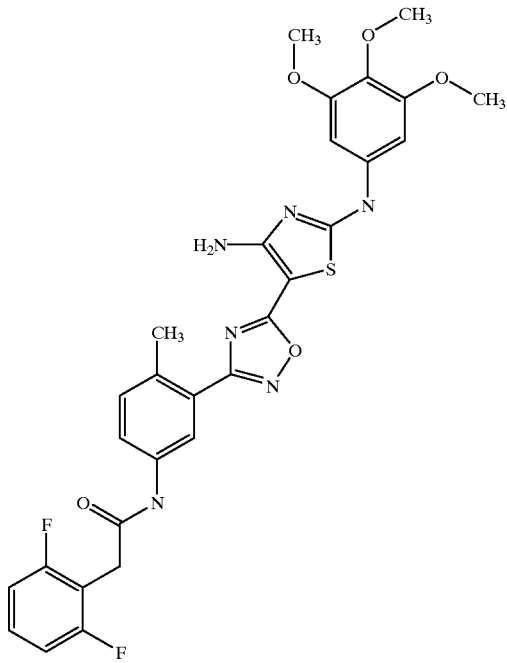 | 42 | −23 |

-continued
| STRUCTURE | % inhibition @ 10 nM | % inhibition @ 1 nM |
|---|---|---|
| 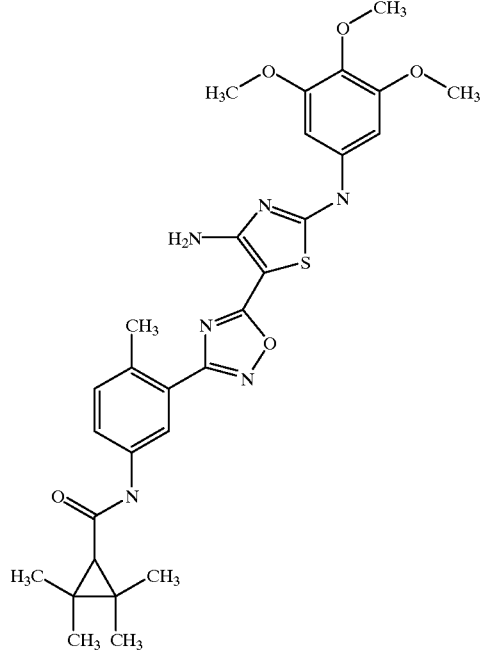 | 32 | −31 |
| 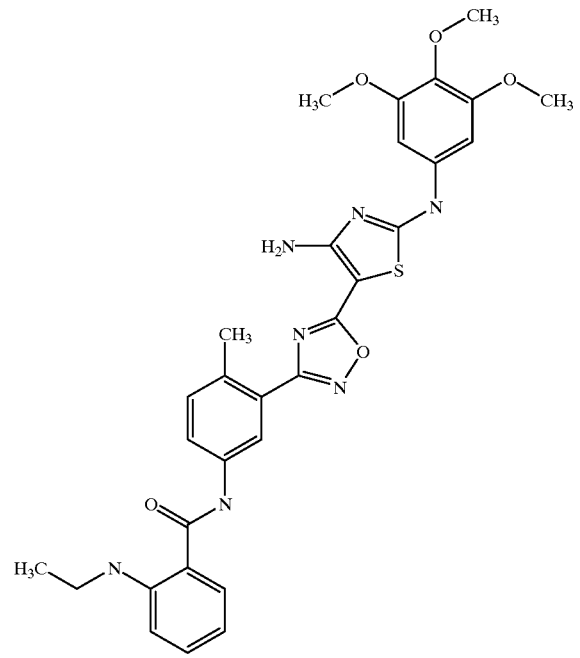 | 18 | −21 |

-continued
| STRUCTURE | % inhibition @ 10 nM | % inhibition @ 1 nM |
|---|---|---|
| 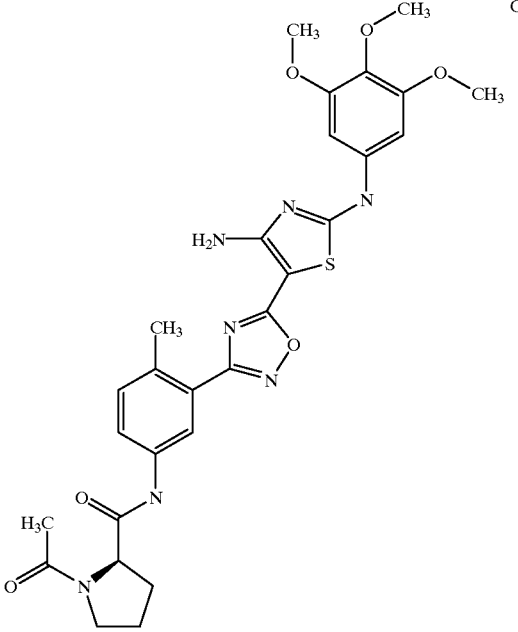 Chiral | −3 | −44 |
| 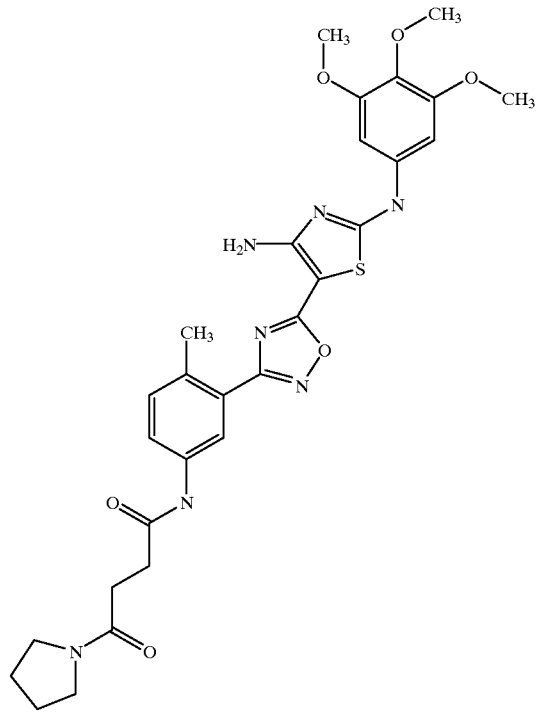 | −20 | −18 |

| STRUCTURE | % inhibition @ 10 nM | % inhibition @ 1 nM |
|---|---|---|
| 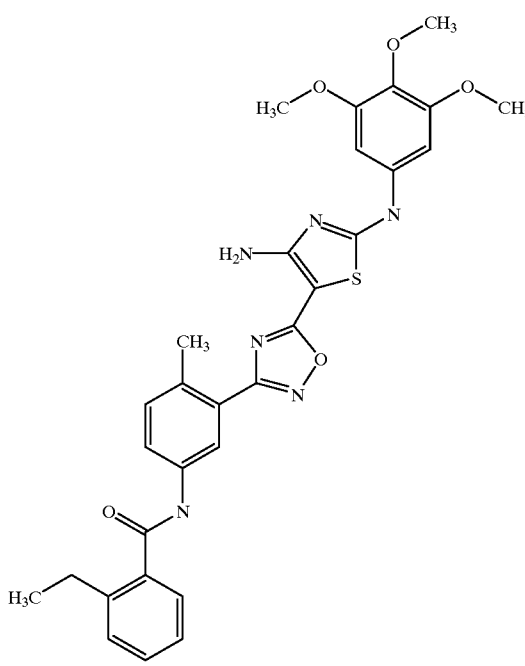 | 59 | −26 |
| 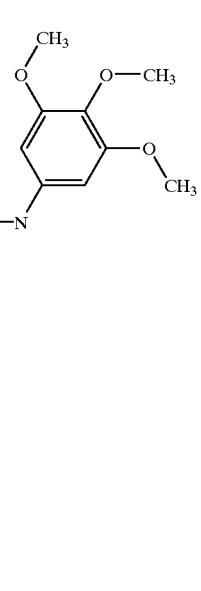 | −7 | 11 |

| STRUCTURE | % inhibition @ 10 nM | % inhibition @ 1 nM |
|---|---|---|
| 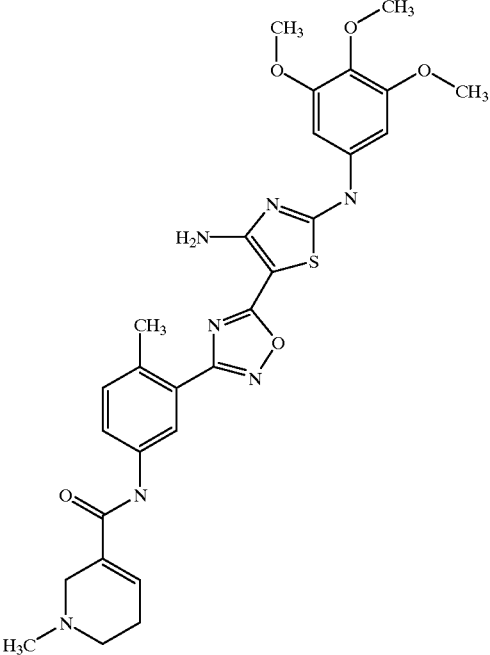 | 1 | 5 |
| 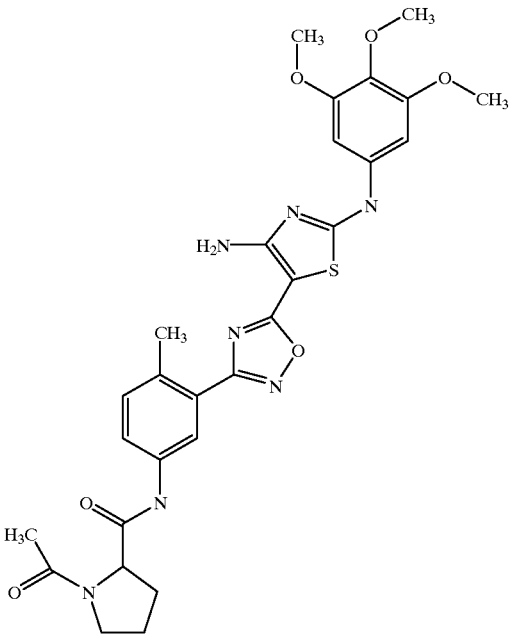 | −24 | −13 |

-continued

| STRUCTURE | % inhibition @ 10 nM | % inhibition @ 1 nM |
|---|---|---|
| 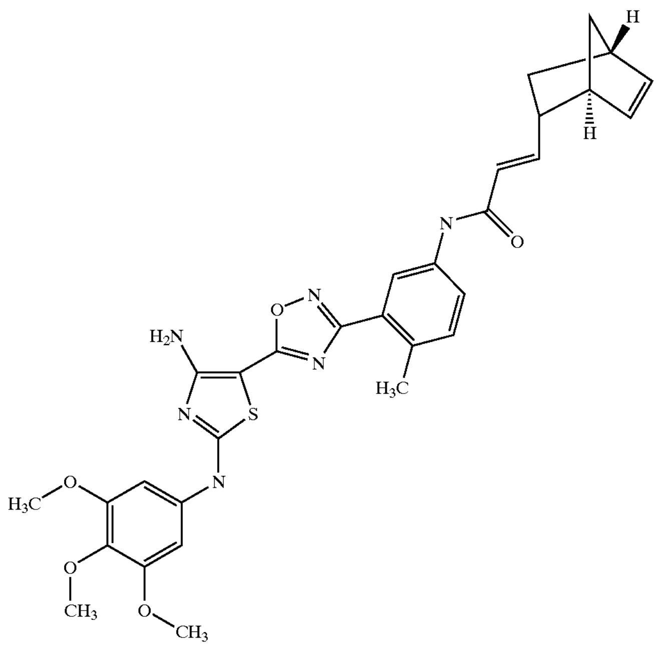 | 25 | −12 |
| 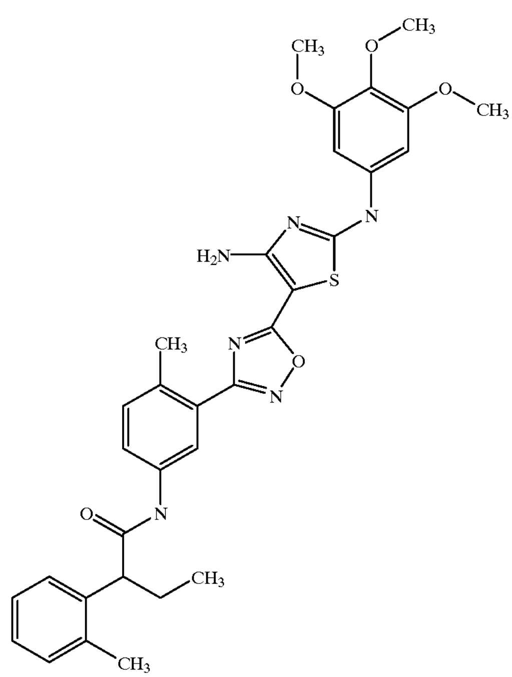 | 13 | −14 |

-continued
| STRUCTURE | % inhibition @ 10 nM | % inhibition @ 1 nM |
|---|---|---|
| 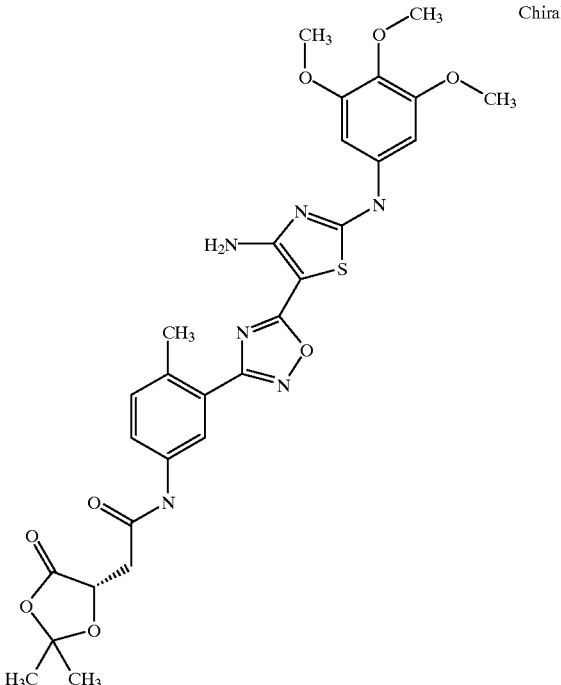 Chiral | 3 | −2 |
| 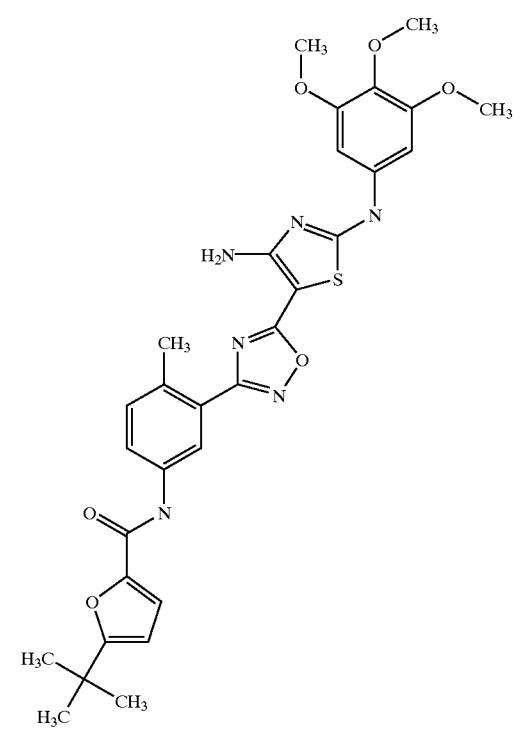 | 48 | −9 |

-continued

| STRUCTURE | % inhibition @ 10 nM | % inhibition @ 1 nM |
|---|---|---|
| (structure) | 8 | −27 |
| (structure) | 93 | 35 |

-continued
| STRUCTURE | % inhibition @ 10 nM | % inhibition @ 1 nM |
|---|---|---|
| 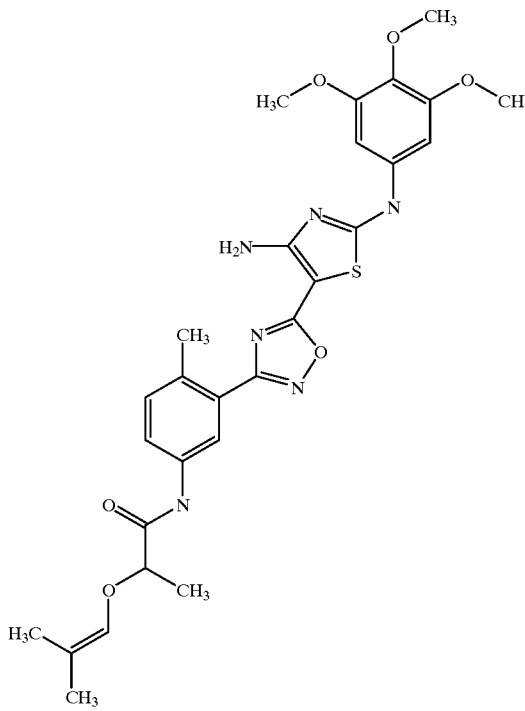 | 11 | −21 |
| 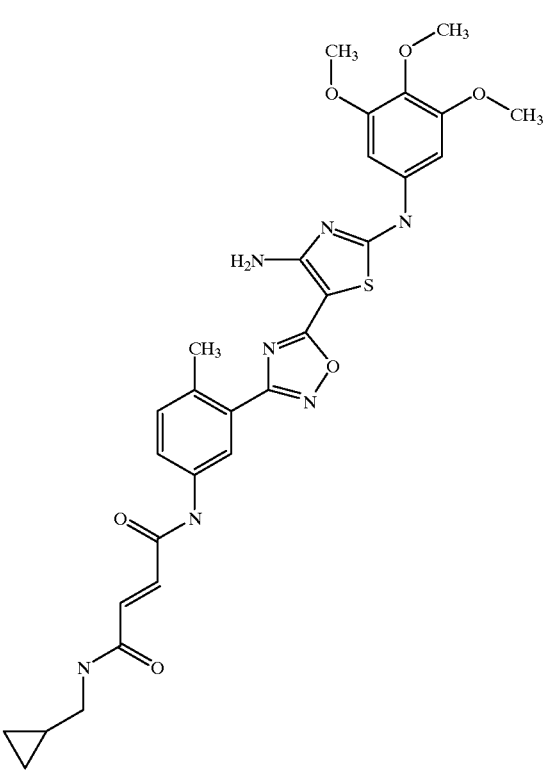 | 5 | 39 |

| STRUCTURE | % inhibition @ 10 nM | % inhibition @ 1 nM |
|---|---|---|
| 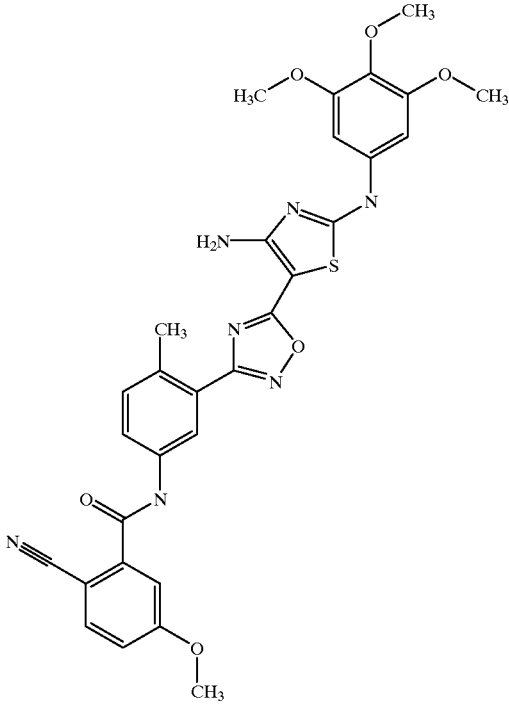 | 1 | 9 |
| 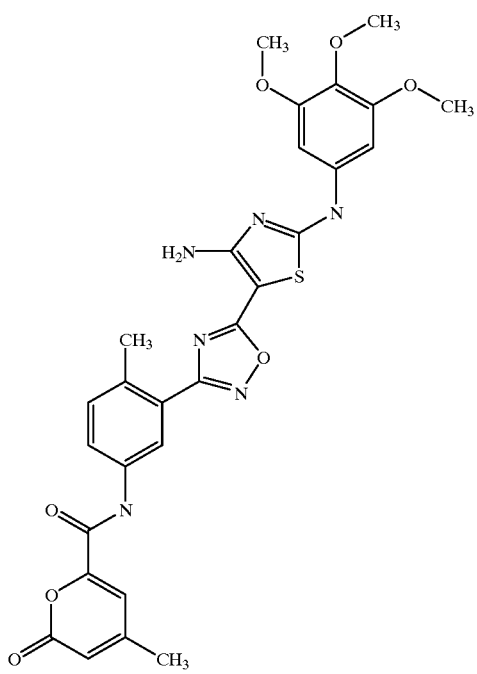 | 66 | −2 |

-continued
| STRUCTURE | % inhibition @ 10 nM | % inhibition @ 1 nM |
|---|---|---|
| 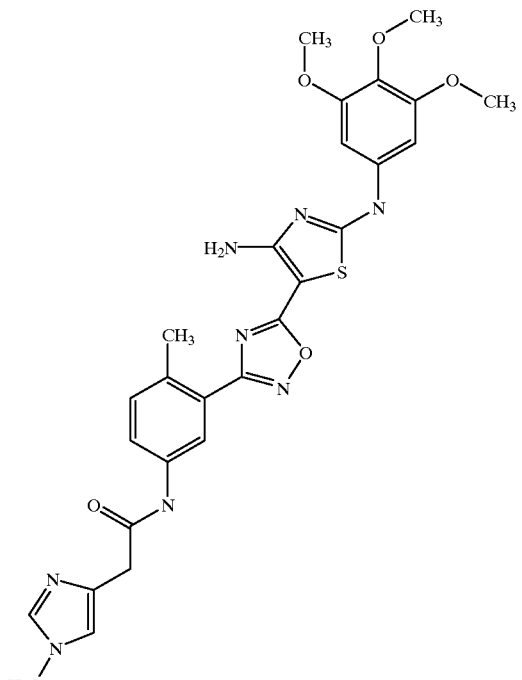 | −14 | −7 |
| 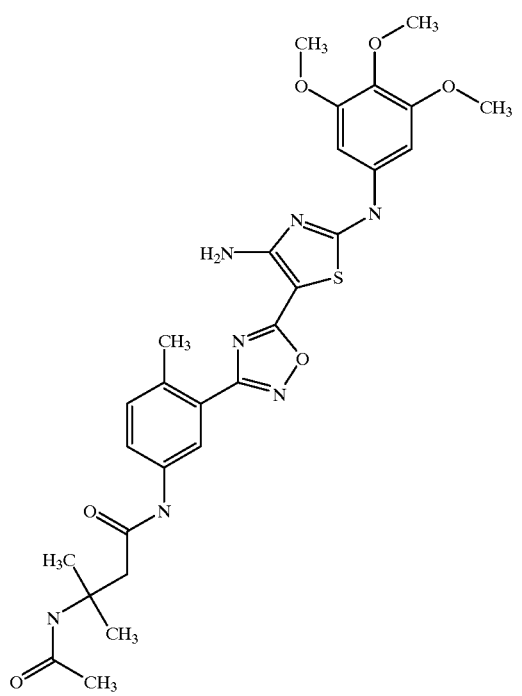 | −11 | 2 |

| STRUCTURE | % inhibition @ 10 nM | % inhibition @ 1 nM |
|---|---|---|
| 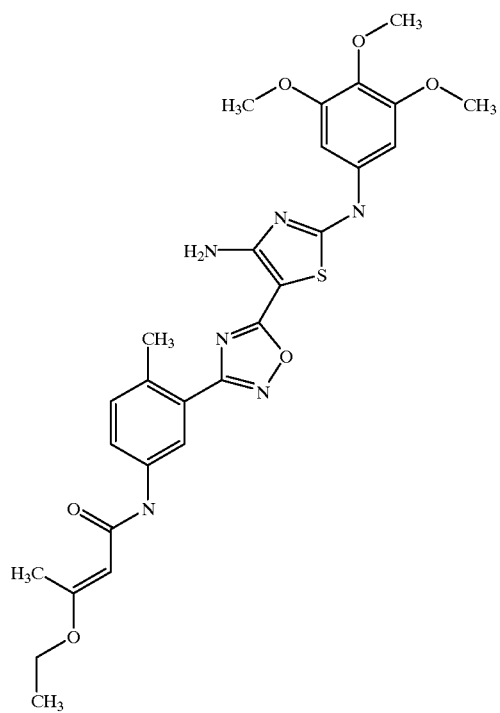 | 78 | 21 |
| 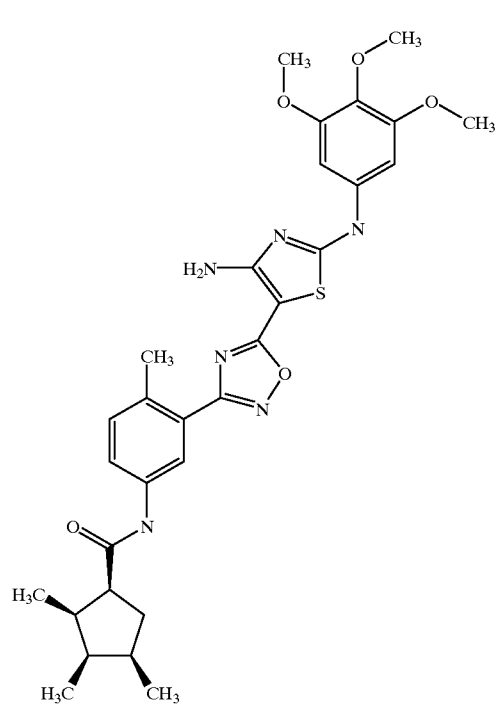 | 5 | −21 |

-continued
| STRUCTURE | % inhibition @ 10 nM | % inhibition @ 1 nM |
|---|---|---|
| 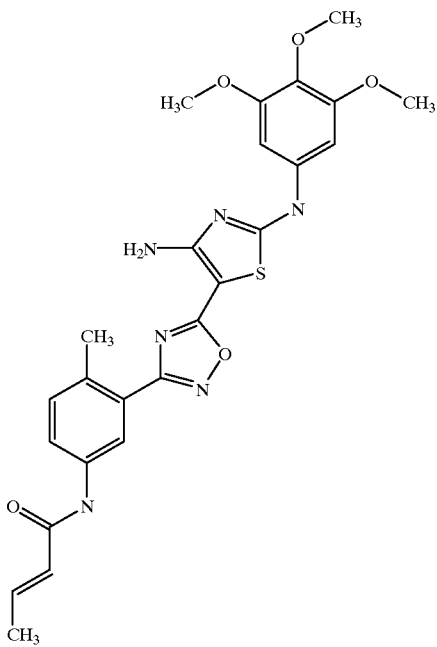 | 65 | 9 |
| 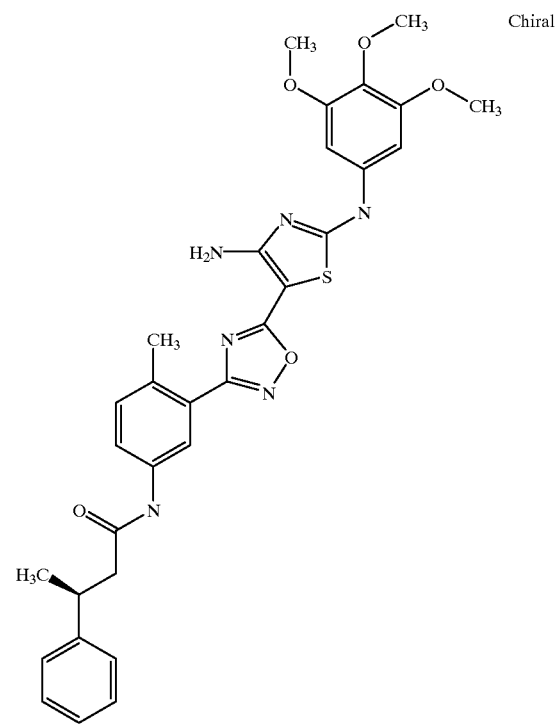 Chiral | 24 | −30 |

-continued
| STRUCTURE | % inhibition @ 10 nM | % inhibition @ 1 nM |
|---|---|---|
| 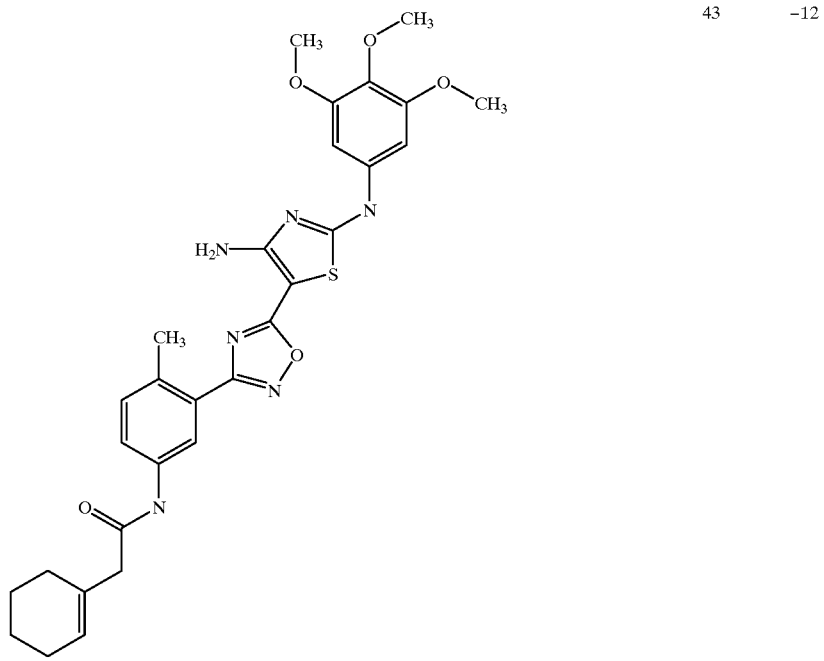 | 43 | −12 |
| 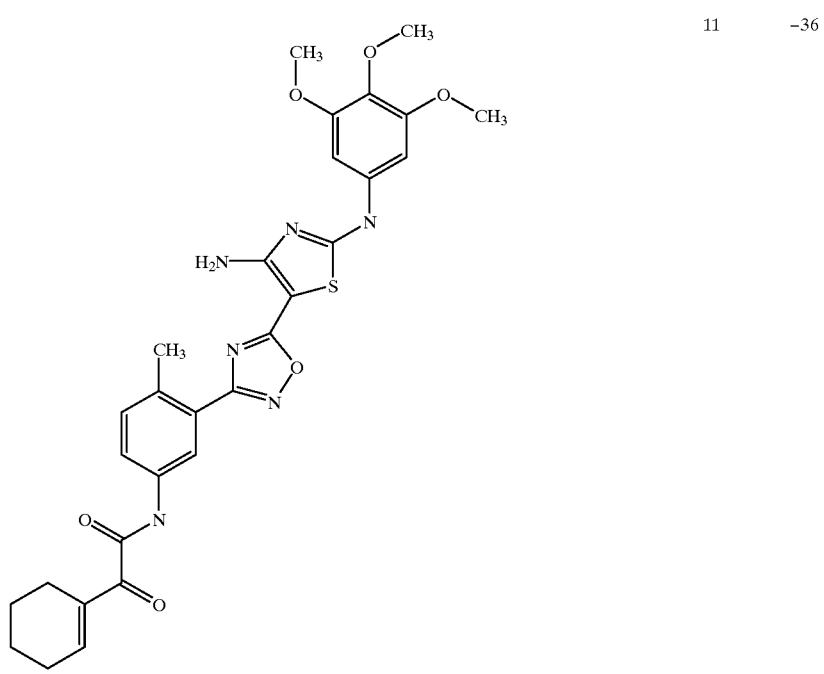 | 11 | −36 |

| STRUCTURE | % inhibition @ 10 nM | % inhibition @ 1 nM |
|---|---|---|
| 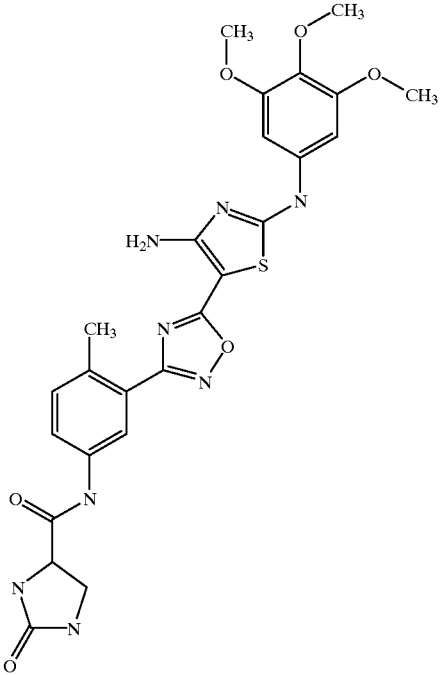 | −7 | −43 |
| 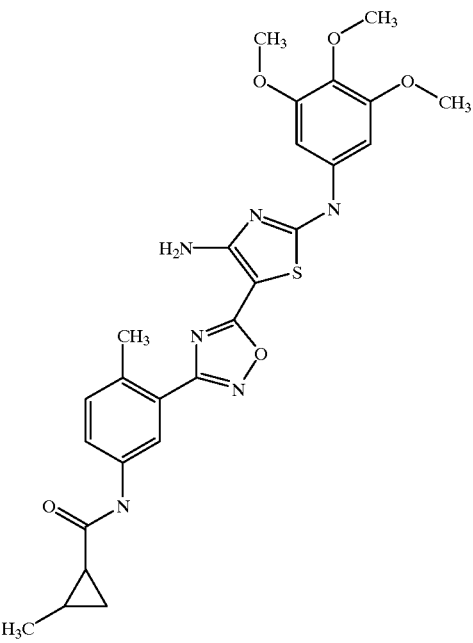 | 6 | 24 |

| STRUCTURE | % inhibition @ 10 nM | % inhibition @ 1 nM |
|---|---|---|
| 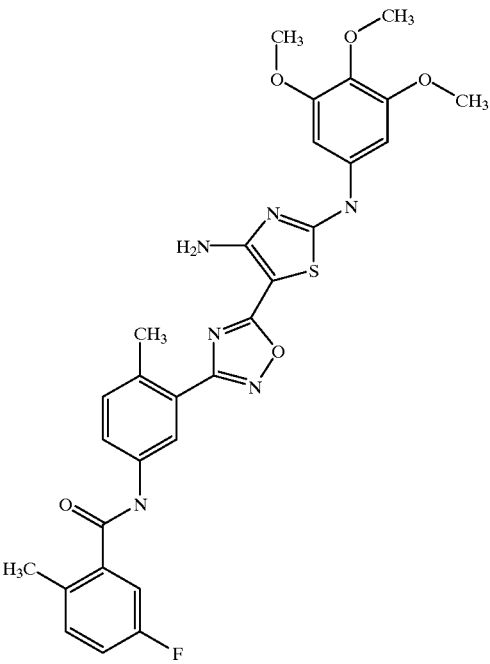 | 64 | 29 |
| 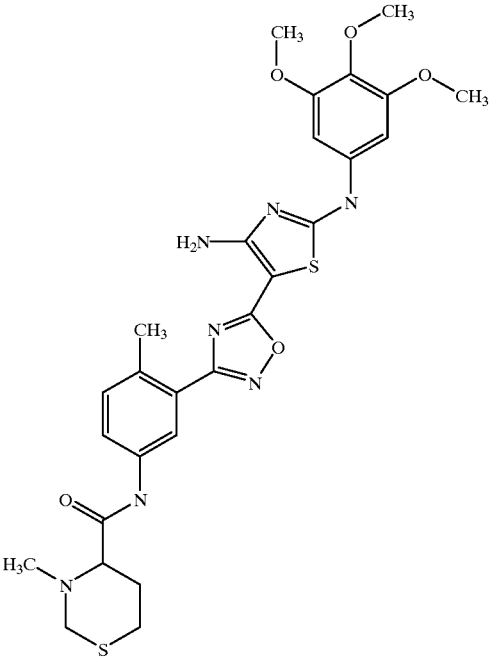 | 29 | 14 |

-continued
| STRUCTURE | % inhibition @ 10 nM | % inhibition @ 1 nM |
|---|---|---|
| 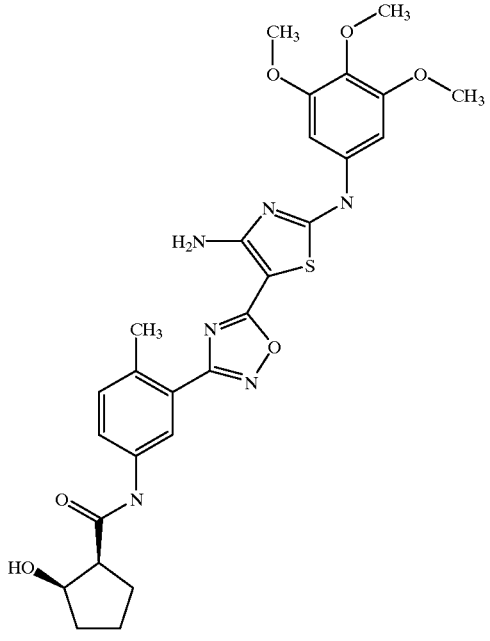 | 9 | 45 |
| 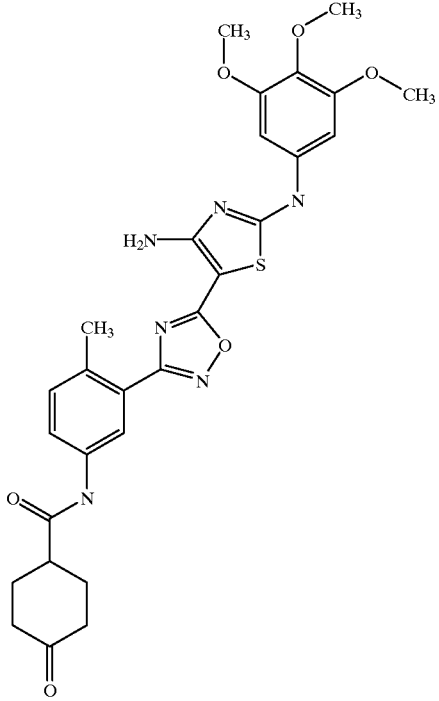 | −24 | 23 |

-continued
| STRUCTURE | % inhibition @ 10 nM | % inhibition @ 1 nM |
|---|---|---|
| 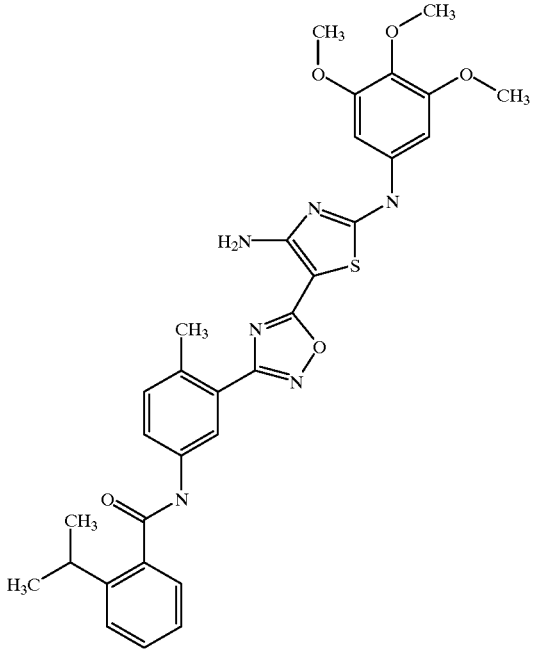 | 11 | 6 |
| 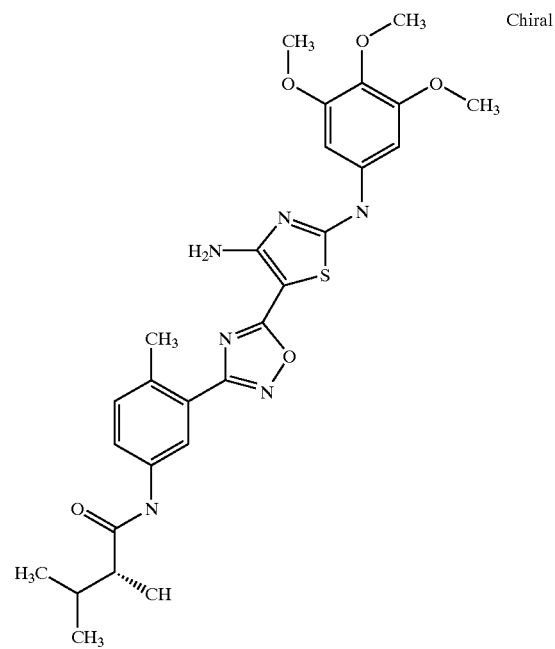 Chiral | −18 | −8 |

-continued
| STRUCTURE | % inhibition @ 10 nM | % inhibition @ 1 nM |
|---|---|---|
| 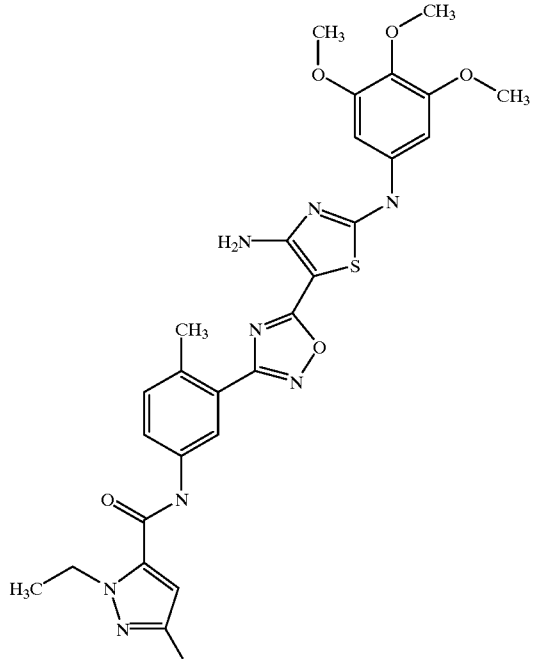 | 44 | −4 |
| 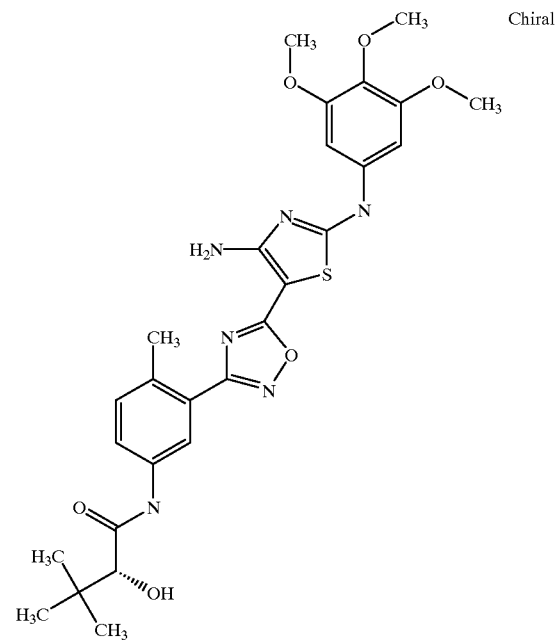 Chiral | −11 | −34 |

-continued
| STRUCTURE | % inhibition @ 10 nM | % inhibition @ 1 nM |
|---|---|---|
| 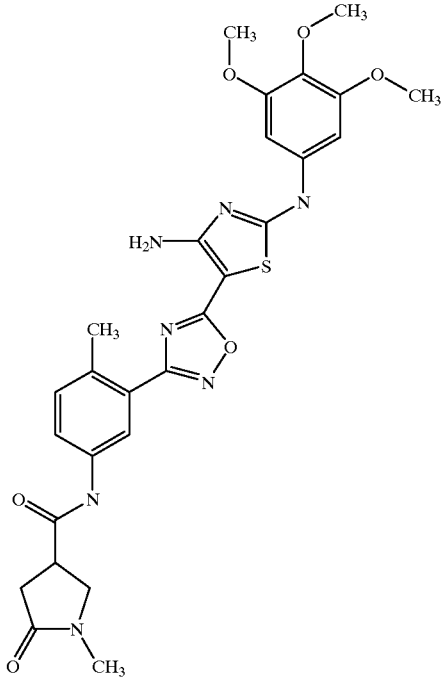 | −18 | 16 |
| 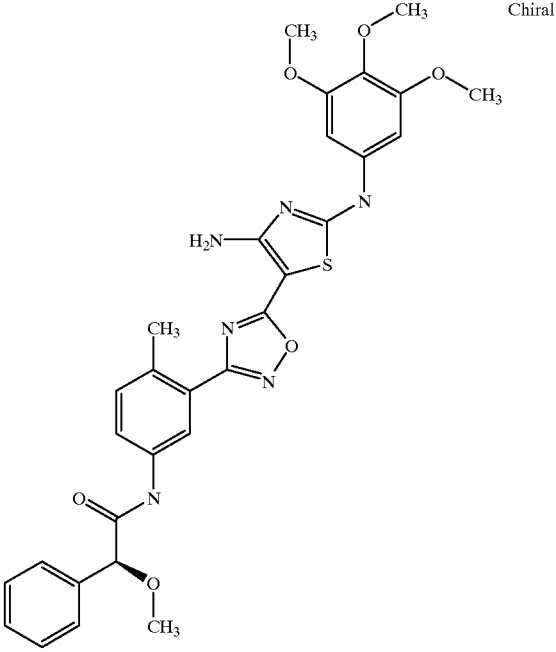 Chiral | 63 | −11 |

-continued

| STRUCTURE | % inhibition @ 10 nM | % inhibition @ 1 nM |
|---|---|---|
| 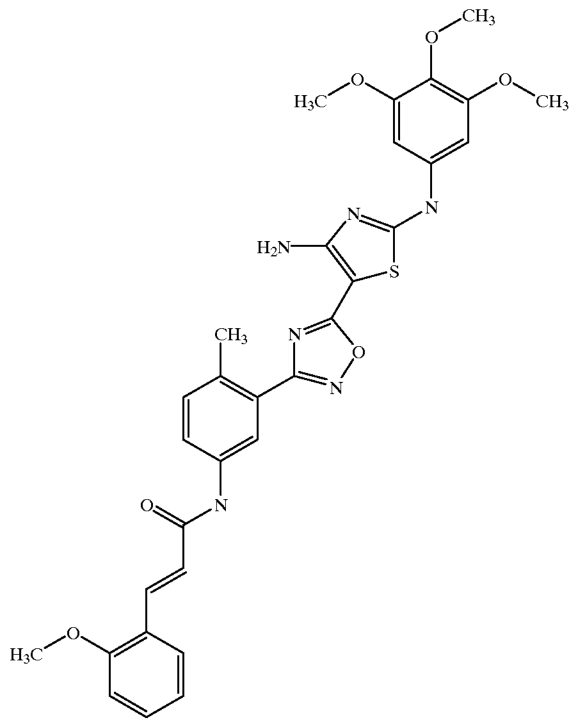 | 31 | 13 |
| 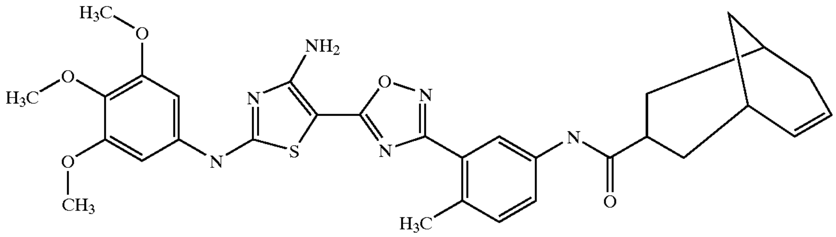 | 18 | 18 |
| 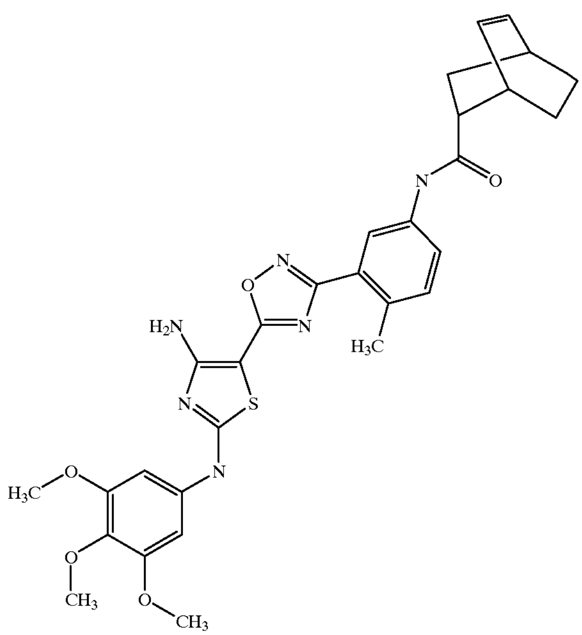 | 21 | 27 |

| STRUCTURE | % inhibition @ 10 nM | % inhibition @ 1 nM |
|---|---|---|
| [chemical structure] | 11 | 10 |
| [chemical structure] | 20 | 7 |

The exemplary compounds described above may be formulated into pharmaceutical compositions according to the following general examples.

EXAMPLE 1
Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

EXAMPLE 2
Oral Composition

To prepare a pharmaceutical composition for oral delivery, 100 mg of a compound of Formula I is mixed with 750 mg of lactose. The mixture is incorporated into an oral dosage unit form, such as a hard gelatin capsule, which is suitable for oral administration.

EXAMPLE 3
Intraocular Composition

To prepare a sustained-release pharmaceutical composition for intraocular delivery, a compound of Formula I is suspended in a neutral, isotonic solution of hyaluronic acid (1.5% conc.) in phosphate buffer (pH 7.4) to form a 1% suspension.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A compound of the Formula I:

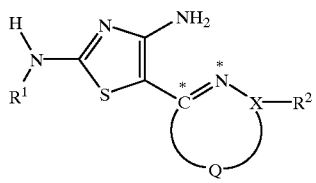

wherein:

$R^1$ is hydrogen, a substituted or unsubstituted alkyl, cycloalkyl, heterocycloalkyl, aryl, or heteroaryl, or a group of the formula $R^6$—CO or $R^6$—CS where $R^6$ is substituted or unsubstituted alkyl, cycloalkyl, heterocycloalkyl, alkenyl, aryl, heteroaryl, alkoxy, or N—$R^7R^8$ where $R^7R^8$ are each independently hydrogen or substituted or unsubstituted alkyl, aryl, or heteroaryl;

$R^2$ is hydroxy, halo, cyano, or nitro, or substituted or unsubstituted alkyl, alkenyl, cycloalkyl, heterocycloalkyl, aryl, or heteroaryl, or a group of the formula (A):

where $R_a$ is hydrogen or substituted or unsubstituted alkyl, cycloalkyl, heterocycloalkyl, aryl, or heteroaryl, or a group of the formula (B):

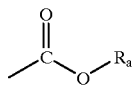

where $R_a$ is hydrogen or substituted or unsubstituted alkyl, cycloalkyl, heterocycloalkyl, aryl, or heteroaryl, or a group of the formula (C):

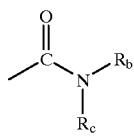

where $R_b$ and $R_c$ are independently hydrogen or substituted or unsubstituted alkyl, cycloalkyl, heterocycloalkyl, aryl, or heteroaryl, or a group of the formula (D):

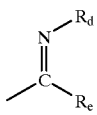

where $R_d$ is hydrogen or substituted or unsubstituted alkyl, cycloalkyl, heterocycloalkyl, aryl, heteroaryl, hydroxy, alkoxy, amino, alkylamino, dialkylamino, or acylamino, and $R_e$ is hydrogen or substituted or unsubstituted alkyl, cycloalkyl, heterocycloalkyl, aryl, heteroaryl, amino, alkylamino, or dialkylamino, or a group of the formula (E):

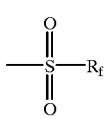

where $R_f$ is substituted or unsubstituted alkyl, cycloalkyl, heterocycloalkyl, aryl, or heteroaryl, or a group of the formula (F):

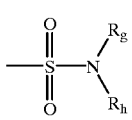

where $R_g$ and $R_h$ are each independently hydrogen or substituted or unsubstituted alkyl, cycloalkyl, heterocycloalkyl, aryl, or heteroaryl, or a group of the formula (G):

where $R_i$ is alkyl or substituted or unsubstituted cycloalkyl, heterocycloalkyl, aryl, or heteroaryl, or a group of formula (A), formula (B), formula (C), formula (H), or formula (I), or a group of the formula (H)

where $R_j$ is hydrogen or substituted or unsubstituted alkyl, cycloalkyl, heterocycloalkyl, aryl, heteroaryl, hydroxy, alkoxy, or amino, or a group of formula (A), formula (B), formula (C) or formula (D), and $R_k$ is hydrogen or substituted or unsubstituted alkyl, cycloalkyl, heterocycloalkyl, aryl, or heteroaryl, or a group of formula (A), formula (B), formula (C), formula (D), formula (E), or formula (F), or a group of the formula (I)

(I)

where $R_1$ is hydrogen or substituted or unsubstituted alkyl, cycloalkyl, heterocycloalkyl, aryl, or heteroaryl, or a group of formula (C),
or $R^2$ is a substituted or unsubstituted cycloalkyl, heterocycloalkyl, or aryl that is fused to Q;

X is C or N; and

Q is a divalent radical having 2 or 3 ring atoms each independently selected from C, N, O, S, C—$R^5$ and N—$R^5$, where $R^5$ hydroxy, halo, cyano, or amino, or substituted or unsubstituted alkyl, aryl, heteroaryl, alkoxy, which together with C* and N* form a five- or six-membered aromatic or nonaromatic ring;

or a pharmaceutically acceptable prodrug, or pharmaceutically acceptable salt thereof.

2. A compound of the Formula II:

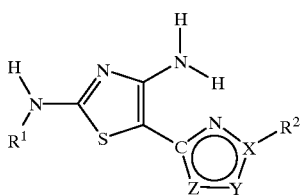

II wherein:

$R^1$ is substituted or unsubstituted aryl or heteroaryl, or a group of the formula $R^6$—CO or $R^6$—CS where $R^6$ is substituted or unsubstituted alkyl, cycloalkyl, heterocycloalkyl, alkenyl, aryl, heteroaryl, alkoxy, or N—$R^7R^8$ where $R^7R^8$ are each independently hydrogen or substituted or unsubstituted alkyl, aryl, or heteroaryl;

$R^2$ is as defined in claim 1;

X is C or N; and

Y and Z are each independently C, N, S, O, C—$R^5$ or N—$R^5$ where $R^5$ is as defined in claim 1;

or a pharmaceutically acceptable prodrug, or pharmaceutically acceptable salt thereof.

3. A compound, pharmaceutically acceptable prodrug, or pharmaceutically acceptable salt according to claim 2, wherein:

$R^1$ is substituted or unsubstituted aryl or heteroaryl, or $R^6$—CO or $R^6$—CS where $R^6$ is substituted or unsubstituted alkyl, cycloalkyl, heterocycloalkyl, alkenyl, aryl, heteroaryl, alkoxy, or N—$R^7R^5$ where $R^7R^8$ are each independently hydrogen or substituted or unsubstituted alkyl, aryl, or heteroaryl;

$R^2$ is substituted or unsubstituted aryl or heteroaryl;

X and Y are each independently C or N; and

Z is S or O.

4. A compound, pharmaceutically acceptable prodrug, or pharmaceutically acceptable salt according to claim 3, wherein:

$R^1$ and $R^2$ are each independently a substituted aryl;

X is C;

Y is C or N; and

Z is S or O.

5. A compound of the Formula III:

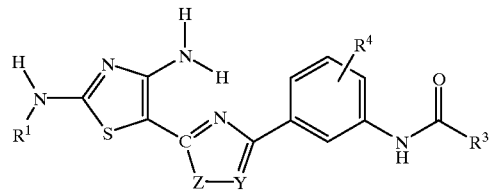

III wherein:

$R^1$ is substituted or unsubstituted aryl or heteroaryl, or $R^6$—CO or $R^6$—CS where $R^6$ is a substituted or unsubstituted alkyl, alkenyl, aryl, heteroaryl, alkoxy, or N—$R^7R^8$ where $R^7R^8$ are each independently hydrogen, alkyl, aryl, or heteroaryl;

$R^3$ is substituted or unsubstituted alkyl, cycloalkyl, heterocycloalkyl, aryl, heteroaryl, alkoxy, aryloxy, or N—$R^7R^8$ where $R^7R^8$ are each independently hydrogen, alkyl, aryl, or heteroaryl;

$R^4$ hydrogen, hydroxy, lower alkyl, halo, lower alkoxy, amino, nitro, or trifluoromethyl; and Y and Z are each independently C, N, S, O, or C—$R^5$ or N—$R^5$ where $R^5$ is unsubstituted or substituted alkyl or aryl;

or a pharmaceutically acceptable prodrug, or pharmaceutically acceptable salt thereof.

6. A compound of the Formula IV:

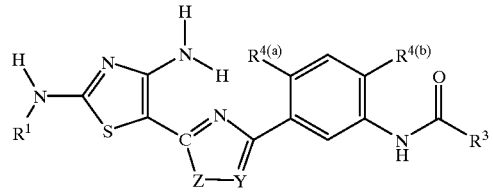

IV wherein:

$R^1$ is substituted or unsubstituted aryl or heteroaryl, or $R^6$—CO where $R^6$ is a substituted or unsubstituted alkyl, alkenyl, aryl, heteroaryl, alkoxy, cycloalkyl, heterocycloalkyl, or N—$R^7R^8$ where $R^7R^8$ are each independently hydrogen, alkyl, aryl, or heteroaryl;

$R^3$ is substituted or unsubstituted alkyl, cycloalkyl, heterocycloalkyl, aryl, heteroaryl, alkoxy, aryloxy, or N—$R^7R^8$ where $R^7R^8$ are each independently hydrogen, alkyl, aryl, or heteroaryl;

$R^4$ is independently hydrogen, hydroxy, lower alkyl, halo, lower alkoxy, amino, nitro, or trifluoromethyl; and Y is C or N; and Z is S or O;

or a pharmaceutically acceptable prodrug, or pharmaceutically acceptable salt thereof.

7. A compound, pharmaceutically acceptable prodrug, or pharmaceutically acceptable salt according to claim 6, wherein: $R^1$ is substituted or unsubstituted aryl or heteroaryl, or $R^6$—CO where $R^6$ is N—$R^7R^8$ where $R^7R^8$ are each independently hydrogen, alkyl, aryl, or heteroaryl; $R^3$ is substituted or unsubstituted alkyl, aryl, heteroaryl, or alkoxy; $R^{4(a)}$ and $R^{4(b)}$ are each independently hydrogen, lower alkyl, or halo; Y is C or N; and Z is S or O.

8. A compound, pharmaceutically acceptable prodrug, or pharmaceutically acceptable salt according to claim 7, wherein: $R^1$ is substituted or unsubstituted aryl or heteroaryl, or $R^6$—CO where $R^6$ is N—$R^7R^8$ where $R^7R^8$ are each independently hydrogen, alkyl, aryl, or heteroaryl; $R^3$ is substituted or unsubstituted aryl, heteroaryl, or alkoxy; $R^{4(a)}$ is chloro, fluoro, or methyl; $R^{4(b)}$ is fluoro; Y is N; and Z is O.

9. A pharmaceutical composition comprising:
   (a) a therapeutically effective amount of a compound, pharmaceutically acceptable prodrug, or pharmaceutically acceptable salt of claim 1; and
   (b) a pharmaceutically acceptable carrier, diluent, vehicle or excipient therefor.

10. A method of treating a mammalian disease condition mediated by protein kinase activity, comprising administering to a mammal in need thereof a therapeutically effective amount of a compound, pharmaceutically acceptable prodrug, or pharmaceutically acceptable salt as defined in claim 1.

11. A method according to claim 10, wherein the mammalian disease condition is associated with tumor growth, cell proliferation, or angiogenesis.

12. A method of modulating the activity of a protein kinase receptor, comprising contacting the kinase receptor with an effective amount of a compound, pharmaceutically acceptable prodrug, or pharmaceutically acceptable salt as defined in claim 1.

13. A method according to claim 12, wherein the protein kinase receptor is a VEGF receptor.

* * * * *